(12) United States Patent
Yaworski et al.

(10) Patent No.: US 12,129,467 B2
(45) Date of Patent: *Oct. 29, 2024

(54) NON-LIPOSOMAL SYSTEMS FOR NUCLEIC ACID DELIVERY

(71) Applicant: ARBUTUS BIOPHARMA CORPORATION, Vancouver (CA)

(72) Inventors: Ed Yaworski, Vancouver (CA); Lloyd B. Jeffs, Vancouver (CA); Lorne R. Palmer, Vancouver (CA)

(73) Assignee: ARBUTUS BIOPHARMA CORPORATION, Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 18/410,136

(22) Filed: Jan. 11, 2024

(65) Prior Publication Data

US 2024/0182895 A1 Jun. 6, 2024

Related U.S. Application Data

(63) Continuation of application No. 18/330,590, filed on Jun. 7, 2023, which is a continuation of application No. 17/203,572, filed on Mar. 16, 2021, now Pat. No. 11,718,852, which is a continuation of application No. 15/892,314, filed on Feb. 8, 2018, now abandoned, which is a continuation of application No. 15/342,020, filed on Nov. 2, 2016, now abandoned, which is a continuation of application No. 15/153,487, filed on May 12, 2016, now Pat. No. 9,518,272, which is a continuation of application No. 14/642,452, filed on Mar. 9, 2015, now Pat. No. 9,404,127, which is a continuation of application No. 13/807,288, filed as application No. PCT/CA2011/000778 on Jun. 30, 2011, now Pat. No. 9,006,417.

(60) Provisional application No. 61/360,480, filed on Jun. 30, 2010.

(51) Int. Cl.
| | |
|---|---|
| C07H 21/04 | (2006.01) |
| A61K 9/107 | (2006.01) |
| A61K 9/50 | (2006.01) |
| A61K 9/51 | (2006.01) |
| A61K 31/7088 | (2006.01) |
| A61K 31/7105 | (2006.01) |
| A61K 31/712 | (2006.01) |
| A61K 31/713 | (2006.01) |
| A61K 47/14 | (2017.01) |
| A61K 47/54 | (2017.01) |
| C12N 15/113 | (2010.01) |
| C12N 15/88 | (2006.01) |
| A61K 9/127 | (2006.01) |

(52) U.S. Cl.
CPC .......... *C12N 15/113* (2013.01); *A61K 9/1075* (2013.01); *A61K 9/5015* (2013.01); *A61K 9/5123* (2013.01); *A61K 31/7088* (2013.01); *A61K 31/7105* (2013.01); *A61K 31/712* (2013.01); *A61K 31/713* (2013.01); *A61K 47/14* (2013.01); *A61K 47/543* (2017.08); *C12N 15/88* (2013.01); *A61K 9/1272* (2013.01); *A61K 9/1274* (2013.01); *C12N 2310/14* (2013.01); *C12N 2310/321* (2013.01); *C12N 2310/3515* (2013.01); *C12N 2320/32* (2013.01)

(58) Field of Classification Search
None
See application file for complete search history.

(56) References Cited

U.S. PATENT DOCUMENTS

| | | | |
|---|---|---|---|
| 4,394,448 | A | 7/1983 | Szoka, Jr. et al. |
| 4,438,052 | A | 3/1984 | Weder et al. |
| 4,515,736 | A | 5/1985 | Deamer |
| 4,598,051 | A | 7/1986 | Papahadjopoulos et al. |
| 4,897,355 | A | 1/1990 | Eppstein et al. |
| 5,013,556 | A | 5/1991 | Woodle et al. |
| 5,171,678 | A | 12/1992 | Behr et al. |
| 5,208,036 | A | 5/1993 | Eppstein et al. |
| 5,225,212 | A | 7/1993 | Martin et al. |
| 5,264,618 | A | 11/1993 | Felgner et al. |
| 5,279,833 | A | 1/1994 | Rose |
| 5,283,185 | A | 2/1994 | Epand et al. |

(Continued)

FOREIGN PATENT DOCUMENTS

| | | |
|---|---|---|
| CA | 2309727 A1 | 4/1999 |
| CA | 2271582 A1 | 11/1999 |

(Continued)

OTHER PUBLICATIONS

Ahmad, A. et al., "New multivalent cationic lipids reveal bell curve for transfection efficiency versus membrane charge density: lipid-DNA complexes for gene delivery," J. Gene Med., 7(6):739-48, 2005.

(Continued)

*Primary Examiner* — Kimberly Chong
(74) *Attorney, Agent, or Firm* — Kilpatrick Townsend & Stockton LLP

(57) ABSTRACT

The present invention provides novel, stable lipid particles having a non-lamellar structure and comprising one or more active agents or therapeutic agents, methods of making such lipid particles, and methods of delivering and/or administering such lipid particles. More particularly, the present invention provides stable nucleic acid-lipid particles (SNALP) that have a non-lamellar structure and that comprise a nucleic acid (such as one or more interfering RNA), methods of making the SNALP, and methods of delivering and/or administering the SNALP.

24 Claims, 24 Drawing Sheets

Specification includes a Sequence Listing.

(56) References Cited

U.S. PATENT DOCUMENTS

| | | |
|---|---|---|
| 5,320,906 A | 6/1994 | Eley et al. |
| 5,334,761 A | 8/1994 | Gebeyehu et al. |
| 5,545,412 A | 8/1996 | Eppstein et al. |
| 5,578,475 A | 11/1996 | Jessee et al. |
| 5,627,159 A | 5/1997 | Shih et al. |
| 5,641,662 A | 6/1997 | Debs et al. |
| 5,656,743 A | 8/1997 | Busch et al. |
| 5,674,908 A | 10/1997 | Haces et al. |
| 5,703,055 A | 12/1997 | Felgner et al. |
| 5,705,385 A | 1/1998 | Bally et al. |
| 5,736,392 A | 4/1998 | Hawley-Nelson et al. |
| 5,753,613 A | 5/1998 | Ansell et al. |
| 5,820,873 A | 10/1998 | Choi et al. |
| 5,877,220 A | 3/1999 | Schwartz et al. |
| 5,885,613 A | 3/1999 | Holland et al. |
| 5,958,901 A | 9/1999 | Dwyer et al. |
| 5,976,567 A | 11/1999 | Wheeler et al. |
| 5,981,501 A | 11/1999 | Wheeler et al. |
| 6,020,202 A | 2/2000 | Jessee |
| 6,020,526 A | 2/2000 | Schwartz et al. |
| 6,034,135 A | 3/2000 | Schwartz et al. |
| 6,051,429 A | 4/2000 | Hawley-Nelson et al. |
| 6,075,012 A | 6/2000 | Gebeyehu et al. |
| 6,165,501 A | 12/2000 | Tirosh et al. |
| 6,172,049 B1 | 1/2001 | Dwyer et al. |
| 6,251,939 B1 | 6/2001 | Schwartz et al. |
| 6,284,267 B1 | 9/2001 | Aneja |
| 6,287,591 B1 | 9/2001 | Semple et al. |
| 6,339,173 B1 | 1/2002 | Schwartz et al. |
| 6,376,248 B1 | 4/2002 | Hawley-Nelson et al. |
| 6,534,484 B1 | 3/2003 | Wheeler et al. |
| 6,586,410 B1 | 7/2003 | Wheeler et al. |
| 6,638,529 B2 | 10/2003 | Schwartz et al. |
| 6,649,780 B1 | 11/2003 | Eibl et al. |
| 6,671,393 B2 | 12/2003 | Hays et al. |
| 6,696,424 B1 | 2/2004 | Wheeler |
| 6,815,432 B2 | 11/2004 | Wheeler et al. |
| 6,858,224 B2 | 2/2005 | Wheeler et al. |
| 7,166,745 B1 | 1/2007 | Chu et al. |
| 7,422,902 B1 | 9/2008 | Wheeler et al. |
| 7,479,573 B2 | 1/2009 | Chu et al. |
| 7,491,409 B1 | 2/2009 | Meers et al. |
| 7,514,099 B2 | 4/2009 | Chen et al. |
| 7,601,872 B2 | 10/2009 | Chu et al. |
| 7,687,070 B2 | 3/2010 | Gebeyehu et al. |
| 7,745,651 B2 | 6/2010 | Heyes et al. |
| 7,799,565 B2 | 9/2010 | MacLachlan et al. |
| 7,803,397 B2 | 9/2010 | Heyes et al. |
| 7,807,815 B2 | 10/2010 | MacLachlan et al. |
| 7,838,658 B2 | 11/2010 | MacLachlan et al. |
| 7,901,708 B2 | 3/2011 | MacLachlan et al. |
| 7,915,450 B2 | 3/2011 | Chu et al. |
| 7,939,505 B2 | 5/2011 | Quay et al. |
| 7,981,027 B2 | 7/2011 | Miyagi et al. |
| 7,982,027 B2 | 7/2011 | MacLachlan et al. |
| 8,058,068 B2 | 11/2011 | Hawley-Nelson et al. |
| 8,058,069 B2 | 11/2011 | Yaworski |
| 8,101,741 B2 | 1/2012 | MacLachlan et al. |
| 8,158,601 B2 | 4/2012 | Chen et al. |
| 8,158,827 B2 | 4/2012 | Chu et al. |
| 8,188,263 B2 | 5/2012 | MacLachlan et al. |
| 8,227,443 B2 | 7/2012 | MacLachlan et al. |
| 8,236,943 B2 | 8/2012 | Lee et al. |
| 8,283,333 B2 | 10/2012 | Yaworski et al. |
| 8,455,455 B1 | 6/2013 | Robbins et al. |
| 8,466,122 B2 | 6/2013 | Heyes et al. |
| 8,492,359 B2 | 7/2013 | Yaworski et al. |
| 8,513,403 B2 | 8/2013 | MacLachlan et al. |
| 8,569,256 B2 | 10/2013 | Heyes et al. |
| 8,598,333 B2 | 12/2013 | MacLachlan et al. |
| 8,716,464 B2 | 5/2014 | Geisbert et al. |
| 8,822,668 B2 | 9/2014 | Yaworski et al. |
| 8,865,675 B2 | 10/2014 | Heyes et al. |
| 8,999,950 B2 | 4/2015 | MacLachlan et al. |
| 9,006,191 B2 | 4/2015 | MacLachlan et al. |
| 9,006,417 B2 | 4/2015 | Yaworski et al. |
| 9,018,187 B2 | 4/2015 | Heyes et al. |
| 9,035,039 B2 | 5/2015 | Dhillon et al. |
| 9,126,966 B2 | 9/2015 | Martin et al. |
| 9,139,554 B2 | 9/2015 | Hope et al. |
| 9,187,748 B2 | 11/2015 | Geisbert et al. |
| 9,364,435 B2 | 6/2016 | Yaworski et al. |
| 9,404,127 B2 | 8/2016 | Yaworski et al. |
| 9,504,651 B2 | 11/2016 | MacLachlan et al. |
| 9,518,272 B2 | 12/2016 | Yaworski et al. |
| 9,878,042 B2 | 1/2018 | Yaworski et al. |
| 10,053,689 B2 | 8/2018 | Fitzgerald et al. |
| 10,077,232 B2 | 9/2018 | Heyes et al. |
| 10,415,037 B2 | 9/2019 | Cross et al. |
| 11,141,378 B2 | 10/2021 | Yaworski et al. |
| 11,718,852 B2 | 8/2023 | Yaworski et al. |
| 2001/0048940 A1 | 12/2001 | Tousignant et al. |
| 2003/0069173 A1 | 4/2003 | Hawley-Nelson et al. |
| 2003/0072794 A1 | 4/2003 | Boulikas |
| 2003/0077829 A1 | 4/2003 | MacLachlan |
| 2003/0143732 A1 | 7/2003 | Fosnaugh et al. |
| 2004/0063654 A1 | 4/2004 | Davis et al. |
| 2004/0142025 A1 | 7/2004 | MacLachlan et al. |
| 2004/0142892 A1 | 7/2004 | Finn et al. |
| 2004/0253723 A1 | 12/2004 | Tachas et al. |
| 2004/0259247 A1 | 12/2004 | Tuschl et al. |
| 2005/0064595 A1 | 3/2005 | MacLachlan et al. |
| 2005/0118253 A1 | 6/2005 | MacLachlan et al. |
| 2005/0260757 A1 | 11/2005 | Gebeyehu et al. |
| 2006/0008910 A1 | 1/2006 | MacLachlan et al. |
| 2006/0025366 A1 | 2/2006 | MacLachlan et al. |
| 2006/0083780 A1 | 4/2006 | Heyes et al. |
| 2006/0134189 A1 | 6/2006 | MacLachlan et al. |
| 2006/0147514 A1 | 7/2006 | Gebeyehu et al. |
| 2006/0228406 A1 | 10/2006 | Chiou et al. |
| 2006/0240093 A1 | 10/2006 | MacLachlan et al. |
| 2006/0240554 A1 | 10/2006 | Chen et al. |
| 2007/0042031 A1 | 2/2007 | MacLachlan et al. |
| 2007/0135372 A1 | 6/2007 | MacLachlan et al. |
| 2007/0202598 A1 | 8/2007 | Chu et al. |
| 2007/0202600 A1 | 8/2007 | Chu et al. |
| 2008/0020058 A1 | 1/2008 | Chen et al. |
| 2008/0317839 A1 | 12/2008 | Quay et al. |
| 2009/0143583 A1 | 6/2009 | Chu et al. |
| 2009/0291131 A1 | 11/2009 | MacLachlan et al. |
| 2010/0130588 A1 | 5/2010 | Yaworski et al. |
| 2010/0159593 A1 | 6/2010 | Chu et al. |
| 2011/0076335 A1 | 3/2011 | Yaworski et al. |
| 2012/0058188 A1 | 3/2012 | MacLachlan et al. |
| 2012/0136073 A1 | 5/2012 | Zhiwei et al. |
| 2012/0148663 A1 | 6/2012 | Nilssen et al. |
| 2012/0183581 A1 | 7/2012 | Yaworski et al. |
| 2012/0238747 A1 | 9/2012 | Chu et al. |
| 2012/0276209 A1 | 11/2012 | Cullis et al. |
| 2013/0116307 A1 | 5/2013 | Heyes et al. |
| 2013/0122104 A1 | 5/2013 | Yaworski et al. |
| 2013/0303587 A1 | 11/2013 | Yaworski et al. |
| 2014/0065228 A1 | 3/2014 | Yaworski et al. |
| 2014/0294937 A1 | 10/2014 | MacLachlan et al. |
| 2015/0164799 A1 | 6/2015 | Yaworski et al. |
| 2015/0374834 A1 | 12/2015 | Yaworski et al. |
| 2016/0032320 A1 | 2/2016 | Yaworski et al. |
| 2016/0251681 A1 | 9/2016 | Yaworski et al. |
| 2017/0042814 A1 | 2/2017 | Yaworski et al. |
| 2017/0260523 A1 | 9/2017 | Yaworski et al. |
| 2017/0307608 A1 | 10/2017 | Bettencourt |
| 2018/0071397 A1 | 3/2018 | Yaworski et al. |
| 2018/0085312 A1 | 3/2018 | Yaworski et al. |
| 2018/0092848 A1 | 4/2018 | Yaworski et al. |
| 2019/0032051 A1 | 1/2019 | Yaworski et al. |
| 2019/0240339 A1 | 8/2019 | Yaworski et al. |
| 2020/0113832 A1 | 4/2020 | Yaworski et al. |
| 2021/0207140 A1 | 7/2021 | Yaworski et al. |
| 2021/0220274 A1 | 7/2021 | Yaworski et al. |

(56) References Cited

U.S. PATENT DOCUMENTS

| | | | |
|---|---|---|---|
| 2021/0267895 | A1 | 9/2021 | Yaworski et al. |
| 2023/0372245 | A1 | 11/2023 | Yaworski et al. |

FOREIGN PATENT DOCUMENTS

| | | | |
|---|---|---|---|
| CA | 2330741 | A1 | 11/1999 |
| CA | 2397016 | A1 | 7/2001 |
| CA | 2513623 | | 8/2004 |
| CA | 2637931 | | 7/2007 |
| EP | 1 648 519 | B1 | 10/2014 |
| EP | 2 567 693 | B1 | 10/2015 |
| JP | 03-126211 | | 5/1991 |
| JP | 05-202085 | | 8/1993 |
| JP | 06-080560 | | 3/1994 |
| JP | 2002-525063 | | 8/2002 |
| JP | 2003-505401 | | 2/2003 |
| JP | 2007-524349 | | 8/2007 |
| WO | 91/16024 | A1 | 10/1991 |
| WO | 93/05162 | A1 | 3/1993 |
| WO | 93/12240 | A1 | 6/1993 |
| WO | 93/12756 | A2 | 7/1993 |
| WO | 93/24640 | A2 | 12/1993 |
| WO | 93/25673 | A1 | 12/1993 |
| WO | 94/03198 | A1 | 2/1994 |
| WO | 95/02698 | A1 | 1/1995 |
| WO | 95/18863 | A1 | 7/1995 |
| WO | 95/35301 | A1 | 12/1995 |
| WO | 96/02655 | A1 | 2/1996 |
| WO | 96/10390 | A1 | 4/1996 |
| WO | 96/40964 | A2 | 12/1996 |
| WO | 96/41873 | A1 | 12/1996 |
| WO | 98/51285 | A2 | 11/1998 |
| WO | 00/03683 | A2 | 1/2000 |
| WO | 00/15820 | A1 | 3/2000 |
| WO | 00/62813 | A2 | 10/2000 |
| WO | 01/05374 | A1 | 1/2001 |
| WO | 01/05873 | A1 | 1/2001 |
| WO | 01/75164 | A2 | 10/2001 |
| WO | 01/93836 | | 12/2001 |
| WO | 02/034236 | A2 | 5/2002 |
| WO | 02/087541 | A1 | 11/2002 |
| WO | 03/097805 | A2 | 11/2003 |
| WO | 2004/065546 | A2 | 8/2004 |
| WO | 2004/110499 | A1 | 12/2004 |
| WO | 2005/007196 | A2 | 1/2005 |
| WO | 2005/026372 | A1 | 3/2005 |
| WO | 2005/035764 | A1 | 4/2005 |
| WO | 2005/120152 | A2 | 12/2005 |
| WO | 2006/002538 | A1 | 1/2006 |
| WO | 2006/053430 | A1 | 5/2006 |
| WO | 2007/012191 | | 2/2007 |
| WO | 2007/056861 | A1 | 5/2007 |
| WO | 2009/082817 | A1 | 7/2009 |
| WO | 2009/086558 | A1 | 7/2009 |
| WO | 2009/111658 | A2 | 9/2009 |
| WO | 2009/127060 | | 10/2009 |
| WO | 2010/042877 | A1 | 4/2010 |
| WO | 2010/048228 | A2 | 4/2010 |
| WO | 2010/088537 | A2 | 8/2010 |
| WO | 2010/105209 | A1 | 9/2010 |
| WO | 2010/144740 | A1 | 12/2010 |
| WO | 2011/000107 | A1 | 1/2011 |
| WO | 2011/140627 | | 11/2011 |
| WO | 2012/019168 | A2 | 2/2012 |
| WO | 2012/045075 | A1 | 4/2012 |
| WO | 2012/135805 | A2 | 10/2012 |
| WO | 2012/158736 | A1 | 11/2012 |
| WO | 2013/090648 | A1 | 6/2013 |
| WO | 2015/011633 | A1 | 1/2015 |
| WO | 2017/223135 | A1 | 12/2017 |
| WO | 2018/232357 | A1 | 12/2018 |

OTHER PUBLICATIONS

Akinc, A. et al., "The Onpattro story and the clinical translation of nanomedicines containing nucleic acid-based drugs," Nature Nanotechnology, 14:1084-1087, 2019.

Alnylam Pharmaceuticals, Inc., ONPATTRO Label, Revised Aug. 2018.

Ambegia, E. et al., "Stabilized plasmid-lipid particles containing PEG-diacylglycerols exhibit extended circulation lifetimes and tumor selective gene expression," Biochimica et Biophysica Acta, 1669:155-163, 2005.

Arbutus Biopharma Corporation, "Arbutus' LNP Licensee Alnylam Announces FDA Approval of ONPATTRO™ (patisiran), for the Treatment of ATTR Amyloidosis," Press Release, https://investor.arbutusbio.com/news-releases/news-release-details/arbutus-lnp-licensee-alnylam-announces-fda-approval-onpattrotm, Aug. 13, 2018, 2 pages.

Arima, Y. et al., "Complement activation on surfaces modified with ethylene glycol units," Biomaterials, 29:551-560, 2008.

Arpicco, S., et al., "Preparation and Characterization of Novel Cationic Lipids Developed for Gene Transfection," Proceed. Int'l Symp. Control. Rel. Bioact. Mater. (Controlled Release Society, Inc.), 1999, vol. 26, pp. 759-760.

Arpicco, S., et al., "Synthesis, characterization and transfection activity of new saturated and unsaturated cationic lipids," IL Farmaco, 2004, vol. 59, pp. 869-878.

Bahl, K. et al., "Preclinical and Clinical Demonstration of Immunogenicity by mRNA Vaccines against H10N8 and H7N9 Influenza Viruses," Molecular Therapy, 25(6):1316-1327, 2017.

Ballas, N., et al., "Liposomes bearing a quaternary ammonium detergent as an efficient vehicle for functional transfer of TMV-RNA into plant protoplasts," Biochimica et Biophysica Acta, 1988, vol. 939, pp. 8-18.

Barinaga, M., "Step Taken Toward Improved Vectors for Gene Transfer," Science, 1994, vol. 266, p. 1326.

Basarkar, A. and J. Singh, "Nanoparticulate systems for polynucleotide delivery," Int. J. Nanomedicine, 2(3):353-360, 2007.

Bass, "The Short Answer," Nature, 2001, 411: 428-9.

Beale, G., et al., "Gene Silencing Nucleic Acids Designed by Scanning Arrays: Anti-EGFR Activity of siRNA, Ribozyme and DNA Enzymes Targeting a Single Hybridization-accessible Region using the Same Delivery System," Journal of Drug Targeting, 2003, vol. 11, No. 7, pp. 449-456.

Behr, J.-P., "Synthetic Gene-Transfer Vectors," Acc. Chem. Res., 1993, vol. 26, pp. 274-278.

Bennett et al., "Cholesterol enhances cationic liposome-mediated DNA transfection of human respiratory epithelial cells," Bioscience Reports, 15:47-53, 1995.

Brigham, K., et al., "Rapid Communication: In vivo Transfection of Murine Lungs with a Functioning Prokaryotic Gene Using a Liposome Vehicle," The American Journal of the Medical Sciences, vol. 298, Oct. 1989, No. 4, pp. 278-281.

Brummelkamp, et al., "A System for Stable Expression of Short Interfering RNAs in Mammalian Cells," Science, 2002, V. 296. pp. 550-553.

Cevc, G., "How Membrane Chain-Melting Phase-Transition Temperature is Affected by the Lipid Chain Asymmetry and Degree of Unsaturation: An Effective Chain-Length Model," Biochemistry, 1991, vol. 30, pp. 7186-7193.

Check, E., "RNA to the Rescue? Disease therapies based on a technique for gene silencing called RNA interference are racing towards the clinic. Erika Check investigates molecular medicine's next big thing," Nature, 425:10-12, 2003.

Choi, S. et al., "Novel cationic solid lipid nanoparticles enhanced p53 gene transfer to lung cancer cells," European J. of Pharmaceutics and Biopharmaceutics, 68:545-554, 2008.

Chonn et al., "Recent advances in liposomal drug-delivery systems," Current Opinion in Biotechnology, 1995, vol. 6, pp. 698-708.

Cortesi, R., et al., "Effect of cationic liposome composition on in vitro cytotoxicity and protective effect on carried DNA," International Journal of Pharmaceutics, 1996, vol. 139, pp. 69-78.

Crystal, R., "Transfer of Genes to Humans: Early Lessons and Obstacles to Success," Science, 1995, vol. 270, pp. 404-410.

(56) References Cited

OTHER PUBLICATIONS

Culver K., "The First Human Gene Therapy Experiment," Gene Therapy: A Handbook for Physicians, 1994, pp. 33-40.
Duzgunes, N., "Membrane Fusion," Subcellular Biochemistry, 1985, vol. 11, pp. 195-286.
Dwarki, V.J., et al., "Cationic Liposome-Mediated RNA Transfection," Methods in Enzymology, 1993, vol. 217, pp. 644-654.
Elbashir, et a., "Duplexes of 21-nucleotide RNAs mediate RNA interference in cultured mammalian cells," Nature, May 2001, pp. 494-498, vol. 411.
Enoch, H., et al., "Formation and properties of 1000-Å-diameter, single-bilayer phospholipid vesicles," Proc. Natl. Acad. Sci. USA, 1979, vol. 76, No. 1, pp. 145-149.
Epand, Richard M. et al., "Phosphatidylcholine structure determines cholesterol solubility and lipid polymorphism," Chemistry and Physics of Lipids, 2005, vol. 135, pp. 39-53.
European Medicines Agency, "New Medicine for Hereditary Rare Disease," Press Release, https://www.ema.europa.eu/en/news/new-medicine-hereditary-rare-disease, Jul. 27, 2018, 2 pages.
Ewert et al., "Cationic Lipid-DNA Complexes for Non-Viral Gene Therapy: Relating Supramolecular Structures to Cellular Pathways," Expert Opin Biol Ther, 5(1):33-53, 2005.
Felgner, J., et al., "Cationic Lipid-Mediated Transfection in Mammalian Cells: 'Lipofection,'" J. Tiss. Cult. Meth., 1993, vol. 15, pp. 63-68.
Felgner, J., et al., "Enhanced Gene Delivery and Mechanism Studies with a Novel Series of Cationic Lipid Formulations," The Journal of Biological Chemistry, 1994, vol. 269, No. 4, pp. 2550-2561.
Felgner, P., et al., "Lipofection: A highly efficient, lipid-mediated DNA-transfection procedure," Proc. Natl. Acad. Sci. USA, 1987, vol. 84, pp. 7413-7417.
Felgner, P. L., et al., "Cationic Liposome Mediated Transfection," Proc. West. Pharmacol. Soc., 1989, vol. 32, pp. 115-121.
Filion, M.C. and Phillips, N.C., "Toxicity and immunomodulatory activity of liposomal vectors formulated with cationic lipids towards immune effector cells," Biochim. Biophys. Acta., 1329(2):345-356, 1997.
Gallie, D., "Introduction of mRNA to plant protoplasts using polyethylene glycol," Plant Cell Reports, 13:119-122, 1993.
Gao, X. et al., "Nonviral gene Delivery: What we know and what is next," AAPS Journal, 9(1): E92-104, 2007.
Gao, X., et al., "A Novel Cationic Liposome Reagent for Efficient Transfection of Mammalian Cells," Biochem. Biophys. Res. Comm., 1991, vol. 179, No. 1, pp. 280-285.
Gershon, H., et al., "Mode of Formation and Structural Feature of DNA-Cationic Liposome Complexes Used for Transfection," Biochemistry, 1993, vol. 32, pp. 7143-7151.
Global Newswire, retrieved from http://globalnewswire.com on Feb. 27, 2013, Tekmira sues Alnylam Pharmaceuticals for repeated misuse of trade secrets and confidential information, Mar. 16, 2011, pp. 1-3.
Guy-Caffey, J., et al., "Novel Polyaminolipids Enhance the Cellular Uptake of Oligonucleotides," The Journal of Biological Chemistry, 1995, vol. 270, No. 52, pp. 31391-31396.
Hausseker, D., "The Business of RNAi Therapeutics in 2012," Molecular Therapy-Nucleic Acids, 2:e8, 2012, 12 pages.
Hawley-Nelson, P., et al., "LipofectAmine™ Reagent: A New, Higher Efficiency Polycationic Liposome Transfection Reagent," Focus, 1993, vol. 15, No. 3, pp. 73-80.
Heyes et al., "Cationic lipid saturation influences intracellular delivery of encapsulated nucleic acids," Journal of Controlled Release, 2005, vol. 107, pp. 276-287.
Heyes et al., "Synthesis of novel cationic lipids: effect of structural modification on the efficiency of gene transfer," J. Med. Chem., 2002, vol. 45, pp. 99-114.
Huang, L. et al., "Liposomal Gene Delivery: A Complex Package," Nature Biotechnology, 15:620-621, 1997.
Hui et al., "The Role of Helper Lipids in Cationic Liposome-Medicated Gene Transfer," Biophysical Journal, 71:590-99, 1996.

Hyde, S., et al., "Correction of the ion transport defect in cystic fibrosis transgenic mice by gene therapy," Nature, 1993, vol. 362, pp. 250-255.
Jeffs, L. et al., "A scalable, extrusion-free method for efficient liposomal encapsulation of plasmid DNA," Pharmaceutical Research, 22(3):362-372, 2005.
Jiang, L., et al., "Comparison of protein precipitation methods for sample preparation prior to proteomic analysis," Journal of Chromatography A, 2004, vol. 1023, pp. 317-320.
Juliano, R., et al., "The Effect of Particle Size and Charge on the Clearance Rates of Liposomes and Liposome Encapsulated Drugs," Biochem. Biophys. Res. Commun., 1975, vol. 63, No. 3, pp. 651-658.
Kauffman, K. et al., "Optimization of Lipid Nanoparticle Formulations for mRNA Delivery in Vivo with Fractional Factorial and Definitive Screening Designs," Nano Letters, 2015.
Keough, K., "Influence of chain unsaturation and chain position on thermotropism and intermolecular interactions in membranes," Biochem. Soc. Transactions, 1990, vol. 18, No. 5, pp. 835-837.
Kim, H. et al., "Cationic solid lipid nanoparticles reconstituted from low density lipoprotein components for delivery of siRNA," Molecular Pharmaceutics, 5(4):622-631, 2008.
Koltover et al., "An Inverted Hexagonal Phase of Cationic Liposome-DNA Complexes Related to DNA Release and Delivery," Science, 281:78-81, 1998.
Krichevsky, A. et al., "RNAi functions in cultured mammalian neurons," PNAS, 99(18): 11926-29, 2002.
Lawrence et al. "The formation, characterization and stability of non-ionic surfactant vesicles," S.T.P. Pharma Sciences, 1996, vol. 6, No. 1, pp. 49-60.
Lawrence et al., "Synthesis and aggregation properties of dialkyl polyoxyethylene glycerol ethers," Chemistry and Physics of Lipids, 1996, 82(2):89-100.
Ledford, H., "Gene-Silencing Drug Approved: US Government Okays First RNA-Interference Drug—After a 20-Year Wait," Nature 560:291-292, 2018.
Legendre, J.-Y et al., "Delivery of Plasmid DNA into Mammalian Cell Lines Using pH-Sensitive Liposomes: Comparison with Cationic Liposomes," Pharm. Res., 1992, vol. 9, No. 10, pp. 1235-1242.
Leventis, R., et al., "Interactions of mammalian cells with lipid dispersions containing novel metabolizable cationic amphiphiles," Biochem. Biophys. Acta, 1990, vol. 1023, pp. 124-132.
Li, H. et al., "The role of the transferrin-transferrin-receptor system in drug delivery and targeting," Trends in Pharmacological Sciences, 23(5):206-209, 2002.
Li and Szoka, "Lipid-based nanoparticles for nucleic acid delivery," Pharmaceutical Research, 2483:438-449, 2007.
Lin, A.J. et al., "Three-dimensional imaging of lipid gene-carriers: Membrane charge density controls universal transfection behavior in lamellar cationic liposome-DNA complexes," Biophys J., 84(5):3307-16, 2003.
Liu, et al., "Cationic Liposome-mediated Intravenous Gene Delivery", J. Biol. Chem., 1995, V. 270, pp. 24864-24870.
Maclachlan, "Liposomal Formulations for Nucleic Acid Delivery," Antisense Drug Technologies, Second Edition; 2007; pp. 237-270.
Maclachlan, I. and Cullis, P., "Diffusible-PEG-Lipid Stabilized Plasmid Lipid Particles," Advances in Genetics, 53:157-188, 2005.
Manickam, D. and D. Oupicky, "Polyplex gene delivery modulated by redox potential gradients," Journal of Drug Targeting, 14(8):519-526, 2006.
Marshall, E., "Gene Therapy's Growing Pains," Science, 1995, vol. 269, pp. 1050-1055.
Middaugh, C. and Ramsey, C., "Analysis of Cationic-Lipid-Plasmid-DNA Complexes," Analytical Chemistry, American Chemical Society, pp. 7240-7248, 2007.
Moghimi, S. et al., "Methylation of the phosphate oxygen moiety of phospholipid-methoxy(polyethylene glycol) conjugate prevents PEGylated liposome-mediated complement activation and anaphylatoxin production," The FASEB Journal, 20:E2057-E2593, 2006.
Montana, G. et al., "Employment of cationic solid-lipid nanoparticles as RNA carriers," Bioconjugate Chemistry, 18:302-308, 2007.
Murahashi et al., "Synthesis and evaluation of neoglycolipid for liposome modification," Biol. Pharm. Bull., 1997, 20(6):704-707.

(56) References Cited

OTHER PUBLICATIONS

Olbrich, C. et al., "Cationic solid-lipid nanoparticles can efficiently bind and transfect plasmid DNA," J. Controlled Release, 77:345-355, 2007.
Orkin, S., et al., NIH Report, Report and Recommendations of the Panel to Assess the NIH Investment in Research on Gene Therapy, 1995.
Ortho Biotech Products, LP, "Doxil® Label—Product Insert, Revised May 2007," https://www.accessdata.fda.gov/drugsatfda_docs/label/2007/ 050718s029lbl.pdf, 33 pages.
Pak, C. et al., "Elastase-activated liposomal delivery to nucleated cells," Biochimica et Biophysica Acta, 1419:111-126, 1999.
Parr et al., Factors influencing the retention and chemical stability of poly(ethylene glycol)-lipid conjugates incorporated into large unilamellar vesicles, Biochimica et Biophysica Acta, 1994, 1195:21-30.
Paul, C., et al., "Effective expression of small interfering RNA in human cells," Nature Biotech., 2002, vol. 20, pp. 505-508.
Puyal, C., et al., "A new cationic liposome encapsulating genetic material: A potential delivery system for polynucleotides," Eur. J. Biochem., 1995, vol. 228, pp. 697-703.
Rotenberg, M. et al., "Physico-chemical characterization of Intralipid™ emulsions," Biochemica et Biophysica Acta, 1086:265-272, 1991.
Rudolph, C et al., "Application of novel solid lipid nanoparticle (SLN)-gene vector formulations based on a dimeric HIV-1 TAT-peptide in vitro and in vivo," Pharmaceutical Research, 21(9):1662-1669, 2004.
Sawada et al., "Microemulsions in supercritical $CO_2$ utilizing the polyethyleneglycol dialkylglycerol and their use for the solubilization of hydrophiles," Dyes and Pigments, 2005, pp. 64-74, vol. 65.
Schmidt, C., "Therapeutic Interference: Small RNA Molecules Act as Blockers of Disease Metabolism," Modern Drug Discovery, American Chemical Society, pp. 37-42, 2003.
Sedic. M. et al., "Safety Evaluation of Lipid Nanoparticle-Formulated Modified mRNA in the Sprague-Dawley Rat and Cynomolgus Monkey," Veterinary Pathology, 2017:1-14, 2017.
Semple, S. et al., "Influence of cholesterol on the association of plasma proteins with liposomes," Biochemistry, 35:2521-2525, 1996.
Semple, S. et al., "Immunogenicity and Rapid Blood Clearance of Liposomes Containing Polyethylene Glycol-Lipid Conjugates and Nucleic Acid," The Journal Of Pharmacology and Experimental Therapeutics, 312(3):1020-1026, 2006.
Semple, S. et al., "Rational Design of Cationic Lipids for siRNA Delivery," Nature Biotechnology, 28(2):172-176, 2010.
Semple, S. et al., "Supplementary Text and Figures, Supplementary Fig. 1, Supplementary Tables 1-4 and Supplementary Syntheses 1 and 2 to Rational Design of Cationic Lipids for siRNA Delivery," Nature Biotechnology, 28(2):172-176, 2010, published online at https://www.nature.com/articles/nbt.1602?draft= collection#supplementary-information, last visited on Nov. 14, 2019, 19 pages.
Shimada, K. et al., "Determination of incorporated amounts of poly(ethylene glycol)-derivatized lipids in liposomes for the physicochemical characterization of stealth liposomes," International Journal of Pharmaceutics, 203:255-263, 2000.
Shin, et al. "Acid-triggered release via dePEGylation of DOPE liposomes containing acid-labile vinyl ether PEG-lipids," Journal of Controlled Release, 2003, vol. 91, pp. 187-200.
Smisterova, J. et al., "Molecular shape of the cationic lipid controls the structure of cationic lipid/dioleylphosphatidylethanolamine-DNA complexes and the efficiency of gene delivery," J. Biol. Chem., 276(50):47615-47622, 2001.
Song et al., "Characterization of the inhibitory effect of PEG-lipid conjugates on the intracellular delivery of plasmid and antisense DNA mediated by cationic lipid liposomes," Biochimica et Biophysica Acta, 2002, 1558:1-13.
Sorensen, et al., "Gene Silencing by Systemic Delivery of Synthetic siRNAs in Adult Mice", J. Biol. Chem., 2003, V. 327, pp. 761-766.

Spagnou, S., et al., "Lipidic Carriers of siRNA: Differences in the Formulation, Cellular Uptake, and Delivery with Plasmid DNA," Biochemistry, 2004, vol. 43, pp. 13348-13356.
Stamatatos, L., et al., "Interactions of Cationic Lipid Vesicles with Negatively Charged Phospholipid Vesicles and Biological Membranes," Biochemistry, 1988, vol. 27, pp. 3917-3925.
Suzuki, Y. et al., "Differences and Similarities of the Intravenously Administered Lipid Nanoparticles in Three Clinical Trials: Potential Linkage between Lipid Nanoparticles and Extracellular Vesicles," Mol. Pharmaceutics, 20(10):4883-4892, 2023.
Szoka, F., et al., "Comparative Properties and Methods of Preparation of Lipid Vesicles (Liposomes)," Ann. Rev. Biophys. Bioeng., 1980, vol. 9, pp. 467-508.
Szoka, F., et al., "Procedure for preparation of liposomes with large internal aqueous space and high capture by reverse-phase evaporation," Proc. Natl. Acad. Sci. USA, 1978, vol. 75, No. 9, pp. 4194-4198.
Tabatt, K. et al., "Effect of cationic lipid and matrix lipid composition on solid lipid nanoparticle-mediated gene transfer," European J. of Pharmaceutics and Biopharmaceutics, 57:155-162, 2004.
Tam P. et al., "Stabilized plasmid-lipid particles for systemic gene therapy," Gene Therapy, 7:1867-74, 2000.
Teixeira, H. et al., "Characterization of oligonucleotide/lipid interactions in submicron cationic emulsions: influence of the cationic lipid structure and the presence of PEG-lipids," Biophysical Chemistry, 92:169-181, 2001.
Tekmira Pharmaceuticals and Protiva Biotherapeutics Inc., Poster entitled "Manufacturing, Safety and Efficacy of SNALP Formulated siRNA," Presented at CHI—Discovery on Target—Oct. 23, 2008, Boston, MA, by Ian MacLachlan.
Templeton, "Cationic Liposome-mediated Gene Delivery In vivo", Bioscience Reports, 2002, vol. 22, No. 2, pp. 283-295.
Timmerman, L. "Merck's Alan Sachs, on RNAi's Big Challenge: Delivery, Delivery, Delivery," Xconomy, Inc., https://xconomy.com/national/2010/01/21/mercks-alan-sachs-on-rnais-big-challenge-delivery-delivery-delivery/ -2016-, last visited on Jan. 21, 2010, 9 pages.
U.S. Department of Health and Human Services, "Liposome Drug Products: Chemistry, Manufacturing, and Controls; Human Pharmacokinetics and Bioavailability; and Labeling Documentation, Guidance for Industry," Food and Drug Administration, Center for Drug Evaluation and Research (CDER), Apr. 2018, 18 pages.
U.S. Food and Drug Administration, "FDA Approves First-of-its Kind Targeted RNA-based Therapy to Treat a Rare Disease," Press Announcement, https://www.fda.gov/newsevents/newsroom/pressannouncements/ucm616518.htm, Aug. 10, 2018, 3 pages.
U.S. Food and Drug Administration, "Orange Book: Approved Drug Products with Therapeutic Equivalence Evaluations, Patent and Exclusivity for: N210922," available at https://www.accessdata.fda.gov/scripts/cder/ob/patent_info.cfm?Product_No=001&Appl_No=210922&Appl_type=N, last visited Dec. 19, 2018, 3 pages.
Uyechi-O'brien, L. and Szoka, F., "Mechanisms for Cationic Lipids in Gene Transfer," Pharmaceutical Gene Delivery Systems, Marcel Dekker, Inc., vol. 131, pp. 79-108, 2003.
Van Der Woude, I., et al., "Parameters influencing the introduction of plasmid DNA into cells by the use of synthetic amphiphiles as a carrier system," Biochimica et Biophysica Acta, 1995, vol. 1240, pp. 34-40.
Wheeler, J. et al., "Stabilized Plasmid-lipid Particles: Constructions and Characterization," Gene Therapy (1999) 6, 271-281.
Wilson, R., et al., "Counterion-Induced Condensation of Deoxyribonucleic Acid," A Light-Scattering Study, Biochemistry, 1979, vol. 18, No. 11, pp. 2192-2196.
Woodle, M.C., et al., "Versatility in lipid compositions showing prolonged circulation with sterically stabilized liposomes," Biochimica et Biophysica Acta, 1992, vol. 1105, pp. 193-200.
Xu, Y. et al., "Physicochemical characterization and purification of cationic lipoplexes," Biophysical Journal, 77:341-353, 1999.
Yew, N.S. and Scheule, R.K., "Toxicity of cationic lipid-DNA complexes," Advances in Genetics, 53:189-214, 2005.
Zhang, P. et al., "Use of small RNA as antiaging cosmeceuticals," J. Cosmetic Sci., 64(6):455-68, 2013 (Abstract only).

(56) References Cited

OTHER PUBLICATIONS

Zhu, N., et al., "Systemic Gene Expression After Intravenous DNA Delivery into Adult Mice," Science, 1993, vol. 261, pp. 209-211.

Zimmermann, T. et al., "RNAi-mediated gene silencing in non-human primates," Nature, 2006, 441(7089):111-114.

Step One: Blending

Step Two: Diluting

| [lipid] mg/mL | Particle size (nm) | Final encapsulation (%) | Number-averaged Diameter size (nm) |
|---|---|---|---|
| 15 | 93 (0.12) | 95 | 46* |

| [lipid] mg/mL | Particle size (nm) | Final encapsulation (%) | Number-averaged Diameter size (nm) |
|---|---|---|---|
| 15 | 95 (0.1) | 96 | 47* |

| [lipid] mg/mL | Particle size (nm) | Final encapsulation (%) | Number-averaged Diameter size (nm) |
|---|---|---|---|
| 15 | 116 (0.06) | 97 | 64* |

| [lipid] mg/mL | Particle size (nm) | Final encapsulation (%) | Number-averaged Diameter size (nm) |
|---|---|---|---|
| 15 | 108 (0.09) | 96 | 59* |

| [lipid] mg/mL | Particle size (nm) | Final encapsulation (%) | Number-averaged Diameter size (nm)* |
|---|---|---|---|
| 15 | 58 (0.07) | 97 | 37 |

| [lipid] mg/mL | Particle size (nm) | Final encapsulation (%) | Number-averaged Diameter size (nm)* |
|---|---|---|---|
| 15 | 65 (0.11) | 97 | 36 |

| [lipid] mg/mL | Particle size (nm) | Final encapsulation (%) | Number-averaged Diameter size (nm) |
|---|---|---|---|
| 15 | 78 (0.03) | 96 | 55* |

| [lipid] mg/mL | Particle size (nm) | Final encapsulation (%) | Number-averaged Diameter size (nm) |
|---|---|---|---|
| 15 | 78 (0.04) | 97 | 55* |

NON-LIPOSOMAL SYSTEMS FOR NUCLEIC ACID DELIVERY

CROSS-REFERENCE TO RELATED APPLICATIONS

This application is a continuation of U.S. application Ser. No. 18/330,590 filed Jun. 7, 2023, which is a continuation of U.S. application Ser. No. 17/203,572, filed Mar. 16, 2021, and which issued on Aug. 8, 2023 as U.S. Pat. No. 11,718, 852, which is a continuation of U.S. application Ser. No. 15/892,314, filed Feb. 8, 2018, which is a continuation of U.S. application Ser. No. 15/342,020, filed Nov. 2, 2016, which is a continuation of U.S. application Ser. No. 15/153, 487, filed May 12, 2016, and which issued on Dec. 13, 2016 as U.S. Pat. No. 9,518,272, which is a continuation of U.S. application Ser. No. 14/642,452, filed Mar. 9, 2015, and which issued on Aug. 2, 2016 as U.S. Pat. No. 9,404,127, which is a continuation of U.S. application Ser. No. 13/807, 288, filed Apr. 18, 2013, and which issued on Apr. 14, 2015 as U.S. Pat. No. 9,006,417, which application is a National Phase application under 35 U.S.C. § 371 of PCT/CA2011/ 000778, filed Jun. 30, 2011, which application claims the benefit of U.S. Provisional Application No. 61/360,480, filed Jun. 30, 2010, the disclosures of which are incorporated herein by reference in their entirety for all purposes.

REFERENCE TO A SEQUENCE LISTING

A Sequence Listing conforming to the rules of WIPO Standard ST.26 is submitted electronically herewith via Patent Center and is hereby incorporated by reference in its entirety. The Sequence Listing file, identified as 104290-010070US-1390929_SEQ.xml, is 13,790 bytes in size and was created on Jun. 21, 2023.

BACKGROUND OF THE INVENTION

RNA interference (RNAi) is an evolutionarily conserved process in which recognition of double-stranded RNA (dsRNA) ultimately leads to posttranscriptional suppression of gene expression. This suppression is mediated by short dsRNA, also called small interfering RNA (siRNA), which induces specific degradation of mRNA through complementary base pairing. In several model systems, this natural response has been developed into a powerful tool for the investigation of gene function (see, e.g., Elbashir et al., *Genes Dev.*, 15:188-200 (2001); Hammond et al., *Nat. Rev. Genet.*, 2:110-119 (2001)). More recently, it was discovered that introducing synthetic 21-nucleotide dsRNA duplexes into mammalian cells could efficiently silence gene expression.

Although the precise mechanism is still unclear, RNAi provides a potential new approach to downregulate or silence the transcription and translation of a gene of interest. For example, it is desirable to modulate (e.g., reduce) the expression of certain genes for the treatment of neoplastic disorders such as cancer. It is also desirable to silence the expression of genes associated with liver diseases and disorders such as hepatitis. It is further desirable to reduce the expression of certain genes for the treatment of atherosclerosis and its manifestations, e.g., hypercholesterolemia, myocardial infarction, and thrombosis.

A safe and effective nucleic acid delivery system is required for RNAi to be therapeutically useful. Viral vectors are relatively efficient gene delivery systems, but suffer from a variety of limitations, such as the potential for reversion to the wild-type as well as immune response concerns. As a result, nonviral gene delivery systems are receiving increasing attention (Worgall et al., *Human Gene Therapy*, 8:37 (1997); Peeters et al., *Human Gene Therapy*, 7:1693 (1996); Yei et al., *Gene Therapy*, 1:192 (1994); Hope et al., *Molecular Membrane Biology*, 15:1 (1998)). Furthermore, viral systems are rapidly cleared from the circulation, limiting transfection to "first-pass" organs such as the lungs, liver, and spleen. In addition, these systems induce immune responses that compromise delivery with subsequent injections.

Plasmid DNA-cationic liposome complexes are currently the most commonly employed nonviral gene delivery vehicles (Felgner, *Scientific American*, 276:102 (1997); Chonn et al., *Current Opinion in Biotechnology*, 6:698 (1995)). For instance, cationic liposome complexes made of an amphipathic compound, a neutral lipid, and a detergent for transfecting insect cells are disclosed in U.S. Pat. No. 6,458,382. Cationic liposome complexes are also disclosed in U.S. Patent Publication No. 20030073640.

Cationic liposome complexes are large, poorly defined systems that are not suited for systemic applications and can elicit considerable toxic side effects (Harrison et al., *Biotechniques*, 19:816 (1995); Li et al., *The Gene*, 4:891 (1997); Tam et al, *Gene Ther.*, 7:1867 (2000)). As large, positively charged aggregates, lipoplexes are rapidly cleared when administered in vivo, with highest expression levels observed in first-pass organs, particularly the lungs (Huang et al., *Nature Biotechnology*, 15:620 (1997); Templeton et al., *Nature Biotechnology*, 15:647 (1997); Hofland et al., *Pharmaceutical Research*, 14:742 (1997)).

Other liposomal delivery systems include, for example, the use of reverse micelles, anionic liposomes, and polymer liposomes. Reverse micelles are disclosed in U.S. Pat. No. 6,429,200. Anionic liposomes are disclosed in U.S. Patent Publication No. 20030026831. Polymer liposomes that incorporate dextrin or glycerol-phosphocholine polymers are disclosed in U.S. Patent Publication Nos. 20020081736 and 20030082103, respectively.

A gene delivery system containing an encapsulated nucleic acid for systemic delivery should be small (i.e., less than about 100 nm diameter) and should remain intact in the circulation for an extended period of time in order to achieve delivery to affected tissues. This requires a highly stable, serum-resistant nucleic acid-containing particle that does not interact with cells and other components of the vascular compartment. The particle should also readily interact with target cells at a disease site in order to facilitate intracellular delivery of a desired nucleic acid.

Recent work has shown that nucleic acids can be encapsulated in small (e.g., about 70 nm diameter) "stabilized plasmid-lipid particles" (SPLP) that consist of a single plasmid encapsulated within a bilayer lipid vesicle (Wheeler et al., *Gene Therapy*, 6:271 (1999)). These SPLPs typically contain the "fusogenic" lipid dioleoylphosphatidylethanolamine (DOPE), low levels of cationic lipid, and are stabilized in aqueous media by the presence of a poly (ethylene glycol) (PEG) coating. SPLPs have systemic application as they exhibit extended circulation lifetimes following intravenous (i.v.) injection, accumulate preferentially at distal tumor sites due to the enhanced vascular permeability in such regions, and can mediate transgene expression at these tumor sites. The levels of transgene expression observed at the tumor site following i.v. injection of SPLPs containing the luciferase marker gene are superior to the levels that can be achieved employing plasmid DNA-cationic liposome complexes (lipoplexes) or naked DNA.

Thus, there remains a strong need in the art for novel and more efficient methods and compositions for introducing nucleic acids such as siRNA into cells. In addition, there is a need in the art for methods of downregulating the expression of genes of interest to treat or prevent diseases and disorders such as cancer and atherosclerosis. The present invention addresses these and other needs.

BRIEF SUMMARY OF THE INVENTION

The present invention is based, in part, upon the surprising discovery that by controlling the lipid composition of a SNALP formulation as well as the formation process used to prepare the SNALP formulation, a novel non-lamellar lipid nanoparticle (i.e., SNALP) can be produced. More particularly, it has surprisingly been found that lipid particles that comprise from about 50 mol % to about 85 mol % of a cationic lipid, from about 13 mol % to about 49.5 mol % of a non-cationic lipid, and from about 0.5 mol % to about 10 mol % of a lipid conjugate, and that are made using the Direct Dilution Method as described herein have a novel non-lamellar (i.e., non-bilayer) morphology and enhanced silencing ability when used to deliver an interfering nucleic acid, such as an siRNA molecule. As such, the present invention provides a composition comprising a plurality of nucleic acid-lipid particles, wherein each particle in the plurality of particles comprises: (a) a nucleic acid; (b) a cationic lipid comprising from about 50 mol % to about 85 mol % of the total lipid present in the particle; (c) a non-cationic lipid comprising from about 13 mol % to about 49.5 mol % of the total lipid present in the particle; and (d) a conjugated lipid that inhibits aggregation of particles comprising from about 0.5 mol % to about 10 mol % of the total lipid present in the particle, wherein at least about 95% of the particles in the plurality of particles have a non-lamellar morphology. In preferred embodiments, greater than 95%, preferably, greater than 96%, preferably, greater than 97%, preferably, greater than 98% and, preferably, greater than 99% of the particles have a non-lamellar morphology, i.e., a non-bilayer structure.

In certain embodiments, the active agent or therapeutic agent is fully encapsulated within the lipid portion of the lipid particles such that the active agent or therapeutic agent in the lipid particle is resistant in aqueous solution to enzymatic degradation, e.g., by a nuclease or protease. In certain other embodiments, the lipid particles are substantially non-toxic to mammals such as humans.

In some embodiments, the active agent or therapeutic agent comprises a nucleic acid. In certain instances, the nucleic acid comprises an interfering RNA molecule such as, e.g., an siRNA, aiRNA, miRNA, or mixtures thereof. In certain other instances, the nucleic acid comprises single-stranded or double-stranded DNA, RNA, or a DNA/RNA hybrid such as, e.g., an antisense oligonucleotide, a ribozyme, a plasmid, an immunostimulatory oligonucleotide, or mixtures thereof.

In preferred embodiments, the active agent or therapeutic agent comprises an siRNA. In one embodiment, the siRNA molecule comprises a double-stranded region of about 15 to about 60 nucleotides in length (e.g., about 15-60, 15-50, 15-40, 15-30, 15-25, or 19-25 nucleotides in length, or 15, 16, 17, 18, 19, 20, 21, 22, 23, 24, or 25 nucleotides in length). The siRNA molecules of the invention are capable of silencing the expression of a target sequence in vitro and/or in vivo.

In some embodiments, the siRNA molecule comprises at least one modified nucleotide. In certain preferred embodiments, the siRNA molecule comprises one, two, three, four, five, six, seven, eight, nine, ten, or more modified nucleotides in the double-stranded region. In certain instances, the siRNA comprises from about 1% to about 100% (e.g., about 1%, 5%, 10%, 15%, 20%, 25%, 30%, 35%, 40%, 45%, 50%, 55%, 60%, 65%, 70%, 75%, 80%, 85%, 90%, 95%, or 100%) modified nucleotides in the double-stranded region. In preferred embodiments, less than about 25% (e.g., less than about 25%, 20%, 15%, 10%, or 5%) or from about 1% to about 25% (e.g., from about 1%-25%, 5%-25%, 10%-25%, 15%-25%, 20%-25%, or 10%-20%) of the nucleotides in the double-stranded region comprise modified nucleotides.

In other embodiments, the siRNA molecule comprises modified nucleotides including, but not limited to, 2'-O-methyl (2'OMe) nucleotides, 2'-deoxy-2'-fluoro (2'F) nucleotides, 2'-deoxy nucleotides, 2'-O-(2-methoxyethyl) (MOE) nucleotides, locked nucleic acid (LNA) nucleotides, and mixtures thereof. In preferred embodiments, the siRNA comprises 2'OMe nucleotides (e.g., 2'OMe purine and/or pyrimidine nucleotides) such as, for example, 2'OMe-guanosine nucleotides, 2'OMe-uridine nucleotides, 2'OMe-adenosine nucleotides, 2'OMe-cytosine nucleotides, and mixtures thereof. In certain instances, the siRNA does not comprise 2'OMe-cytosine nucleotides. In other embodiments, the siRNA comprises a hairpin loop structure.

The siRNA may comprise modified nucleotides in one strand (i.e., sense or antisense) or both strands of the double-stranded region of the siRNA molecule. Preferably, uridine and/or guanosine nucleotides are modified at selective positions in the double-stranded region of the siRNA duplex. With regard to uridine nucleotide modifications, at least one, two, three, four, five, six, or more of the uridine nucleotides in the sense and/or antisense strand can be a modified uridine nucleotide such as a 2'OMe-uridine nucleotide. In some embodiments, every uridine nucleotide in the sense and/or antisense strand is a 2'OMe-uridine nucleotide. With regard to guanosine nucleotide modifications, at least one, two, three, four, five, six, or more of the guanosine nucleotides in the sense and/or antisense strand can be a modified guanosine nucleotide such as a 2'OMe-guanosine nucleotide. In some embodiments, every guanosine nucleotide in the sense and/or antisense strand is a 2'OMe-guanosine nucleotide.

In the lipid particles of the invention (e.g., SNALP comprising an interfering RNA such as siRNA), the cationic lipid may comprise, e.g., one or more of the following: the cationic lipids of Formula I as disclosed herein, including, for example, MC3, LenMC3, CP-LenMC3, γ-LenMC3, CP-T-LenMC3, MC3MC, MC2MC, MC3 Ether, MC4 Ether, MC3 Amide, Pan-MC3, Pan-MC4 and Pan MC5, 1,2-dilinoleyloxy-N,N-dimethylaminopropane (DLinDMA), 1,2-dilinolenyloxy-N,N-dimethylaminopropane (DLenDMA), 2,2-dilinoleyl-4-(2-dimethylaminoethyl)-[1,3]-dioxolane (DLin-K-C2-DMA; "XTC2"), 2,2-dilinoleyl-4-(3-dimethylaminopropyl)-[1,3]-dioxolane (DLin-K-C3-DMA), 2,2-dilinoleyl-4-(4-dimethylaminobutyl)-[1,3]-dioxolane (DLin-K-C4-DMA), 2,2-dilinoleyl-5-dimethylaminomethyl-[1,3]-dioxane (DLin-K6-DMA), 2,2-dilinoleyl-4-N-methylpepiazino-[1,3]-dioxolane (DLin-K-MPZ), 2,2-dilinoleyl-4-dimethylaminomethyl-[1,3]-dioxolane (DLin-K-DMA), 1,2-dilinoleylcarbamoyloxy-3-dimethylaminopropane (DLin-C-DAP), 1,2-dilinoleyoxy-3-(dimethylamino)acetoxypropane (DLin-DAC), 1,2-dilinoleyoxy-3-morpholinopropane (DLin-MA), 1,2-dilinoleoyl-3-dimethylaminopropane (DLinDAP), 1,2-dilinoleylthio-3-dimethylaminopropane (DLin-S-DMA), 1-linoleoyl-2-linoleyloxy-3-dimethylaminopropane (DLin-2-DMAP), 1,2-dilinoleyloxy-3-trimethylaminopropane chloride salt (DLin-TMA.Cl), 1,2-dilinoleoyl-3-trimethylaminopropane chloride salt (DLin-TAP.Cl), 1,2-dilinoleyloxy-3-(N-methylpiperazino)propane (DLin-MPZ), 3-(N,N-dilinoleylamino)-1,2-propanediol (DLinAP), 3-(N,N-dioleylamino)-1,2-propanedio (DOAP), 1,2-dilinoleyloxo-3-(2-N,N-dimethylamino)ethoxypropane (DLin-EG-DMA), N,N-dioleyl-N,N-dimethylammonium chloride (DODAC), 1,2-dioleyloxy-N,N-dimethylaminopropane (DODMA), 1,2-distearyloxy-N,N-dimethylaminopropane (DSDMA), N-(1-(2,3-dioleyloxy)propyl)-N,N,N-trimethylammonium chloride (DOTMA), N,N-distearyl-N,N-dimethylammonium bromide (DDAB), N-(1-(2,3-dioleoyloxy)propyl)-N,N,N-trimethylammonium chloride (DOTAP), 3-(N—(N',N'-dimethylaminoethane)-carbamoyl)cholesterol (DC-Chol), N-(1,2-dimyristyloxyprop-3-yl)-N,N-dimethyl-N-hydroxyethyl ammonium bromide (DMRIE), 2,3-dioleyloxy-N-[2 (spermine-carboxamido)ethyl]-N,N-dimethyl-1-propan-aminiumtrifluoroacetate (DOSPA), dioctadecylamidoglycyl spermine (DOGS), 3-dimethylamino-2-(cholest-5-en-3-beta-oxybutan-4-oxy)-1-(cis,cis-9,12-octadecadienoxy)propane (CLinDMA), 2-[5'-(cholest-5-en-3-beta-oxy)-3'-oxapentoxy)-3-dimethy-1-(cis,cis-9',1-2'-octadecadienoxy) propane (CpLinDMA), N,N-dimethyl-3,4-dioleyloxybenzylamine (DMOBA), 1,2-N,N'-dioleylcarbamyl-3-dimethylaminopropane (DOcarbDAP), 1,2-N,N'-dilinoleylcarbamyl-3-dimethylaminopropane (DLincarbDAP), or mixtures thereof. In certain preferred embodiments, the cationic lipid is DLinDMA, DLin-K-C2-DMA ("XTC2"), MC3, LenMC3, CP-LenMC3, γ-LenMC3, CP-γ-LenMC3, MC3MC, MC2MC, MC3 Ether, MC4 Ether, MC3 Amide, Pan-MC3, Pan-MC4, Pan MC5, or mixtures thereof.

In the lipid particles of the invention (e.g., SNALP comprising an interfering RNA such as siRNA), the non-cationic lipid may comprise, e.g., one or more anionic lipids and/or neutral lipids. In preferred embodiments, the non-cationic lipid comprises one of the following neutral lipid components: (1) cholesterol or a derivative thereof, (2) a phospholipid; or (3) a mixture of a phospholipid and cholesterol or a derivative thereof.

Examples of cholesterol derivatives include, but are not limited to, cholestanol, cholestanone, cholestenone, coprostanol, cholesteryl-2'-hydroxyethyl ether, cholesteryl-4'-hydroxybutyl ether, and mixtures thereof. The synthesis of cholesteryl-2'-hydroxyethyl ether is described herein.

The phospholipid may be a neutral lipid including, but not limited to, dipalmitoylphosphatidylcholine (DPPC), distearoylphosphatidylcholine (DSPC), dioleoylphosphatidylethanolamine (DOPE), palmitoyloleoyl-phosphatidylcholine (POPC), palmitoyloleoyl-phosphatidylethanolamine (POPE), palmitoyloleyol-phosphatidylglycerol (POPG), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethyl-phosphatidylethanolamine, dielaidoyl-phosphatidylethanolamine (DEPE), stearoyloleoyl-phosphatidylethanolamine (SOPE), egg phosphatidylcholine (EPC), and mixtures thereof. In certain preferred embodiments, the phospholipid is DPPC, DSPC, or mixtures thereof.

In the lipid particles of the invention (e.g., SNALP comprising an interfering RNA such as siRNA), the conjugated lipid that inhibits aggregation of particles may comprise, e.g., one or more of the following: a polyethyleneglycol (PEG)-lipid conjugate, a polyamide (ATTA)-lipid conjugate, a cationic-polymer-lipid conjugates (CPLs), or mixtures thereof. In one preferred embodiment, the nucleic acid-lipid particles comprise either a PEG-lipid conjugate or an ATTA-lipid conjugate. In certain embodiments, the PEG-lipid conjugate or ATTA-lipid conjugate is used together with a CPL. The conjugated lipid that inhibits aggregation of particles may comprise a PEG-lipid including, e.g., a PEG-diacylglycerol (DAG), a PEG dialkyloxypropyl (DAA), a PEG-phospholipid, a PEG-ceramide (Cer), or mixtures thereof. The PEG-DAA conjugate may be PEG-dilauryloxypropyl (C12), a PEG-dimyristyloxypropyl (C14), a PEG-dipalmityloxypropyl (C16), a PEG-distearyloxypropyl (C18), or mixtures thereof.

In one specific embodiment, the composition of the present invention comprises: a plurality of nucleic acid-lipid particles, wherein each particle in the plurality of particles comprises: (a) one or more unmodified and/or modified interfering RNA (e.g., siRNA, aiRNA, miRNA) that silence target gene expression; (b) a cationic lipid comprising from about 56.5 mol % to about 66.5 mol % of the total lipid present in the particle; (c) a non-cationic lipid comprising from about 31.5 mol % to about 42.5 mol % of the total lipid present in the particle; and (d) a conjugated lipid that inhibits aggregation of particles comprising from about 1 mol % to about 2 mol % of the total lipid present in the particle, wherein at least about 95% of the particles in the plurality of particles have a non-lamellar morphology. This specific embodiment of SNALP is generally referred to herein as the "1:62" formulation. In a preferred embodiment, the cationic lipid is DLinDMA or DLin-K-C2-DMA ("XTC2"), the non-cationic lipid is cholesterol, and the conjugated lipid is a PEG-DAA conjugate. Although these are preferred embodiments of the 1:62 formulation, those of skill in the art will appreciate that other cationic lipids, non-cationic lipids (including other cholesterol derivatives), and conjugated lipids can be used in the 1:62 formulation as described herein.

In another specific embodiment, the composition of the present invention comprises: a plurality of nucleic acid-lipid particles, wherein each particle in the plurality of particles comprises: (a) one or more unmodified and/or modified interfering RNA (e.g., siRNA, aiRNA, miRNA) that silence target gene expression; (b) a cationic lipid comprising from about 52 mol % to about 62 mol % of the total lipid present in the particle; (c) a non-cationic lipid comprising from about 36 mol % to about 47 mol % of the total lipid present in the particle; and (d) a conjugated lipid that inhibits aggregation of particles comprising from about 1 mol % to about 2 mol % of the total lipid present in the particle, wherein at least about 95% of the particles in the plurality of particles have a non-lamellar morphology. This specific embodiment of SNALP is generally referred to herein as the "1:57" formulation. In one preferred embodiment, the cationic lipid is DLinDMA or DLin-K-C2-DMA ("XTC2"), the non-cationic lipid is a mixture of a phospholipid (such as DPPC) and cholesterol, wherein the phospholipid comprises from about 5 mol % to about 9 mol % of the total lipid present in the particle (e.g., about 7.1 mol %) and the cholesterol (or cholesterol derivative) comprises from about 32 mol % to about 37 mol % of the total lipid present in the particle (e.g., about 34.3 mol %), and the PEG-lipid is a PEG-DAA (e.g., PEG-cDMA). In another preferred embodiment, the cationic lipid is DLinDMA or DLin-K-C2-DMA ("XTC2"), the non-cationic lipid is a mixture of a phospholipid (such as DPPC) and cholesterol, wherein the phospholipid comprises from about 15 mol % to about 25 mol % of the total lipid present in the particle (e.g., about 20 mol %)

and the cholesterol (or cholesterol derivative) comprises from about 15 mol % to about 25 mol % of the total lipid present in the particle (e.g., about 20 mol %), and the PEG-lipid is a PEG-DAA (e.g., PEG-cDMA). Although these are preferred embodiments of the 1:57 formulation, those of skill in the art will appreciate that other cationic lipids, non-cationic lipids (including other phospholipids and other cholesterol derivatives), and conjugated lipids can be used in the 1:57 formulation as described herein.

In yet another specific embodiment, the composition of the present invention comprises: a plurality of nucleic acid-lipid particles, wherein each particle in the plurality of particles comprises: (a) a nucleic acid (e.g., an interfering RNA); (b) a cationic lipid comprising from about 50 mol % to about 60 mol % of the total lipid present in the particle; (c) a mixture of a phospholipid and cholesterol or a derivative thereof comprising from about 35 mol % to about 45 mol % of the total lipid present in the particle; and (d) a PEG-lipid conjugate comprising from about 5 mol % to about 10 mol % of the total lipid present in the particle, wherein at least about 95% of the particles in the plurality of particles have a non-lamellar morphology. This embodiment of nucleic acid-lipid particle is generally referred to herein as the "7:54" formulation.

In still another specific embodiment, the composition of the present invention comprises: a plurality of nucleic acid-lipid particles, wherein each particle in the plurality of particles comprises: (a) a nucleic acid (e.g., an interfering RNA); (b) a cationic lipid comprising from about 55 mol % to about 65 mol % of the total lipid present in the particle; (c) cholesterol or a derivative thereof comprising from about 30 mol % to about 40 mol % of the total lipid present in the particle; and (d) a PEG-lipid conjugate comprising from about 5 mol % to about 10 mol % of the total lipid present in the particle, wherein at least about 95% of the particles in the plurality of particles have a non-lamellar morphology. This embodiment of nucleic acid-lipid particle is generally referred to herein as the "7:58" formulation.

The present invention also provides a pharmaceutical composition comprising a composition of a plurality of nucleic acid lipid particles (e.g., SNALP), wherein at least about 95% of the particles in the plurality of particles have a non-lamellar morphology as described herein and a pharmaceutically acceptable carrier.

In a further aspect, the present invention provides a method for introducing one or more active agents or therapeutic agents (e.g., nucleic acid) into a cell, comprising contacting the cell with a composition comprising a plurality of nucleic acid lipid particles (e.g., SNALP), wherein at least about 95% of the particles in the plurality of particles have a non-lamellar morphology as described herein. In one embodiment, the cell is in a mammal and the mammal is a human. In another embodiment, the present invention provides a method for the in vivo delivery of one or more active agents or therapeutic agents (e.g., nucleic acid), comprising administering to a mammalian subject a composition comprising a plurality of nucleic acid lipid particles (e.g., SNALP), wherein at least about 95% of the particles in the plurality of particles have a non-lamellar morphology as described herein. In a preferred embodiment, the mode of administration includes, but is not limited to, oral, intranasal, intravenous, intraperitoneal, intramuscular, intra-articular, intralesional, intratracheal, subcutaneous, and intradermal. Preferably, the mammalian subject is a human.

Other objects, features, and advantages of the present invention will be apparent to one of skill in the art from the following detailed description and figures.

DETAILED DESCRIPTION OF THE INVENTION

I. Introduction

The present invention is based, in part, upon the surprising discovery that by controlling the lipid composition of a SNALP formulation as well as the formation process used to prepare the SNALP formulation, a novel non-lamellar lipid nanoparticle (i.e., SNALP) can be produced. More particularly, it has surprisingly been found that lipid particles that comprise from about 50 mol % to about 85 mol % of a cationic lipid, from about 13 mol % to about 49.5 mol % of a non-cationic lipid, and from about 0.5 mol % to about 10 mol % of a lipid conjugate, and that are made using the Direct Dilution Method as described herein have a novel non-lamellar (i.e., non-bilayer) morphology and enhanced silencing ability when used to deliver an interfering nucleic acid, such as an siRNA molecule. As such, the present invention provides a composition comprising a plurality of nucleic acid-lipid particles, wherein each particle in the plurality of particles comprises: (a) a nucleic acid; (b) a cationic lipid comprising from about 50 mol % to about 85 mol % of the total lipid present in the particle; (c) a non-cationic lipid comprising from about 13 mol % to about 49.5 mol % of the total lipid present in the particle; and (d) a conjugated lipid that inhibits aggregation of particles comprising from about 0.5 mol % to about 10 mol % of the total lipid present in the particle, wherein at least about 95% of the particles in the plurality of particles have a non-lamellar morphology. In preferred embodiments, greater than 95%, preferably, greater than 96%, preferably, greater than 97%, preferably, greater than 98% and, preferably, greater than 99% of the particles have a non-lamellar morphology, i.e., a non-bilayer structure.

Figure 21:
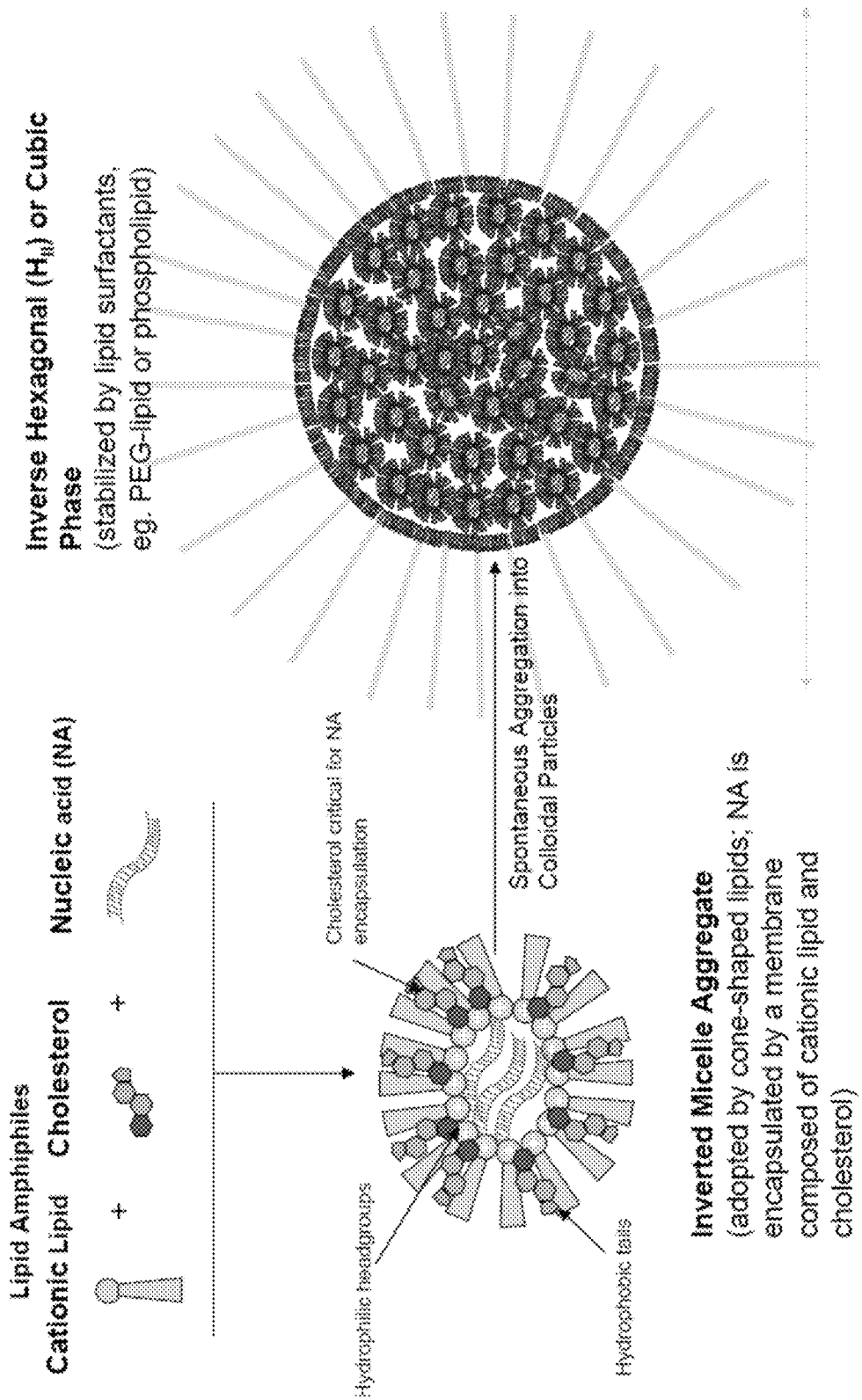
FIG. 21 illustrates an inverse Hexagonal ($H_{II}$) or Cubic Phase structure of the non-lamellar stable nucleic acid-lipid particles prepared by the Direct Dilution Method.

As illustrated in FIG. 21 and without intending to be bound by any theory, it is believed that the cationic lipid and cholesterol combine together with the nucleic acid to form inverted micelle aggregates, wherein the nucleic acid is encapsulated by a membrane composed of cationic lipid and cholesterol present in the formulation and, thereafter, spontaneous aggregation of the inverted micelles results in colloidal particles that are stabilized by the lipid surfactants (e.g., the PEG-lipids and/or phospholipids present in the formulation). It is thought that the resulting non-lamellar (i.e., non-bilayer structure) particle has an inverse Hexagonal ($H_{II}$) or Cubic phase structure. In essence, it is thought that the resulting non-bilayer lipid packing provides a 3-dimensional network of lipid cylinders with water and nucleic on the inside, i.e., essentially, a lipid droplet interpenetrated with aqueous channels containing the nucleic acid.

The non-lamellar morphology (i.e., non-bilayer structure) of the resulting lipid particles can readily be determined using techniques known to and used by those of skill in the art. Such techniques include, but are not limited to, Cryo-Transmission Electron Microscopy ("Cryo-TEM"), Differential Scanning Calorimetry ("DSC"), X-Ray Diffraction, etc. As illustrated in FIGS. 3-6 and 8-11, the morphology of the lipid particles (lamellar vs. non-lamellar) can readily be assessed and characterized using, e.g., Cryo-TEM analysis as described herein.

It has been found that the SNALP of the present invention provide advantages when used for the in vitro or in vivo delivery of an active agent, such as a therapeutic nucleic acid (e.g., an interfering RNA). In particular, as illustrated by the Examples herein, the present invention provides stable nucleic acid-lipid particles (SNALP) that advantageously impart increased activity of the encapsulated nucleic acid (e.g., an interfering RNA such as siRNA) and improved tolerability of the formulations in vivo, resulting in a significant increase in the therapeutic index as compared to nucleic acid-lipid particle compositions previously described. Additionally, the SNALP of the invention are stable in circulation, e.g., resistant to degradation by nucleases in serum, and are substantially non-toxic to mammals such as humans. As a non-limiting example, FIG. 17 of Example 5 shows that one SNALP embodiment of the invention ("1:57 SNALP") was more efficacious as compared to a nucleic acid-lipid particle previously described ("2:30 SNALP") in mediating target gene silencing at a 10-fold lower dose. Similarly, FIG. 18 of Example 6 shows that the "1:57 SNALP" formulation was substantially more effective at silencing the expression of a target gene as compared to nucleic acid-lipid particles previously described ("2:40 SNALP"). Moreover, FIG. 20 of Example 8 shows that the "7:54 SNALP" PLK-1 displayed increased potency in SC tumors and that this formulation can be used to preferentially target tumors outside of the liver.

In certain embodiments, the present invention provides improved compositions for the delivery of interfering RNA such as siRNA molecules. In particular, the Examples herein illustrate that the improved lipid particle formulations of the invention are highly effective in downregulating the mRNA and/or protein levels of target genes. Furthermore, the Examples herein illustrate that the presence of certain molar ratios of lipid component ts results in improved or enhanced activity of these lipid particle formulations of the present invention. For instance, the "1:57 SNALP," "1:62 SNALP," "7:54 SNALP" and "7:58 SNALP" formulations described herein are exemplary formulations of the present invention that are particularly advantageous because they provide improved efficacy and tolerability in vivo, are serum-stable, are substantially non-toxic, are smaller in size, with smaller polydispersities, are capable of accessing extravascular sites, and are capable of reaching target cell populations.

The lipid particles and compositions of the present invention may be used for a variety of purposes, including the delivery of associated or encapsulated therapeutic agents to cells, both in vitro and in vivo. Accordingly, the present invention provides methods for treating diseases or disorders in a subject in need thereof, by contacting the subject with a lipid particle described herein comprising one or more suitable therapeutic agents.

Various exemplary embodiments of the lipid particles of the invention, as well as compositions and formulations comprising the same, and their use to deliver therapeutic agents and modulate target gene and protein expression, are described in further detail below.

II. Definitions

As used herein, the following terms have the meanings ascribed to them unless specified otherwise.

The term "interfering RNA" or "RNAi" or "interfering RNA sequence" as used herein includes single-stranded RNA (e.g., mature miRNA, ssRNAi oligonucleotides, ssDNAi oligonucleotides), double-stranded RNA (i.e., duplex RNA such as siRNA, Dicer-substrate dsRNA, shRNA, aiRNA, or pre-miRNA), a DNA-RNA hybrid (see, e.g., PCT Publication No. WO 2004/078941), or a DNA-DNA hybrid (see, e.g., PCT Publication No. WO 2004/104199) that is capable of reducing or inhibiting the expression of a target gene or sequence (e.g., by mediating the degradation or inhibiting the translation of mRNAs which are complementary to the interfering RNA sequence) when the interfering RNA is in the same cell as the target gene or sequence. Interfering RNA thus refers to the single-stranded RNA that is complementary to a target mRNA sequence or to the double-stranded RNA formed by two complementary strands or by a single, self-complementary strand. Interfering RNA may have substantial or complete identity to the target gene or sequence, or may comprise a region of mismatch (i.e., a mismatch motif). The sequence of the interfering RNA can correspond to the full-length target gene, or a subsequence thereof. Preferably, the interfering RNA molecules are chemically synthesized. The disclosures of each of the above patent documents are herein incorporated by reference in their entirety for all purposes.

Interfering RNA includes "small-interfering RNA" or "siRNA," e.g., interfering RNA of about 15-60, 15-50, or 15-40 (duplex) nucleotides in length, more typically about 15-30, 15-25, or 19-25 (duplex) nucleotides in length, and is preferably about 20-24, 21-22, or 21-23 (duplex) nucleotides in length (e.g., each complementary sequence of the double-stranded siRNA is 15-60, 15-50, 15-40, 15-30, 15-25, or 19-25 nucleotides in length, preferably about 20-24, 21-22, or 21-23 nucleotides in length, and the double-stranded siRNA is about 15-60, 15-50, 15-40, 15-30, 15-25, or 19-25 base pairs in length, preferably about 18-22, 19-20, or 19-21 base pairs in length). siRNA duplexes may comprise 3' overhangs of about 1 to about 4 nucleotides or about 2 to about 3 nucleotides and 5' phosphate termini. Examples of siRNA include, without limitation, a double-stranded polynucleotide molecule assembled from two separate stranded molecules, wherein one strand is the sense strand and the other is the complementary antisense strand; a double-stranded polynucleotide molecule assembled from a single stranded molecule, where the sense and antisense regions are linked by a nucleic acid-based or non-nucleic acid-based linker; a double-stranded polynucleotide molecule with a hairpin secondary structure having self-complementary sense and antisense regions; and a circular single-stranded polynucleotide molecule with two or more loop structures and a stem having self-complementary sense and antisense regions, where the circular polynucleotide can be processed in vivo or in vitro to generate an active double-stranded siRNA molecule. As used herein, the term "siRNA" includes RNA-RNA duplexes as well as DNA-RNA hybrids (see, e.g., PCT Publication No. WO 2004/078941).

Preferably, siRNA are chemically synthesized. siRNA can also be generated by cleavage of longer dsRNA (e.g., dsRNA greater than about 25 nucleotides in length) with the E. coli RNase III or Dicer. These enzymes process the dsRNA into biologically active siRNA (see, e.g., Yang et al., *Proc. Natl. Acad. Sci. USA*, 99:9942-9947 (2002); Calegari et al., *Proc. Natl. Acad. Sci. USA*, 99:14236 (2002); Byrom et al., *Ambion TechNotes*, 10(1):4-6 (2003); Kawasaki et al., *Nucleic Acids Res.*, 31:981-987 (2003); Knight et al., *Science*, 293:2269-2271 (2001); and Robertson et al., *J. Biol. Chem.*, 243:82 (1968)). Preferably, dsRNA are at least 50 nucleotides to about 100, 200, 300, 400, or 500 nucleotides in length. A dsRNA may be as long as 1000, 1500, 2000, 5000 nucleotides in length, or longer. The dsRNA can encode for an entire gene transcript or a partial gene transcript. In certain instances, siRNA may be encoded by a plasmid (e.g., transcribed as sequences that automatically fold into duplexes with hairpin loops).

As used herein, the term "mismatch motif" or "mismatch region" refers to a portion of an interfering RNA (e.g., siRNA) sequence that does not have 100% complementarity to its target sequence. An interfering RNA may have at least one, two, three, four, five, six, or more mismatch regions. The mismatch regions may be contiguous or may be separated by 1, 2, 3, 4, 5, 6, 7, 8, 9, 10, 11, 12, or more nucleotides. The mismatch motifs or regions may comprise a single nucleotide or may comprise two, three, four, five, or more nucleotides.

The phrase "inhibiting expression of a target gene" refers to the ability of an interfering RNA (e.g., siRNA) to silence, reduce, or inhibit the expression of a target gene (e.g., PLK-1). To examine the extent of gene silencing, a test sample (e.g., a sample of cells in culture expressing the target gene) or a test mammal (e.g., a mammal such as a human or an animal model such as a rodent (e.g., mouse) or a non-human primate (e.g., monkey) model) is contacted with an interfering RNA (e.g., siRNA) that silences, reduces, or inhibits expression of the target gene. Expression of the target gene in the test sample or test animal is compared to expression of the target gene in a control sample (e.g., a sample of cells in culture expressing the target gene) or a control mammal (e.g., a mammal such as a human or an animal model such as a rodent (e.g., mouse) or non-human primate (e.g., monkey) model) that is not contacted with or administered the interfering RNA (e.g., siRNA). The expression of the target gene in a control sample or a control mammal may be assigned a value of 100%. In particular embodiments, silencing, inhibition, or reduction of expression of a target gene is achieved when the level of target gene expression in the test sample or the test mammal relative to the level of target gene expression in the control sample or the control mammal is about 95%, 90%, 85%, 80%, 75%, 70%, 65%, 60%, 55%, 50%, 45%, 40%, 35%, 30%, 25%, 20%, 15%, 10%, 5%, or 0%. In other words, the interfering RNAs (e.g., siRNAs) of the present invention are capable of silencing, reducing, or inhibiting the expression of a target gene (e.g., PLK-1) by at least about 5%, 10%, 15%, 20%, 25%, 30%, 35%, 40%, 45%, 50%, 55%, 60%, 65%, 70%, 75%, 80%, 85%, 90%, 95%, or 100% in a test sample or a test mammal relative to the level of target gene expression in a control sample or a control mammal not contacted with or administered the interfering RNA. Suitable assays for determining the level of target gene expression include, without limitation, examination of protein or mRNA levels using techniques known to those of skill in the art, such as, e.g., dot blots, Northern blots, in situ hybridization, ELISA, immunoprecipitation, enzyme function, as well as phenotypic assays known to those of skill in the art.

An "effective amount" or "therapeutically effective amount" of an active agent or therapeutic agent such as an interfering RNA is an amount sufficient to produce the desired effect, e.g., an inhibition of expression of a target sequence in comparison to the normal expression level detected in the absence of an interfering RNA. Inhibition of expression of a target gene or target sequence is achieved when the value obtained with an interfering RNA relative to the control is about 95%, 90%, 85%, 80%, 75%, 70%, 65%, 60%, 55%, 50%, 45%, 40%, 35%, 30%, 25%, 20%, 15%, 10%, 5%, or 0%. Suitable assays for measuring expression of a target gene or target sequence include, e.g., examination of protein or RNA levels using techniques known to those of skill in the art such as dot blots, northern blots, in situ hybridization, ELISA, immunoprecipitation, enzyme function, as well as phenotypic assays known to those of skill in the art.

By "decrease," "decreasing," "reduce," or "reducing" of an immune response by an interfering RNA is intended to mean a detectable decrease of an immune response to a given interfering RNA (e.g., a modified interfering RNA). The amount of decrease of an immune response by a modified interfering RNA may be determined relative to the level of an immune response in the presence of an unmodified interfering RNA. A detectable decrease can be about 5%, 10%, 15%, 20%, 25%, 30%, 35%, 40%, 45%, 50%, 55%, 60%, 65%, 70%, 75%, 80%, 85%, 90%, 95%, 100%, or more lower than the immune response detected in the presence of the unmodified interfering RNA. A decrease in the immune response to interfering RNA is typically measured by a decrease in cytokine production (e.g., IFNγ, IFNα, TNFα, IL-6, IL-8, or IL-12) by a responder cell in vitro or a decrease in cytokine production in the sera of a mammalian subject after administration of the interfering RNA.

As used herein, the term "responder cell" refers to a cell, preferably a mammalian cell, that produces a detectable immune response when contacted with an immunostimulatory interfering RNA such as an unmodified siRNA. Exemplary responder cells include, e.g., dendritic cells, macrophages, peripheral blood mononuclear cells (PBMCs), splenocytes, and the like. Detectable immune responses include, e.g., production of cytokines or growth factors such as TNF-α, IFN-α, IFN-β, IFN-γ, IL-1, IL-2, IL-3, IL-4, IL-5, IL-6, IL-8, IL-10, IL-12, IL-13, TGF, and combinations thereof. Detectable immune responses also include, e.g., induction of interferon-induced protein with tetratricopeptide repeats 1 (IFIT1) mRNA.

"Substantial identity" refers to a sequence that hybridizes to a reference sequence under stringent conditions, or to a sequence that has a specified percent identity over a specified region of a reference sequence.

The phrase "stringent hybridization conditions" refers to conditions under which a nucleic acid will hybridize to its target sequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point (Tm) for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions may also be achieved with the addition of destabilizing agents such as formamide. For selective or specific hybridization, a positive signal is at least two times background, preferably 10 times background hybridization.

Exemplary stringent hybridization conditions can be as follows: 50% formamide, 5×SSC, and 1% SDS, incubating at 42° C., or, 5×SSC, 1% SDS, incubating at 65° C., with wash in 0.2×SSC, and 0.1% SDS at 65° C. For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec.-2 min., an annealing phase lasting 30 sec.-2 min., and an extension phase of about 72° C. for 1-2 min. Protocols and guidelines for low and high stringency amplification reactions are provided, e.g., in Innis et al., *PCR Protocols, A Guide to Methods and Applications*, Academic Press, Inc. N.Y. (1990).

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous references, e.g., Current Protocols in Molecular Biology, Ausubel et al., eds.

The terms "substantially identical" or "substantial identity," in the context of two or more nucleic acids, refer to two or more sequences or subsequences that are the same or have a specified percentage of nucleotides that are the same (i.e., at least about 60%, preferably at least about 65%, 70%, 75%, 80%, 85%, 90%, or 95% identity over a specified region), when compared and aligned for maximum correspondence over a comparison window, or designated region as measured using one of the following sequence comparison algorithms or by manual alignment and visual inspection. This definition, when the context indicates, also refers analogously to the complement of a sequence. Preferably, the substantial identity exists over a region that is at least about 5, 10, 15, 20, 25, 30, 35, 40, 45, 50, 55, or 60 nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of a number of contiguous positions selected from the group consisting of from about 5 to about 60, usually about 10 to about 45, more usually about 15 to about 30, in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman, *Adv. Appl. Math.*, 2:482 (1981), by the homology alignment algorithm of Needleman and Wunsch, *J. Mol. Biol.*, 48:443 (1970), by the search for similarity method of Pearson and Lipman, *Proc. Natl. Acad. Sci. USA*, 85:2444 (1988), by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., *Current Protocols in Molecular Biology*, Ausubel et al., eds. (1995 supplement)).

Non-limiting examples of algorithms that are suitable for determining percent sequence identity and sequence similarity are the BLAST and BLAST 2.0 algorithms, which are described in Altschul et al., *Nuc. Acids Res.*, 25:3389-3402 (1977) and Altschul et al., *J. Mol. Biol.*, 215:403-410 (1990), respectively. BLAST and BLAST 2.0 are used, with the parameters described herein, to determine percent sequence identity for the nucleic acids of the invention. Software for performing BLAST analyses is publicly available through the National Center for Biotechnology Information (http://www.ncbi.nlm.nih.gov/). Another example is a global alignment algorithm for determining percent sequence identity such as the Needleman-Wunsch algorithm for aligning protein or nucleotide (e.g., RNA) sequences.

The BLAST algorithm also performs a statistical analysis of the similarity between two sequences (see, e.g., Karlin and Altschul, *Proc. Natl. Acad. Sci. USA*, 90:5873-5787 (1993)). One measure of similarity provided by the BLAST algorithm is the smallest sum probability (P(N)), which provides an indication of the probability by which a match between two nucleotide sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The term "nucleic acid" as used herein refers to a polymer containing at least two deoxyribonucleotides or ribonucleotides in either single- or double-stranded form and includes DNA, RNA, and hybrids thereof. DNA may be in the form of, e.g., antisense molecules, plasmid DNA, DNA-DNA duplexes, pre-condensed DNA, PCR products, vectors (P1, PAC, BAC, YAC, artificial chromosomes), expression cassettes, chimeric sequences, chromosomal DNA, or derivatives and combinations of these groups. RNA may be in the form of small interfering RNA (siRNA), Dicer-substrate dsRNA, small hairpin RNA (shRNA), asymmetrical interfering RNA (aiRNA), microRNA (miRNA), mRNA, tRNA, rRNA, tRNA, viral RNA (vRNA), and combinations thereof. Nucleic acids include nucleic acids containing known nucleotide analogs or modified backbone residues or linkages, which are synthetic, naturally occurring, and non-naturally occurring, and which have similar binding properties as the reference nucleic acid. Examples of such analogs include, without limitation, phosphorothioates, phosphoramidates, methyl phosphonates, chiral-methyl phosphonates, 2'-O-methyl ribonucleotides, and peptide-nucleic acids (PNAs). Unless specifically limited, the term encompasses nucleic acids containing known analogues of natural nucleotides that have similar binding properties as the reference nucleic acid. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.*, 19:5081 (1991); Ohtsuka et al., *J. Biol. Chem.*, 260:2605-2608 (1985); Rossolini et al., *Mol. Cell. Probes*, 8:91-98 (1994)). "Nucleotides" contain a sugar deoxyribose (DNA) or ribose (RNA), a base, and a phosphate group. Nucleotides are linked together through the phosphate groups. "Bases" include purines and pyrimidines, which further include natural compounds adenine, thymine, guanine, cytosine, uracil, inosine, and natural analogs, and synthetic derivatives of purines and pyrimidines, which include, but are not limited to, modifications which place new reactive groups such as, but not limited to, amines, alcohols, thiols, carboxylates, and alkylhalides.

The term "gene" refers to a nucleic acid (e.g., DNA or RNA) sequence that comprises partial length or entire length coding sequences necessary for the production of a polypeptide or precursor polypeptide (e.g., PLK-1).

"Gene product," as used herein, refers to a product of a gene such as an RNA transcript or a polypeptide.

The term "lipid" refers to a group of organic compounds that include, but are not limited to, esters of fatty acids and are characterized by being insoluble in water, but soluble in many organic solvents. They are usually divided into at least three classes: (1) "simple lipids," which include fats and oils as well as waxes; (2) "compound lipids," which include phospholipids and glycolipids; and (3) "derived lipids" such as steroids.

The term "lipid particle" includes a lipid formulation that can be used to deliver an active agent or therapeutic agent, such as a nucleic acid (e.g., an interfering RNA), to a target site of interest (e.g., cell, tissue, organ, and the like). In preferred embodiments, the lipid particle of the invention is a nucleic acid-lipid particle, which is typically formed from a cationic lipid, a non-cationic lipid, and optionally a conjugated lipid that prevents aggregation of the particle. In other preferred embodiments, the active agent or therapeutic agent, such as a nucleic acid, may be encapsulated in the lipid portion of the particle, thereby protecting it from enzymatic degradation.

As used herein, the term "SNALP" refers to a stable nucleic acid-lipid particle. A SNALP represents a particle made from lipids (e.g., a cationic lipid, a non-cationic lipid, and optionally a conjugated lipid that prevents aggregation of the particle), wherein the nucleic acid (e.g., an interfering RNA) is fully encapsulated within the lipid. In certain instances, SNALP are extremely useful for systemic applications, as they can exhibit extended circulation lifetimes following intravenous (i.v.) injection, they can accumulate at distal sites (e.g., sites physically separated from the administration site), and they can mediate silencing of target gene expression at these distal sites. The nucleic acid may be complexed with a condensing agent and encapsulated within a SNALP as set forth in PCT Publication No. WO 00/03683, the disclosure of which is herein incorporated by reference in its entirety for all purposes.

The lipid particles of the invention (e.g., SNALP) typically have a mean diameter of from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, or about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm, and are substantially non-toxic. In addition, nucleic acids, when present in the lipid particles of the present invention, are resistant in aqueous solution to degradation with a nuclease. Nucleic acid-lipid particles and their method of preparation are disclosed in, e.g., U.S. Patent Publication Nos. 20040142025 and 20070042031, the disclosures of which are herein incorporated by reference in their entirety for all purposes.

As used herein, "lipid encapsulated" can refer to a lipid particle that provides an active agent or therapeutic agent, such as a nucleic acid (e.g., an interfering RNA that targets PLK-1), with full encapsulation, partial encapsulation, or both. In a preferred embodiment, the nucleic acid is fully encapsulated in the lipid particle (e.g., to form a SNALP or other nucleic acid-lipid particle).

The term "lipid conjugate" refers to a conjugated lipid that inhibits aggregation of lipid particles. Such lipid conjugates include, but are not limited to, PEG-lipid conjugates such as, e.g., PEG coupled to dialkyloxypropyls (e.g., PEG-DAA conjugates), PEG coupled to diacylglycerols (e.g., PEG-DAG conjugates), PEG coupled to cholesterol, PEG coupled to phosphatidylethanolamines, and PEG conjugated to ceramides (see, e.g., U.S. Pat. No. 5,885,613), cationic PEG lipids, polyoxazoline (POZ)-lipid conjugates (e.g., POZ-DAA conjugates; see, e.g., U.S. Provisional Application No. 61/294,828, filed Jan. 13, 2010, and U.S. Provisional Application No. 61/295,140, filed Jan. 14, 2010), polyamide oligomers (e.g., ATTA-lipid conjugates), and mixtures thereof. Additional examples of POZ-lipid conjugates are described in PCT Publication No. WO 2010/006282. PEG or POZ can be conjugated directly to the lipid or may be linked to the lipid via a linker moiety. Any linker moiety suitable for coupling the PEG or the POZ to a lipid can be used including, e.g., non-ester containing linker moieties and ester-containing linker moieties. In certain preferred embodiments, non-ester containing linker moieties, such as amides or carbamates, are used. The disclosures of each of the above patent documents are herein incorporated by reference in their entirety for all purposes.

The term "amphipathic lipid" refers, in part, to any suitable material wherein the hydrophobic portion of the lipid material orients into a hydrophobic phase, while the hydrophilic portion orients toward the aqueous phase. Hydrophilic characteristics derive from the presence of polar or charged groups such as carbohydrates, phosphate, carboxylic, sulfato, amino, sulfhydryl, nitro, hydroxyl, and other like groups. Hydrophobicity can be conferred by the inclusion of apolar groups that include, but are not limited to, long-chain saturated and unsaturated aliphatic hydrocarbon groups and such groups substituted by one or more aromatic, cycloaliphatic, or heterocyclic group(s). Examples of amphipathic compounds include, but are not limited to, phospholipids, aminolipids, and sphingolipids.

Representative examples of phospholipids include, but are not limited to, phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine, and dilinoleoylphosphatidylcholine. Other compounds lacking in phosphorus, such as sphingolipid, glycosphingolipid families, diacylglycerols, and β-acyloxyacids, are also within the group designated as amphipathic lipids. Additionally, the amphipathic lipids described above can be mixed with other lipids including triglycerides and sterols.

The term "neutral lipid" refers to any of a number of lipid species that exist either in an uncharged or neutral zwitterionic form at a selected pH. At physiological pH, such lipids include, for example, diacylphosphatidylcholine, diacylphosphatidylethanolamine, ceramide, sphingomyelin, cephalin, cholesterol, cerebrosides, and diacylglycerols.

The term "non-cationic lipid" refers to any amphipathic lipid as well as any other neutral lipid or anionic lipid.

The term "anionic lipid" refers to any lipid that is negatively charged at physiological pH. These lipids include, but are not limited to, phosphatidylglycerols, cardiolipins, diacylphosphatidylserines, diacylphosphatidic acids, N-dodecanoyl phosphatidylethanolamines, N-succinyl phosphatidylethanolamines, N-glutarylphosphatidylethanolamines, lysylphosphatidylglycerols, palmitoyloleyolphosphatidylglycerol (POPG), and other anionic modifying groups joined to neutral lipids.

The term "hydrophobic lipid" refers to compounds having apolar groups that include, but are not limited to, long-chain saturated and unsaturated aliphatic hydrocarbon groups and such groups optionally substituted by one or more aromatic, cycloaliphatic, or heterocyclic group(s). Suitable examples include, but are not limited to, diacylglycerol, dialkylglycerol, N—N-dialkylamino, 1,2-diacyloxy-3-aminopropane, and 1,2-dialkyl-3-aminopropane.

The term "fusogenic" refers to the ability of a lipid particle, such as a SNALP, to fuse with the membranes of a cell. The membranes can be either the plasma membrane or membranes surrounding organelles, e.g., endosome, nucleus, etc.

The term "non-lamellar morphology" refer to a non-bilayer structure. The non-bilayer morphology can include, for example, three dimensional tubes, rods, cubic symmetries, etc. The non-lamellar morphology (i.e., non-bilayer structure) of the lipid particles disclosed herein can be determined using analytical techniques including Cryo-Transmission Electron Microscopy ("Cryo-TEM"), Differential Scanning Calorimetry ("DSC"), X-Ray Diffraction, etc.

The term "a plurality of nucleic acid-lipid particles" refers to at least 2 particles, more preferably more than 10, $10^2$, $10^1$, $10^4$, $10^5$, $10^6$ or more particles (or any fraction thereof or range therein). In certain embodiments, the plurality of nucleic acid-lipid particles includes 50-100, 50-200, 50-300, 50-400, 50-500, 50-600, 50-700, 50-800, 50-900, 50-1000, 50-1100, 50-1200, 50-1300, 50-1400, 50-1500, 50-1600, 50-1700, 50-1800, 50-1900, 50-2000, 50-2500, 50-3000, 50-3500, 50-4000, 50-4500, 50-5000, 50-5500, 50-6000, 50-6500, 50-7000, 50-7500, 50-8000, 50-8500, 50-9000, 50-9500, 50-10,000 or more particles. It will be apparent to those of skill in the art that the plurality of nucleic acid-lipid particles can include any fraction of the foregoing ranges or any range therein. In certain other embodiments, the plurality of nucleic acid-lipid particles is the number of particles (or a representative subset of particles) observed in a Cryo-TEM image similar to those illustrated in FIGS. 3-6 and 8-11, wherein the Cryo-TEM analysis is carried out using a method similar to that set forth in Example 2.

As used herein, the term "aqueous solution" refers to a composition comprising in whole, or in part, water.

As used herein, the term "organic lipid solution" refers to a composition comprising in whole, or in part, an organic solvent having a lipid.

"Distal site," as used herein, refers to a physically separated site, which is not limited to an adjacent capillary bed, but includes sites broadly distributed throughout an organism.

"Serum-stable" in relation to nucleic acid-lipid particles such as SNALP means that the particle is not significantly degraded after exposure to a serum or nuclease assay that would significantly degrade free DNA or RNA. Suitable assays include, for example, a standard serum assay, a DNAse assay, or an RNAse assay.

"Systemic delivery," as used herein, refers to delivery of lipid particles that leads to a broad biodistribution of an active agent such as an interfering RNA (e.g., siRNA) within an organism. Some techniques of administration can lead to the systemic delivery of certain agents, but not others. Systemic delivery means that a useful, preferably therapeutic, amount of an agent is exposed to most parts of the body. To obtain broad biodistribution generally requires a blood lifetime such that the agent is not rapidly degraded or cleared (such as by first pass organs (liver, lung, etc.) or by rapid, nonspecific cell binding) before reaching a disease site distal to the site of administration. Systemic delivery of lipid particles can be by any means known in the art including, for example, intravenous, subcutaneous, and intraperitoneal. In a preferred embodiment, systemic delivery of lipid particles is by intravenous delivery.

"Local delivery," as used herein, refers to delivery of an active agent such as an interfering RNA (e.g., siRNA) directly to a target site within an organism. For example, an agent can be locally delivered by direct injection into a disease site such as a tumor or other target site such as a site of inflammation or a target organ such as the liver, heart, pancreas, kidney, and the like.

The term "mammal" refers to any mammalian species such as a human, mouse, rat, dog, cat, hamster, guinea pig, rabbit, livestock, and the like.

The term "cancer" refers to any member of a class of diseases characterized by the uncontrolled growth of aberrant cells. The term includes all known cancers and neoplastic conditions, whether characterized as malignant, benign, soft tissue, or solid, and cancers of all stages and grades including pre- and post-metastatic cancers. Examples of different types of cancer include, but are not limited to, liver cancer, lung cancer, colon cancer, rectal cancer, anal cancer, bile duct cancer, small intestine cancer, stomach (gastric) cancer, esophageal cancer; gallbladder cancer, pancreatic cancer, appendix cancer, breast cancer, ovarian cancer; cervical cancer, prostate cancer, renal cancer (e.g., renal cell carcinoma), cancer of the central nervous system, glioblastoma, skin cancer, lymphomas, choriocarcinomas, head and neck cancers, osteogenic sarcomas, and blood cancers. Non-limiting examples of specific types of liver cancer include hepatocellular carcinoma (HCC), secondary liver cancer (e.g., caused by metastasis of some other non-liver cancer cell type), and hepatoblastoma. As used herein, a "tumor" comprises one or more cancerous cells.

The term "polo-like kinase 1," "PLK-1," "polo-like kinase," or "PLK" refers to a serine/threonine kinase containing two functional domains: (1) a kinase domain; and (2) a polo-box domain (see, e.g., Barr et al., *Nat. Rev. Mol. Cell Biol.*, 5:429-440 (2004)). The activity and cellular concentration of PLK-1 are crucial for the precise regulation of cell division. PLK-1 expression and activity are low throughout the G0, G1, and S phases of the cell cycle, but begin to rise in G2 and peak during M phase. PLK-1 is essential for mitosis and cell division and contributes to the following processes: centrosome maturation and the activation of maturation-promoting factors by Cdc25C and cyclinB1 phosphorylation; bipolar spindle formation; and DNA damage checkpoint adaptation (DNA damage inhibits PLK-1 in G2 and mitosis). PLK-1 is also involved in the activation of components of the anaphase promoting complex for mitotic exit and cytokinesis. PLK-1 is overexpressed in many cancer types including hepatoma and colon cancer, and PLK-1 expression often correlates with poor patient prognosis. Overexpression of PLK-1 (wild-type or kinase inactive) results in multinucleation (genetic instability). Hyperactive PLK-1 overrides the DNA damage checkpoint. Constitutive PLK-1 expression causes transformation of NIH 3T3 cells. PLK-1 phosphorylates the p53 tumor suppressor, thereby inhibiting the pro-apoptotic effects of p53. Human PLK-1 mRNA sequences are set forth in Genbank Accession Nos. NM_005030, X73458, BC014846, BC003002, HSU01038, and L19559. A mouse PLK-1 mRNA sequence is set forth in Genbank Accession No. NM_011121. PLK-1 is also known as serine/threonine protein kinase 13 (STPK13).

III. Description of the Embodiments

The present invention provides novel, serum-stable lipid particles comprising one or more active agents or therapeutic agents, methods of making the lipid particles, and methods of delivering and/or administering the lipid particles (e.g., for the treatment of a disease or disorder).

In one aspect, the present invention provides a composition comprising a plurality of nucleic acid-lipid particles, wherein each particle in the plurality of particles comprises: (a) a nucleic acid; (b) a cationic lipid comprising from about 50 mol % to about 85 mol % of the total lipid present in the particle; (c) a non-cationic lipid comprising from about 13 mol % to about 49.5 mol % of the total lipid present in the particle; and (d) a conjugated lipid that inhibits aggregation of particles comprising from about 0.5 mol % to about 10 mol % of the total lipid present in the particle, wherein at least about 95% of the particles in the plurality of particles have a non-lamellar morphology. In preferred embodiments, greater than 95%, preferably, greater than 96%, preferably, greater than 97%, preferably, greater than 98% and, preferably, greater than 99% of the particles have a non-lamellar morphology, i.e., a non-bilayer structure.

In certain embodiments, the active agent or therapeutic agent is fully encapsulated within the lipid portion of the lipid particles such that the active agent or therapeutic agent in the lipid particle is resistant in aqueous solution to enzymatic degradation, e.g., by a nuclease or protease. In certain other embodiments, the lipid particles are substantially non-toxic to mammals such as humans.

In some embodiments, the active agent or therapeutic agent comprises a nucleic acid. In certain instances, the nucleic acid comprises an interfering RNA molecule such as, e.g., an siRNA, aiRNA, miRNA, or mixtures thereof. In certain other instances, the nucleic acid comprises single-stranded or double-stranded DNA, RNA, or a DNA/RNA hybrid such as, e.g., an antisense oligonucleotide, a ribozyme, a plasmid, an immunostimulatory oligonucleotide, or mixtures thereof.

In other embodiments, the active agent or therapeutic agent comprises a peptide or polypeptide. In certain instances, the peptide or polypeptide comprises an antibody such as, e.g., a polyclonal antibody, a monoclonal antibody, an antibody fragment; a humanized antibody, a recombinant antibody, a recombinant human antibody, a Primatized™ antibody, or mixtures thereof. In certain other instances, the peptide or polypeptide comprises a cytokine, a growth factor, an apoptotic factor, a differentiation-inducing factor, a cell-surface receptor, a ligand, a hormone, a small molecule (e.g., small organic molecule or compound), or mixtures thereof.

In preferred embodiments, the active agent or therapeutic agent comprises an siRNA. In one embodiment, the siRNA molecule comprises a double-stranded region of about 15 to about 60 nucleotides in length (e.g., about 15-60, 15-50, 15-40, 15-30, 15-25, or 19-25 nucleotides in length, or 15, 16, 17, 18, 19, 20, 21, 22, 23, 24, or 25 nucleotides in length). The siRNA molecules of the invention are capable of silencing the expression of a target sequence in vitro and/or in vivo.

In some embodiments, the siRNA molecule comprises at least one modified nucleotide. In certain preferred embodiments, the siRNA molecule comprises one, two, three, four, five, six, seven, eight, nine, ten, or more modified nucleotides in the double-stranded region. In certain instances, the siRNA comprises from about 1% to about 100% (e.g., about 1%, 5%, 10%, 15%, 20%, 25%, 30%, 35%, 40%, 45%, 50%, 55%, 60%, 65%, 70%, 75%, 80%, 85%, 90%, 95%, or 100%) modified nucleotides in the double-stranded region. In preferred embodiments, less than about 25% (e.g., less than about 25%, 20%, 15%, 10%, or 5%) or from about 1% to about 25% (e.g., from about 1%-25%, 5%-25%, 10%-25%, 15%-25%, 20%-25%, or 10%-20%) of the nucleotides in the double-stranded region comprise modified nucleotides.

In other embodiments, the siRNA molecule comprises modified nucleotides including, but not limited to, 2'-O-methyl (2'OMe) nucleotides, 2'-deoxy-2'-fluoro (2'F) nucleotides, 2'-deoxy nucleotides, 2'-O-(2-methoxyethyl) (MOE) nucleotides, locked nucleic acid (LNA) nucleotides, and mixtures thereof. In preferred embodiments, the siRNA comprises 2'OMe nucleotides (e.g., 2'OMe purine and/or pyrimidine nucleotides) such as, for example, 2'OMe-guanosine nucleotides, 2'OMe-uridine nucleotides, 2'OMe-adenosine nucleotides, 2'OMe-cytosine nucleotides, and mixtures thereof. In certain instances, the siRNA does not comprise 2'OMe-cytosine nucleotides. In other embodiments, the siRNA comprises a hairpin loop structure.

The siRNA may comprise modified nucleotides in one strand (i.e., sense or antisense) or both strands of the double-stranded region of the siRNA molecule. Preferably, uridine and/or guanosine nucleotides are modified at selective positions in the double-stranded region of the siRNA duplex. With regard to uridine nucleotide modifications, at least one, two, three, four, five, six, or more of the uridine nucleotides in the sense and/or antisense strand can be a modified uridine nucleotide such as a 2'OMe-uridine nucleotide. In some embodiments, every uridine nucleotide in the sense and/or antisense strand is a 2'OMe-uridine nucleotide. With regard to guanosine nucleotide modifications, at least one, two, three, four, five, six, or more of the guanosine nucleotides in the sense and/or antisense strand can be a modified guanosine nucleotide such as a 2'OMe-guanosine nucleotide. In some embodiments, every guanosine nucleotide in the sense and/or antisense strand is a 2'OMe-guanosine nucleotide.

In certain embodiments, at least one, two, three, four, five, six, seven, or more 5'-GU-3' motifs in an siRNA sequence may be modified, e.g., by introducing mismatches to eliminate the 5'-GU-3' motifs and/or by introducing modified nucleotides such as 2'OMe nucleotides. The 5'-GU-3' motif can be in the sense strand, the antisense strand, or both strands of the siRNA sequence. The 5'-GU-3' motifs may be adjacent to each other or, alternatively, they may be separated by 1, 2, 3, 4, 5, 6, 7, 8, 9, 10, 11, 12, or more nucleotides.

In some preferred embodiments, a modified siRNA molecule is less immunostimulatory than a corresponding unmodified siRNA sequence. In such embodiments, the modified siRNA molecule with reduced immunostimulatory properties advantageously retains RNAi activity against the target sequence. In another embodiment, the immunostimulatory properties of the modified siRNA molecule and its ability to silence target gene expression can be balanced or optimized by the introduction of minimal and selective 2'OMe modifications within the siRNA sequence such as, e.g., within the double-stranded region of the siRNA duplex. In certain instances, the modified siRNA is at least about 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% less immunostimulatory than the corresponding unmodified siRNA. It will be readily apparent to those of skill in the art that the immunostimulatory properties of the modified siRNA molecule and the corresponding unmodified siRNA molecule can be determined by, for example, measuring INF-α and/or IL-6 levels from about two to about twelve hours after systemic administration in a mammal or transfection of a mammalian responder cell using an appropriate lipid-based delivery system (such as the SNALP delivery system disclosed herein).

In certain embodiments, a modified siRNA molecule has an IC50 (i.e., half-maximal inhibitory concentration) less than or equal to ten-fold that of the corresponding unmodified siRNA (i.e., the modified siRNA has an IC50 that is less than or equal to ten-times the IC50 of the corresponding unmodified siRNA). In other embodiments, the modified siRNA has an IC50 less than or equal to three-fold that of the corresponding unmodified siRNA sequence. In yet other embodiments, the modified siRNA has an IC50 less than or equal to two-fold that of the corresponding unmodified siRNA. It will be readily apparent to those of skill in the art that a dose-response curve can be generated and the IC50 values for the modified siRNA and the corresponding unmodified siRNA can be readily determined using methods known to those of skill in the art.

In yet another embodiment, a modified siRNA molecule is capable of silencing at least about 5%, 10%, 15%, 20%, 25%, 30%, 35%, 40%, 45%, 50%, 55%, 60%, 65%, 70%, 75%, 80%, 85%, 90%, 95%, or 100% of the expression of the target sequence relative to the corresponding unmodified siRNA sequence.

In some embodiments, the siRNA molecule does not comprise phosphate backbone modifications, e.g., in the sense and/or antisense strand of the double-stranded region. In other embodiments, the siRNA comprises one, two, three, four, or more phosphate backbone modifications, e.g., in the sense and/or antisense strand of the double-stranded region. In preferred embodiments, the siRNA does not comprise phosphate backbone modifications.

In further embodiments, the siRNA does not comprise 2'-deoxy nucleotides, e.g., in the sense and/or antisense strand of the double-stranded region. In yet further embodiments, the siRNA comprises one, two, three, four, or more 2'-deoxy nucleotides, e.g., in the sense and/or antisense strand of the double-stranded region. In preferred embodiments, the siRNA does not comprise 2'-deoxy nucleotides.

In certain instances, the nucleotide at the 3'-end of the double-stranded region in the sense and/or antisense strand is not a modified nucleotide. In certain other instances, the nucleotides near the 3'-end (e.g., within one, two, three, or four nucleotides of the 3'-end) of the double-stranded region in the sense and/or antisense strand are not modified nucleotides.

The siRNA molecules described herein may have 3' overhangs of one, two, three, four, or more nucleotides on one or both sides of the double-stranded region, or may lack overhangs (i.e., have blunt ends) on one or both sides of the double-stranded region. Preferably, the siRNA has 3' overhangs of two nucleotides on each side of the double-stranded region. In certain instances, the 3' overhang on the antisense strand has complementarity to the target sequence and the 3' overhang on the sense strand has complementarity to a complementary strand of the target sequence. Alternatively, the 3' overhangs do not have complementarity to the target sequence or the complementary strand thereof. In some embodiments, the 3' overhangs comprise one, two, three, four, or more nucleotides such as 2'-deoxy (2'H) nucleotides. In certain preferred embodiments, the 3' overhangs comprise deoxythymidine (dT) and/or uridine nucleotides. In other embodiments, one or more of the nucleotides in the 3' overhangs on one or both sides of the double-stranded region comprise modified nucleotides. Non-limiting examples of modified nucleotides are described above and include 2'OMe nucleotides, 2'-deoxy-2'F nucleotides, 2'-deoxy nucleotides, 2'-O-2-MOE nucleotides, LNA nucleotides, and mixtures thereof. In preferred embodiments, one, two, three, four, or more nucleotides in the 3' overhangs present on the sense and/or antisense strand of the siRNA comprise 2'OMe nucleotides (e.g., 2'OMe purine and/or pyrimidine nucleotides) such as, for example, 2'OMe-guanosine nucleotides, 2'OMe-uridine nucleotides, 2'OMe-adenosine nucleotides, 2'OMe-cytosine nucleotides, and mixtures thereof.

The siRNA may comprise at least one or a cocktail (e.g., at least two, three, four, five, six, seven, eight, nine, ten, or more) of unmodified and/or modified siRNA sequences that silence target gene expression. The cocktail of siRNA may comprise sequences which are directed to the same region or domain (e.g., a "hot spot") and/or to different regions or domains of one or more target genes. In certain instances, one or more (e.g., at least two, three, four, five, six, seven, eight, nine, ten, or more) modified siRNA that silence target gene expression are present in a cocktail. In certain other instances, one or more (e.g., at least two, three, four, five, six, seven, eight, nine, ten, or more) unmodified siRNA sequences that silence target gene expression are present in a cocktail.

In some embodiments, the antisense strand of the siRNA molecule comprises or consists of a sequence that is at least about 80%, 85%, 90%, 95%, 96%, 97%, 98%, or 99% complementary to the target sequence or a portion thereof. In other embodiments, the antisense strand of the siRNA molecule comprises or consists of a sequence that is 100% complementary to the target sequence or a portion thereof. In further embodiments, the antisense strand of the siRNA molecule comprises or consists of a sequence that specifically hybridizes to the target sequence or a portion thereof.

In further embodiments, the sense strand of the siRNA molecule comprises or consists of a sequence that is at least about 80%, 85%, 90%, 95%, 96%, 97%, 98%, or 99% identical to the target sequence or a portion thereof. In additional embodiments, the sense strand of the siRNA molecule comprises or consists of a sequence that is 100% identical to the target sequence or a portion thereof.

In the lipid particles of the invention (e.g., SNALP comprising an interfering RNA such as siRNA), the cationic lipid may comprise, e.g., one or more of the following: the cationic lipids of Formula I as disclosed herein, including, for example, MC3, LenMC3, CP-LenMC3, γ-LenMC3, CP-T-LenMC3, MC3MC, MC2MC, MC3 Ether, MC4 Ether, MC3 Amide, Pan-MC3, Pan-MC4 and Pan MC5, 1,2-dilinoleyloxy-N,N-dimethylaminopropane (DLinDMA), 1,2-dilinolenyloxy-N,N-dimethylaminopropane (DLenDMA), 2,2-dilinoleyl-4-(2-dimethylaminoethyl)-[1,3]-dioxolane (DLin-K-C2-DMA; "XTC2"), 2,2-dilinoleyl-4-(3-dimethylaminopropyl)-[1,3]-dioxolane (DLin-K-C3-DMA), 2,2-dilinoleyl-4-(4-dimethylaminobutyl)-[1,3]-dioxolane (DLin-K-C4-DMA), 2,2-dilinoleyl-5-dimethylaminomethyl-[1,3]-dioxane (DLin-K6-DMA), 2,2-dilinoleyl-4-N-methylpepiazino-[1,3]-dioxolane (DLin-K-MPZ), 2,2-dilinoleyl-4-dimethylaminomethyl-[1,3]-dioxolane (DLin-K-DMA), 1,2-dilinoleylcarbamoyloxy-3-dimethylaminopropane (DLin-C-DAP), 1,2-dilinoleyoxy-3-(dimethylamino)acetoxypropane (DLin-DAC), 1,2-dilinoleyoxy-3-morpholinopropane (DLin-MA), 1,2-dilinoleoyl-3-dimethylaminopropane (DLinDAP), 1,2-dilinoleylthio-3-dimethylaminopropane (DLin-S-DMA), 1-linoleoyl-2-linoleyloxy-3-dimethylaminopropane (DLin-2-DMAP), 1,2-dilinoleyloxy-3-trimethylaminopropane chloride salt (DLin-TMA.Cl), 1,2-dilinoleoyl-3-trimethylaminopropane chloride salt (DLin-TAP.Cl), 1,2-dilinoleyloxy-3-(N-methylpiperazino)propane (DLin-MPZ), 3-(N,N-dilinoleylamino)-1,2-propanediol (DLinAP), 3-(N,N-dioleylamino)-1,2-propanedio (DOAP), 1,2-dilinoleyloxo-3-(2-N,N-dimethylamino)ethoxypropane (DLin-EG-DMA), N,N-dioleyl-N,N-dimethylammonium chloride (DODAC), 1,2-dioleyloxy-N,N-dimethylaminopropane (DODMA), 1,2-distearyloxy-N,N-dimethylaminopropane (DSDMA), N-(1-(2,3-dioleyloxy)propyl)-N,N,N-trimethylammonium chloride (DOTMA), N,N-distearyl-N,N-dimethylammonium bromide (DDAB), N-(1-(2,3-dioleoyloxy)propyl)-N,N,N-trimethylammonium chloride (DOTAP), 3-(N—(N',N'-dimethylaminoethane)-carbamoyl)cholesterol (DC-Chol), N-(1,2-dimyristyloxyprop-3-yl)-N,N-dimethyl-N-hydroxyethyl ammonium bromide (DMRIE), 2,3-dioleyloxy-N-[2 (spermine-carboxamido)ethyl]-N,N-dimethyl-1-propanaminiumtrifluoroacetate (DOSPA), dioctadecylamidoglycyl spermine (DOGS), 3-dimethylamino-2-(cholest-5-en-3-beta-oxybutan-4-oxy)-1-(cis,cis-9,12-octadecadienoxy)propane (CLinDMA), 2-[5'-(cholest-5-en-3-beta-oxy)-3'-oxapentoxy)-3-dimethy-1-(cis,cis-9',1-2'-octadecadienoxy) propane (CpLinDMA), N,N-dimethyl-3,4-dioleyloxybenzylamine (DMOBA), 1,2-N,N'-dioleylcarbamyl-3-dimethylaminopropane (DOcarbDAP), 1,2-N,N'-dilinoleylcarbamyl-3-dimethylaminopropane (DLincarbDAP), or mixtures thereof. In certain preferred embodiments, the cationic lipid is DLinDMA, DLin-K-C2-DMA ("XTC2"), MC3, LenMC3, CP-LenMC3, γ-LenMC3, CP-γ-LenMC3, MC3MC, MC2MC, MC3 Ether, MC4 Ether, MC3 Amide, Pan-MC3, Pan-MC4, Pan MC5, or mixtures thereof.

The synthesis of cationic lipids such as DLin-K-C2-DMA ("XTC2"), DLin-K-C3-DMA, DLin-K-C4-DMA, DLin-K6-DMA, and DLin-K-MPZ, as well as additional cationic lipids, is described in U.S. Provisional Application No. 61/104,212, filed Oct. 9, 2008, the disclosure of which is herein incorporated by reference in its entirety for all purposes. The synthesis of cationic lipids such as DLin-K-DMA, DLin-C-DAP, DLin-DAC, DLin-MA, DLinDAP, DLin-S-DMA, DLin-2-DMAP, DLin-TMA.Cl, DLin-TAP.Cl, DLin-MPZ, DLinAP, DOAP, and DLin-EG-DMA, as well as additional cationic lipids, is described in PCT Application No. PCT/US08/88676, filed Dec. 31, 2008, the disclosure of which is herein incorporated by reference in its entirety for all purposes. The synthesis of cationic lipids such as CLinDMA, as well as additional cationic lipids, is described in U.S. Patent Publication No. 20060240554, the disclosure of which is herein incorporated by reference in its entirety for all purposes.

In some embodiments, the cationic lipid may comprise from about 50 mol % to about 90 mol %, from about 50 mol % to about 85 mol %, from about 50 mol % to about 80 mol %, from about 50 mol % to about 75 mol %, from about 50 mol % to about 70 mol %, from about 50 mol % to about 65 mol %, or from about 50 mol % to about 60 mol % of the total lipid present in the particle.

In other embodiments, the cationic lipid may comprise from about 55 mol % to about 90 mol %, from about 55 mol % to about 85 mol %, from about 55 mol % to about 80 mol %, from about 55 mol % to about 75 mol %, from about 55 mol % to about 70 mol %, or from about 55 mol % to about 65 mol % of the total lipid present in the particle.

In yet other embodiments, the cationic lipid may comprise from about 60 mol % to about 90 mol %, from about 60 mol % to about 85 mol %, from about 60 mol % to about 80 mol %, from about 60 mol % to about 75 mol %, or from about 60 mol % to about 70 mol % of the total lipid present in the particle.

In still yet other embodiments, the cationic lipid may comprise from about 65 mol % to about 90 mol %, from about 65 mol % to about 85 mol %, from about 65 mol % to about 80 mol %, or from about 65 mol % to about 75 mol % of the total lipid present in the particle.

In further embodiments, the cationic lipid may comprise from about 70 mol % to about 90 mol %, from about 70 mol % to about 85 mol %, from about 70 mol % to about 80 mol %, from about 75 mol % to about 90 mol %, from about 75 mol % to about 85 mol %, or from about 80 mol % to about 90 mol % of the total lipid present in the particle.

In additional embodiments, the cationic lipid may comprise (at least) about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 mol % (or any fraction thereof or range therein) of the total lipid present in the particle.

In the lipid particles of the invention (e.g., SNALP comprising an interfering RNA such as siRNA), the non-cationic lipid may comprise, e.g., one or more anionic lipids and/or neutral lipids. In preferred embodiments, the non-cationic lipid comprises one of the following neutral lipid components: (1) cholesterol or a derivative thereof, (2) a phospholipid; or (3) a mixture of a phospholipid and cholesterol or a derivative thereof.

Examples of cholesterol derivatives include, but are not limited to, cholestanol, cholestanone, cholestenone, coprostanol, cholesteryl-2'-hydroxyethyl ether, cholesteryl-4'-hydroxybutyl ether, and mixtures thereof. The synthesis of cholesteryl-2'-hydroxyethyl ether is described herein.

The phospholipid may be a neutral lipid including, but not limited to, dipalmitoylphosphatidylcholine (DPPC), distearoylphosphatidylcholine (DSPC), dioleoylphosphatidylethanolamine (DOPE), palmitoyloleoyl-phosphatidylcholine (POPC), palmitoyloleoyl-phosphatidylethanolamine (POPE), palmitoyloleoyl-phosphatidylglycerol (POPG), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethyl-phosphatidylethanolamine, dielaidoyl-phosphatidylethanolamine (DEPE), stearoyloleoyl-phosphatidylethanolamine (SOPE), egg phosphatidylcholine (EPC), and mixtures thereof. In certain preferred embodiments, the phospholipid is DPPC, DSPC, or mixtures thereof.

In some embodiments, the non-cationic lipid (e.g., one or more phospholipids and/or cholesterol) may comprise from about 10 mol % to about 60 mol %, from about 15 mol % to about 60 mol %, from about 20 mol % to about 60 mol %, from about 25 mol % to about 60 mol %, from about 30 mol % to about 60 mol %, from about 10 mol % to about 55 mol %, from about 15 mol % to about 55 mol %, from about 20 mol % to about 55 mol %, from about 25 mol % to about 55 mol %, from about 30 mol % to about 55 mol %, from about 13 mol % to about 50 mol %, from about 15 mol % to about 50 mol % or from about 20 mol % to about 50 mol % of the total lipid present in the particle. When the non-cationic lipid is a mixture of a phospholipid and cholesterol or a cholesterol derivative, the mixture may comprise up to about 40, 50, or 60 mol % of the total lipid present in the particle.

In other embodiments, the non-cationic lipid (e.g., one or more phospholipids and/or cholesterol) may comprise from about 10 mol % to about 49.5 mol %, from about 13 mol % to about 49.5 mol %, from about 15 mol % to about 49.5 mol %, from about 20 mol % to about 49.5 mol %, from about 25 mol % to about 49.5 mol %, from about 30 mol % to about 49.5 mol %, from about 35 mol % to about 49.5 mol %, or from about 40 mol % to about 49.5 mol % of the total lipid present in the particle.

In yet other embodiments, the non-cationic lipid (e.g., one or more phospholipids and/or cholesterol) may comprise from about 10 mol % to about 45 mol %, from about 13 mol % to about 45 mol %, from about 15 mol % to about 45 mol %, from about 20 mol % to about 45 mol %, from about 25 mol % to about 45 mol %, from about 30 mol % to about 45 mol %, or from about 35 mol % to about 45 mol % of the total lipid present in the particle.

In still yet other embodiments, the non-cationic lipid (e.g., one or more phospholipids and/or cholesterol) may comprise from about 10 mol % to about 40 mol %, from about 13 mol % to about 40 mol %, from about 15 mol % to about 40 mol %, from about 20 mol % to about 40 mol %, from about 25 mol % to about 40 mol %, or from about 30 mol % to about 40 mol % of the total lipid present in the particle.

In further embodiments, the non-cationic lipid (e.g., one or more phospholipids and/or cholesterol) may comprise from about 10 mol % to about 35 mol %, from about 13 mol % to about 35 mol %, from about 15 mol % to about 35 mol %, from about 20 mol % to about 35 mol %, or from about 25 mol % to about 35 mol % of the total lipid present in the particle.

In yet further embodiments, the non-cationic lipid (e.g., one or more phospholipids and/or cholesterol) may comprise from about 10 mol % to about 30 mol %, from about 13 mol % to about 30 mol %, from about 15 mol % to about 30 mol %, from about 20 mol % to about 30 mol %, from about 10 mol % to about 25 mol %, from about 13 mol % to about 25 mol %, or from about 15 mol % to about 25 mol % of the total lipid present in the particle.

In additional embodiments, the non-cationic lipid (e.g., one or more phospholipids and/or cholesterol) may comprise (at least) about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 mol % (or any fraction thereof or range therein) of the total lipid present in the particle.

In certain preferred embodiments, the non-cationic lipid comprises cholesterol or a derivative thereof of from about 31.5 mol % to about 42.5 mol % of the total lipid present in the particle. As a non-limiting example, a phospholipid-free lipid particle of the invention may comprise cholesterol or a derivative thereof at about 37 mol % of the total lipid present in the particle. In other preferred embodiments, a phospholipid-free lipid particle of the invention may comprise cholesterol or a derivative thereof of from about 30 mol % to about 45 mol %, from about 30 mol % to about 40 mol %, from about 30 mol % to about 35 mol %, from about 35 mol % to about 45 mol %, from about 40 mol % to about 45 mol %, from about 32 mol % to about 45 mol %, from about 32 mol % to about 42 mol %, from about 32 mol % to about 40 mol %, from about 34 mol % to about 45 mol %, from about 34 mol % to about 42 mol %, from about 34 mol % to about 40 mol %, or about 30, 31, 32, 33, 34, 35, 36, 37, 38, 39, 40, 41, 42, 43, 44, or 45 mol % (or any fraction thereof or range therein) of the total lipid present in the particle.

In certain other preferred embodiments, the non-cationic lipid comprises a mixture of: (i) a phospholipid of from about 4 mol % to about 10 mol % of the total lipid present in the particle; and (ii) cholesterol or a derivative thereof of from about 30 mol % to about 40 mol % of the total lipid present in the particle. As a non-limiting example, a lipid particle comprising a mixture of a phospholipid and cholesterol may comprise DPPC at about 7 mol % and cholesterol at about 34 mol % of the total lipid present in the particle. In other embodiments, the non-cationic lipid comprises a mixture of: (i) a phospholipid of from about 3 mol % to about 15 mol %, from about 4 mol % to about 15 mol %, from about 4 mol % to about 12 mol %, from about 4 mol % to about 10 mol %, from about 4 mol % to about 8 mol %, from about 5 mol % to about 12 mol %, from about 5 mol % to about 9 mol %, from about 6 mol % to about 12 mol %, from about 6 mol % to about 10 mol %, or about 3, 4, 5, 6, 7, 8, 9, 10, 11, 12, 13, 14, or 15 mol % (or any fraction thereof or range therein) of the total lipid present in the particle; and (ii) cholesterol or a derivative thereof of from about 25 mol % to about 45 mol %, from about 30 mol % to about 45 mol %, from about 25 mol % to about 40 mol %, from about 30 mol % to about 40 mol %, from about 25 mol % to about 35 mol %, from about 30 mol % to about 35 mol %, from about 35 mol % to about 45 mol %, from about 40 mol % to about 45 mol %, from about 28 mol % to about 40 mol %, from about 28 mol % to about 38 mol %, from about 30 mol % to about 38 mol %, from about 32 mol % to about 36 mol %, or about 25, 26, 27, 28, 29, 30, 31, 32, 33, 34, 35, 36, 37, 38, 39, 40, 41, 42, 43, 44, or 45 mol % (or any fraction thereof or range therein) of the total lipid present in the particle.

In further preferred embodiments, the non-cationic lipid comprises a mixture of: (i) a phospholipid of from about 10 mol % to about 30 mol % of the total lipid present in the particle; and (ii) cholesterol or a derivative thereof of from about 10 mol % to about 30 mol % of the total lipid present in the particle. As a non-limiting example, a lipid particle comprising a mixture of a phospholipid and cholesterol may comprise DPPC at about 20 mol % and cholesterol at about 20 mol % of the total lipid present in the particle. In other embodiments, the non-cationic lipid comprises a mixture of: (i) a phospholipid of from about 10 mol % to about 30 mol %, from about 10 mol % to about 25 mol %, from about 10 mol % to about 20 mol %, from about 15 mol % to about 30 mol %, from about 20 mol % to about 30 mol %, from about 15 mol % to about 25 mol %, from about 12 mol % to about 28 mol %, from about 14 mol % to about 26 mol %, or about 10, 11, 12, 13, 14, 15, 16, 17, 18, 19, 20, 21, 22, 23, 24, 25, 26, 27, 28, 29, or 30 mol % (or any fraction thereof or range therein) of the total lipid present in the particle; and (ii) cholesterol or a derivative thereof of from about 10 mol % to about 30 mol %, from about 10 mol % to about 25 mol %, from about 10 mol % to about 20 mol %, from about 15 mol % to about 30 mol %, from about 20 mol % to about 30 mol %, from about 15 mol % to about 25 mol %, from about 12 mol % to about 28 mol %, from about 14 mol % to about 26 mol %, or about 10, 11, 12, 13, 14, 15, 16, 17, 18, 19, 20, 21, 22, 23, 24, 25, 26, 27, 28, 29, or 30 mol % (or any fraction thereof or range therein) of the total lipid present in the particle.

In the lipid particles of the invention (e.g., SNALP comprising an interfering RNA such as siRNA), the conjugated lipid that inhibits aggregation of particles may comprise, e.g., one or more of the following: a polyethyleneglycol (PEG)-lipid conjugate, a polyamide (ATTA)-lipid conjugate, a cationic-polymer-lipid conjugates (CPLs), or mixtures thereof. In one preferred embodiment, the nucleic acid-lipid particles comprise either a PEG-lipid conjugate or an ATTA-lipid conjugate. In certain embodiments, the PEG-lipid conjugate or ATTA-lipid conjugate is used together with a CPL. The conjugated lipid that inhibits aggregation of particles may comprise a PEG-lipid including, e.g., a PEG-diacylglycerol (DAG), a PEG dialkyloxypropyl (DAA), a PEG-phospholipid, a PEG-ceramide (Cer), or mixtures thereof. The PEG-DAA conjugate may be PEG-dilauryloxypropyl (C12), a PEG-dimyristyloxypropyl (C14), a PEG-dipalmityloxypropyl (C16), a PEG-distearyloxypropyl (C18), or mixtures thereof.

Additional PEG-lipid conjugates suitable for use in the invention include, but are not limited to, mPEG2000-1,2-di-O-alkyl-sn3-carbomoylglyceride (PEG-C-DOMG). The synthesis of PEG-C-DOMG is described in PCT Application No. PCT/US08/88676, filed Dec. 31, 2008, the disclosure of which is herein incorporated by reference in its entirety for all purposes. Yet additional PEG-lipid conjugates suitable for use in the invention include, without limitation, 1-[8'-(1,2-dimyristoyl-3-propanoxy)-carboxamido-3',6'-dioxaoctanyl]carbamoyl-o-methyl-poly(ethylene glycol) (2KPEG-DMG). The synthesis of 2KPEG-DMG is described in U.S. Pat. No. 7,404,969, the disclosure of which is herein incorporated by reference in its entirety for all purposes.

The PEG moiety of the PEG-lipid conjugates described herein may comprise an average molecular weight ranging from about 550 daltons to about 10,000 daltons. In certain instances, the PEG moiety has an average molecular weight of from about 750 daltons to about 5,000 daltons (e.g., from about 1,000 daltons to about 5,000 daltons, from about 1,500 daltons to about 3,000 daltons, from about 750 daltons to about 3,000 daltons, from about 750 daltons to about 2,000 daltons, etc.). In preferred embodiments, the PEG moiety has an average molecular weight of about 2,000 daltons or about 750 daltons.

In some embodiments, the conjugated lipid that inhibits aggregation of particles is a CPL that has the formula: A-W-Y, wherein A is a lipid moiety, W is a hydrophilic polymer, and Y is a polycationic moiety. W may be a polymer selected from the group consisting of polyethyleneglycol (PEG), polyamide, polylactic acid, polyglycolic acid, polylactic acid/polyglycolic acid copolymers, or combinations thereof, the polymer having a molecular weight of from about 250 to about 7000 daltons. In some embodiments, Y has at least 4 positive charges at a selected pH. In some embodiments, Y may be lysine, arginine, asparagine, glutamine, derivatives thereof, or combinations thereof.

In certain instances, such as with the "1:57 SNALP" and "1:62 SNALP" formulations, the conjugated lipid that inhibits aggregation of particles (e.g., PEG-lipid conjugate) may comprise from about 0.1 mol % to about 2 mol %, from about 0.5 mol % to about 2 mol %, from about 1 mol % to about 2 mol %, from about 0.6 mol % to about 1.9 mol %, from about 0.7 mol % to about 1.8 mol %, from about 0.8 mol % to about 1.7 mol %, from about 1 mol % to about 1.8 mol %, from about 1.2 mol % to about 1.8 mol %, from about 1.2 mol % to about 1.7 mol %, from about 1.3 mol % to about 1.6 mol %, from about 1.4 mol % to about 1.5 mol %, or about 1, 1.1, 1.2, 1.3, 1.4, 1.5, 1.6, 1.7, 1.8, 1.9, or 2 mol % (or any fraction thereof or range therein) of the total lipid present in the particle. Typically, in such instances, the PEG moiety has an average molecular weight of about 2,000 daltons.

In certain other instances, such as with the "7:54 SNALP" and "7:58 SNALP" formulations, the conjugated lipid that inhibits aggregation of particles (e.g., PEG-lipid conjugate) may comprise from about 5.0 mol % to about 10 mol %, from about 5 mol % to about 9 mol %, from about 5 mol % to about 8 mol %, from about 6 mol % to about 9 mol %, from about 6 mol % to about 8 mol %, or about 5 mol %, 6 mol %, 7 mol %, 8 mol %, 9 mol %, or 10 mol % (or any fraction thereof or range therein) of the total lipid present in the particle. Typically, in such instances, the PEG moiety has an average molecular weight of about 750 daltons.

In the lipid particles of the invention, the active agent or therapeutic agent may be fully encapsulated within the lipid portion of the particle, thereby protecting the active agent or therapeutic agent from enzymatic degradation. In preferred embodiments, a SNALP comprising a nucleic acid such as an interfering RNA (e.g., siRNA) is fully encapsulated within the lipid portion of the particle, thereby protecting the nucleic acid from nuclease degradation. In certain instances, the nucleic acid in the SNALP is not substantially degraded after exposure of the particle to a nuclease at 37° C. for at least about 20, 30, 45, or 60 minutes. In certain other instances, the nucleic acid in the SNALP is not substantially degraded after incubation of the particle in serum at 37° C. for at least about 30, 45, or 60 minutes or at least about 2, 3, 4, 5, 6, 7, 8, 9, 10, 12, 14, 16, 18, 20, 22, 24, 26, 28, 30, 32, 34, or 36 hours. In other embodiments, the active agent or therapeutic agent (e.g., nucleic acid such as siRNA) is complexed with the lipid portion of the particle. One of the benefits of the formulations of the present invention is that the lipid particle compositions are substantially non-toxic to mammals such as humans.

The term "fully encapsulated" indicates that the active agent or therapeutic agent in the lipid particle is not significantly degraded after exposure to serum or a nuclease or protease assay that would significantly degrade free DNA, RNA, or protein. In a fully encapsulated system, preferably less than about 25% of the active agent or therapeutic agent in the particle is degraded in a treatment that would normally degrade 100% of free active agent or therapeutic agent, more preferably less than about 10%, and most preferably less than about 5% of the active agent or therapeutic agent in the particle is degraded. In the context of nucleic acid therapeutic agents, full encapsulation may be determined by an Oligreen® assay. Oligreen® is an ultra-sensitive fluorescent nucleic acid stain for quantitating oligonucleotides and single-stranded DNA or RNA in solution (available from Invitrogen Corporation; Carlsbad, CA). "Fully encapsulated" also indicates that the lipid particles are serum-stable, that is, that they do not rapidly decompose into their component parts upon in vivo administration.

In another aspect, the present invention provides a lipid particle (e.g., SNALP) composition comprising a plurality of lipid particles. In preferred embodiments, the active agent or therapeutic agent (e.g., nucleic acid) is fully encapsulated within the lipid portion of the lipid particles (e.g., SNALP), such that from about 30% to about 100%, from about 40% to about 100%, from about 50% to about 100%, from about 60% to about 100%, from about 70% to about 100%, from about 80% to about 100%, from about 90% to about 100%, from about 30% to about 95%, from about 40% to about 95%, from about 50% to about 95%, from about 60% to about 95%, %, from about 70% to about 95%, from about 80% to about 95%, from about 85% to about 95%, from about 90% to about 95%, from about 30% to about 90%, from about 40% to about 90%, from about 50% to about 90%, from about 60% to about 90%, from about 70% to about 90%, from about 80% to about 90%, or at least about 30%, 35%, 40%, 45%, 50%, 55%, 60%, 65%, 70%, 75%, 80%, 85%, 90%, 91%, 92%, 93%, 94%, 95%, 96%, 97%, 98%, or 99% (or any fraction thereof or range therein) of the lipid particles (e.g., SNALP) have the active agent or therapeutic agent encapsulated therein.

Typically, the lipid particles (e.g., SNALP) of the invention have a lipid:active agent (e.g., lipid:nucleic acid) ratio (mass/mass ratio) of from about 1 to about 100. In some instances, the lipid:active agent (e.g., lipid:nucleic acid) ratio (mass/mass ratio) ranges from about 1 to about 50, from about 2 to about 25, from about 3 to about 20, from about 4 to about 15, or from about 5 to about 10. In preferred embodiments, the lipid particles of the invention have a lipid:active agent (e.g., lipid:nucleic acid) ratio (mass/mass ratio) of from about 5 to about 15, e.g., about 5, 6, 7, 8, 9, 10, 11, 12, 13, 14, or 15 (or any fraction thereof or range therein).

Typically, the lipid particles (e.g., SNALP) of the invention have a mean diameter of from about 40 nm to about 150 nm. In preferred embodiments, the lipid particles (e.g., SNALP) of the invention have a mean diameter of from about 40 nm to about 130 nm, from about 40 nm to about 120 nm, from about 40 nm to about 100 nm, from about 50 nm to about 120 nm, from about 50 nm to about 100 nm, from about 60 nm to about 120 nm, from about 60 nm to about 110 nm, from about 60 nm to about 100 nm, from about 60 nm to about 90 nm, from about 60 nm to about 80 nm, from about 70 nm to about 120 nm, from about 70 nm to about 110 nm, from about 70 nm to about 100 nm, from about 70 nm to about 90 nm, from about 70 nm to about 80 nm, from about 40 nm to about 90 nm, from about 45 nm to about 85, or from about 50 nm to abut 80 nm, or less than about 120 nm, 110 nm, 100 nm, 90 nm, 80 nm, 70 nm or 60 nm (or any fraction thereof or range therein).

In one specific embodiment of the invention, the composition comprises: a plurality of nucleic acid-lipid particles, wherein each particle in the plurality of particles comprises: (a) one or more unmodified and/or modified interfering RNA (e.g., siRNA, aiRNA, miRNA) that silence target gene expression; (b) a cationic lipid comprising from about 56.5 mol % to about 66.5 mol % of the total lipid present in the particle; (c) a non-cationic lipid comprising from about 31.5 mol % to about 42.5 mol % of the total lipid present in the particle; and (d) a conjugated lipid that inhibits aggregation of particles comprising from about 1 mol % to about 2 mol % of the total lipid present in the particle, wherein at least about 95% of the particles in the plurality of particles have a non-lamellar morphology. This specific embodiment of SNALP is generally referred to herein as the "1:62" formulation. In a preferred embodiment, the cationic lipid is DLinDMA or DLin-K-C2-DMA ("XTC2"), the non-cationic lipid is cholesterol, and the conjugated lipid is a PEG-DAA conjugate. Although these are preferred embodiments of the 1:62 formulation, those of skill in the art will appreciate that other cationic lipids, non-cationic lipids (including other cholesterol derivatives), and conjugated lipids can be used in the 1:62 formulation as described herein.

In another specific embodiment of the invention, the composition comprises: a plurality of nucleic acid-lipid particles, wherein each particle in the plurality of particles comprises: (a) one or more unmodified and/or modified interfering RNA (e.g., siRNA, aiRNA, miRNA) that silence target gene expression; (b) a cationic lipid comprising from about 52 mol % to about 62 mol % of the total lipid present in the particle; (c) a non-cationic lipid comprising from about 36 mol % to about 47 mol % of the total lipid present in the particle; and (d) a conjugated lipid that inhibits aggregation of particles comprising from about 1 mol % to about 2 mol % of the total lipid present in the particle, wherein at least about 95% of the particles in the plurality of particles have a non-lamellar morphology. This specific embodiment of SNALP is generally referred to herein as the "1:57" formulation. In one preferred embodiment, the cationic lipid is DLinDMA or DLin-K-C2-DMA ("XTC2"), the non-cationic lipid is a mixture of a phospholipid (such as DPPC) and cholesterol, wherein the phospholipid comprises from about 5 mol % to about 9 mol % of the total lipid present in the particle (e.g., about 7.1 mol %) and the cholesterol (or cholesterol derivative) comprises from about 32 mol % to about 37 mol % of the total lipid present in the particle (e.g., about 34.3 mol %), and the PEG-lipid is a PEG-DAA (e.g., PEG-cDMA). In another preferred embodiment, the cationic lipid is DLinDMA or DLin-K-C2-DMA ("XTC2"), the non-cationic lipid is a mixture of a phospholipid (such as DPPC) and cholesterol, wherein the phospholipid comprises from about 15 mol % to about 25 mol % of the total lipid present in the particle (e.g., about 20 mol %) and the cholesterol (or cholesterol derivative) comprises from about 15 mol % to about 25 mol % of the total lipid present in the particle (e.g., about 20 mol %), and the PEG-lipid is a PEG-DAA (e.g., PEG-cDMA). Although these are preferred embodiments of the 1:57 formulation, those of skill in the art will appreciate that other cationic lipids, non-cationic lipids (including other phospholipids and other cholesterol derivatives), and conjugated lipids can be used in the 1:57 formulation as described herein.

In preferred embodiments, the 1:62 SNALP formulation is a three-component system which is phospholipid-free and comprises about 1.5 mol % PEG-cDMA (or PEG-cDSA), about 61.5 mol % DLinDMA (or XTC2), and about 36.9 mol % cholesterol (or derivative thereof). In other preferred embodiments, the 1:57 SNALP formulation is a four-component system which comprises about 1.4 mol % PEG-cDMA (or PEG-cDSA), about 57.1 mol % DLinDMA (or XTC2), about 7.1 mol % DPPC, and about 34.3 mol % cholesterol (or derivative thereof). In yet other preferred embodiments, the 1:57 SNALP formulation is a four-component system which comprises about 1.4 mol % PEG-cDMA (or PEG-cDSA), about 57.1 mol % DLinDMA (or XTC2), about 20 mol % DPPC, and about 20 mol % cholesterol (or derivative thereof). It should be understood that these SNALP formulations are target formulations, and that the amount of lipid (both cationic and non-cationic) present and the amount of lipid conjugate present in the SNALP formulations may vary.

In yet another specific embodiment of the invention, the composition comprises: a plurality of nucleic acid-lipid particles, wherein each particle in the plurality of particles comprises: (a) a nucleic acid (e.g., an interfering RNA); (b) a cationic lipid comprising from about 50 mol % to about 60 mol % of the total lipid present in the particle; (c) a mixture of a phospholipid and cholesterol or a derivative thereof comprising from about 35 mol % to about 45 mol % of the total lipid present in the particle; and (d) a PEG-lipid conjugate comprising from about 5 mol % to about 10 mol % of the total lipid present in the particle, wherein at least about 95% of the particles in the plurality of particles have a non-lamellar morphology. This embodiment of nucleic acid-lipid particle is generally referred to herein as the "7:54" formulation.

In still another specific embodiment of the invention, the composition comprises: a plurality of nucleic acid-lipid particles, wherein each particle in the plurality of particles comprises: (a) a nucleic acid (e.g., an interfering RNA); (b) a cationic lipid comprising from about 55 mol % to about 65 mol % of the total lipid present in the particle; (c) cholesterol or a derivative thereof comprising from about 30 mol % to about 40 mol % of the total lipid present in the particle; and (d) a PEG-lipid conjugate comprising from about 5 mol % to about 10 mol % of the total lipid present in the particle, wherein at least about 95% of the particles in the plurality of particles have a non-lamellar morphology. This embodiment of nucleic acid-lipid particle is generally referred to herein as the "7:58" formulation.

The present invention also provides a pharmaceutical composition comprising a lipid particle (e.g., SNALP) described herein and a pharmaceutically acceptable carrier.

In a further aspect, the present invention provides a method for introducing one or more active agents or therapeutic agents (e.g., nucleic acid) into a cell, comprising contacting the cell with a lipid particle (e.g., SNALP) described herein. In one embodiment, the cell is in a mammal and the mammal is a human. In another embodiment, the present invention provides a method for the in vivo delivery of one or more active agents or therapeutic agents (e.g., nucleic acid), comprising administering to a mammalian subject a lipid particle (e.g., SNALP) described herein. In a preferred embodiment, the mode of administration includes, but is not limited to, oral, intranasal, intravenous, intraperitoneal, intramuscular, intra-articular, intralesional, intratracheal, subcutaneous, and intradermal. Preferably, the mammalian subject is a human.

In one embodiment, at least about 5%, 10%, 15%, 20%, or 25% of the total injected dose of the lipid particles (e.g., SNALP) is present in plasma about 8, 12, 24, 36, or 48 hours after injection. In other embodiments, more than about 20%, 30%, 40% and as much as about 60%, 70% or 80% of the total injected dose of the lipid particles (e.g., SNALP) is present in plasma about 8, 12, 24, 36, or 48 hours after injection. In certain instances, more than about 10% of a plurality of the particles is present in the plasma of a mammal about 1 hour after administration. In certain other instances, the presence of the lipid particles (e.g., SNALP) is detectable at least about 1 hour after administration of the particle. In certain embodiments, the presence of an active agent or therapeutic agent such as an interfering RNA (e.g., siRNA) is detectable in cells of the lung, liver, tumor, or at a site of inflammation at about 8, 12, 24, 36, 48, 60, 72 or 96 hours after administration. In other embodiments, down-regulation of expression of a target sequence by an active agent or therapeutic agent such as an interfering RNA (e.g., siRNA) is detectable at about 8, 12, 24, 36, 48, 60, 72 or 96 hours after administration. In yet other embodiments, down-regulation of expression of a target sequence by an active agent or therapeutic agent such as an interfering RNA (e.g., siRNA) occurs preferentially in tumor cells or in cells at a site of inflammation. In further embodiments, the presence or effect of an active agent or therapeutic agent such as an interfering RNA (e.g., siRNA) in cells at a site proximal or distal to the site of administration or in cells of the lung, liver, or a tumor is detectable at about 12, 24, 48, 72, or 96 hours, or at about 6, 8, 10, 12, 14, 16, 18, 19, 20, 22, 24, 26, or 28 days after administration. In additional embodiments, the lipid particles (e.g., SNALP) of the invention are administered parenterally or intraperitoneally.

In some embodiments, the lipid particles (e.g., SNALP) of the invention are particularly useful in methods for the therapeutic delivery of one or more nucleic acids comprising an interfering RNA sequence (e.g., siRNA). In particular, it is an object of this invention to provide in vitro and in vivo methods for treatment of a disease or disorder in a mammal (e.g., a rodent such as a mouse or a primate such as a human, chimpanzee, or monkey) by downregulating or silencing the transcription and/or translation of one or more target nucleic acid sequences or genes of interest. As a non-limiting example, the methods of the invention are useful for in vivo delivery of interfering RNA (e.g., siRNA) to the liver and/or tumor of a mammalian subject. In certain embodiments, the disease or disorder is associated with expression and/or overexpression of a gene and expression or overexpression of the gene is reduced by the interfering RNA (e.g., siRNA). In certain other embodiments, a therapeutically effective amount of the lipid particle (e.g., SNALP) may be administered to the mammal. In some instances, an interfering RNA (e.g., siRNA) is formulated into a SNALP, and the particles are administered to patients requiring such treatment. In other instances, cells are removed from a patient, the interfering RNA (e.g., siRNA) is delivered in vitro (e.g., using a SNALP described herein), and the cells are reinjected into the patient.

In an additional aspect, the present invention provides lipid particles (e.g., SNALP) comprising asymmetrical interfering RNA (aiRNA) molecules that silence the expression of a target gene and methods of using such particles to silence target gene expression.

In one embodiment, the aiRNA molecule comprises a double-stranded (duplex) region of about 10 to about 25 (base paired) nucleotides in length, wherein the aiRNA molecule comprises an antisense strand comprising 5' and 3' overhangs, and wherein the aiRNA molecule is capable of silencing target gene expression.

In certain instances, the aiRNA molecule comprises a double-stranded (duplex) region of about 12-20, 12-19, 12-18, 13-17, or 14-17 (base paired) nucleotides in length, more typically 12, 13, 14, 15, 16, 17, 18, 19, or 20 (base paired) nucleotides in length. In certain other instances, the 5' and 3' overhangs on the antisense strand comprise sequences that are complementary to the target RNA sequence, and may optionally further comprise nontargeting sequences. In some embodiments, each of the 5' and 3' overhangs on the antisense strand comprises or consists of one, two, three, four, five, six, seven, or more nucleotides.

In other embodiments, the aiRNA molecule comprises modified nucleotides selected from the group consisting of 2'OMe nucleotides, 2'F nucleotides, 2'-deoxy nucleotides, 2'-O-MOE nucleotides, LNA nucleotides, and mixtures thereof. In a preferred embodiment, the aiRNA molecule comprises 2'OMe nucleotides. As a non-limiting example, the 2'OMe nucleotides may be selected from the group consisting of 2'OMe-guanosine nucleotides, 2'OMe-uridine nucleotides, and mixtures thereof.

In a related aspect, the present invention provides lipid particles (e.g., SNALP) comprising microRNA (miRNA) molecules that silence the expression of a target gene and methods of using such compositions to silence target gene expression.

In one embodiment, the miRNA molecule comprises about 15 to about 60 nucleotides in length, wherein the miRNA molecule is capable of silencing target gene expression.

In certain instances, the miRNA molecule comprises about 15-50, 15-40, or 15-30 nucleotides in length, more typically about 15-25 or 19-25 nucleotides in length, and are preferably about 20-24, 21-22, or 21-23 nucleotides in length. In a preferred embodiment, the miRNA molecule is a mature miRNA molecule targeting an RNA sequence of interest.

In some embodiments, the miRNA molecule comprises modified nucleotides selected from the group consisting of 2'OMe nucleotides, 2'F nucleotides, 2'-deoxy nucleotides, 2'-O-MOE nucleotides, LNA nucleotides, and mixtures thereof. In a preferred embodiment, the miRNA molecule comprises 2'OMe nucleotides. As a non-limiting example, the 2'OMe nucleotides may be selected from the group consisting of 2'OMe-guanosine nucleotides, 2'OMe-uridine nucleotides, and mixtures thereof.

As such, the lipid particles of the invention (e.g., SNALP) are advantageous and suitable for use in the administration of active agents or therapeutic agents such as nucleic acid (e.g., interfering RNA such as siRNA, aiRNA, and/or miRNA) to a subject (e.g., a mammal such as a human) because they are stable in circulation, of a size required for pharmacodynamic behavior resulting in access to extravascular sites, and are capable of reaching target cell populations.

IV. Active Agents

Active agents (e.g., therapeutic agents) include any molecule or compound capable of exerting a desired effect on a cell, tissue, organ, or subject. Such effects may be, e.g., biological, physiological, and/or cosmetic. Active agents may be any type of molecule or compound including, but not limited to, nucleic acids, peptides, polypeptides, small molecules, and mixtures thereof. Non-limiting examples of nucleic acids include interfering RNA molecules (e.g., dsRNA such as siRNA, Dicer-substrate dsRNA, shRNA, aiRNA, and/or miRNA), antisense oligonucleotides, plasmids, ribozymes, immunostimulatory oligonucleotides, and mixtures thereof. Examples of peptides or polypeptides include, without limitation, antibodies (e.g., polyclonal antibodies, monoclonal antibodies, antibody fragments; humanized antibodies, recombinant antibodies, recombinant human antibodies, and/or Primatized™ antibodies), cytokines, growth factors, apoptotic factors, differentiation-inducing factors, cell-surface receptors and their ligands, hormones, and mixtures thereof. Examples of small molecules include, but are not limited to, small organic molecules or compounds such as any conventional agent or drug known to those of skill in the art.

In some embodiments, the active agent is a therapeutic agent, or a salt or derivative thereof. Therapeutic agent derivatives may be therapeutically active themselves or they may be prodrugs, which become active upon further modification. Thus, in one embodiment, a therapeutic agent derivative retains some or all of the therapeutic activity as compared to the unmodified agent, while in another embodiment, a therapeutic agent derivative is a prodrug that lacks therapeutic activity, but becomes active upon further modification.

A. Nucleic Acids

In certain embodiments, lipid particles of the present invention are associated with a nucleic acid, resulting in a nucleic acid-lipid particle (e.g., SNALP). In some embodiments, the nucleic acid is fully encapsulated in the lipid particle. As used herein, the term "nucleic acid" includes any oligonucleotide or polynucleotide, with fragments containing up to 60 nucleotides generally termed oligonucleotides, and longer fragments termed polynucleotides. In particular embodiments, oligonucleotides of the invention are from about 15 to about 60 nucleotides in length. Nucleic acid may be administered alone in the lipid particles of the invention, or in combination (e.g., co-administered) with lipid particles of the invention comprising peptides, polypeptides, or small molecules such as conventional drugs. Similarly, when used to treat a cell proliferative disorder such as cancer, the nucleic acid, such as the interfering RNA molecule (e.g., siRNA), can be administered alone or co-administered (i.e., concurrently or consecutively) with conventional agents used to treat, e.g., a cell proliferative disorder such as cancer. Such agents include chemotherapy drugs as well as conventional hormonal, immunotherapeutic, and/or radiotherapeutic agents.

In the context of this invention, the terms "polynucleotide" and "oligonucleotide" refer to a polymer or oligomer of nucleotide or nucleoside monomers consisting of naturally-occurring bases, sugars and intersugar (backbone) linkages. The terms "polynucleotide" and "oligonucleotide" also include polymers or oligomers comprising non-naturally occurring monomers, or portions thereof, which function similarly. Such modified or substituted oligonucleotides are often preferred over native forms because of properties such as, for example, enhanced cellular uptake, reduced immunogenicity, and increased stability in the presence of nucleases.

Oligonucleotides are generally classified as deoxyribooligonucleotides or ribooligonucleotides. A deoxyribooligonucleotide consists of a 5-carbon sugar called deoxyribose joined covalently to phosphate at the 5' and 3' carbons of this sugar to form an alternating, unbranched polymer. A ribooligonucleotide consists of a similar repeating structure where the 5-carbon sugar is ribose.

The nucleic acid that is present in a nucleic acid-lipid particle according to this invention includes any form of nucleic acid that is known. The nucleic acids used herein can be single-stranded DNA or RNA, or double-stranded DNA or RNA, or DNA-RNA hybrids. In preferred embodiments, the nucleic acids are double-stranded RNA. Examples of double-stranded RNA are described herein and include, e.g., siRNA and other RNAi agents such as Dicer-substrate dsRNA, shRNA, aiRNA, and pre-miRNA. In other preferred embodiments, the nucleic acids are single-stranded nucleic acids. Single-stranded nucleic acids include, e.g., antisense oligonucleotides, ribozymes, mature miRNA, and triplex-forming oligonucleotides. In further embodiments, the nucleic acids are double-stranded DNA. Examples of double-stranded DNA include, e.g., DNA-DNA hybrids comprising a DNA sense strand and a DNA antisense strand as described in PCT Publication No. WO 2004/104199, the disclosure of which is herein incorporated by reference in its entirety for all purposes.

Nucleic acids of the invention may be of various lengths, generally dependent upon the particular form of nucleic acid. For example, in particular embodiments, plasmids or genes may be from about 1,000 to about 100,000 nucleotide residues in length. In particular embodiments, oligonucleotides may range from about 10 to about 100 nucleotides in length. In various related embodiments, oligonucleotides, both single-stranded, double-stranded, and triple-stranded, may range in length from about 10 to about 60 nucleotides, from about 15 to about 60 nucleotides, from about 20 to about 50 nucleotides, from about 15 to about 30 nucleotides, or from about 20 to about 30 nucleotides in length.

In particular embodiments, an oligonucleotide (or a strand thereof) of the invention specifically hybridizes to or is complementary to a target polynucleotide sequence. The terms "specifically hybridizable" and "complementary" as used herein indicate a sufficient degree of complementarity such that stable and specific binding occurs between the DNA or RNA target and the oligonucleotide. It is understood that an oligonucleotide need not be 100% complementary to its target nucleic acid sequence to be specifically hybridizable. In preferred embodiments, an oligonucleotide is specifically hybridizable when binding of the oligonucleotide to the target sequence interferes with the normal function of the target sequence to cause a loss of utility or expression there from, and there is a sufficient degree of complementarity to avoid non-specific binding of the oligonucleotide to non-target sequences under conditions in which specific binding is desired, i.e., under physiological conditions in the case of in vivo assays or therapeutic treatment, or, in the case of in vitro assays, under conditions in which the assays are conducted. Thus, the oligonucleotide may include 1, 2, 3, or more base substitutions as compared to the region of a gene or mRNA sequence that it is targeting or to which it specifically hybridizes.

1. siRNA

The siRNA component of the nucleic acid-lipid particles of the present invention is capable of silencing the expression of a target gene of interest, such as PLK-1. Each strand of the siRNA duplex is typically about 15 to about 60 nucleotides in length, preferably about 15 to about 30 nucleotides in length. In certain embodiments, the siRNA comprises at least one modified nucleotide. The modified siRNA is generally less immunostimulatory than a corresponding unmodified siRNA sequence and retains RNAi activity against the target gene of interest. In some embodiments, the modified siRNA contains at least one 2'OMe purine or pyrimidine nucleotide such as a 2'OMe-guanosine, 2'OMe-uridine, 2'OMe-adenosine, and/or 2'OMe-cytosine nucleotide. The modified nucleotides can be present in one strand (i.e., sense or antisense) or both strands of the siRNA. In some preferred embodiments, one or more of the uridine and/or guanosine nucleotides are modified (e.g., 2'OMe-modified) in one strand (i.e., sense or antisense) or both strands of the siRNA. In these embodiments, the modified siRNA can further comprise one or more modified (e.g., 2'OMe-modified) adenosine and/or modified (e.g., 2'OMe-modified) cytosine nucleotides. In other preferred embodiments, only uridine and/or guanosine nucleotides are modified (e.g., 2'OMe-modified) in one strand (i.e., sense or antisense) or both strands of the siRNA. The siRNA sequences may have overhangs (e.g., 3' or 5' overhangs as described in Elbashir et al., *Genes Dev.*, 15:188 (2001) or Nykanen et al., *Cell*, 107:309 (2001)), or may lack overhangs (i.e., have blunt ends).

In particular embodiments, the selective incorporation of modified nucleotides such as 2'OMe uridine and/or guanosine nucleotides into the double-stranded region of either or both strands of the siRNA reduces or completely abrogates the immune response to that siRNA molecule. In certain instances, the immunostimulatory properties of specific siRNA sequences and their ability to silence gene expression can be balanced or optimized by the introduction of minimal and selective 2'OMe modifications within the double-stranded region of the siRNA duplex. This can be achieved at therapeutically viable siRNA doses without cytokine induction, toxicity, and off-target effects associated with the use of unmodified siRNA.

The modified siRNA generally comprises from about 1% to about 100% (e.g., about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, or 100%) modified nucleotides in the double-stranded region of the siRNA duplex. In certain embodiments, one, two, three, four, five, six, seven, eight, nine, ten, or more of the nucleotides in the double-stranded region of the siRNA comprise modified nucleotides. In certain other embodiments, some or all of the modified nucleotides in the double-stranded region of the siRNA are 1, 2, 3, 4, 5, 6, 7, 8, 9, 10, or more nucleotides apart from each other. In one preferred embodiment, none of the modified nucleotides in the double-stranded region of the siRNA are adjacent to each other (e.g., there is a gap of at least 1, 2, 3, 4, 5, 6, 7, 8, 9, or 10 unmodified nucleotides between each modified nucleotide). In another preferred embodiment, at least two of the modified nucleotides in the double-stranded region of the siRNA are adjacent to each other (e.g., there are no unmodified nucleotides between two or more modified nucleotides). In other preferred embodiments, at least three, at least four, or at least five of the modified nucleotides in the double-stranded region of the siRNA are adjacent to each other.

In some embodiments, less than about 50% (e.g., less than about 49%, 48%, 47%, 46%, 45%, 44%, 43%, 42%, 41%, 40%, 39%, 38%, 37%, or 36%, preferably less than about 35%, 34%, 33%, 32%, 31%, or 30%) of the nucleotides in the double-stranded region of the siRNA comprise modified (e.g., 2'OMe) nucleotides. In one aspect of these embodiments, less than about 50% of the uridine and/or guanosine nucleotides in the double-stranded region of one or both strands of the siRNA are selectively (e.g., only) modified. In another aspect of these embodiments, less than about 50% of the nucleotides in the double-stranded region of the siRNA comprise 2'OMe nucleotides, wherein the siRNA comprises 2'OMe nucleotides in both strands of the siRNA, wherein the siRNA comprises at least one 2'OMe-guanosine nucleotide and at least one 2'OMe-uridine nucleotide, and wherein 2'OMe-guanosine nucleotides and 2'OMe-uridine nucleotides are the only 2'OMe nucleotides present in the double-stranded region. In yet another aspect of these embodiments, less than about 50% of the nucleotides in the double-stranded region of the siRNA comprise 2'OMe nucleotides, wherein the siRNA comprises 2'OMe nucleotides in both strands of the modified siRNA, wherein the siRNA comprises 2'OMe nucleotides selected from the group consisting of 2'OMe-guanosine nucleotides, 2'OMe-uridine nucleotides, 2'OMe-adenosine nucleotides, and mixtures thereof, and wherein the siRNA does not comprise 2'OMe-cytosine nucleotides in the double-stranded region. In a further aspect of these embodiments, less than about 50% of the nucleotides in the double-stranded region of the siRNA comprise 2'OMe nucleotides, wherein the siRNA comprises 2'OMe nucleotides in both strands of the siRNA, wherein the siRNA comprises at least one 2'OMe-guanosine nucleotide and at least one 2'OMe-uridine nucleotide, and wherein the siRNA does not comprise 2'OMe-cytosine nucleotides in the double-stranded region. In another aspect of these embodiments, less than about 50% of the nucleotides in the double-stranded region of the siRNA comprise 2'OMe nucleotides, wherein the siRNA comprises 2'OMe nucleotides in both strands of the modified siRNA, wherein the siRNA comprises 2'OMe nucleotides selected from the group consisting of 2'OMe-guanosine nucleotides, 2'OMe-uridine nucleotides, 2'OMe-adenosine nucleotides, and mixtures thereof, and wherein the 2'OMe nucleotides in the double-stranded region are not adjacent to each other.

In other embodiments, from about 1% to about 50% (e.g., from about 5%-50%, 10%-50%, 15%-50%, 20%-50%, 25%-50%, 30%-50%, 35%-50%, 40%-50%, 45%-50%, 5%-45%, 10%-45%, 15%-45%, 20%-45%, 25%-45%, 30%-45%, 35%-45%, 40%-45%, 5%-40%, 10%-40%, 15%-40%, 20%-40%, 25%-40%, 25%-39%, 25%-38%, 25%-37%, 25%-36%, 26%-39%, 26%-38%, 26%-37%, 26%-36%, 27%-39%, 27%-38%, 27%-37%, 27%-36%, 28%-39%, 28%-38%, 28%-37%, 28%-36%, 29%-39%, 29%-38%, 29%-37%, 29%-36%, 30%-40%, 30%-39%, 30%-38%, 30%-37%, 30%-36%, 31%-39%, 31%-38%, 31%-37%, 31%-36%, 32%-39%, 32%-38%, 32%-37%, 32%-36%, 33%-39%, 33%-38%, 33%-37%, 33%-36%, 34%-39%, 34%-38%, 34%-37%, 34%-36%, 35%-40%, 5%-35%, 10%-35%, 15%-35%, 20%-35%, 21%-35%, 22%-35%, 23%-35%, 24%-35%, 25%-35%, 26%-35%, 27%-35%, 28%-35%, 29%-35%, 30%-35%, 31%-35%, 32%-35%, 33%-35%, 34%-35%, 30%-34%, 31%-34%, 32%-34%, 33%-34%, 30%-33%, 31%-33%, 32%-33%, 30%-32%, 31%-32%, 25%-34%, 25%-33%, 25%-32%, 25%-31%, 26%-34%, 26%-33%, 26%-32%, 26%-31%, 27%-34%, 27%-33%, 27%-32%, 27%-31%, 28%-34%, 28%-33%, 28%-32%, 28%-31%, 29%-34%, 29%-33%, 29%-32%, 29%-31%, 5%-30%, 10%-30%, 15%-30%, 20%-34%, 20%-33%, 20%-32%, 20%-31%, 20%-30%, 21%-30%, 22%-30%, 23%-30%, 24%-30%, 25%-30%, 25%-29%, 25%-28%, 25%-27%, 25%-26%, 26%-30%, 26%-29%, 26%-28%, 26%-27%, 27%-30%, 27%-29%, 27%-28%, 28%-30%, 28%-29%, 29%-30%, 5%-25%, 10%-25%, 15%-25%, 20%-29%, 20%-28%, 20%-27%, 20%-26%, 20%-25%, 5%-20%, 10%-20%, 15%-20%, 5%-15%, 10%-15%, or 5%-10%) of the nucleotides in the double-stranded region of the siRNA comprise modified nucleotides. In one aspect of these embodiments, from about 1% to about 50% of the uridine and/or guanosine nucleotides in the double-stranded region of one or both strands of the siRNA are selectively (e.g., only) modified. In another aspect of these embodiments, from about 1% to about 50% of the nucleotides in the double-stranded region of the siRNA comprise 2'OMe nucleotides, wherein the siRNA comprises 2'OMe nucleotides in both strands of the siRNA, wherein the siRNA comprises at least one 2'OMe-guanosine nucleotide and at least one 2'OMe-uridine nucleotide, and wherein 2'OMe-guanosine nucleotides and 2'OMe-uridine nucleotides are the only 2'OMe nucleotides present in the double-stranded region. In yet another aspect of these embodiments, from about 1% to about 50% of the nucleotides in the double-stranded region of the siRNA comprise 2'OMe nucleotides, wherein the siRNA comprises 2'OMe nucleotides in both strands of the modified siRNA, wherein the siRNA comprises 2'OMe nucleotides selected from the group consisting of 2'OMe-guanosine nucleotides, 2'OMe-uridine nucleotides, 2'OMe-adenosine nucleotides, and mixtures thereof, and wherein the siRNA does not comprise 2'OMe-cytosine nucleotides in the double-stranded region. In a further aspect of these embodiments, from about 1% to about 50% of the nucleotides in the double-stranded region of the siRNA comprise 2'OMe nucleotides, wherein the siRNA comprises 2'OMe nucleotides in both strands of the siRNA, wherein the siRNA comprises at least one 2'OMe-guanosine nucleotide and at least one 2'OMe-uridine nucleotide, and wherein the siRNA does not comprise 2'OMe-cytosine nucleotides in the double-stranded region. In another aspect of these embodiments, from about 1% to about 50% of the nucleotides in the double-stranded region of the siRNA comprise 2'OMe nucleotides, wherein the siRNA comprises 2'OMe nucleotides in both strands of the modified siRNA, wherein the siRNA comprises 2'OMe nucleotides selected from the group consisting of 2'OMe-guanosine nucleotides, 2'OMe-uridine nucleotides, 2'OMe-adenosine nucleotides, and mixtures thereof, and wherein the 2'OMe nucleotides in the double-stranded region are not adjacent to each other.

In certain embodiments, the siRNA component of the nucleic acid-lipid particles of the present invention (e.g., SNALP) comprises an asymmetric siRNA duplex as described in PCT Publication No. WO 2004/078941, which comprises a double-stranded region consisting of a DNA sense strand and an RNA antisense strand (e.g., a DNA-RNA hybrid), wherein a blocking agent is located on the siRNA duplex. In some instances, the asymmetric siRNA duplex can be chemically modified as described herein. Other non-limiting examples of asymmetric siRNA duplexes are described in PCT Publication No. WO 2006/074108, which discloses self-protected oligonucleotides comprising a region having a sequence complementary to one, two, three, or more same or different target mRNA sequences (e.g., multivalent siRNAs) and one or more self-complementary regions. Yet other non-limiting examples of asymmetric siRNA duplexes are described in PCT Publication No. WO 2009/076321, which discloses self-forming asymmetric precursor polynucleotides comprising a targeting region comprising a polynucleotide sequence complementary to a region of one, two, three, or more same or different target mRNA sequences (e.g., multivalent siRNAs); a first self-complementary region; and a second self-complementary region, wherein the first and second self-complementary regions are located one at each end of the targeting region and both self-complementary regions form stem-loop structures, wherein the first self-complementary region is capable of being cleaved by a RNase III endoribonuclease that is not a class IV DICER endoribonuclease, and wherein both self-complementary regions comprise a nucleotide sequence that is complementary to a region of the target gene sequence, but wherein a portion of the target sequence present in the targeting region does not have a complementary sequence in either of the self-complementary regions. The disclosures of each of the above patent documents are herein incorporated by reference in their entirety for all purposes.

Additional ranges, percentages, and patterns of modifications that may be introduced into siRNA are described in U.S. Patent Publication No. 20070135372, the disclosure of which is herein incorporated by reference in its entirety for all purposes.

a) Selection of siRNA Sequences

Suitable siRNA sequences can be identified using any means known in the art. Typically, the methods described in Elbashir et al., *Nature,* 411:494-498 (2001) and Elbashir et al., *EMBO J,* 20:6877-6888 (2001) are combined with rational design rules set forth in Reynolds et al., *Nature Biotech.,* 22(3):326-330 (2004).

As a non-limiting example, the nucleotide sequence 3' of the AUG start codon of a transcript from the target gene of interest may be scanned for dinucleotide sequences (e.g., AA, NA, CC, GG, or UU, wherein N=C, G, or U) (see, e.g., Elbashir et al., *EMBO J.,* 20:6877-6888 (2001)). The nucleotides immediately 3' to the dinucleotide sequences are identified as potential siRNA sequences (i.e., a target sequence or a sense strand sequence). Typically, the 19, 21, 23, 25, 27, 29, 31, 33, 35, or more nucleotides immediately 3' to the dinucleotide sequences are identified as potential siRNA sequences. In some embodiments, the dinucleotide sequence is an AA or NA sequence and the 19 nucleotides immediately 3' to the AA or NA dinucleotide are identified as potential siRNA sequences. siRNA sequences are usually spaced at different positions along the length of the target gene. To further enhance silencing efficiency of the siRNA sequences, potential siRNA sequences may be analyzed to identify sites that do not contain regions of homology to other coding sequences, e.g., in the target cell or organism. For example, a suitable siRNA sequence of about 21 base pairs typically will not have more than 16-17 contiguous base pairs of homology to coding sequences in the target cell or organism. If the siRNA sequences are to be expressed from an RNA Pol III promoter, siRNA sequences lacking more than 4 contiguous A's or T's are selected.

Once a potential siRNA sequence has been identified, a complementary sequence (i.e., an antisense strand sequence) can be designed. A potential siRNA sequence can also be analyzed using a variety of criteria known in the art. For example, to enhance their silencing efficiency, the siRNA sequences may be analyzed by a rational design algorithm to identify sequences that have one or more of the following features: (1) G/C content of about 25% to about 60% G/C; (2) at least 3 A/Us at positions 15-19 of the sense strand; (3) no internal repeats; (4) an A at position 19 of the sense strand; (5) an A at position 3 of the sense strand; (6) a U at position 10 of the sense strand; (7) no G/C at position 19 of the sense strand; and (8) no G at position 13 of the sense strand. siRNA design tools that incorporate algorithms that assign suitable values of each of these features and are useful for selection of siRNA can be found at, e.g., http://ihome.ust.hk/~bokcmho/siRNA/siRNA.html. One of skill in the art will appreciate that sequences with one or more of the foregoing characteristics may be selected for further analysis and testing as potential siRNA sequences.

Additionally, potential siRNA sequences with one or more of the following criteria can often be eliminated as siRNA: (1) sequences comprising a stretch of 4 or more of the same base in a row; (2) sequences comprising homopolymers of Gs (i.e., to reduce possible non-specific effects due to structural characteristics of these polymers; (3) sequences comprising triple base motifs (e.g., GGG, CCC, AAA, or TTT); (4) sequences comprising stretches of 7 or more G/Cs in a row; and (5) sequences comprising direct repeats of 4 or more bases within the candidates resulting in internal foldback structures. However, one of skill in the art will appreciate that sequences with one or more of the foregoing characteristics may still be selected for further analysis and testing as potential siRNA sequences.

In some embodiments, potential siRNA sequences may be further analyzed based on siRNA duplex asymmetry as described in, e.g., Khvorova et al., Cell, 115:209-216 (2003); and Schwarz et al., Cell, 115:199-208 (2003). In other embodiments, potential siRNA sequences may be further analyzed based on secondary structure at the target site as described in, e.g., Luo et al., Biophys. Res. Commun., 318:303-310 (2004). For example, secondary structure at the target site can be modeled using the Mfold algorithm (available at http://mfold.burnet.edu.au/rna_form) to select siRNA sequences which favor accessibility at the target site where less secondary structure in the form of base-pairing and stem-loops is present.

Once a potential siRNA sequence has been identified, the sequence can be analyzed for the presence of any immunostimulatory properties, e.g., using an in vitro cytokine assay or an in vivo animal model. Motifs in the sense and/or antisense strand of the siRNA sequence such as GU-rich motifs (e.g., 5'-GU-3', 5'-UGU-3', 5'-GUGU-3', 5'-UGUGU-3', etc.) can also provide an indication of whether the sequence may be immunostimulatory. Once an siRNA molecule is found to be immunostimulatory, it can then be modified to decrease its immunostimulatory properties as described herein. As a non-limiting example, an siRNA sequence can be contacted with a mammalian responder cell under conditions such that the cell produces a detectable immune response to determine whether the siRNA is an immunostimulatory or a non-immunostimulatory siRNA. The mammalian responder cell may be from a naïve mammal (i.e., a mammal that has not previously been in contact with the gene product of the siRNA sequence). The mammalian responder cell may be, e.g., a peripheral blood mononuclear cell (PBMC), a macrophage, and the like. The detectable immune response may comprise production of a cytokine or growth factor such as, e.g., TNF-α, IFN-α, IFN-β, IFN-γ, IL-6, IL-8, IL-12, or a combination thereof. An siRNA identified as being immunostimulatory can then be modified to decrease its immunostimulatory properties by replacing at least one of the nucleotides on the sense and/or antisense strand with modified nucleotides. For example, less than about 30% (e.g., less than about 30%, 25%, 20%, 15%, 10%, or 5%) of the nucleotides in the double-stranded region of the siRNA duplex can be replaced with modified nucleotides such as 2'OMe nucleotides. The modified siRNA can then be contacted with a mammalian responder cell as described above to confirm that its immunostimulatory properties have been reduced or abrogated.

Suitable in vitro assays for detecting an immune response include, but are not limited to, the double monoclonal antibody sandwich immunoassay technique of David et al. (U.S. Pat. No. 4,376,110); monoclonal-polyclonal antibody sandwich assays (Wide et al., in Kirkham and Hunter, eds., Radioimmunoassay Methods, E. and S. Livingstone, Edinburgh (1970)); the "Western blot" method of Gordon et al. (U.S. Pat. No. 4,452,901); immunoprecipitation of labeled ligand (Brown et al., J. Biol. Chem., 255:4980-4983 (1980)); enzyme-linked immunosorbent assays (ELISA) as described, for example, by Raines et al., J. Biol. Chem., 257:5154-5160 (1982); immunocytochemical techniques, including the use of fluorochromes (Brooks et al., Clin. Exp. Immunol., 39:477 (1980)); and neutralization of activity (Bowen-Pope et al., Proc. Natl. Acad. Sci. USA, 81:2396-2400 (1984)). In addition to the immunoassays described above, a number of other immunoassays are available, including those described in U.S. Pat. Nos. 3,817,827; 3,850,752; 3,901,654; 3,935,074; 3,984,533; 3,996,345; 4,034,074; and 4,098,876. The disclosures of these references are herein incorporated by reference in their entirety for all purposes.

A non-limiting example of an in vivo model for detecting an immune response includes an in vivo mouse cytokine induction assay as described in, e.g., Judge et al., Mol. Ther., 13:494-505 (2006). In certain embodiments, the assay that can be performed as follows: (1) siRNA can be administered by standard intravenous injection in the lateral tail vein; (2) blood can be collected by cardiac puncture about 6 hours after administration and processed as plasma for cytokine analysis; and (3) cytokines can be quantified using sandwich ELISA kits according to the manufacturer's instructions (e.g., mouse and human IFN-α (PBL Biomedical; Piscataway, NJ); human IL-6 and TNF-α (eBioscience; San Diego, CA); and mouse IL-6, TNF-α, and IFN-γ (BD Biosciences; San Diego, CA)).

Monoclonal antibodies that specifically bind cytokines and growth factors are commercially available from multiple sources and can be generated using methods known in the art (see, e.g., Kohler et al., Nature, 256: 495-497 (1975) and Harlow and Lane, ANTIBODIES, A LABORATORY MANUAL, Cold Spring Harbor Publication, New York (1999)). Generation of monoclonal antibodies has been previously described and can be accomplished by any means known in the art (Buhring et al., in Hybridoma, Vol. 10, No. 1, pp. 77-78 (1991)). In some methods, the monoclonal antibody is labeled (e.g., with any composition detectable by spectroscopic, photochemical, biochemical, electrical, optical, or chemical means) to facilitate detection.

b) Generating siRNA Molecules siRNA can be provided in several forms including, e.g., as one or more isolated small-interfering RNA (siRNA) duplexes, as longer double-stranded RNA (dsRNA), or as siRNA or dsRNA transcribed from a transcriptional cassette in a DNA plasmid. In some embodiments, siRNA may be produced enzymatically or by partial/total organic synthesis, and modified ribonucleotides can be introduced by in vitro enzymatic or organic synthesis. In certain instances, each strand is prepared chemically. Methods of synthesizing RNA molecules are known in the art, e.g., the chemical synthesis methods as described in Verma and Eckstein (1998) or as described herein.

An RNA population can be used to provide long precursor RNAs, or long precursor RNAs that have substantial or complete identity to a selected target sequence can be used to make the siRNA. The RNAs can be isolated from cells or tissue, synthesized, and/or cloned according to methods well known to those of skill in the art. The RNA can be a mixed population (obtained from cells or tissue, transcribed from cDNA, subtracted, selected, etc.), or can represent a single target sequence. RNA can be naturally occurring (e.g., isolated from tissue or cell samples), synthesized in vitro (e.g., using T7 or SP6 polymerase and PCR products or a cloned cDNA), or chemically synthesized.

To form a long dsRNA, for synthetic RNAs, the complement is also transcribed in vitro and hybridized to form a dsRNA. If a naturally occurring RNA population is used, the RNA complements are also provided (e.g., to form dsRNA for digestion by *E. coli* RNAse III or Dicer), e.g., by transcribing cDNAs corresponding to the RNA population, or by using RNA polymerases. The precursor RNAs are then hybridized to form double stranded RNAs for digestion. The dsRNAs can be directly administered to a subject or can be digested in vitro prior to administration.

Methods for isolating RNA, synthesizing RNA, hybridizing nucleic acids, making and screening cDNA libraries, and performing PCR are well known in the art (see, e.g., Gubler and Hoffman, Gene, 25:263-269 (1983); Sambrook et al., supra; Ausubel et al., supra), as are PCR methods (see, U.S. Pat. Nos. 4,683,195 and 4,683,202; *PCR Protocols: A Guide to Methods and Applications* (Innis et al., eds, 1990)). Expression libraries are also well known to those of skill in the art. Additional basic texts disclosing the general methods of use in this invention include Sambrook et al., *Molecular Cloning, A Laboratory Manual* (2nd ed. 1989); Kriegler, Gene *Transfer and Expression: A Laboratory Manual* (1990); and *Current Protocols in Molecular Biology* (Ausubel et al., eds., 1994). The disclosures of these references are herein incorporated by reference in their entirety for all purposes.

Preferably, siRNA are chemically synthesized. The oligonucleotides that comprise the siRNA molecules of the invention can be synthesized using any of a variety of techniques known in the art, such as those described in Usman et al., *J. Am. Chem. Soc.*, 109:7845 (1987); Scaringe et al., *Nucl. Acids Res.*, 18:5433 (1990); Wincott et al., *Nucl. Acids Res.*, 23:2677-2684 (1995); and Wincott et al., *Methods Mol. Bio.*, 74:59 (1997). The synthesis of oligonucleotides makes use of common nucleic acid protecting and coupling groups, such as dimethoxytrityl at the 5'-end and phosphoramidites at the 3'-end. As a non-limiting example, small scale syntheses can be conducted on an Applied Biosystems synthesizer using a 0.2 μmol scale protocol. Alternatively, syntheses at the 0.2 μmol scale can be performed on a 96-well plate synthesizer from Protogene (Palo Alto, CA). However, a larger or smaller scale of synthesis is also within the scope of this invention. Suitable reagents for oligonucleotide synthesis, methods for RNA deprotection, and methods for RNA purification are known to those of skill in the art.

siRNA molecules can also be synthesized via a tandem synthesis technique, wherein both strands are synthesized as a single continuous oligonucleotide fragment or strand separated by a cleavable linker that is subsequently cleaved to provide separate fragments or strands that hybridize to form the siRNA duplex. The linker can be a polynucleotide linker or a non-nucleotide linker. The tandem synthesis of siRNA can be readily adapted to both multiwell/multiplate synthesis platforms as well as large scale synthesis platforms employing batch reactors, synthesis columns, and the like. Alternatively, siRNA molecules can be assembled from two distinct oligonucleotides, wherein one oligonucleotide comprises the sense strand and the other comprises the antisense strand of the siRNA. For example, each strand can be synthesized separately and joined together by hybridization or ligation following synthesis and/or deprotection. In certain other instances, siRNA molecules can be synthesized as a single continuous oligonucleotide fragment, where the self-complementary sense and antisense regions hybridize to form an siRNA duplex having hairpin secondary structure.

c) Modifying siRNA Sequences

In certain aspects, siRNA molecules comprise a duplex having two strands and at least one modified nucleotide in the double-stranded region, wherein each strand is about 15 to about 60 nucleotides in length. Advantageously, the modified siRNA is less immunostimulatory than a corresponding unmodified siRNA sequence, but retains the capability of silencing the expression of a target sequence. In preferred embodiments, the degree of chemical modifications introduced into the siRNA strikes a balance between reduction or abrogation of the immunostimulatory properties of the siRNA and retention of RNAi activity. As a non-limiting example, an siRNA molecule that targets a gene of interest can be minimally modified (e.g., less than about 30%, 25%, 20%, 15%, 10%, or 5% modified) at selective uridine and/or guanosine nucleotides within the siRNA duplex to eliminate the immune response generated by the siRNA while retaining its capability to silence target gene expression.

Examples of modified nucleotides suitable for use in the invention include, but are not limited to, ribonucleotides having a 2'-O-methyl (2'OMe), 2'-deoxy-2'-fluoro (2'F), 2'-deoxy, 5-C-methyl, 2'-O-(2-methoxyethyl) (MOE), 4'-thio, 2'-amino, or 2'-C-allyl group. Modified nucleotides having a Northern conformation such as those described in, e.g., Saenger, *Principles of Nucleic Acid Structure*, Springer-Verlag Ed. (1984), are also suitable for use in siRNA molecules. Such modified nucleotides include, without limitation, locked nucleic acid (LNA) nucleotides (e.g., 2'-O, 4'-C-methylene-(D-ribofuranosyl) nucleotides), 2'-O-(2-methoxyethyl) (MOE) nucleotides, 2'-methyl-thio-ethyl nucleotides, 2'-deoxy-2'-fluoro (2'F) nucleotides, 2'-deoxy-2'-chloro (2'Cl) nucleotides, and 2'-azido nucleotides. In certain instances, the siRNA molecules described herein include one or more G-clamp nucleotides. A G-clamp nucleotide refers to a modified cytosine analog wherein the modifications confer the ability to hydrogen bond both Watson-Crick and Hoogsteen faces of a complementary guanine nucleotide within a duplex (see, e.g., Lin et al., *J. Am. Chem. Soc.*, 120:8531-8532 (1998)). In addition, nucleotides having a nucleotide base analog such as, for example, C-phenyl, C-naphthyl, other aromatic derivatives, inosine, azole carboxamides, and nitroazole derivatives such as 3-nitropyrrole, 4-nitroindole, 5-nitroindole, and 6-nitroindole (see, e.g., Loakes, *Nucl. Acids Res.*, 29:2437-2447 (2001)) can be incorporated into siRNA molecules.

In certain embodiments, siRNA molecules may further comprise one or more chemical modifications such as terminal cap moieties, phosphate backbone modifications, and the like. Examples of terminal cap moieties include, without limitation, inverted deoxy abasic residues, glyceryl modifications, 4',5'-methylene nucleotides, 1-(β-D-erythrofuranosyl) nucleotides, 4'-thio nucleotides, carbocyclic nucleotides, 1,5-anhydrohexitol nucleotides, L-nucleotides, α-nucleotides, modified base nucleotides, threo-pentofuranosyl nucleotides, acyclic 3',4'-seco nucleotides, acyclic 3,4-dihydroxybutyl nucleotides, acyclic 3,5-dihydroxypentyl nucleotides, 3'-3'-inverted nucleotide moieties, 3'-3'-inverted abasic moieties, 3'-2'-inverted nucleotide moieties, 3'-2'-inverted abasic moieties, 5'-5'-inverted nucleotide moieties, 5'-5'-inverted abasic moieties, 3'-5'-inverted deoxy abasic moieties, 5'-amino-alkyl phosphate, 1,3-diamino-2-propyl phosphate, 3-aminopropyl phosphate, 6-aminohexyl phosphate, 1,2-aminododecyl phosphate, hydroxypropyl phosphate, 1,4-butanediol phosphate, 3'-phosphoramidate, 5'-phosphoramidate, hexylphosphate, aminohexyl phosphate, 3'-phosphate, 5'-amino, 3'-phosphorothioate, 5'-phosphorothioate, phosphorodithioate, and bridging or non-bridging methylphosphonate or 5'-mercapto moieties (see, e.g., U.S. Pat. No. 5,998,203; Beaucage et al., *Tetrahedron*

49:1925 (1993)). Non-limiting examples of phosphate backbone modifications (i.e., resulting in modified internucleotide linkages) include phosphorothioate, phosphorodithioate, methylphosphonate, phosphotriester, morpholino, amidate, carbamate, carboxymethyl, acetamidate, polyamide, sulfonate, sulfonamide, sulfamate, formacetal, thioformacetal, and alkylsilyl substitutions (see, e.g., Hunziker et al., *Nucleic Acid Analogues: Synthesis and Properties*, in *Modern Synthetic Methods, VCH*, 331-417 (1995); Mesmaeker et al., *Novel Backbone Replacements for Oligonucleotides*, in *Carbohydrate Modifications in Antisense Research*, ACS, 24-39 (1994)). Such chemical modifications can occur at the 5'-end and/or 3'-end of the sense strand, antisense strand, or both strands of the siRNA. The disclosures of these references are herein incorporated by reference in their entirety for all purposes.

In some embodiments, the sense and/or antisense strand of the siRNA molecule can further comprise a 3'-terminal overhang having about 1 to about 4 (e.g., 1, 2, 3, or 4) 2'-deoxy ribonucleotides, modified (e.g., 2'OMe) and/or unmodified uridine ribonucleotides, and/or any other combination of modified (e.g., 2'OMe) and unmodified nucleotides.

Additional examples of modified nucleotides and types of chemical modifications that can be introduced into siRNA molecules are described, e.g., in UK Patent No. GB 2,397,818 B and U.S. Patent Publication Nos. 20040192626, 20050282188, and 20070135372, the disclosures of which are herein incorporated by reference in their entirety for all purposes.

The siRNA molecules described herein can optionally comprise one or more non-nucleotides in one or both strands of the siRNA. As used herein, the term "non-nucleotide" refers to any group or compound that can be incorporated into a nucleic acid chain in the place of one or more nucleotide units, including sugar and/or phosphate substitutions, and allows the remaining bases to exhibit their activity. The group or compound is abasic in that it does not contain a commonly recognized nucleotide base such as adenosine, guanine, cytosine, uracil, or thymine and therefore lacks a base at the 1'-position.

In other embodiments, chemical modification of the siRNA comprises attaching a conjugate to the siRNA molecule. The conjugate can be attached at the 5' and/or 3'-end of the sense and/or antisense strand of the siRNA via a covalent attachment such as, e.g., a biodegradable linker. The conjugate can also be attached to the siRNA, e.g., through a carbamate group or other linking group (see, e.g., U.S. Patent Publication Nos. 20050074771, 20050043219, and 20050158727). In certain instances, the conjugate is a molecule that facilitates the delivery of the siRNA into a cell. Examples of conjugate molecules suitable for attachment to siRNA include, without limitation, steroids such as cholesterol, glycols such as polyethylene glycol (PEG), human serum albumin (HSA), fatty acids, carotenoids, terpenes, bile acids, folates (e.g., folic acid, folate analogs and derivatives thereof), sugars (e.g., galactose, galactosamine, N-acetyl galactosamine, glucose, mannose, fructose, fucose, etc.), phospholipids, peptides, ligands for cellular receptors capable of mediating cellular uptake, and combinations thereof (see, e.g., U.S. Patent Publication Nos. 20030130186, 20040110296, and 20040249178; U.S. Pat. No. 6,753,423). Other examples include the lipophilic moiety, vitamin, polymer, peptide, protein, nucleic acid, small molecule, oligosaccharide, carbohydrate cluster, intercalator, minor groove binder, cleaving agent, and cross-linking agent conjugate molecules described in U.S. Patent Publication Nos. 20050119470 and 20050107325. Yet other examples include the 2'-O-alkyl amine, 2'-O-alkoxyalkyl amine, polyamine, C5-cationic modified pyrimidine, cationic peptide, guanidinium group, amidininium group, cationic amino acid conjugate molecules described in U.S. Patent Publication No. 20050153337. Additional examples include the hydrophobic group, membrane active compound, cell penetrating compound, cell targeting signal, interaction modifier, and steric stabilizer conjugate molecules described in U.S. Patent Publication No. 20040167090. Further examples include the conjugate molecules described in U.S. Patent Publication No. 20050239739. The type of conjugate used and the extent of conjugation to the siRNA molecule can be evaluated for improved pharmacokinetic profiles, bioavailability, and/or stability of the siRNA while retaining RNAi activity. As such, one skilled in the art can screen siRNA molecules having various conjugates attached thereto to identify ones having improved properties and full RNAi activity using any of a variety of well-known in vitro cell culture or in vivo animal models. The disclosures of the above-described patent documents are herein incorporated by reference in their entirety for all purposes.

d) Target Genes

The siRNA component of the nucleic acid-lipid particles of the present invention (e.g., SNALP) can be used to downregulate or silence the translation (i.e., expression) of a gene of interest. As previously mentioned, it has been unexpectedly found that the nucleic acid-lipid particles of the present invention (i.e., SNALP formulations) containing at least one siRNA as disclosed herein show increased potency (i.e., increased silencing) and/or increased tolerability (e.g., decreased toxicity) when targeting a gene of interest in a tumor cell, when compared to other nucleic acid-lipid particle compositions previously described. In preferred embodiments, the siRNA silences the expression of a gene associated with cell proliferation, tumorigenesis, and/or cell transformation (e.g., a cell proliferative disorder such as cancer). Other genes of interest include, but are not limited to, angiogenic genes, receptor ligand genes, immunomodulator genes (e.g., those associated with inflammatory and autoimmune responses), genes associated with metabolic diseases and disorders (e.g., liver diseases and disorders), genes associated with viral infection and survival, and genes associated with neurodegenerative disorders.

Genes associated with tumorigenesis or cell transformation (e.g., cancer or other neoplasia) include, for example, genes involved in p53 ubiquitination, c-Jun ubiquitination, histone deacetylation, cell cycle regulation, transcriptional regulation, and combinations thereof. Non-limiting examples of gene sequences associated with tumorigenesis or cell transformation include serine/threonine kinases such as polo-like kinase 1 (PLK-1) (Genbank Accession No. NM_005030; Barr et al., *Nat. Rev. Mol. Cell Biol.*, 5:429-440 (2004)) and cyclin-dependent kinase 4 (CDK4) (Genbank Accession No. NM_000075); ubiquitin ligases such as COP1 (RFWD2; Genbank Accession Nos. NM_022457 and NM_001001740) and ring-box 1 (RBX1) (ROC1; Genbank Accession No. NM_014248); tyrosine kinases such as WEE1 (Genbank Accession Nos. NM_003390 and NM_001143976); mitotic kinesins such as Eg5 (KSP, KIF11; Genbank Accession No. NM_004523); transcription factors such as forkhead box M1 (FOXM1) (Genbank Accession Nos. NM_202002, NM_021953, and NM_202003) and RAM2 (R1 or CDCA7L; Genbank Accession Nos. NM_018719, NM_001127370, and NM_001127371); inhibitors of apoptosis such as XIAP (Genbank Accession No. NM_001167); COP9 signalosome subunits such as CSN1, CSN2, CSN3, CSN4, CSN5 (JAB1; Genbank Accession No. NM_006837); CSN6, CSN7A, CSN7B, and CSN8; and histone deacetylases such as HDAC1, HDAC2 (Genbank Accession No. NM_001527), HDAC3, HDAC4, HDAC5, HDAC6, HDAC7, HDAC8, HDAC9, etc.

Non-limiting examples of siRNA molecules targeting the PLK-1 gene include those described herein and in U.S. Patent Publication Nos. 20050107316 and 20070265438; and PCT Publication No. WO 09/082817, the disclosures of which are herein incorporated by reference in their entirety for all purposes. Non-limiting examples of siRNA molecules targeting the Eg5 and XIAP genes include those described in U.S. Patent Publication No. 20090149403, the disclosure of which is herein incorporated by reference in its entirety for all purposes. Non-limiting examples of siRNA molecules targeting the CSN5 gene include those described in PCT Publication No. WO 09/129319, the disclosure of which is herein incorporated by reference in its entirety for all purposes. Non-limiting examples of siRNA molecules targeting the COP1, CSN5, RBX1, HDAC2, CDK4, WEE1, FOXM1, and RAM2 genes include those described in U.S. Provisional Application No. 61/245,143, filed Sep. 23, 2009, the disclosure of which is herein incorporated by reference in its entirety for all purposes.

Additional examples of gene sequences associated with tumorigenesis or cell transformation include translocation sequences such as MLL fusion genes, BCR-ABL (Wilda et al., *Oncogene*, 21:5716 (2002); Scherr et al., *Blood*, 101: 1566 (2003)), TEL-AML1, EWS-FLI1, TLS-FUS, PAX3-FKHR, BCL-2, AML1-ETO, and AML1-MTG8 (Heidenreich et al., *Blood*, 101:3157 (2003)); overexpressed sequences such as multidrug resistance genes (Nieth et al., *FEBS Lett.*, 545:144 (2003); Wu et al, *Cancer Res.* 63:1515 (2003)), cyclins (Li et al., *Cancer Res.*, 63:3593 (2003); Zou et al., *Genes Dev.*, 16:2923 (2002)), beta-catenin (Verma et al., *Clin Cancer Res.*, 9:1291 (2003)), telomerase genes (Kosciolek et al., *Mol Cancer Ther.*, 2:209 (2003)), c-MYC, N-MYC, BCL-2, growth factor receptors (e.g., EGFR/ErbB1 (Genbank Accession Nos. NM_005228, NM_201282, NM_201283, and NM_201284; see also, Nagy et al. *Exp. Cell Res.*, 285:39-49 (2003)), ErbB2/HER-2 (Genbank Accession Nos. NM_004448 and NM_001005862), ErbB3 (Genbank Accession Nos. NM_001982 and NM_001005915), and ErbB4 (Genbank Accession Nos. NM_005235 and NM_001042599)), and mutated sequences such as RAS (Tuschl and Borkhardt, *Mol. Interventions*, 2:158 (2002)). Non-limiting examples of siRNA molecules targeting the EGFR gene include those described in U.S. Patent Publication No. 20090149403, the disclosure of which is herein incorporated by reference in its entirety for all purposes. siRNA molecules that target VEGFR genes are set forth in, e.g., GB 2396864; U.S. Patent Publication No. 20040142895; and CA 2456444, the disclosures of which are herein incorporated by reference in their entirety for all purposes.

Silencing of sequences that encode DNA repair enzymes find use in combination with the administration of chemotherapeutic agents (Collis et al., *Cancer Res.*, 63:1550 (2003)). Genes encoding proteins associated with tumor migration are also target sequences of interest, for example, integrins, selectins, and metalloproteinases. The foregoing examples are not exclusive. Those of skill in the art will understand that any whole or partial gene sequence that facilitates or promotes tumorigenesis or cell transformation, tumor growth, or tumor migration can be included as a template sequence.

Angiogenic genes are able to promote the formation of new vessels. Angiogenic genes of particular interest include, but are not limited to, vascular endothelial growth factor (VEGF) (Reich et al., *Mol. Vis.*, 9:210 (2003)), placental growth factor (PGF), VEGFR-1 (Flt-1), VEGFR-2 (KDR/Flk-1), and the like. siRNA molecules that target VEGFR genes are set forth in, e.g., GB 2396864; U.S. Patent Publication No. 20040142895; and CA 2456444, the disclosures of which are herein incorporated by reference in their entirety for all purposes.

Immunomodulator genes are genes that modulate one or more immune responses. Examples of immunomodulator genes include, without limitation, growth factors (e.g., TGF-α, TGF-β, EGF, FGF, IGF, NGF, PDGF, CGF, GM-CSF, SCF, etc.), interleukins (e.g., IL-2, IL-4, IL-12 (Hill et al., *J. Immunol.*, 171:691 (2003)), IL-15, IL-18, IL-20, etc.), interferons (e.g., IFN-α, IFN-0, IFN-γ, etc.), and TNF. Fas and Fas ligand genes are also immunomodulator target sequences of interest (Song et al., *Nat. Med.*, 9:347 (2003)). Genes encoding secondary signaling molecules in hematopoietic and lymphoid cells are also included in the present invention, for example, Tec family kinases such as Bruton's tyrosine kinase (Btk) (Heinonen et al., *FEBS Lett.*, 527:274 (2002)).

Cell receptor ligand genes include ligands that are able to bind to cell surface receptors (e.g., cytokine receptors, growth factor receptors, receptors with tyrosine kinase activity, G-protein coupled receptors, insulin receptor, EPO receptor, etc.) to modulate (e.g., inhibit) the physiological pathway that the receptor is involved in (e.g., cell proliferation, tumorigenesis, cell transformation, mitogenesis, etc.). Non-limiting examples of cell receptor ligand genes include cytokines (e.g., TNF-α, interferons such as IFN-α, IFN-β, and IFN-γ, interleukins such as IL-1α, IL-1β, IL-2, IL-4, IL-5, IL-6, IL-7, IL-8, IL-9, IL-10, IL-12, IL-13, IL-15, IL-17, IL-23, IL-27, chemokines, etc.), growth factors (e.g., EGF, HB-EGF, VEGF, PEDF, SDGF, bFGF, HGF, TGF-α, TGF-β, BMP1-BMP15, PDGF, IGF, NGF, R-NGF, BDNF, NT3, NT4, GDF-9, CGF, G-CSF, GM-CSF, GDF-8, EPO, TPO, etc.), insulin, glucagon, G-protein coupled receptor ligands, etc.

Genes associated with viral infection and survival include those expressed by a host (e.g., a host factor such as tissue factor (TF)) or a virus in order to bind, enter, and replicate in a cell. Of particular interest are viral sequences associated with chronic viral diseases. Viral sequences of particular interest include sequences of Filoviruses such as Ebola virus and Marburg virus (see, e.g., Geisbert et al., *J. Infect. Dis.*, 193:1650-1657 (2006)); Arenaviruses such as Lassa virus, Junin virus, Machupo virus, Guanarito virus, and Sabia virus (Buchmeier et al., *Arenaviridae*: the viruses and their replication, In: FIELDS VIROLOGY, Knipe et al. (eds.), 4th ed., Lippincott-Raven, Philadelphia, (2001)); Influenza viruses such as Influenza A, B, and C viruses, (see, e.g., Steinhauer et al., *Annu Rev Genet.*, 36:305-332 (2002); and Neumann et al., *J Gen Virol.*, 83:2635-2662 (2002)); Hepatitis viruses (see, e.g., Hamasaki et al., *FEBS Lett.*, 543:51 (2003); Yokota et al., *EMBO Rep.*, 4:602 (2003); Schlomai et al., *Hepatology*, 37:764 (2003); Wilson et al., *Proc. Natl. Acad. Sci. USA*, 100:2783 (2003); Kapadia et al., *Proc. Natl. Acad. Sci. USA*, 100:2014 (2003); and FIELDS VIROLOGY, Knipe et al. (eds.), 4th ed., Lippincott-Raven, Philadelphia (2001)); Human Immunodeficiency Virus (HIV) (Banerjea et al., *Mol. Ther.*, 8:62 (2003); Song et al., *J. Virol.*, 77:7174 (2003); Stephenson, *JAMA*, 289:1494 (2003); Qin et al., *Proc. Natl. Acad. Sci. USA*, 100:183 (2003)); Herpes viruses (Jia et al., *J. Virol.*, 77:3301 (2003)); and Human Papilloma Viruses (HPV) (Hall et al., *J. Virol.*, 77:6066 (2003); Jiang et al., *Oncogene*, 21:6041 (2002)).

Exemplary Filovirus nucleic acid sequences that can be silenced include, but are not limited to, nucleic acid sequences encoding structural proteins (e.g., VP30, VP35, nucleoprotein (NP), polymerase protein (L-pol)) and membrane-associated proteins (e.g., VP40, glycoprotein (GP), VP24). Complete genome sequences for Ebola virus are set forth in, e.g., Genbank Accession Nos. NC_002549; AY769362; NC_006432; NC_004161; AY729654; AY354458; AY142960; AB050936; AF522874; AF499101; AF272001; and AF086833. Ebola virus VP24 sequences are set forth in, e.g., Genbank Accession Nos. U77385 and AY058897. Ebola virus L-pol sequences are set forth in, e.g., Genbank Accession No. X67110. Ebola virus VP40 sequences are set forth in, e.g., Genbank Accession No. AY058896. Ebola virus NP sequences are set forth in, e.g., Genbank Accession No. AY058895. Ebola virus GP sequences are set forth in, e.g., Genbank Accession No. AY058898; Sanchez et al., *Virus Res.*, 29:215-240 (1993); Will et al., *J. Virol.*, 67:1203-1210 (1993); Volchkov et al., *FEBS Lett.*, 305:181-184 (1992); and U.S. Pat. No. 6,713, 069. Additional Ebola virus sequences are set forth in, e.g., Genbank Accession Nos. L11365 and X61274. Complete genome sequences for Marburg virus are set forth in, e.g., Genbank Accession Nos. NC_001608; AY430365; AY430366; and AY358025. Marburg virus GP sequences are set forth in, e.g., Genbank Accession Nos. AF005734; AF005733; and AF005732. Marburg virus VP35 sequences are set forth in, e.g., Genbank Accession Nos. AF005731 and AF005730. Additional Marburg virus sequences are set forth in, e.g., Genbank Accession Nos. X64406; Z29337; AF005735; and Z12132. Non-limiting examples of siRNA molecules targeting Ebola virus and Marburg virus nucleic acid sequences include those described in U.S. Patent Publication No. 20070135370 and U.S. Provisional Application No. 61/286,741, filed Dec. 15, 2009, the disclosures of which are herein incorporated by reference in their entirety for all purposes.

Exemplary Arenavirus nucleic acid sequences that can be silenced include, but are not limited to, nucleic acid sequences encoding nucleoprotein (NP), glycoprotein (GP), L-polymerase (L), and Z protein (Z). Complete genome sequences for Lassa virus are set forth in, e.g., Genbank Accession Nos. NC_004296 (LASV segment S) and NC_004297 (LASV segment L). Non-limiting examples of siRNA molecules targeting Lassa virus nucleic acid sequences include those described in U.S. Provisional Application No. 61/319,855, filed Mar. 31, 2010, the disclosure of which is herein incorporated by reference in its entirety for all purposes.

Exemplary host nucleic acid sequences that can be silenced include, but are not limited to, nucleic acid sequences encoding host factors such as tissue factor (TF) that are known to play a role in the pathogenesis of hemorrhagic fever viruses. The mRNA sequence of TF is set forth in Genbank Accession No. NM_001993. Those of skill in the art will appreciate that TF is also known as F3, coagulation factor III, thromboplastin, and CD142. Non-limiting examples of siRNA molecules targeting TF nucleic acid sequences include those described in U.S. Provisional Application No. 61/319,855, filed Mar. 31, 2010, the disclosure of which is herein incorporated by reference in its entirety for all purposes.

Exemplary Influenza virus nucleic acid sequences that can be silenced include, but are not limited to, nucleic acid sequences encoding nucleoprotein (NP), matrix proteins (M1 and M2), nonstructural proteins (NS1 and NS2), RNA polymerase (PA, PB1, PB2), neuraminidase (NA), and haemagglutinin (HA). Influenza A NP sequences are set forth in, e.g., Genbank Accession Nos. NC_004522; AY818138; AB166863; AB188817; AB189046; AB189054; AB189062; AY646169; AY646177; AY651486; AY651493; AY651494; AY651495; AY651496; AY651497; AY651498; AY651499; AY651500; AY651501; AY651502; AY651503; AY651504; AY651505; AY651506; AY651507; AY651509; AY651528; AY770996; AY790308; AY818138; and AY818140. Influenza A PA sequences are set forth in, e.g., Genbank Accession Nos. AY818132; AY790280; AY646171; AY818132; AY818133; AY646179; AY818134; AY551934; AY651613; AY651610; AY651620; AY651617; AY651600; AY651611; AY651606; AY651618; AY651608; AY651607; AY651605; AY651609; AY651615; AY651616; AY651640; AY651614; AY651612; AY651621; AY651619; AY770995; and AY724786. Non-limiting examples of siRNA molecules targeting Influenza virus nucleic acid sequences include those described in U.S. Patent Publication No. 20070218122, the disclosure of which is herein incorporated by reference in its entirety for all purposes.

Exemplary hepatitis virus nucleic acid sequences that can be silenced include, but are not limited to, nucleic acid sequences involved in transcription and translation (e.g., En1, En2, X, P) and nucleic acid sequences encoding structural proteins (e.g., core proteins including C and C-related proteins, capsid and envelope proteins including S, M, and/or L proteins, or fragments thereof) (see, e.g., FIELDS VIROLOGY, supra). Exemplary Hepatitis C virus (HCV) nucleic acid sequences that can be silenced include, but are not limited to, the 5'-untranslated region (5'-UTR), the 3'-untranslated region (3'-UTR), the polyprotein translation initiation codon region, the internal ribosome entry site (IRES) sequence, and/or nucleic acid sequences encoding the core protein, the E1 protein, the E2 protein, the p7 protein, the NS2 protein, the NS3 protease/helicase, the NS4A protein, the NS4B protein, the NS5A protein, and/or the NS5B RNA-dependent RNA polymerase. HCV genome sequences are set forth in, e.g., Genbank Accession Nos. NC_004102 (HCV genotype 1a), AJ238799 (HCV genotype 1b), NC_009823 (HCV genotype 2), NC_009824 (HCV genotype 3), NC_009825 (HCV genotype 4), NC_009826 (HCV genotype 5), and NC_009827 (HCV genotype 6). Hepatitis A virus nucleic acid sequences are set forth in, e.g., Genbank Accession No. NC_001489; Hepatitis B virus nucleic acid sequences are set forth in, e.g., Genbank Accession No. NC_003977; Hepatitis D virus nucleic acid sequence are set forth in, e.g., Genbank Accession No. NC_001653; Hepatitis E virus nucleic acid sequences are set forth in, e.g., Genbank Accession No. NC_001434; and Hepatitis G virus nucleic acid sequences are set forth in, e.g., Genbank Accession No. NC_001710. Silencing of sequences that encode genes associated with viral infection and survival can conveniently be used in combination with the administration of conventional agents used to treat the viral condition. Non-limiting examples of siRNA molecules targeting hepatitis virus nucleic acid sequences include those described in U.S. Patent Publication Nos. 20060281175, 20050058982, and 20070149470; U.S. Pat. No. 7,348,314; and PCT Application No. PCT/CA2010/000444, entitled "Compositions and Methods for Silencing Hepatitis C Virus Expression," filed Mar. 19, 2010, the disclosures of which are herein incorporated by reference in their entirety for all purposes.

Genes associated with metabolic diseases and disorders (e.g., disorders in which the liver is the target and liver diseases and disorders) include, but are not limited to, genes expressed in dyslipidemia, such as, e.g., apolipoprotein B (APOB) (Genbank Accession No. NM_000384), apolipoprotein CIII (APOC3) (Genbank Accession Nos. NM_000040 and NG_008949 REGION: 5001 . . . 8164), apolipoprotein E (APOE) (Genbank Accession Nos. NM_000041 and NG_007084 REGION: 5001 . . . 8612), proprotein convertase subtilisin/kexin type 9 (PCSK9) (Genbank Accession No. NM_174936), diacylglycerol O-acyltransferase type 1 (DGAT1) (Genbank Accession No. NM_012079), diacylglyerol O-acyltransferase type 2 (DGAT2) (Genbank Accession No. NM_032564), liver X receptors such as LXRα, and LXRβ (Genback Accession No. NM_007121), farnesoid X receptors (FXR) (Genbank Accession No. NM_005123), sterol-regulatory element binding protein (SREBP), site-1 protease (SiP), 3-hydroxy-3-methylglutaryl coenzyme-A reductase (HMG coenzyme-A reductase); and genes expressed in diabetes, such as, e.g., glucose 6-phosphatase (see, e.g., Forman et al., *Cell,* 81:687 (1995); Seol et al., *Mol. Endocrinol.,* 9:72 (1995); Zavacki et al., *Proc. Natl. Acad. Sci. USA,* 94:7909 (1997); Sakai et al., *Cell,* 85:1037-1046 (1996); Duncan et al., *J. Biol. Chem.,* 272:12778-12785 (1997); Willy et al., *Genes Dev.,* 9:1033-1045 (1995); Lehmann et al., *J. Biol. Chem.,* 272:3137-3140 (1997); Janowski et al., *Nature,* 383:728-731 (1996); and Peet et al., *Cell,* 93:693-704 (1998)).

One of skill in the art will appreciate that genes associated with metabolic diseases and disorders (e.g., diseases and disorders in which the liver is a target and liver diseases and disorders) include genes that are expressed in the liver itself as well as and genes expressed in other organs and tissues. Silencing of sequences that encode genes associated with metabolic diseases and disorders can conveniently be used in combination with the administration of conventional agents used to treat the disease or disorder. Non-limiting examples of siRNA molecules targeting the APOB gene include those described in U.S. Patent Publication Nos. 20060134189, 20060105976, and 20070135372, and PCT Publication No. WO 04/091515, the disclosures of which are herein incorporated by reference in their entirety for all purposes. Non-limiting examples of siRNA molecules targeting the APOC3 gene include those described in PCT Application No. PCT/CA2010/000120, filed Jan. 26, 2010, the disclosure of which is herein incorporated by reference in its entirety for all purposes. Non-limiting examples of siRNA molecules targeting the PCSK9 gene include those described in U.S. Patent Publication Nos. 20070173473, 20080113930, and 20080306015, the disclosures of which are herein incorporated by reference in their entirety for all purposes. Exemplary siRNA molecules targeting the DGAT1 gene may be designed using the antisense compounds described in U.S. Patent Publication No. 20040185559, the disclosure of which is herein incorporated by reference in its entirety for all purposes. Exemplary siRNA molecules targeting the DGAT2 gene may be designed using the antisense compounds described in U.S. Patent Publication No. 20050043524, the disclosure of which is herein incorporated by reference in its entirety for all purposes.

Templates coding for an expansion of trinucleotide repeats (e.g., CAG repeats) find use in silencing pathogenic sequences in neurodegenerative disorders caused by the expansion of trinucleotide repeats, such as spinobulbular muscular atrophy and Huntington's Disease (Caplen et al., *Hum. Mol. Genet.,* 11:175 (2002)).

In addition to its utility in silencing the expression of any of the above-described genes for therapeutic purposes, the siRNA described herein are also useful in research and development applications as well as diagnostic, prophylactic, prognostic, clinical, and other healthcare applications. As a non-limiting example, the siRNA can be used in target validation studies directed at testing whether a gene of interest has the potential to be a therapeutic target. The siRNA can also be used in target identification studies aimed at discovering genes as potential therapeutic targets.

e) Exemplary siRNA Embodiments

In some embodiments, each strand of the siRNA molecule comprises from about 15 to about 60 nucleotides in length (e.g., about 15-60, 15-50, 15-40, 15-30, 15-25, or 19-25 nucleotides in length, or 15, 16, 17, 18, 19, 20, 21, 22, 23, 24, or 25 nucleotides in length). In one particular embodiment, the siRNA is chemically synthesized. The siRNA molecules of the invention are capable of silencing the expression of a target sequence in vitro and/or in vivo.

In other embodiments, the siRNA comprises at least one modified nucleotide. In certain embodiments, the siRNA comprises one, two, three, four, five, six, seven, eight, nine, ten, or more modified nucleotides in the double-stranded region. In particular embodiments, less than about 50% (e.g., less than about 50%, 45%, 40%, 35%, 30%, 25%, 20%, 15%, 10%, or 5%) of the nucleotides in the double-stranded region of the siRNA comprise modified nucleotides. In preferred embodiments, from about 1% to about 50% (e.g., from about 5%-50%, 10%-50%, 15%-50%, 20%-50%, 25%-50%, 30%-50%, 35%-50%, 40%-50%, 45%-50%, 5%-45%, 10%-45%, 15%-45%, 20%-45%, 25%-45%, 30%-45%, 35%-45%, 40%-45%, 5%-40%, 10%-40%, 15%-40%, 20%-40%, 25%-40%, 30%-40%, 35%-40%, 5%-35%, 10%-35%, 15%-35%, 20%-35%, 25%-35%, 30%-35%, 5%-30%, 10%-30%, 15%-30%, 20%-30%, 25%-30%, 5%-25%, 10%-25%, 15%-25%, 20%-25%, 5%-20%, 10%-20%, 15%-20%, 5%-15%, 10%-15%, or 5%-10%) of the nucleotides in the double-stranded region of the siRNA comprise modified nucleotides.

In further embodiments, the siRNA comprises modified nucleotides including, but not limited to, 2'-O-methyl (2'OMe) nucleotides, 2'-deoxy-2'-fluoro (2'F) nucleotides, 2'-deoxy nucleotides, 2'-O-(2-methoxyethyl) (MOE) nucleotides, locked nucleic acid (LNA) nucleotides, and mixtures thereof. In preferred embodiments, the siRNA comprises 2'OMe nucleotides (e.g., 2'OMe purine and/or pyrimidine nucleotides) such as, e.g., 2'OMe-guanosine nucleotides, 2'OMe-uridine nucleotides, 2'OMe-adenosine nucleotides, 2'OMe-cytosine nucleotides, or mixtures thereof. In one particular embodiment, the siRNA comprises at least one 2'OMe-guanosine nucleotide, 2'OMe-uridine nucleotide, or mixtures thereof. In certain instances, the siRNA does not comprise 2'OMe-cytosine nucleotides. In other embodiments, the siRNA comprises a hairpin loop structure.

In certain embodiments, the siRNA comprises modified nucleotides in one strand (i.e., sense or antisense) or both strands of the double-stranded region of the siRNA molecule. Preferably, uridine and/or guanosine nucleotides are modified at selective positions in the double-stranded region of the siRNA duplex. With regard to uridine nucleotide modifications, at least one, two, three, four, five, six, or more of the uridine nucleotides in the sense and/or antisense strand can be a modified uridine nucleotide such as a 2'OMe-uridine nucleotide. In some embodiments, every uridine nucleotide in the sense and/or antisense strand is a 2'OMe-uridine nucleotide. With regard to guanosine nucleotide modifications, at least one, two, three, four, five, six, or more of the guanosine nucleotides in the sense and/or antisense strand can be a modified guanosine nucleotide such as a 2'OMe-guanosine nucleotide. In some embodiments, every guanosine nucleotide in the sense and/or antisense strand is a 2'OMe-guanosine nucleotide.

In certain embodiments, at least one, two, three, four, five, six, seven, or more 5'-GU-3' motifs in an siRNA sequence may be modified, e.g., by introducing mismatches to eliminate the 5'-GU-3' motifs and/or by introducing modified nucleotides such as 2'OMe nucleotides. The 5'-GU-3' motif can be in the sense strand, the antisense strand, or both strands of the siRNA sequence. The 5'-GU-3' motifs may be adjacent to each other or, alternatively, they may be separated by 1, 2, 3, 4, 5, 6, 7, 8, 9, 10, 11, 12, or more nucleotides.

In some embodiments, a modified siRNA molecule is less immunostimulatory than a corresponding unmodified siRNA sequence. In such embodiments, the modified siRNA molecule with reduced immunostimulatory properties advantageously retains RNAi activity against the target sequence. In another embodiment, the immunostimulatory properties of the modified siRNA molecule and its ability to silence target gene expression can be balanced or optimized by the introduction of minimal and selective 2'OMe modifications within the siRNA sequence such as, e.g., within the double-stranded region of the siRNA duplex. In certain instances, the modified siRNA is at least about 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% less immunostimulatory than the corresponding unmodified siRNA. It will be readily apparent to those of skill in the art that the immunostimulatory properties of the modified siRNA molecule and the corresponding unmodified siRNA molecule can be determined by, for example, measuring INF-α and/or IL-6 levels from about two to about twelve hours after systemic administration in a mammal or transfection of a mammalian responder cell using an appropriate lipid-based delivery system (such as the SNALP delivery system disclosed herein).

In other embodiments, a modified siRNA molecule has an $IC_{50}$ (i.e., half-maximal inhibitory concentration) less than or equal to ten-fold that of the corresponding unmodified siRNA (i.e., the modified siRNA has an $IC_{50}$ that is less than or equal to ten-times the $IC_{50}$ of the corresponding unmodified siRNA). In other embodiments, the modified siRNA has an $IC_{50}$ less than or equal to three-fold that of the corresponding unmodified siRNA sequence. In yet other embodiments, the modified siRNA has an $IC_{50}$ less than or equal to two-fold that of the corresponding unmodified siRNA. It will be readily apparent to those of skill in the art that a dose-response curve can be generated and the $IC_{50}$ values for the modified siRNA and the corresponding unmodified siRNA can be readily determined using methods known to those of skill in the art.

In another embodiment, an unmodified or modified siRNA molecule is capable of silencing at least about 5%, 10%, 15%, 20%, 25%, 30%, 35%, 40%, 45%, 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% of the expression of the target sequence relative to a negative control (e.g., buffer only, an siRNA sequence that targets a different gene, a scrambled siRNA sequence, etc.).

In yet another embodiment, a modified siRNA molecule is capable of silencing at least about 5%, 10%, 15%, 20%, 25%, 30%, 35%, 40%, 45%, 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% of the expression of the target sequence relative to the corresponding unmodified siRNA sequence.

In some embodiments, the siRNA molecule does not comprise phosphate backbone modifications, e.g., in the sense and/or antisense strand of the double-stranded region. In other embodiments, the siRNA comprises one, two, three, four, or more phosphate backbone modifications, e.g., in the sense and/or antisense strand of the double-stranded region. In preferred embodiments, the siRNA does not comprise phosphate backbone modifications.

In further embodiments, the siRNA does not comprise 2'-deoxy nucleotides, e.g., in the sense and/or antisense strand of the double-stranded region. In yet further embodiments, the siRNA comprises one, two, three, four, or more 2'-deoxy nucleotides, e.g., in the sense and/or antisense strand of the double-stranded region. In preferred embodiments, the siRNA does not comprise 2'-deoxy nucleotides.

In certain instances, the nucleotide at the 3'-end of the double-stranded region in the sense and/or antisense strand is not a modified nucleotide. In certain other instances, the nucleotides near the 3'-end (e.g., within one, two, three, or four nucleotides of the 3'-end) of the double-stranded region in the sense and/or antisense strand are not modified nucleotides.

The siRNA molecules described herein may have 3' overhangs of one, two, three, four, or more nucleotides on one or both sides of the double-stranded region, or may lack overhangs (i.e., have blunt ends) on one or both sides of the double-stranded region. In certain embodiments, the 3' overhang on the sense and/or antisense strand independently comprises one, two, three, four, or more modified nucleotides such as 2'OMe nucleotides and/or any other modified nucleotide described herein or known in the art.

In particular embodiments, siRNAs are administered using a carrier system such as a nucleic acid-lipid particle. In a preferred embodiment, the nucleic acid-lipid particle comprises: (a) one or more siRNA molecules targeting one or more genes associated with cell proliferation, tumorigenesis, and/or cell transformation (e.g., PLK-1); (b) one or more cationic lipids (e.g., one or more cationic lipids of Formula I-XVI or salts thereof as set forth herein); (c) one or more non-cationic lipids (e.g., DPPC, DSPC, DSPE, and/or cholesterol); and (d) one or more conjugated lipids that inhibit aggregation of the particles (e.g., one or more PEG-lipid conjugates having an average molecular weight of from about 550 daltons to about 1000 daltons such as PEG750-C-DMA).

2. Dicer-Substrate dsRNA

As used herein, the term "Dicer-substrate dsRNA" or "precursor RNAi molecule" is intended to include any precursor molecule that is processed in vivo by Dicer to produce an active siRNA which is incorporated into the RISC complex for RNA interference of a target gene, such as PLK-1.

In one embodiment, the Dicer-substrate dsRNA has a length sufficient such that it is processed by Dicer to produce an siRNA. According to this embodiment, the Dicer-substrate dsRNA comprises (i) a first oligonucleotide sequence (also termed the sense strand) that is between about 25 and about 60 nucleotides in length (e.g., about 25-60, 25-55, 25-50, 25-45, 25-40, 25-35, or 25-30 nucleotides in length), preferably between about 25 and about 30 nucleotides in length (e.g., 25, 26, 27, 28, 29, or 30 nucleotides in length), and (ii) a second oligonucleotide sequence (also termed the antisense strand) that anneals to the first sequence under biological conditions, such as the conditions found in the cytoplasm of a cell. The second oligonucleotide sequence may be between about 25 and about 60 nucleotides in length (e.g., about 25-60, 25-55, 25-50, 25-45, 25-40, 25-35, or 25-30 nucleotides in length), and is preferably between about 25 and about 30 nucleotides in length (e.g., 25, 26, 27, 28, 29, or 30 nucleotides in length). In addition, a region of one of the sequences, particularly of the antisense strand, of the Dicer-substrate dsRNA has a sequence length of at least about 19 nucleotides, for example, from about 19 to about 60 nucleotides (e.g., about 19-60, 19-55, 19-50, 19-45, 19-40, 19-35, 19-30, or 19-25 nucleotides), preferably from about 19 to about 23 nucleotides (e.g., 19, 20, 21, 22, or 23 nucleotides) that are sufficiently complementary to a nucleotide sequence of the RNA produced from the target gene to trigger an RNAi response.

In a second embodiment, the Dicer-substrate dsRNA has several properties which enhance its processing by Dicer. According to this embodiment, the dsRNA has a length sufficient such that it is processed by Dicer to produce an siRNA and has at least one of the following properties: (i) the dsRNA is asymmetric, e.g., has a 3'-overhang on the antisense strand; and/or (ii) the dsRNA has a modified 3'-end on the sense strand to direct orientation of Dicer binding and processing of the dsRNA to an active siRNA. According to this latter embodiment, the sense strand comprises from about 22 to about 28 nucleotides and the antisense strand comprises from about 24 to about 30 nucleotides.

In one embodiment, the Dicer-substrate dsRNA has an overhang on the 3'-end of the antisense strand. In another embodiment, the sense strand is modified for Dicer binding and processing by suitable modifiers located at the 3'-end of the sense strand. Suitable modifiers include nucleotides such as deoxyribonucleotides, acyclonucleotides, and the like, and sterically hindered molecules such as fluorescent molecules and the like. When nucleotide modifiers are used, they replace ribonucleotides in the dsRNA such that the length of the dsRNA does not change. In another embodiment, the Dicer-substrate dsRNA has an overhang on the 3'-end of the antisense strand and the sense strand is modified for Dicer processing. In another embodiment, the 5'-end of the sense strand has a phosphate. In another embodiment, the 5'-end of the antisense strand has a phosphate. In another embodiment, the antisense strand or the sense strand or both strands have one or more 2'-O-methyl (2'OMe) modified nucleotides. In another embodiment, the antisense strand contains 2'OMe modified nucleotides. In another embodiment, the antisense stand contains a 3'-overhang that is comprised of 2'OMe modified nucleotides. The antisense strand could also include additional 2'OMe modified nucleotides. The sense and antisense strands anneal under biological conditions, such as the conditions found in the cytoplasm of a cell. In addition, a region of one of the sequences, particularly of the antisense strand, of the Dicer-substrate dsRNA has a sequence length of at least about 19 nucleotides, wherein these nucleotides are in the 21-nucleotide region adjacent to the 3'-end of the antisense strand and are sufficiently complementary to a nucleotide sequence of the RNA produced from the target gene, such as PLK-1. Further, in accordance with this embodiment, the Dicer-substrate dsRNA may also have one or more of the following additional properties: (a) the antisense strand has a right shift from the typical 21-mer (i.e., the antisense strand includes nucleotides on the right side of the molecule when compared to the typical 21-mer); (b) the strands may not be completely complementary, i.e., the strands may contain simple mismatch pairings; and (c) base modifications such as locked nucleic acid(s) may be included in the 5'-end of the sense strand.

In a third embodiment, the sense strand comprises from about 25 to about 28 nucleotides (e.g., 25, 26, 27, or 28 nucleotides), wherein the 2 nucleotides on the 3'-end of the sense strand are deoxyribonucleotides. The sense strand contains a phosphate at the 5'-end. The antisense strand comprises from about 26 to about 30 nucleotides (e.g., 26, 27, 28, 29, or 30 nucleotides) and contains a 3'-overhang of 1-4 nucleotides. The nucleotides comprising the 3'-overhang are modified with 2'OMe modified ribonucleotides. The antisense strand contains alternating 2'OMe modified nucleotides beginning at the first monomer of the antisense strand adjacent to the 3'-overhang, and extending 15-19 nucleotides from the first monomer adjacent to the 3'-overhang. For example, for a 27-nucleotide antisense strand and counting the first base at the 5'-end of the antisense strand as position number 1, 2'OMe modifications would be placed at bases 9, 11, 13, 15, 17, 19, 21, 23, 25, 26, and 27. In one embodiment, the Dicer-substrate dsRNA has the following structure:

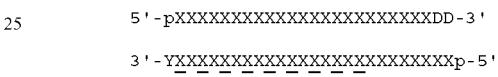

wherein "X"=RNA, "p"=a phosphate group, "X̲"=2'OMe RNA, "Y" is an overhang domain comprised of 1, 2, 3, or 4 RNA monomers that are optionally 2'OMe RNA monomers, and "D"=DNA. The top strand is the sense strand, and the bottom strand is the antisense strand.

In a fourth embodiment, the Dicer-substrate dsRNA has several properties which enhance its processing by Dicer. According to this embodiment, the dsRNA has a length sufficient such that it is processed by Dicer to produce an siRNA and at least one of the following properties: (i) the dsRNA is asymmetric, e.g., has a 3'-overhang on the sense strand; and (ii) the dsRNA has a modified 3'-end on the antisense strand to direct orientation of Dicer binding and processing of the dsRNA to an active siRNA. According to this embodiment, the sense strand comprises from about 24 to about 30 nucleotides (e.g., 24, 25, 26, 27, 28, 29, or 30 nucleotides) and the antisense strand comprises from about 22 to about 28 nucleotides (e.g., 22, 23, 24, 25, 26, 27, or 28 nucleotides). In one embodiment, the Dicer-substrate dsRNA has an overhang on the 3'-end of the sense strand. In another embodiment, the antisense strand is modified for Dicer binding and processing by suitable modifiers located at the 3'-end of the antisense strand. Suitable modifiers include nucleotides such as deoxyribonucleotides, acyclonucleotides, and the like, and sterically hindered molecules such as fluorescent molecules and the like. When nucleotide modifiers are used, they replace ribonucleotides in the dsRNA such that the length of the dsRNA does not change. In another embodiment, the dsRNA has an overhang on the 3'-end of the sense strand and the antisense strand is modified for Dicer processing. In one embodiment, the antisense strand has a 5'-phosphate. The sense and antisense strands anneal under biological conditions, such as the conditions found in the cytoplasm of a cell. In addition, a region of one of the sequences, particularly of the antisense strand, of the dsRNA has a sequence length of at least 19 nucleotides, wherein these nucleotides are adjacent to the 3'-end of antisense strand and are sufficiently complementary to a nucleotide sequence of the RNA produced from the target gene, such as PLK-1. Further, in accordance with this embodiment, the Dicer-substrate dsRNA may also have one or more of the following additional properties: (a) the antisense strand has a left shift from the typical 21-mer (i.e., the antisense strand includes nucleotides on the left side of the molecule when compared to the typical 21-mer); and (b) the strands may not be completely complementary, i.e., the strands may contain simple mismatch pairings.

In a preferred embodiment, the Dicer-substrate dsRNA has an asymmetric structure, with the sense strand having a 25-base pair length, and the antisense strand having a 27-base pair length with a 2 base 3'-overhang. In certain instances, this dsRNA having an asymmetric structure further contains 2 deoxynucleotides at the 3'-end of the sense strand in place of two of the ribonucleotides. In certain other instances, this dsRNA having an asymmetric structure further contains 2'OMe modifications at positions 9, 11, 13, 15, 17, 19, 21, 23, and 25 of the antisense strand (wherein the first base at the 5'-end of the antisense strand is position 1). In certain additional instances, this dsRNA having an asymmetric structure further contains a 3'-overhang on the antisense strand comprising 1, 2, 3, or 4 2'OMe nucleotides (e.g., a 3'-overhang of 2'OMe nucleotides at positions 26 and 27 on the antisense strand).

In another embodiment, Dicer-substrate dsRNAs may be designed by first selecting an antisense strand siRNA sequence having a length of at least 19 nucleotides. In some instances, the antisense siRNA is modified to include about 5 to about 11 ribonucleotides on the 5'-end to provide a length of about 24 to about 30 nucleotides. When the antisense strand has a length of 21 nucleotides, 3-9, preferably 4-7, or more preferably 6 nucleotides may be added on the 5'-end. Although the added ribonucleotides may be complementary to the target gene sequence, full complementarity between the target sequence and the antisense siRNA is not required. That is, the resultant antisense siRNA is sufficiently complementary with the target sequence. A sense strand is then produced that has about 22 to about 28 nucleotides. The sense strand is substantially complementary with the antisense strand to anneal to the antisense strand under biological conditions. In one embodiment, the sense strand is synthesized to contain a modified 3'-end to direct Dicer processing of the antisense strand. In another embodiment, the antisense strand of the dsRNA has a 3'-overhang. In a further embodiment, the sense strand is synthesized to contain a modified 3'-end for Dicer binding and processing and the antisense strand of the dsRNA has a 3'-overhang.

In a related embodiment, the antisense siRNA may be modified to include about 1 to about 9 ribonucleotides on the 5'-end to provide a length of about 22 to about 28 nucleotides. When the antisense strand has a length of 21 nucleotides, 1-7, preferably 2-5, or more preferably 4 ribonucleotides may be added on the 3'-end. The added ribonucleotides may have any sequence. Although the added ribonucleotides may be complementary to the target gene sequence, full complementarity between the target sequence and the antisense siRNA is not required. That is, the resultant antisense siRNA is sufficiently complementary with the target sequence. A sense strand is then produced that has about 24 to about 30 nucleotides. The sense strand is substantially complementary with the antisense strand to anneal to the antisense strand under biological conditions. In one embodiment, the antisense strand is synthesized to contain a modified 3'-end to direct Dicer processing. In another embodiment, the sense strand of the dsRNA has a 3'-overhang. In a further embodiment, the antisense strand is synthesized to contain a modified 3'-end for Dicer binding and processing and the sense strand of the dsRNA has a 3'-overhang.

Suitable Dicer-substrate dsRNA sequences can be identified, synthesized, and modified using any means known in the art for designing, synthesizing, and modifying siRNA sequences. In particular embodiments, Dicer-substrate dsRNAs are administered using a carrier system such as a nucleic acid-lipid particle. In a preferred embodiment, the nucleic acid-lipid particle comprises: (a) one or more Dicer-substrate dsRNA molecules targeting one or more genes associated with cell proliferation, tumorigenesis, and/or cell transformation (e.g., PLK-1); (b) one or more cationic lipids (e.g., one or more cationic lipids of Formula I-XVI or salts thereof as set forth herein); (c) one or more non-cationic lipids (e.g., DPPC, DSPC, DSPE, and/or cholesterol); and (d) one or more conjugated lipids that inhibit aggregation of the particles (e.g., one or more PEG-lipid conjugates having an average molecular weight of from about 550 daltons to about 1000 daltons such as PEG750-C-DMA).

Additional embodiments related to the Dicer-substrate dsRNAs of the invention, as well as methods of designing and synthesizing such dsRNAs, are described in U.S. Patent Publication Nos. 20050244858, 20050277610, and 20070265220, and U.S. application Ser. No. 12/794,701, filed Jun. 4, 2010, the disclosures of which are herein incorporated by reference in their entirety for all purposes.

3. Small Hairpin RNA (shRNA)

A "small hairpin RNA" or "short hairpin RNA" or "shRNA" includes a short RNA sequence that makes a tight hairpin turn that can be used to silence gene expression via RNA interference. The shRNAs of the invention may be chemically synthesized or transcribed from a transcriptional cassette in a DNA plasmid. The shRNA hairpin structure is cleaved by the cellular machinery into siRNA, which is then bound to the RNA-induced silencing complex (RISC).

The shRNAs of the invention are typically about 15-60, 15-50, or 15-40 (duplex) nucleotides in length, more typically about 15-30, 15-25, or 19-25 (duplex) nucleotides in length, and are preferably about 20-24, 21-22, or 21-23 (duplex) nucleotides in length (e.g., each complementary sequence of the double-stranded shRNA is 15-60, 15-50, 15-40, 15-30, 15-25, or 19-25 nucleotides in length, preferably about 20-24, 21-22, or 21-23 nucleotides in length, and the double-stranded shRNA is about 15-60, 15-50, 15-40, 15-30, 15-25, or 19-25 base pairs in length, preferably about 18-22, 19-20, or 19-21 base pairs in length). shRNA duplexes may comprise 3' overhangs of about 1 to about 4 nucleotides or about 2 to about 3 nucleotides on the antisense strand and/or 5'-phosphate termini on the sense strand. In some embodiments, the shRNA comprises a sense strand and/or antisense strand sequence of from about 15 to about 60 nucleotides in length (e.g., about 15-60, 15-55, 15-50, 15-45, 15-40, 15-35, 15-30, or 15-25 nucleotides in length), preferably from about 19 to about 40 nucleotides in length (e.g., about 19-40, 19-35, 19-30, or 19-25 nucleotides in length), more preferably from about 19 to about 23 nucleotides in length (e.g., 19, 20, 21, 22, or 23 nucleotides in length).

Non-limiting examples of shRNA include a double-stranded polynucleotide molecule assembled from a single-stranded molecule, where the sense and antisense regions are linked by a nucleic acid-based or non-nucleic acid-based linker; and a double-stranded polynucleotide molecule with a hairpin secondary structure having self-complementary sense and antisense regions. In preferred embodiments, the sense and antisense strands of the shRNA are linked by a loop structure comprising from about 1 to about 25 nucleotides, from about 2 to about 20 nucleotides, from about 4 to about 15 nucleotides, from about 5 to about 12 nucleotides, or 1, 2, 3, 4, 5, 6, 7, 8, 9, 10, 11, 12, 13, 14, 15, 16, 17, 18, 19, 20, 21, 22, 23, 24, 25, or more nucleotides.

Additional shRNA sequences include, but are not limited to, asymmetric shRNA precursor polynucleotides such as those described in PCT Publication Nos. WO 2006/074108 and WO 2009/076321, the disclosures of which are herein incorporated by reference in their entirety for all purposes. For example, PCT Publication No. WO 2006/074108 discloses self-protected oligonucleotides comprising a region having a sequence complementary to one, two, three, or more same or different target mRNA sequences (e.g., multivalent shRNAs) and one or more self-complementary regions. Similarly, PCT Publication No. WO 2009/076321 discloses self-forming asymmetric precursor polynucleotides comprising a targeting region comprising a polynucleotide sequence complementary to a region of one, two, three, or more same or different target mRNA sequences (e.g., multivalent shRNAs); a first self-complementary region; and a second self-complementary region, wherein the first and second self-complementary regions are located one at each end of the targeting region and both self-complementary regions form stem-loop structures, wherein the first self-complementary region is capable of being cleaved by a RNase III endoribonuclease that is not a class IV DICER endoribonuclease, and wherein both self-complementary regions comprise a nucleotide sequence that is complementary to a region of the target gene sequence, but wherein a portion of the target sequence present in the targeting region does not have a complementary sequence in either of the self-complementary regions.

Suitable shRNA sequences can be identified, synthesized, and modified using any means known in the art for designing, synthesizing, and modifying siRNA sequences. In particular embodiments, shRNAs are administered using a carrier system such as a nucleic acid-lipid particle. In a preferred embodiment, the nucleic acid-lipid particle comprises: (a) one or more shRNA molecules targeting one or more genes associated with cell proliferation, tumorigenesis, and/or cell transformation (e.g., PLK-1); (b) one or more cationic lipids (e.g., one or more cationic lipids of Formula I-XVI or salts thereof as set forth herein); (c) one or more non-cationic lipids (e.g., DPPC, DSPC, DSPE, and/or cholesterol); and (d) one or more conjugated lipids that inhibit aggregation of the particles (e.g., one or more PEG-lipid conjugates having an average molecular weight of from about 550 daltons to about 1000 daltons such as PEG750-C-DMA).

Additional embodiments related to the shRNAs of the invention, as well as methods of designing and synthesizing such shRNAs, are described in U.S. patent application Ser. No. 12/794,701, filed Jun. 4, 2010, the disclosure of which is herein incorporated by reference in its entirety for all purposes.

4. aiRNA

Like siRNA, asymmetrical interfering RNA (aiRNA) can recruit the RNA-induced silencing complex (RISC) and lead to effective silencing of a variety of genes in mammalian cells by mediating sequence-specific cleavage of the target sequence between nucleotide 10 and 11 relative to the 5' end of the antisense strand (Sun et al., *Nat. Biotech.*, 26:1379-1382 (2008)). Typically, an aiRNA molecule comprises a short RNA duplex having a sense strand and an antisense strand, wherein the duplex contains overhangs at the 3' and 5' ends of the antisense strand. The aiRNA is generally asymmetric because the sense strand is shorter on both ends when compared to the complementary antisense strand. In some aspects, aiRNA molecules may be designed, synthesized, and annealed under conditions similar to those used for siRNA molecules. As a non-limiting example, aiRNA sequences may be selected and generated using the methods described above for selecting siRNA sequences.

In another embodiment, aiRNA duplexes of various lengths (e.g., about 10-25, 12-20, 12-19, 12-18, 13-17, or 14-17 base pairs, more typically 12, 13, 14, 15, 16, 17, 18, 19, or 20 base pairs) may be designed with overhangs at the 3' and 5' ends of the antisense strand to target an mRNA of interest. In certain instances, the sense strand of the aiRNA molecule is about 10-25, 12-20, 12-19, 12-18, 13-17, or 14-17 nucleotides in length, more typically 12, 13, 14, 15, 16, 17, 18, 19, or 20 nucleotides in length. In certain other instances, the antisense strand of the aiRNA molecule is about 15-60, 15-50, or 15-40 nucleotides in length, more typically about 15-30, 15-25, or 19-25 nucleotides in length, and is preferably about 20-24, 21-22, or 21-23 nucleotides in length.

In some embodiments, the 5' antisense overhang contains one, two, three, four, or more nontargeting nucleotides (e.g., "AA", "UU", "dTdT", etc.). In other embodiments, the 3' antisense overhang contains one, two, three, four, or more nontargeting nucleotides (e.g., "AA", "UU", "dTdT", etc.). In certain aspects, the aiRNA molecules described herein may comprise one or more modified nucleotides, e.g., in the double-stranded (duplex) region and/or in the antisense overhangs. As a non-limiting example, aiRNA sequences may comprise one or more of the modified nucleotides described above for siRNA sequences. In a preferred embodiment, the aiRNA molecule comprises 2'OMe nucleotides such as, for example, 2'OMe-guanosine nucleotides, 2'OMe-uridine nucleotides, or mixtures thereof.

In certain embodiments, aiRNA molecules may comprise an antisense strand which corresponds to the antisense strand of an siRNA molecule, e.g., one of the siRNA molecules described herein. In particular embodiments, aiRNAs are administered using a carrier system such as a nucleic acid-lipid particle. In a preferred embodiment, the nucleic acid-lipid particle comprises: (a) one or more aiRNA molecules targeting one or more genes associated with cell proliferation, tumorigenesis, and/or cell transformation (e.g., PLK-1); (b) one or more cationic lipids (e.g., one or more cationic lipids of Formula I-XVI or salts thereof as set forth herein); (c) one or more non-cationic lipids (e.g., DPPC, DSPC, DSPE, and/or cholesterol); and (d) one or more conjugated lipids that inhibit aggregation of the particles (e.g., one or more PEG-lipid conjugates having an average molecular weight of from about 550 daltons to about 1000 daltons such as PEG750-C-DMA).

Suitable aiRNA sequences can be identified, synthesized, and modified using any means known in the art for designing, synthesizing, and modifying siRNA sequences. Additional embodiments related to the aiRNA molecules of the invention are described in U.S. Patent Publication No. 20090291131 and PCT Publication No. WO 09/127060, the disclosures of which are herein incorporated by reference in their entirety for all purposes.

5. miRNA

Generally, microRNAs (miRNA) are single-stranded RNA molecules of about 21-23 nucleotides in length which regulate gene expression. miRNAs are encoded by genes from whose DNA they are transcribed, but miRNAs are not translated into protein (non-coding RNA); instead, each primary transcript (a pri-miRNA) is processed into a short stem-loop structure called a pre-miRNA and finally into a functional mature miRNA. Mature miRNA molecules are either partially or completely complementary to one or more messenger RNA (mRNA) molecules, and their main function is to downregulate gene expression. The identification of miRNA molecules is described, e.g., in Lagos-Quintana et al., *Science,* 294:853-858; Lau et al., *Science,* 294:858-862; and Lee et al., *Science,* 294:862-864.

The genes encoding miRNA are much longer than the processed mature miRNA molecule. miRNA are first transcribed as primary transcripts or pri-miRNA with a cap and poly-A tail and processed to short, ~70-nucleotide stem-loop structures known as pre-miRNA in the cell nucleus. This processing is performed in animals by a protein complex known as the Microprocessor complex, consisting of the nuclease Drosha and the double-stranded RNA binding protein Pasha (Denli et al., *Nature,* 432:231-235 (2004)). These pre-miRNA are then processed to mature miRNA in the cytoplasm by interaction with the endonuclease Dicer, which also initiates the formation of the RNA-induced silencing complex (RISC) (Bernstein et al., *Nature,* 409: 363-366 (2001). Either the sense strand or antisense strand of DNA can function as templates to give rise to miRNA.

When Dicer cleaves the pre-miRNA stem-loop, two complementary short RNA molecules are formed, but only one is integrated into the RISC complex. This strand is known as the guide strand and is selected by the argonaute protein, the catalytically active RNase in the RISC complex, on the basis of the stability of the 5' end (Preall et al., *Curr. Biol.,* 16:530-535 (2006)). The remaining strand, known as the anti-guide or passenger strand, is degraded as a RISC complex substrate (Gregory et al., *Cell,* 123:631-640 (2005)). After integration into the active RISC complex, miRNAs base pair with their complementary mRNA molecules and induce target mRNA degradation and/or translational silencing.

Mammalian miRNA molecules are usually complementary to a site in the 3' UTR of the target mRNA sequence. In certain instances, the annealing of the miRNA to the target mRNA inhibits protein translation by blocking the protein translation machinery. In certain other instances, the annealing of the miRNA to the target mRNA facilitates the cleavage and degradation of the target mRNA through a process similar to RNA interference (RNAi). miRNA may also target methylation of genomic sites which correspond to targeted mRNA. Generally, miRNA function in association with a complement of proteins collectively termed the miRNP.

In certain aspects, the miRNA molecules described herein are about 15-100, 15-90, 15-80, 15-75, 15-70, 15-60, 15-50, or 15-40 nucleotides in length, more typically about 15-30, 15-25, or 19-25 nucleotides in length, and are preferably about 20-24, 21-22, or 21-23 nucleotides in length. In certain other aspects, miRNA molecules may comprise one or more modified nucleotides. As a non-limiting example, miRNA sequences may comprise one or more of the modified nucleotides described above for siRNA sequences. In a preferred embodiment, the miRNA molecule comprises 2'OMe nucleotides such as, for example, 2'OMe-guanosine nucleotides, 2'OMe-uridine nucleotides, or mixtures thereof.

In some embodiments, miRNA molecules may be used to silence the expression of any of the target genes described above for siRNA sequences, and preferably silence genes associated with cell proliferation, tumorigenesis, and/or cell transformation. In particular embodiments, miRNAs are administered using a carrier system such as a nucleic acid-lipid particle. In a preferred embodiment, the nucleic acid-lipid particle comprises: (a) one or more miRNA molecules targeting one or more genes associated with cell proliferation, tumorigenesis, and/or cell transformation (e.g., PLK-1); (b) one or more cationic lipids (e.g., one or more cationic lipids of Formula I-XVI or salts thereof as set forth herein); (c) one or more non-cationic lipids (e.g., DPPC, DSPC, DSPE, and/or cholesterol); and (d) one or more conjugated lipids that inhibit aggregation of the particles (e.g., one or more PEG-lipid conjugates having an average molecular weight of from about 550 daltons to about 1000 daltons such as PEG750-C-DMA).

In other embodiments, one or more agents that block the activity of an miRNA targeting an mRNA of interest (e.g., PLK-1 mRNA) are administered using a lipid particle of the invention (e.g., a nucleic acid-lipid particle such as SNALP). Examples of blocking agents include, but are not limited to, steric blocking oligonucleotides, locked nucleic acid oligonucleotides, and Morpholino oligonucleotides. Such blocking agents may bind directly to the miRNA or to the miRNA binding site on the target mRNA.

Additional embodiments related to the miRNA molecules of the invention are described in U.S. Patent Publication No. 20090291131 and PCT Publication No. WO 09/127060, the disclosures of which are herein incorporated by reference in their entirety for all purposes.

6. Antisense Oligonucleotides

In one embodiment, the nucleic acid is an antisense oligonucleotide directed to a target gene or sequence of interest. The terms "antisense oligonucleotide" or "antisense" include oligonucleotides that are complementary to a targeted polynucleotide sequence. Antisense oligonucleotides are single strands of DNA or RNA that are complementary to a chosen sequence. Antisense RNA oligonucleotides prevent the translation of complementary RNA strands by binding to the RNA. Antisense DNA oligonucleotides can be used to target a specific, complementary (coding or non-coding) RNA. If binding occurs, this DNA/RNA hybrid can be degraded by the enzyme RNase H. In a particular embodiment, antisense oligonucleotides comprise from about 10 to about 60 nucleotides, more preferably from about 15 to about 30 nucleotides. The term also encompasses antisense oligonucleotides that may not be exactly complementary to the desired target gene. Thus, the invention can be utilized in instances where non-target specific-activities are found with antisense, or where an antisense sequence containing one or more mismatches with the target sequence is the most preferred for a particular use.

Antisense oligonucleotides have been demonstrated to be effective and targeted inhibitors of protein synthesis, and, consequently, can be used to specifically inhibit protein synthesis by a targeted gene. The efficacy of antisense oligonucleotides for inhibiting protein synthesis is well established. For example, the synthesis of polygalacturonase and the muscarine type 2 acetylcholine receptor are inhibited by antisense oligonucleotides directed to their respective mRNA sequences (see, U.S. Pat. Nos. 5,739,119 and 5,759,829). Furthermore, examples of antisense inhibition have been demonstrated with the nuclear protein cyclin, the multiple drug resistance gene (MDR1), ICAM-1, E-selectin, STK-1, striatal GABAA receptor, and human EGF (see, Jaskulski et al., *Science,* 240:1544-6 (1988); Vasanthakumar et al., *Cancer Commun.,* 1:225-32 (1989); Peris et al., *Brain Res Mol Brain Res.,* 15; 57:310-20 (1998); and U.S. Pat. Nos. 5,801,154; 5,789,573; 5,718,709 and 5,610,288). Moreover, antisense constructs have also been described that inhibit and can be used to treat a variety of abnormal cellular proliferations, e.g., cancer (see, U.S. Pat. Nos. 5,747,470;

5,591,317; and 5,783,683). The disclosures of these references are herein incorporated by reference in their entirety for all purposes.

Methods of producing antisense oligonucleotides are known in the art and can be readily adapted to produce an antisense oligonucleotide that targets any polynucleotide sequence. Selection of antisense oligonucleotide sequences specific for a given target sequence is based upon analysis of the chosen target sequence and determination of secondary structure, Tm, binding energy, and relative stability. Antisense oligonucleotides may be selected based upon their relative inability to form dimers, hairpins, or other secondary structures that would reduce or prohibit specific binding to the target mRNA in a host cell. Highly preferred target regions of the mRNA include those regions at or near the AUG translation initiation codon and those sequences that are substantially complementary to 5' regions of the mRNA. These secondary structure analyses and target site selection considerations can be performed, for example, using v.4 of the OLIGO primer analysis software (Molecular Biology Insights) and/or the BLASTN 2.0.5 algorithm software (Altschul et al., *Nucleic Acids Res.*, 25:3389-402 (1997)).

7. Ribozymes

According to another embodiment of the invention, nucleic acid-lipid particles are associated with ribozymes. Ribozymes are RNA-protein complexes having specific catalytic domains that possess endonuclease activity (see, Kim et al., *Proc. Natl. Acad. Sci. USA*, 84:8788-92 (1987); and Forster et al., *Cell*, 49:211-20 (1987)). For example, a large number of ribozymes accelerate phosphoester transfer reactions with a high degree of specificity, often cleaving only one of several phosphoesters in an oligonucleotide substrate (see, Cech et al., *Cell*, 27:487-96 (1981); Michel et al., *J. Mol. Biol.*, 216:585-610 (1990); Reinhold-Hurek et al., *Nature*, 357:173-6 (1992)). This specificity has been attributed to the requirement that the substrate bind via specific base-pairing interactions to the internal guide sequence ("IGS") of the ribozyme prior to chemical reaction.

At least six basic varieties of naturally-occurring enzymatic RNA molecules are known presently. Each can catalyze the hydrolysis of RNA phosphodiester bonds in trans (and thus can cleave other RNA molecules) under physiological conditions. In general, enzymatic nucleic acids act by first binding to a target RNA. Such binding occurs through the target binding portion of an enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nucleic acid molecule may be formed in a hammerhead, hairpin, hepatitis δ virus, group I intron or RNaseP RNA (in association with an RNA guide sequence), or *Neurospora* VS RNA motif, for example. Specific examples of hammerhead motifs are described in, e.g., Rossi et al., *Nucleic Acids Res.*, 20:4559-65 (1992). Examples of hairpin motifs are described in, e.g., EP 0360257, Hampel et al., *Biochemistry*, 28:4929-33 (1989); Hampel et al., *Nucleic Acids Res.*, 18:299-304 (1990); and U.S. Pat. No. 5,631,359. An example of the hepatitis δ virus motif is described in, e.g., Perrotta et al., *Biochemistry*, 31:11843-52 (1992). An example of the RNaseP motif is described in, e.g., Guerrier-Takada et al., *Cell*, 35:849-57 (1983). Examples of the *Neurospora* VS RNA ribozyme motif is described in, e.g., Saville et al., *Cell*, 61:685-96 (1990); Saville et al., *Proc. Natl. Acad. Sci. USA*, 88:8826-30 (1991); Collins et al., *Biochemistry*, 32:2795-9 (1993). An example of the Group I intron is described in, e.g., U.S. Pat. No. 4,987,071. Important characteristics of enzymatic nucleic acid molecules used according to the invention are that they have a specific substrate binding site which is complementary to one or more of the target gene DNA or RNA regions, and that they have nucleotide sequences within or surrounding that substrate binding site which impart an RNA cleaving activity to the molecule. Thus, the ribozyme constructs need not be limited to specific motifs mentioned herein. The disclosures of these references are herein incorporated by reference in their entirety for all purposes.

Methods of producing a ribozyme targeted to any polynucleotide sequence are known in the art. Ribozymes may be designed as described in, e.g., PCT Publication Nos. WO 93/23569 and WO 94/02595, and synthesized to be tested in vitro and/or in vivo as described therein. The disclosures of these PCT publications are herein incorporated by reference in their entirety for all purposes.

Ribozyme activity can be optimized by altering the length of the ribozyme binding arms or chemically synthesizing ribozymes with modifications that prevent their degradation by serum ribonucleases (see, e.g., PCT Publication Nos. WO 92/07065, WO 93/15187, WO 91/03162, and WO 94/13688; EP 92110298.4; and U.S. Pat. No. 5,334,711, which describe various chemical modifications that can be made to the sugar moieties of enzymatic RNA molecules, the disclosures of which are each herein incorporated by reference in their entirety for all purposes), modifications which enhance their efficacy in cells, and removal of stem II bases to shorten RNA synthesis times and reduce chemical requirements.

8. Immunostimulatory Oligonucleotides

Nucleic acids associated with lipid particles of the present invention may be immunostimulatory, including immunostimulatory oligonucleotides (ISS; single- or double-stranded) capable of inducing an immune response when administered to a subject, which may be a mammal such as a human. ISS include, e.g., certain palindromes leading to hairpin secondary structures (see, Yamamoto et al., *J. Immunol.*, 148:4072-6 (1992)), or CpG motifs, as well as other known ISS features (such as multi-G domains; see; PCT Publication No. WO 96/11266, the disclosure of which is herein incorporated by reference in its entirety for all purposes).

Immunostimulatory nucleic acids are considered to be non-sequence specific when it is not required that they specifically bind to and reduce the expression of a target sequence in order to provoke an immune response. Thus, certain immunostimulatory nucleic acids may comprise a sequence corresponding to a region of a naturally-occurring gene or mRNA, but they may still be considered non-sequence specific immunostimulatory nucleic acids.

In one embodiment, the immunostimulatory nucleic acid or oligonucleotide comprises at least one CpG dinucleotide. The oligonucleotide or CpG dinucleotide may be unmethylated or methylated. In another embodiment, the immunostimulatory nucleic acid comprises at least one CpG dinucleotide having a methylated cytosine. In one embodiment, the nucleic acid comprises a single CpG dinucleotide, wherein the cytosine in the CpG dinucleotide is methylated. In an alternative embodiment, the nucleic acid comprises at least two CpG dinucleotides, wherein at least one cytosine in the CpG dinucleotides is methylated. In a further embodiment, each cytosine in the CpG dinucleotides present in the sequence is methylated. In another embodiment, the nucleic acid comprises a plurality of CpG dinucleotides, wherein at least one of the CpG dinucleotides comprises a methylated cytosine. Examples of immunostimulatory oligonucleotides suitable for use in the compositions and methods of the present invention are described in PCT Publication Nos. WO 02/069369, WO 01/15726, and WO 09/086558; U.S. Pat. No. 6,406,705; and Raney et al., *J. Pharm. Exper. Ther.*, 298:1185-92 (2001), the disclosures of which are herein incorporated by reference in their entirety for all purposes. In certain embodiments, the oligonucleotides used in the compositions and methods of the invention have a phosphodiester ("PO") backbone or a phosphorothioate ("PS") backbone, and/or at least one methylated cytosine residue in a CpG motif.

B. Other Active Agents

In certain embodiments, the active agent associated with the lipid particles of the invention may comprise one or more therapeutic proteins, polypeptides, or small organic molecules or compounds. Non-limiting examples of such therapeutically effective agents or drugs include oncology drugs (e.g., chemotherapy drugs, hormonal therapeutic agents, immunotherapeutic agents, radiotherapeutic agents, etc.), lipid-lowering agents, anti-viral drugs, anti-inflammatory compounds, antidepressants, stimulants, analgesics, antibiotics, birth control medication, antipyretics, vasodilators, anti-angiogenics, cytovascular agents, signal transduction inhibitors, cardiovascular drugs such as anti-arrhythmic agents, hormones, vasoconstrictors, and steroids. These active agents may be administered alone in the lipid particles of the invention, or in combination (e.g., co-administered) with lipid particles of the invention comprising nucleic acid such as interfering RNA.

Non-limiting examples of chemotherapy drugs include platinum-based drugs (e.g., oxaliplatin, cisplatin, carboplatin, spiroplatin, iproplatin, satraplatin, etc.), alkylating agents (e.g., cyclophosphamide, ifosfamide, chlorambucil, busulfan, melphalan, mechlorethamine, uramustine, thiotepa, nitrosoureas, etc.), anti-metabolites (e.g., 5-fluorouracil (5-FU), azathioprine, methotrexate, leucovorin, capecitabine, cytarabine, floxuridine, fludarabine, gemcitabine, pemetrexed, raltitrexed, etc.), plant alkaloids (e.g., vincristine, vinblastine, vinorelbine, vindesine, podophyllotoxin, paclitaxel (taxol), docetaxel, etc.), topoisomerase inhibitors (e.g., irinotecan (CPT-11; Camptosar), topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), tyrosine kinase inhibitors (e.g., gefitinib (Iressa®), sunitinib (Sutent®; SU11248), erlotinib (Tarceva®; OSI-1774), lapatinib (GW572016; GW2016), canertinib (CI 1033), semaxinib (SU5416), vatalanib (PTK787/ZK222584), sorafenib (BAY 43-9006), imatinib (Gleevec®; STI571), dasatinib (BMS-354825), leflunomide (SU101), vandetanib (Zactima™; ZD6474), etc.), pharmaceutically acceptable salts thereof, stereoisomers thereof, derivatives thereof, analogs thereof, and combinations thereof.

Examples of conventional hormonal therapeutic agents include, without limitation, steroids (e.g., dexamethasone), finasteride, aromatase inhibitors, tamoxifen, and goserelin as well as other gonadotropin-releasing hormone agonists (GnRH).

Examples of conventional immunotherapeutic agents include, but are not limited to, immunostimulants (e.g., *Bacillus* Calmette-Guerin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), and radioimmunotherapy (e.g., anti-CD20 monoclonal antibody conjugated to $^{111}$In, $^{90}$Y, or $^{131}$I, etc.).

Examples of conventional radiotherapeutic agents include, but are not limited to, radionuclides such as $^{47}$Sc, $^{64}$Cu, $^{67}$Cu, $^{89}$Sr, $^{86}$Y, $^{87}$Y, $^{90}$Y, $^{105}$R, $^{111}$Ag, $^{111}$In, $^{117m}$Sn, $^{149}$Pm, $^{153}$Sm, $^{166}$Ho, $^{177}$Lu, $^{186}$Re, $^{188}$Re, $^{211}$At, and $^{212}$Bi, optionally conjugated to antibodies directed against tumor antigens.

Additional oncology drugs that may be used according to the invention include, but are not limited to, alkeran, allopurinol, altretamine, amifostine, anastrozole, araC, arsenic trioxide, bexarotene, biCNU, carmustine, CCNU, celecoxib, cladribine, cyclosporin A, cytosine arabinoside, cytoxan, dexrazoxane, DTIC, estramustine, exemestane, FK506, gemtuzumab-ozogamicin, hydrea, hydroxyurea, idarubicin, interferon, letrozole, leustatin, leuprolide, litretinoin, megastrol, L-PAM, mesna, methoxsalen, mithramycin, nitrogen mustard, pamidronate, Pegademase, pentostatin, porfimer sodium, prednisone, rituxan, streptozocin, STI-571, taxotere, temozolamide, VM-26, toremifene, tretinoin, ATRA, valrubicin, and velban. Other examples of oncology drugs that may be used according to the invention are ellipticin and ellipticin analogs or derivatives, epothilones, intracellular kinase inhibitors, and camptothecins.

Non-limiting examples of lipid-lowering agents for treating a lipid disease or disorder associated with elevated triglycerides, cholesterol, and/or glucose include statins, fibrates, ezetimibe, thiazolidinediones, niacin, beta-blockers, nitroglycerin, calcium antagonists, fish oil, and mixtures thereof.

Examples of anti-viral drugs include, but are not limited to, abacavir, aciclovir, acyclovir, adefovir, amantadine, amprenavir, arbidol, atazanavir, atripla, cidofovir, combivir, darunavir, delavirdine, didanosine, docosanol, edoxudine, efavirenz, emtricitabine, enfuvirtide, entecavir, entry inhibitors, famciclovir, fixed dose combinations, fomivirsen, fosamprenavir, foscarnet, fosfonet, fusion inhibitors, ganciclovir, ibacitabine, imunovir, idoxuridine, imiquimod, indinavir, inosine, integrase inhibitors, interferon type III (e.g., IFN-k molecules such as IFN-k1, IFN-k2, and IFN-k3), interferon type II (e.g., IFN-γ), interferon type I (e.g., IFN-α such as PEGylated IFN-α, IFN-β, IFN-κ, IFN-δ, IFN-ε, IFN-τ, IFN-ω, and IFN-ζ), interferon, lamivudine, lopinavir, loviride, MK-0518, maraviroc, moroxydine, nelfinavir, nevirapine, nexavir, nucleoside analogues, oseltamivir, penciclovir, peramivir, pleconaril, podophyllotoxin, protease inhibitors, reverse transcriptase inhibitors, ribavirin, rimantadine, ritonavir, saquinavir, stavudine, synergistic enhancers, tenofovir, tenofovir disoproxil, tipranavir, trifluridine, trizivir, tromantadine, truvada, valaciclovir, valganciclovir, vicriviroc, vidarabine, viramidine, zalcitabine, zanamivir, zidovudine, pharmaceutically acceptable salts thereof, stereoisomers thereof, derivatives thereof, analogs thereof, and mixtures thereof.

V. Lipid Particles

In certain aspects, the present invention provides lipid particles comprising one or more of the cationic (amino) lipids or salts thereof described herein. In some embodiments, the lipid particles of the invention further comprise one or more non-cationic lipids. In other embodiments, the lipid particles further comprise one or more conjugated lipids capable of reducing or inhibiting particle aggregation. In additional embodiments, the lipid particles further comprise one or more active agents or therapeutic agents such as therapeutic nucleic acids (e.g., interfering RNA such as siRNA).

The lipid particles of the present invention have a non-lamellar morphology, i.e., a non-bilayer structure. More particularly, the present invention provides a composition comprising a plurality of nucleic acid-lipid particles, wherein each particle in the plurality of particles comprises: (a) a nucleic acid; (b) a cationic lipid comprising from about 50 mol % to about 85 mol % of the total lipid present in the particle; (c) a non-cationic lipid comprising from about 13 mol % to about 49.5 mol % of the total lipid present in the particle; and (d) a conjugated lipid that inhibits aggregation of particles comprising from about 0.5 mol % to about 10 mol % of the total lipid present in the particle, wherein at least about 95% of the particles in the plurality of particles have a non-lamellar morphology. In preferred embodiments, greater than 95%, preferably, greater than 96%, preferably, greater than 97%, preferably, greater than 98% and, preferably, greater than 99% of the particles have a non-lamellar morphology, i.e., a non-bilayer structure.

The lipid particles of the invention typically comprise an active agent or therapeutic agent, a cationic lipid, a non-cationic lipid, and a conjugated lipid that inhibits aggregation of particles. In some embodiments, the active agent or therapeutic agent is fully encapsulated within the lipid portion of the lipid particle such that the active agent or therapeutic agent in the lipid particle is resistant in aqueous solution to enzymatic degradation, e.g., by a nuclease or protease. In other embodiments, the lipid particles described herein are substantially non-toxic to mammals such as humans. The lipid particles of the invention typically have a mean diameter of from about 30 nm to about 150 nm, from about 40 nm to about 150 nm, from about 50 nm to about 150 nm, from about 60 nm to about 130 nm, from about 70 nm to about 110 nm, from about 70 to about 90 nm, from about 40 nm to about 90 nm, from about 45 nm to about 85, or from about 50 nm to abut 80 nm. The lipid particles of the invention also typically have a lipid:therapeutic agent (e.g., lipid:nucleic acid) ratio (mass/mass ratio) of from about 1:1 to about 100:1, from about 1:1 to about 50:1, from about 2:1 to about 25:1, from about 3:1 to about 20:1, from about 5:1 to about 15:1, or from about 5:1 to about 10:1.

In preferred embodiments, the lipid particles of the invention are serum-stable nucleic acid-lipid particles (SNALP) which comprise an interfering RNA (e.g., siRNA, Dicer-substrate dsRNA, shRNA, aiRNA, and/or miRNA), a cationic lipid (e.g., one or more cationic lipids of Formula I or salts thereof as set forth herein), a non-cationic lipid (e.g., mixtures of one or more phospholipids and cholesterol), and a conjugated lipid that inhibits aggregation of the particles (e.g., one or more PEG-lipid and/or POZ-lipid conjugates). The SNALP may comprise at least 1, 2, 3, 4, 5, 6, 7, 8, 9, 10, or more unmodified and/or modified interfering RNA molecules. Nucleic acid-lipid particles and their method of preparation are described in, e.g., U.S. Pat. Nos. 5,753,613; 5,785,992; 5,705,385; 5,976,567; 5,981,501; 6,110,745; and 6,320,017; and PCT Publication No. WO 96/40964, the disclosures of which are each herein incorporated by reference in their entirety for all purposes.

In the nucleic acid-lipid particles of the invention, the nucleic acid may be fully encapsulated within the lipid portion of the particle, thereby protecting the nucleic acid from nuclease degradation. In preferred embodiments, a SNALP comprising a nucleic acid such as an interfering RNA is fully encapsulated within the lipid portion of the particle, thereby protecting the nucleic acid from nuclease degradation. In certain instances, the nucleic acid in the SNALP is not substantially degraded after exposure of the particle to a nuclease at 37° C. for at least about 20, 30, 45, or 60 minutes. In certain other instances, the nucleic acid in the SNALP is not substantially degraded after incubation of the particle in serum at 37° C. for at least about 30, 45, or 60 minutes or at least about 2, 3, 4, 5, 6, 7, 8, 9, 10, 12, 14, 16, 18, 20, 22, 24, 26, 28, 30, 32, 34, or 36 hours. In other embodiments, the nucleic acid is complexed with the lipid portion of the particle. One of the benefits of the formulations of the present invention is that the nucleic acid-lipid particle compositions are substantially non-toxic to mammals such as humans.

The term "fully encapsulated" indicates that the nucleic acid in the nucleic acid-lipid particle is not significantly degraded after exposure to serum or a nuclease assay that would significantly degrade free DNA or RNA. In a fully encapsulated system, preferably less than about 25% of the nucleic acid in the particle is degraded in a treatment that would normally degrade 100% of free nucleic acid, more preferably less than about 10%, and most preferably less than about 5% of the nucleic acid in the particle is degraded. "Fully encapsulated" also indicates that the nucleic acid-lipid particles are serum-stable, that is, that they do not rapidly decompose into their component parts upon in vivo administration.

In the context of nucleic acids, full encapsulation may be determined by performing a membrane-impermeable fluorescent dye exclusion assay, which uses a dye that has enhanced fluorescence when associated with nucleic acid. Specific dyes such as OliGreen® and RiboGreen® (Invitrogen Corp.; Carlsbad, CA) are available for the quantitative determination of plasmid DNA, single-stranded deoxyribonucleotides, and/or single- or double-stranded ribonucleotides. Encapsulation is determined by adding the dye to a liposomal formulation, measuring the resulting fluorescence, and comparing it to the fluorescence observed upon addition of a small amount of nonionic detergent. Detergent-mediated disruption of the liposomal bilayer releases the encapsulated nucleic acid, allowing it to interact with the membrane-impermeable dye. Nucleic acid encapsulation may be calculated as $E=(I_o-I)/I_o$, where I and $I_o$ refer to the fluorescence intensities before and after the addition of detergent (see, Wheeler et al., *Gene Ther.*, 6:271-281 (1999)).

In other embodiments, the present invention provides a nucleic acid-lipid particle (e.g., SNALP) composition comprising a plurality of nucleic acid-lipid particles.

In some instances, the SNALP composition comprises nucleic acid that is fully encapsulated within the lipid portion of the particles, such that from about 30% to about 100%, from about 40% to about 100%, from about 50% to about 100%, from about 60% to about 100%, from about 70% to about 100%, from about 80% to about 100%, from about 90% to about 100%, from about 30% to about 95%, from about 40% to about 95%, from about 50% to about 95%, from about 60% to about 95%, from about 70% to about 95%, from about 80% to about 95%, from about 85% to about 95%, from about 90% to about 95%, from about 30% to about 90%, from about 40% to about 90%, from about 50% to about 90%, from about 60% to about 90%, from about 70% to about 90%, from about 80% to about 90%, or at least about 30%, 35%, 40%, 45%, 50%, 55%

60%, 65%, 70%, 75%, 80%, 85%, 90%, 91%, 92%, 93%, 94%, 95%, 96%, 97%, 98%, or 99% (or any fraction thereof or range therein) of the particles have the nucleic acid encapsulated therein.

In other instances, the SNALP composition comprises nucleic acid that is fully encapsulated within the lipid portion of the particles, such that from about 30% to about 100%, from about 40% to about 100%, from about 50% to about 100%, from about 60% to about 100%, from about 70% to about 100%, from about 80% to about 100%, from about 90% to about 100%, from about 30% to about 95%, from about 40% to about 95%, from about 50% to about 95%, from about 60% to about 95%, from about 70% to about 95%, from about 80% to about 95%, from about 85% to about 95%, from about 90% to about 95%, from about 30% to about 90%, from about 40% to about 90%, from about 50% to about 90%, from about 60% to about 90%, from about 70% to about 90%, from about 80% to about 90%, or at least about 30%, 35%, 40%, 45%, 50%, 55%, 60%, 65%, 70%, 75% 80%, 85%, 90%, 91%, 92%, 93%, 94%, 95%, 96%, 97%, 98%, or 99% (or any fraction thereof or range therein) of the input nucleic acid is encapsulated in the particles.

Depending on the intended use of the lipid particles of the invention, the proportions of the components can be varied and the delivery efficiency of a particular formulation can be measured using, e.g., an endosomal release parameter (ERP) assay.

In particular embodiments, the present invention provides a lipid particle (e.g., SNALP) composition comprising a plurality of lipid particles described herein and an antioxidant. In certain instances, the antioxidant in the lipid particle composition reduces, prevents, and/or inhibits the degradation of a cationic lipid present in the lipid particle. In instances wherein the active agent is a therapeutic nucleic acid such as an interfering RNA (e.g., siRNA), the antioxidant in the lipid particle composition reduces, prevents, and/or inhibits the degradation of the nucleic acid payload, e.g., by reducing, preventing, and/or inhibiting the formation of adducts between the nucleic acid and the cationic lipid. Non-limiting examples of antioxidants include hydrophilic antioxidants such as chelating agents (e.g., metal chelators such as ethylenediaminetetraacetic acid (EDTA), citrate, and the like), lipophilic antioxidants (e.g., vitamin E isomers, polyphenols, and the like), salts thereof; and mixtures thereof. If needed, the antioxidant is typically present in an amount sufficient to prevent, inhibit, and/or reduce the degradation of the cationic lipid and/or active agent present in the particle, e.g., at least about 20 mM EDTA or a salt thereof, or at least about 100 mM citrate or a salt thereof. An antioxidant such as EDTA and/or citrate may be included at any step or at multiple steps in the lipid particle formation process described in Section VI (e.g., prior to, during, and/or after lipid particle formation).

Additional embodiments related to methods of preventing the degradation of cationic lipids and/or active agents (e.g., therapeutic nucleic acids) present in lipid particles, compositions comprising lipid particles stabilized by these methods, methods of making these lipid particles, and methods of delivering and/or administering these lipid particles are described in U.S. Provisional Application No. 61/265,671, entitled "SNALP Formulations Containing Antioxidants," filed Dec. 1, 2009, the disclosure of which is herein incorporated by reference in its entirety for all purposes.

A. Cationic Lipids

Any of the novel cationic lipids of Formula I or salts thereof as set forth herein may be used in the lipid particles of the present invention (e.g., SNALP), either alone or in combination with one or more other cationic lipid species or non-cationic lipid species.

1. Novel Cationic Lipids

The present invention provides, inter alia, novel cationic (amino) lipids that can advantageously be used in the lipid particles described herein for the in vitro and/or in vivo delivery of therapeutic agents such as nucleic acids to cells. The novel cationic lipids of the present invention have the structure set forth in Formula I herein, and include the (R) and/or (S) enantiomers thereof.

In some embodiments, a lipid of the present invention comprises a racemic mixture. In other embodiments, a lipid of the present invention comprises a mixture of one or more diastereomers. In certain embodiments, a lipid of the present invention is enriched in one enantiomer, such that the lipid comprises at least about 55%, 60%, 65%, 70%, 75%, 80%, 85%, 90%, or 95% enantiomeric excess. In certain other embodiments, a lipid of the present invention is enriched in one diastereomer, such that the lipid comprises at least about 55%, 60%, 65%, 70%, 75%, 80%, 85%, 90%, or 95% diastereomeric excess. In certain additional embodiments, a lipid of the present invention is chirally pure (e.g., comprises a single optical isomer). In further embodiments, a lipid of the present invention is enriched in one optical isomer (e.g., an optically active isomer), such that the lipid comprises at least about 55%, 60%, 65%, 70%, 75%, 80%, 85%, 90%, or 95% isomeric excess. The present invention provides the synthesis of the cationic lipids of Formula I as a racemic mixture or in optically pure form.

The terms "cationic lipid" and "amino lipid" are used interchangeably herein to include those lipids and salts thereof having one, two, three, or more fatty acid or fatty alkyl chains and a pH-titratable amino head group (e.g., an alkylamino or dialkylamino head group). The cationic lipid is typically protonated (i.e., positively charged) at a pH below the $pK_a$ of the cationic lipid and is substantially neutral at a pH above the $pK_a$. The cationic lipids of the invention may also be termed titratable cationic lipids.

The term "salts" includes any anionic and cationic complex, such as the complex formed between a cationic lipid disclosed herein and one or more anions. Non-limiting examples of anions include inorganic and organic anions, e.g., hydride, fluoride, chloride, bromide, iodide, oxalate (e.g., hemioxalate), phosphate, phosphonate, hydrogen phosphate, dihydrogen phosphate, oxide, carbonate, bicarbonate, nitrate, nitrite, nitride, bisulfite, sulfide, sulfite, bisulfate, sulfate, thiosulfate, hydrogen sulfate, borate, formate, acetate, benzoate, citrate, tartrate, lactate, acrylate, polyacrylate, fumarate, maleate, itaconate, glycolate, gluconate, malate, mandelate, tiglate, ascorbate, salicylate, polymethacrylate, perchlorate, chlorate, chlorite, hypochlorite, bromate, hypobromite, iodate, an alkylsulfonate, an arylsulfonate, arsenate, arsenite, chromate, dichromate, cyanide, cyanate, thiocyanate, hydroxide, peroxide, permanganate, and mixtures thereof. In particular embodiments, the salts of the cationic lipids disclosed herein are crystalline salts.

The term "alkyl" includes a straight chain or branched, noncyclic or cyclic, saturated aliphatic hydrocarbon containing from 1 to 24 carbon atoms. Representative saturated straight chain alkyls include, but are not limited to, methyl, ethyl, n-propyl, n-butyl, n-pentyl, n-hexyl, and the like, while saturated branched alkyls include, without limitation, isopropyl, sec-butyl, isobutyl, tert-butyl, isopentyl, and the like. Representative saturated cyclic alkyls include, but are not limited to, the C3-8 cycloalkyls described herein, while unsaturated cyclic alkyls include, without limitation, the C3-8 cycloalkenyls described herein.

The term "heteroalkyl," includes a straight chain or branched, noncyclic or cyclic, saturated aliphatic hydrocarbon as defined above having from about 1 to about 5 heteroatoms (i.e., 1, 2, 3, 4, or 5 heteroatoms) such as, for example, O, N, Si, and/or S, wherein the nitrogen and sulfur atoms may optionally be oxidized and the nitrogen heteroatom may optionally be quaternized. The heteroalkyl group can be attached to the remainder of the molecule through a carbon atom or a heteroatom.

The term "cyclic alkyl" includes any of the substituted or unsubstituted cycloalkyl, heterocycloalkyl, cycloalkenyl, and heterocycloalkenyl groups described below.

The term "cycloalkyl" includes a substituted or unsubstituted cyclic alkyl group having from about 3 to about 8 carbon atoms (i.e., 3, 4, 5, 6, 7, or 8 carbon atoms) as ring vertices. Preferred cycloalkyl groups include those having from about 3 to about 6 carbon atoms as ring vertices. Examples of C3-8 cycloalkyl groups include, but are not limited to, cyclopropyl, methyl-cyclopropyl, dimethyl-cyclopropyl, cyclobutyl, methyl-cyclobutyl, cyclopentyl, methyl-cyclopentyl, cyclohexyl, methyl-cyclohexyl, dimethyl-cyclohexyl, cycloheptyl, and cyclooctyl, as well as other substituted C3-8 cycloalkyl groups.

The term "heterocycloalkyl" includes a substituted or unsubstituted cyclic alkyl group as defined above having from about 1 to about 3 heteroatoms as ring members selected from the group consisting of O, N, Si and S, wherein the nitrogen and sulfur atoms may optionally be oxidized and the nitrogen heteroatom may optionally be quaternized. The heterocycloalkyl group can be attached to the remainder of the molecule through a carbon atom or a heteroatom.

The term "cycloalkenyl" includes a substituted or unsubstituted cyclic alkenyl group having from about 3 to about 8 carbon atoms (i.e., 3, 4, 5, 6, 7, or 8 carbon atoms) as ring vertices. Preferred cycloalkenyl groups are those having from about 3 to about 6 carbon atoms as ring vertices. Examples of $C_{3-8}$ cycloalkenyl groups include, but are not limited to, cyclopropenyl, methyl-cyclopropenyl, dimethyl-cyclopropenyl, cyclobutenyl, cyclopentenyl, cyclohexenyl, cycloheptenyl, and cyclooctenyl, as well as other substituted $C_{3-8}$ cycloalkenyl groups.

The term "heterocycloalkenyl" includes a substituted or unsubstituted cyclic alkenyl group as defined above having from about 1 to about 3 heteroatoms as ring members selected from the group consisting of O, N, Si and S, wherein the nitrogen and sulfur atoms may optionally be oxidized and the nitrogen heteroatom may optionally be quaternized. The heterocycloalkenyl group can be attached to the remainder of the molecule through a carbon atom or a heteroatom.

The term "alkoxy" includes a group of the formula alkyl-O—, wherein "alkyl" has the previously given definition. Non-limiting examples of alkoxy groups include methoxy, ethoxy, n-propoxy, iso-propoxy, n-butoxy, iso-butoxy, sec-butoxy and tert-butoxy.

The term "alkenyl" includes an alkyl, as defined above, containing at least one double bond between adjacent carbon atoms. Alkenyls include both cis and trans isomers. Representative straight chain and branched alkenyls include, but are not limited to, ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like. Representative cyclic alkenyls are described above.

The term "alkynyl" includes any alkyl or alkenyl, as defined above, which additionally contains at least one triple bond between adjacent carbons. Representative straight chain and branched alkynyls include, without limitation, acetylenyl, propynyl, 1-butynyl, 2-butynyl, 1-pentynyl, 2-pentynyl, 3-methyl-1 butynyl, and the like.

The term "aryl" includes a polyunsaturated, typically aromatic, hydrocarbon group which can be a single ring or multiple rings (up to three rings) which are fused together or linked covalently, and which optionally carries one or more substituents, such as, for example, halogen, trifluoromethyl, amino, alkyl, alkoxy, alkylcarbonyl, cyano, carbamoyl, alkoxycarbamoyl, methylendioxy, carboxy, alkoxycarbonyl, aminocarbonyl, alkylaminocarbonyl, dialkylaminocarbonyl, hydroxy, nitro, and the like. Non-limiting examples of unsubstituted aryl groups include phenyl, naphthyl, and biphenyl. Examples of substituted aryl groups include, but are not limited to, phenyl, chlorophenyl, trifluoromethylphenyl, chlorofluorophenyl, and aminophenyl.

The terms "alkylthio," "alkylsulfonyl," "alkylsulfinyl," and "arylsulfonyl" include groups having the formula —S—$R^i$, —$S(O)_2$—$R^i$, —$S(O)$—$R^i$ and —$S(O)_2R^j$, respectively, wherein $R^i$ is an alkyl group as previously defined and $R^j$ is an aryl group as previously defined.

The terms "alkenyloxy" and "alkynyloxy" include groups having the formula —O—$R^k$, wherein $R^k$ is an alkenyl or alkynyl group, respectively.

The terms "alkenylthio" and "alkynylthio" include groups having the formula —S—$R^k$, wherein $R^k$ is an alkenyl or alkynyl group, respectively.

The term "alkoxycarbonyl" includes a group having the formula —C(O)O—$R^i$, wherein $R^i$ is an alkyl group as defined above and wherein the total number of carbon atoms refers to the combined alkyl and carbonyl moieties.

The term "acyl" includes any alkyl, alkenyl, or alkynyl wherein the carbon at the point of attachment is substituted with an oxo group, as defined below. The following are non-limiting examples of acyl groups: —C(=O)alkyl, —C(=O)alkenyl, and —C(=O)alkynyl.

The term "heterocycle" includes a 5- to 7-membered monocyclic, or 7- to 10-membered bicyclic, heterocyclic ring which is either saturated, unsaturated, or aromatic, and which contains from 1 or 2 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles include, but are not limited to, heteroaryls as defined below, as well as morpholinyl, pyrrolidinonyl, pyrrolidinyl, piperidinyl, piperizynyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

The term "heteroaryl" includes an aromatic 5- to 10-membered heterocycle which contains one, two, or more heteroatoms selected from nitrogen (N), oxygen (O), and sulfur (S). The heteroaryl can be substituted on one or more carbon atoms with substituents such as, for example, halogen, alkyl, alkoxy, cyano, haloalkyl (e.g., trifluoromethyl), heterocyclyl (e.g., morpholinyl or pyrrolidinyl), and the like. Non-limiting examples of heteroaryls include pyridinyl and furanyl.

The term "halogen" includes fluoro, chloro, bromo, and iodo.

The terms "optionally substituted alkyl," "optionally substituted cyclic alkyl," "optionally substituted alkenyl," "optionally substituted alkynyl," "optionally substituted acyl," and "optionally substituted heterocycle" mean that, when substituted, at least one hydrogen atom is replaced with a substituent. In the case of an "oxo" substituent (=O), two hydrogen atoms are replaced. Non-limiting examples of substituents include oxo, halogen, heterocycle, —CN, —OR$^x$, —NR$^x$R$^y$, —NR$^x$C(=O)R$^y$, —NR$^x$SO$_2$R$^y$, —C(=O)R$^x$, —C(=O)OR$^x$, —C(=O)NR$^x$R$^y$, —SO$_n$R$^x$, and —SO$_n$NR$^x$R$^y$, wherein n is 0, 1, or 2, R$^x$ and R$^y$ are the same or different and are independently hydrogen, alkyl, or heterocycle, and each of the alkyl and heterocycle substituents may be further substituted with one or more of oxo, halogen, —OH, —CN, alkyl, —OR$^x$, heterocycle, —NR$^x$R$^y$, —NR$^x$C(=O)R$^y$, —NR$^x$SO$_2$R$^y$, —C(=O)R$^x$, —C(=O)OR$^x$, —C(=O)NR$^x$R$^y$, —SO$_n$R$^x$, and —SO$_n$NR$^x$R$^y$. The term "optionally substituted," when used before a list of substituents, means that each of the substituents in the list may be optionally substituted as described herein.

In one aspect, the present invention provides a cationic lipid of Formula I having the following structure:

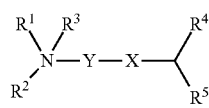

(I)

or salts thereof, wherein:

R$^1$ and R$^2$ are either the same or different and are independently hydrogen (H) or an optionally substituted C$_1$-C$_6$ alkyl, C$_2$-C$_6$ alkenyl, or C$_2$-C$_6$ alkynyl, or R$^1$ and R$^2$ may join to form an optionally substituted heterocyclic ring of 4 to 6 carbon atoms and 1 or 2 heteroatoms selected from the group consisting of nitrogen (N), oxygen (O), and mixtures thereof;

R$^3$ is either absent or is hydrogen (H) or a C$_1$-C$_6$ alkyl to provide a quaternary amine;

R$^4$ and R$^5$ are either the same or different and are independently an optionally substituted C$_{10}$-C$_{24}$ alkyl, C$_{10}$-C$_{24}$ alkenyl, C$_{10}$-C$_{24}$ alkynyl, or C$_{10}$-C$_{24}$ acyl;

X is O, S, N(R$^6$), C(O), C(O)O, OC(O), C(O)N(R$^6$), N(R$^6$)C(O), OC(O)N(R$^6$), N(R$^6$)C(O)O, C(O)S, C(S)O, S(O), S(O)(O), or C(S), wherein R$^6$ is hydrogen (H) or an optionally substituted C$_1$-C$_6$ alkyl, C$_2$-C$_6$ alkenyl, or C$_2$-C$_6$ alkynyl; and Y is either absent or is an optionally substituted C$_1$-C$_6$ alkyl, C$_2$-C$_6$ alkenyl, or C$_2$-C$_6$ alkynyl.

In some embodiments, R$^1$, R$^2$, and R$^6$ are each independently hydrogen (H) or an optionally substituted C$_1$-C$_2$ alkyl, C$_1$-C$_3$ alkyl, C$_1$-C$_4$ alkyl, C$_1$-C$_5$ alkyl, C$_2$-C$_3$ alkyl, C$_2$-C$_4$ alkyl, C$_2$-C$_5$ alkyl, C$_2$-C$_6$ alkyl, C$_3$-C$_4$ alkyl, C$_3$-C$_5$ alkyl, C$_3$-C$_6$ alkyl, C$_4$-C$_5$ alkyl, C$_4$-C$_6$ alkyl, C$_5$-C$_6$ alkyl, C$_2$-C$_3$ alkenyl, C$_2$-C$_4$ alkenyl, C$_2$-C$_5$ alkenyl, C$_2$-C$_6$ alkenyl, C$_3$-C$_4$ alkenyl, C$_3$-C$_5$ alkenyl, C$_3$-C$_6$ alkenyl, C$_4$-C$_5$ alkenyl, C$_4$-C$_6$ alkenyl, C$_5$-C$_6$ alkenyl, C$_2$-C$_3$ alkynyl, C$_2$-C$_4$ alkynyl, C$_2$-C$_5$ alkynyl, C$_2$-C$_6$ alkynyl, C$_3$-C$_4$ alkynyl, C$_3$-C$_5$ alkynyl, C$_3$-C$_6$ alkynyl, C$_4$-C$_5$ alkynyl, C$_4$-C$_6$ alkynyl, or C$_5$-C$_6$ alkynyl. In other embodiments, R$^1$ and R$^2$ are joined to form a heterocyclic ring of 5 carbon atoms and 1 nitrogen atom, wherein the heterocyclic ring can be substituted with a substituent such as a hydroxyl (—OH) group at the ortho, meta, and/or para positions. In particular embodiments, R$^1$ and R$^2$ are both methyl groups. In certain instances, R$^3$ is absent when the pH is above the pK$_a$ of the cationic lipid and R$^3$ is hydrogen (H) when the pH is below the pK$_a$ of the cationic lipid such that the amino head group is protonated. In certain other instances, R$^3$ is an optionally substituted C$_1$-C$_2$ alkyl, C$_1$-C$_3$ alkyl, C$_1$-C$_4$ alkyl, C$_1$-C$_5$ alkyl, C$_2$-C$_3$ alkyl, C$_2$-C$_4$ alkyl, C$_2$-C$_5$ alkyl, C$_2$-C$_6$ alkyl, C$_3$-C$_4$ alkyl, C$_3$-C$_5$ alkyl, C$_3$-C$_6$ alkyl, C$_4$-C$_5$ alkyl, C$_4$-C$_6$ alkyl, or C$_5$-C$_6$ alkyl to provide a quaternary amine. In one particular embodiment, X is C(O)O. In another particular embodiment, X is O. In certain other embodiments, X is C(O)N(R$^6$), N(R$^6$)C(O)O, or C(O)S. In one particular embodiment, X is N(R$^6$)C(O)O and R$^6$ is hydrogen (H) or a methyl group. In other instances, R$^1$ and R$^2$ are not both methyl groups when X is C(O)O, Y is (CH$_2$)$_2$ or (CH$_2$)$_3$, and R$^4$ and R$^5$ are both linoleyl moieties.

In certain embodiments, at least one or both R$^4$ and R$^5$ independently comprises an optionally substituted C$_{12}$-C$_{24}$, C$_{12}$-C$_{22}$, C$_{12}$-C$_{20}$, C$_{14}$-C$_{24}$, C$_{14}$-C$_{22}$, C$_{14}$-C$_{20}$, C$_{16}$-C$_{24}$, C$_{16}$-C$_{22}$, or C$_{16}$-C$_{20}$ alkyl or acyl group (i.e., C$_{12}$, C$_{13}$, C$_{14}$, C$_{15}$, C$_{16}$, C$_{17}$, C$_{18}$, C$_{19}$, C$_{20}$, C$_{21}$, C$_{22}$, C$_{23}$, or C$_{24}$ alkyl or acyl group). In other embodiments, at least one or both R$^4$ and R$^5$ independently comprises at least 1, 2, 3, 4, 5, or 6 sites of unsaturation (e.g., 1-2, 1-3, 1-4, 1-5, 1-6, 2-3, 2-4, 2-5, or 2-6 sites of unsaturation) or a substituted alkyl or acyl group. In certain instances, the unsaturated side-chain may comprise a myristoleyl moiety, a palmitoleyl moiety, an oleyl moiety, a dodecadienyl moiety, a tetradecadienyl moiety, a hexadecadienyl moiety, an octadecadienyl moiety, an icosadienyl moiety, a dodecatrienyl moiety, a tetradectrienyl moiety, a hexadecatrienyl moiety, an octadecatrienyl moiety, an icosatrienyl moiety, or an acyl derivative thereof (e.g., linoleoyl, linolenoyl, γ-linolenoyl, etc.). In some instances, the octadecadienyl moiety is a linoleyl moiety. In particular embodiments, R$^4$ and R$^5$ are both linoleyl moieties. In other instances, the octadecatrienyl moiety is a linolenyl moiety or a γ-linolenyl moiety. In particular embodiments, R$^4$ and R$^5$ are both linolenyl moieties or γ-linolenyl moieties. In embodiments where one or both R$^4$ and R$^5$ independently comprises a branched alkyl or acyl group (e.g., a substituted alkyl or acyl group), the branched alkyl or acyl group may comprise a C$_{12}$-C$_{24}$ alkyl or acyl having at least 1-6 (e.g., 1, 2, 3, 4, 5, 6, or more) C$_1$-C$_6$ alkyl substituents. In particular embodiments, the branched alkyl or acyl group comprises a C$_{12}$-C$_{20}$ or C$_{14}$-C$_{22}$ alkyl or acyl with 1-6 (e.g., 1, 2, 3, 4, 5, 6) C$_1$-C$_4$ alkyl (e.g., methyl, ethyl, propyl, or butyl) substituents. In some embodiments, the branched alkyl group comprises a phytanyl (3,7,11,15-tetramethyl-hexadecanyl) moiety and the branched acyl group comprises a phytanoyl (3,7,11,15-tetramethyl-hexadecanoyl) moiety. In particular embodiments, R$^4$ and R$^5$ are both phytanyl moieties.

In other embodiments, at least one or both R$^4$ and R$^5$ independently comprises at least 1, 2, 3, 4, 5, 6, or more optionally substituted cyclic alkyl groups (e.g., 1-2, 1-3, 1-4, 1-5, 1-6, 2-3, 2-4, 2-5, or 2-6 optionally substituted cyclic alkyl groups). In certain instances, at least one or both R$^4$ and R$^5$ independently comprises an optionally substituted C$_{12}$-C$_{24}$, C$_{12}$-C$_{22}$, C$_{12}$-C$_{20}$, C$_{14}$-C$_{24}$, C$_{14}$-C$_{22}$, C$_{14}$-C$_{20}$, C$_{16}$-C$_{24}$, C$_{16}$-C$_{22}$, or C$_{16}$-C$_{20}$ alkyl, alkenyl, alkynyl, or acyl group (i.e., C$_{12}$, C$_{13}$, C$_{14}$, C$_{15}$, C$_{16}$, C$_{17}$, C$_{18}$, C$_{19}$, C$_{20}$, C$_{21}$, C$_{22}$, C$_{23}$, or C$_{24}$ alkyl, alkenyl, alkynyl, or acyl group), wherein at least one of R$^4$ and R$^5$ comprises at least 1, 2, 3, 4, 5, or 6 optionally substituted cyclic alkyl groups (e.g., 1-2, 1-3, 1-4, 1-5, 1-6, 2-3, 2-4, 2-5, or 2-6 optionally substituted cyclic alkyl groups).

In particular embodiments, one or more of the optionally substituted cyclic alkyl groups present in R$^4$ and/or R$^5$ are independently selected from the group consisting of an optionally substituted saturated cyclic alkyl group, an optionally substituted unsaturated cyclic alkyl group, and combinations thereof. In certain instances, the optionally substituted saturated cyclic alkyl group comprises an optionally substituted $C_{3-8}$ cycloalkyl group (e.g., cyclopropyl, cyclobutyl, cyclopentyl, cyclohexyl, cycloheptyl, cyclooctyl, etc.). In preferred embodiments, the optionally substituted saturated cyclic alkyl group comprises a cyclopropyl group, optionally containing one or more substituents and/or heteroatoms. In other instances, the optionally substituted unsaturated cyclic alkyl group comprises an optionally substituted $C_{3-8}$ cycloalkenyl group (e.g., cyclopropenyl, cyclobutenyl, cyclopentenyl, cyclohexenyl, cycloheptenyl, cyclooctenyl, etc.).

In some embodiments, one of $R^4$ or $R^5$ comprises at least 1, 2, 3, 4, 5, or 6 sites of unsaturation (e.g., 1-2, 1-3, 1-4, 1-5, 1-6, 2-3, 2-4, 2-5, or 2-6 sites of unsaturation) or a substituted alkyl or acyl group, and the other side-chain comprises at least 1, 2, 3, 4, 5, or 6 optionally substituted cyclic alkyl groups (e.g., 1-2, 1-3, 1-4, 1-5, 1-6, 2-3, 2-4, 2-5, or 2-6 optionally substituted cyclic alkyl groups). In embodiments where one of $R^4$ or $R^5$ comprises at least 1, 2, 3, 4, 5, or 6 sites of unsaturation, the unsaturated side-chain may comprise a myristoleyl moiety, a palmitoleyl moiety, an oleyl moiety, a dodecadienyl moiety, a tetradecadienyl moiety, a hexadecadienyl moiety, an octadecadienyl moiety, an icosadienyl moiety, a dodecatrienyl moiety, a tetradectrienyl moiety, a hexadecatrienyl moiety, an octadecatrienyl moiety, an icosatrienyl moiety, or an acyl derivative thereof (e.g., linoleoyl, linolenoyl, γ-linolenoyl, etc.). In some instances, the octadecadienyl moiety is a linoleyl moiety. In other instances, the octadecatrienyl moiety is a linolenyl moiety or a γ-linolenyl moiety. In embodiments where one of $R^4$ or $R^5$ comprises a branched alkyl or acyl group (e.g., a substituted alkyl or acyl group), the branched alkyl or acyl group may comprise a $C_{12}$-$C_{24}$ alkyl or acyl having at least 1-6 (e.g., 1, 2, 3, 4, 5, 6, or more) $C_1$-$C_6$ alkyl substituents. In particular embodiments, the branched alkyl or acyl group comprises a $C_{12}$-$C_{20}$ or $C_{14}$-$C_{22}$ alkyl or acyl with 1-6 (e.g., 1, 2, 3, 4, 5, 6) $C_1$-$C_4$ alkyl (e.g., methyl, ethyl, propyl, or butyl) substituents. In some embodiments, the branched alkyl group comprises a phytanyl moiety and the branched acyl group comprises a phytanoyl moiety.

In particular embodiments, $R^4$ and $R^5$ are both independently selected $C_{12}$-$C_{20}$ alkyl groups (i.e., $C_{12}$, $C_{13}$, $C_{14}$, $C_{15}$, $C_{16}$, $C_{17}$, $C_{18}$, $C_{19}$, or $C_{20}$ alkyl groups) having at least 1, 2, 3, 4, 5, or 6 optionally substituted cyclic alkyl groups (e.g., 1-2, 1-3, 1-4, 1-5, 1-6, 2-3, 2-4, 2-5, or 2-6 optionally substituted cyclic alkyl groups). In preferred embodiments, $R^4$ and $R^5$ are both $C_{18}$ alkyl groups having at least one, two, three, or more optionally substituted cyclic alkyl groups such as, for example, an optionally substituted $C_{3-8}$ cycloalkyl group (e.g., a cyclopropyl group, optionally containing one or more substituents and/or heteroatoms). In certain embodiments, each of the optionally substituted cyclic alkyl groups is independently selected and can be the same cyclic alkyl group (e.g., all cyclopropyl groups) or different cyclic alkyl groups (e.g., cyclopropyl and other cycloalkyl, heterocycloalkyl, cycloalkenyl, and/or heterocycloalkenyl groups).

In preferred embodiments, the optionally substituted cyclic alkyl groups present in $R^4$ and/or $R^5$ are located at the site(s) of unsaturation in the corresponding unsaturated side-chain. As a non-limiting example, one or both of $R^4$ and $R^5$ are $C_{18}$ alkyl groups having 1, 2, or 3 optionally substituted cyclic alkyl groups, wherein the optionally substituted cyclic alkyl groups (e.g., independently selected cyclopropyl groups) are located at one or more (e.g., all) of the sites of unsaturation present in a corresponding linoleyl moiety, linolenyl moiety, or γ-linolenyl moiety.

In alternative embodiments to the cationic lipid of Formula I, $R^4$ and $R^5$ are different and are independently an optionally substituted $C_1$-$C_{24}$ alkyl, $C_2$-$C_{24}$ alkenyl, $C_2$-$C_{24}$ alkynyl, or $C_1$-$C_{24}$ acyl. In particular embodiments, at least one or both $R^4$ and $R^5$ comprises at least 1, 2, 3, 4, 5, or 6 optionally substituted cyclic alkyl groups (e.g., 1-2, 1-3, 1-4, 1-5, 1-6, 2-3, 2-4, 2-5, or 2-6 optionally substituted cyclic alkyl groups). In certain embodiments, $R^4$ and $R^5$ are different and are independently an optionally substituted $C_4$-$C_{20}$ alkyl, $C_4$-$C_{20}$ alkenyl, $C_4$-$C_{20}$ alkynyl, or $C_4$-$C_{20}$ acyl. In some instances, $R^4$ is an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl, and $R^5$ is an optionally substituted $C_4$-$C_{10}$ alkyl, $C_4$-$C_{10}$ alkenyl, $C_4$-$C_{10}$ alkynyl, or $C_4$-$C_{10}$ acyl. In other instances, $R^4$ is an optionally substituted $C_{12}$-$C_{20}$ or $C_{14}$-$C_{22}$ alkyl, $C_{12}$-$C_{20}$ or $C_{14}$-$C_{22}$ alkenyl, $C_{12}$-$C_{20}$ or $C_{14}$-$C_{22}$ alkynyl, or $C_{12}$-$C_{20}$ or $C_{14}$-$C_{22}$ acyl, and $R^5$ is an optionally substituted $C_4$-$C_8$ or $C_6$ alkyl, $C_4$-$C_8$ or $C_6$ alkenyl, $C_4$-$C_8$ or $C_6$ alkynyl, or $C_4$-$C_8$ or $C_6$ acyl. In certain instances, $R^4$ is an optionally substituted $C_4$-$C_{10}$ alkyl, $C_4$-$C_{10}$ alkenyl, $C_4$-$C_{10}$ alkynyl, or $C_4$-$C_{10}$ acyl, and $R^5$ is an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl. In certain other instances, $R^4$ is an optionally substituted $C_4$-$C_8$ or $C_6$ alkyl, $C_4$-$C_8$ or $C_6$ alkenyl, $C_4$-$C_8$ or $C_6$ alkynyl, or $C_4$-$C_8$ or $C_6$ acyl, and $R^5$ is an optionally substituted $C_{12}$-$C_{20}$ or $C_{14}$-$C_{22}$ alkyl, $C_{12}$-$C_{20}$ or $C_{14}$-$C_{22}$ alkenyl, $C_{12}$-$C_{20}$ or $C_{14}$-$C_{22}$ alkynyl, or $C_{12}$-$C_{20}$ or $C_{14}$-$C_{22}$ acyl. In particular embodiments, one or more of the optionally substituted cyclic alkyl groups, when present in $R^4$ and/or $R^5$, are as described above.

In some groups of embodiments to the cationic lipid of Formula I, $R^4$ and $R^5$ are either the same or different and are independently selected from the group consisting of:

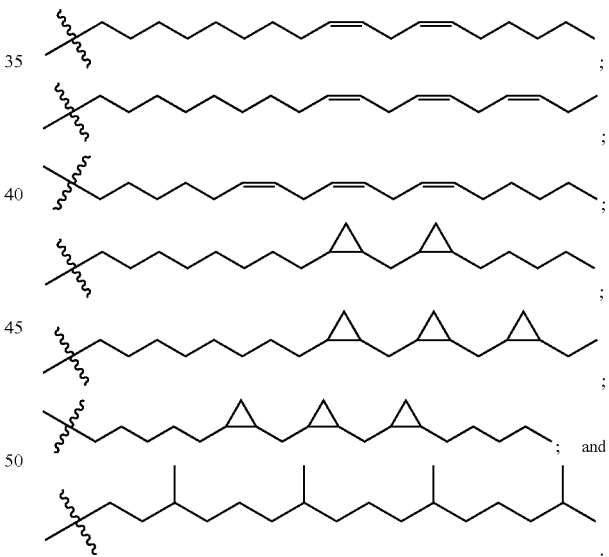

In certain embodiments, Y is an optionally substituted $C_1$-$C_2$ alkyl, $C_1$-$C_3$ alkyl, $C_1$-$C_4$ alkyl, $C_1$-$C_5$ alkyl, $C_2$-$C_3$ alkyl, $C_2$-$C_4$ alkyl, $C_2$-$C_5$ alkyl, $C_2$-$C_6$ alkyl, $C_3$-$C_4$ alkyl, $C_3$-$C_5$alkyl, $C_3$-$C_6$ alkyl, $C_4$-$C_5$ alkyl, $C_4$-$C_6$ alkyl, $C_5$-$C_6$ alkyl, $C_2$-$C_3$ alkenyl, $C_2$-$C_4$ alkenyl, $C_2$-$C_5$ alkenyl, $C_2$-$C_6$ alkenyl, $C_3$-$C_4$ alkenyl, $C_3$-$C_5$ alkenyl, $C_3$-$C_6$ alkenyl, $C_4$-$C_5$ alkenyl, $C_4$-$C_6$ alkenyl, $C_5$-$C_6$ alkenyl, $C_2$-$C_3$ alkynyl, $C_2$-$C_4$ alkynyl, $C_2$-$C_5$ alkynyl, $C_2$-$C_6$ alkynyl, $C_3$-$C_4$ alkynyl, $C_3$-$C_5$ alkynyl, $C_3$-$C_6$ alkynyl, $C_4$-$C_5$ alkynyl, $C_4$-$C_6$ alkynyl, or $C_5$-$C_6$ alkynyl. In one particular embodiment, Y is $(CH_2)_n$ and n is 0, 1, 2, 3, 4, 5, or 6 (e.g., 1-2, 1-3, 1-4, 1-5, 1-6, 2-3, 2-4, 2-5, or 2-6). In a preferred embodiment, n is 2, 3, or 4.

In particular embodiments, the cationic lipid of Formula I has the following structure:

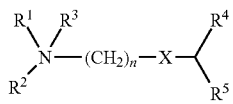

or salts thereof, wherein $R_1$, $R^2$, $R^3$, $R^4$, $R^5$, X, and n are the same as described above.

In some embodiments, the cationic lipid of Formula I forms a salt (preferably a crystalline salt) with one or more anions. In one particular embodiment, the cationic lipid of Formula I is the oxalate (e.g., hemioxalate) salt thereof, which is preferably a crystalline salt.

In particularly preferred embodiments, the cationic lipid of Formula I has one of the following structures:

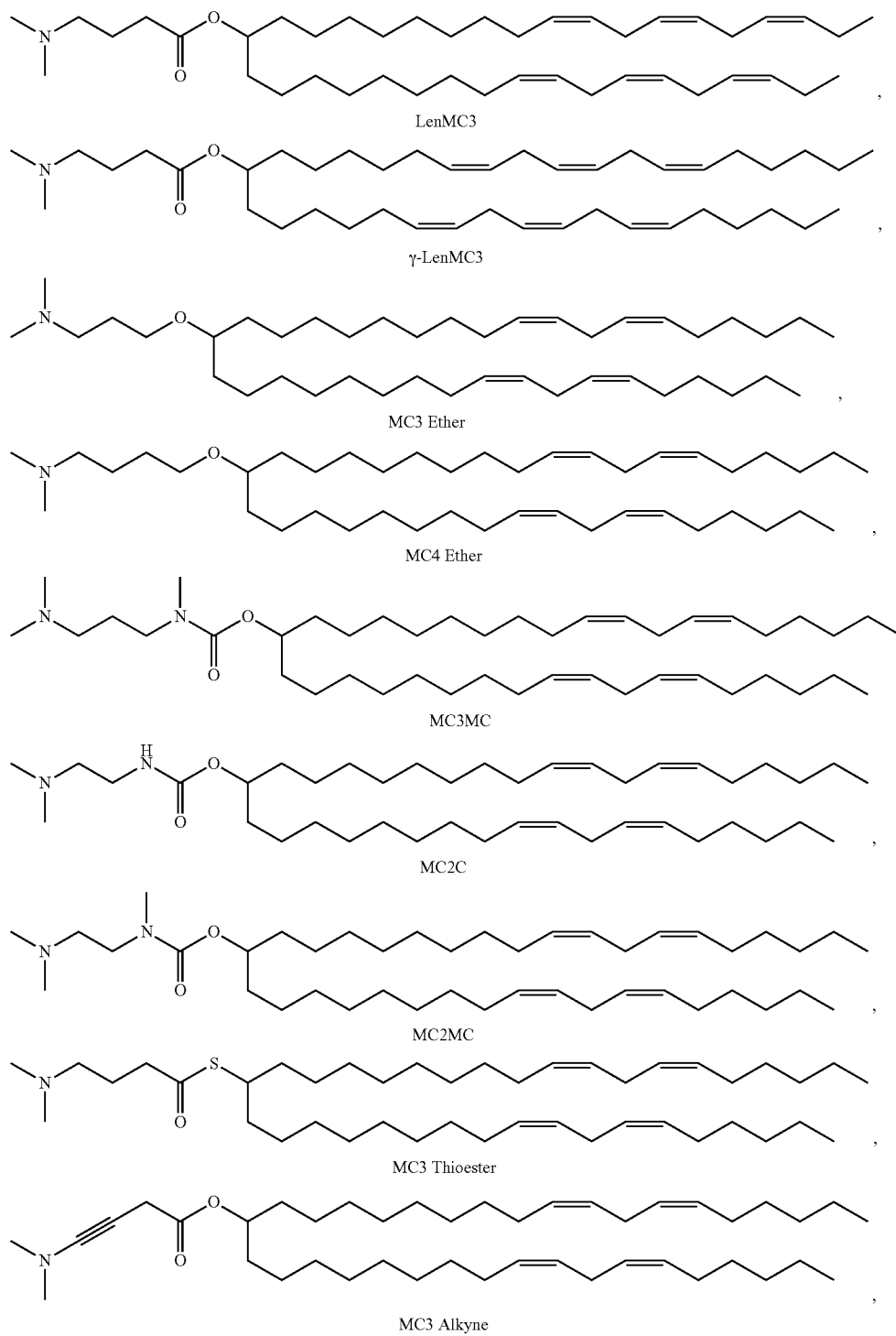

-continued

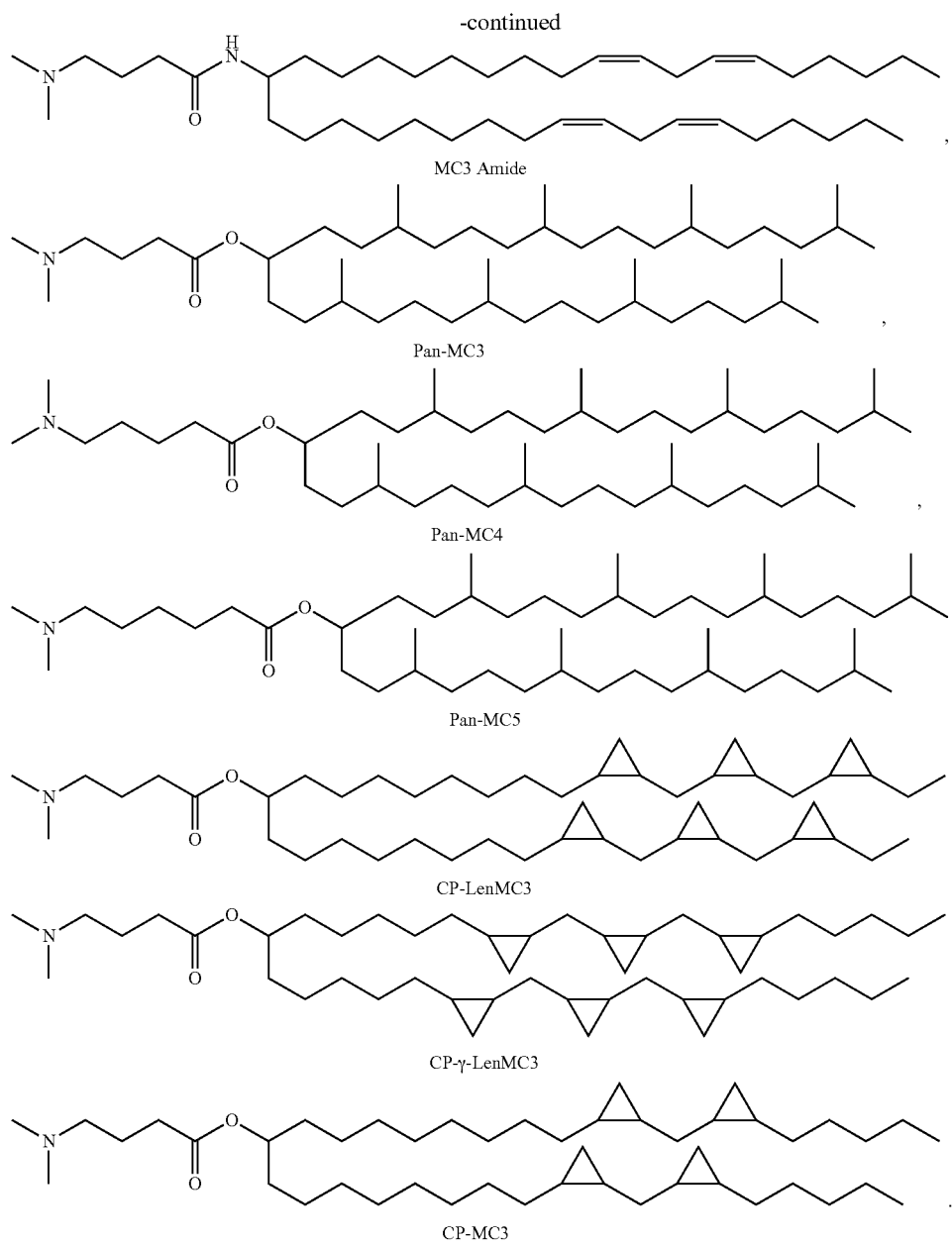

The compounds of the invention may be prepared by known organic synthesis techniques, including the methods described in the Examples. In some embodiments, the synthesis of the cationic lipids of the invention may require the use of protecting groups. Protecting group methodology is well known to those skilled in the art (see, e.g., PROTECTIVE GROUPS IN ORGANIC SYNTHESIS, Green, T. W. et. al., Wiley-Interscience, New York City, 1999). Briefly, protecting groups within the context of this invention are any group that reduces or eliminates the unwanted reactivity of a functional group. A protecting group can be added to a functional group to mask its reactivity during certain reactions and then removed to reveal the original functional group. In certain instances, an "alcohol protecting group" is used. An "alcohol protecting group" is any group which decreases or eliminates the unwanted reactivity of an alcohol functional group. Protecting groups can be added and removed using techniques well known in the art.

In certain embodiments, the cationic lipids of the present invention have at least one protonatable or deprotonatable group, such that the lipid is positively charged at a pH at or below physiological pH (e.g., pH 7.4), and neutral at a second pH, preferably at or above physiological pH. It will be understood by one of ordinary skill in the art that the addition or removal of protons as a function of pH is an equilibrium process, and that the reference to a charged or a neutral lipid refers to the nature of the predominant species and does not require that all of the lipid be present in the charged or neutral form. Lipids that have more than one protonatable or deprotonatable group, or which are zwiterrionic, are not excluded from use in the invention.

In certain other embodiments, protonatable lipids according to the invention have a $pK_a$ of the protonatable group in the range of about 4 to about 11. Most preferred is a $pK_a$ of about 4 to about 7, because these lipids will be cationic at a lower pH formulation stage, while particles will be largely (though not completely) surface neutralized at physiological pH of around pH 7.4. One of the benefits of this pK$_a$ is that at least some nucleic acid associated with the outside surface of the particle will lose its electrostatic interaction at physiological pH and be removed by simple dialysis, thus greatly reducing the particle's susceptibility to clearance.

2. Other Cationic Lipids

Other cationic lipids or salts thereof which may also be included in the lipid particles of the present invention include, but are not limited to, 1,2-dilinoleyloxy-N,N-dimethylaminopropane (DLinDMA), 1,2-dilinolenyloxy-N,N-dimethylaminopropane (DLenDMA), 1,2-di-7-linolenyloxy-N,N-dimethylaminopropane (7-DLenDMA), 1,2-dilinoleyloxy-(N,N-dimethyl)-butyl-4-amine (C2-DLinDMA), 1,2-dilinoleoyloxy-(N,N-dimethyl)-butyl-4-amine (C2-DLinDAP), 2,2-dilinoleyl-4-(2-dimethylaminoethyl)-[1,3]-dioxolane (DLin-K-C2-DMA; also known as "XTC2" or "C2K"), 2,2-dilinoleyl-4-(3-dimethylaminopropyl)-[1,3]-dioxolane (DLin-K-C3-DMA; "C3K"), 2,2-dilinoleyl-4-(4-dimethylaminobutyl)-[1,3]-dioxolane (DLin-K-C4-DMA; "C4K"), 2,2-dilinoleyl-5-dimethylaminomethyl-[1,3]-dioxane (DLin-K6-DMA), 2,2-dilinoleyl-4-N-methylpepiazino-[1,3]-dioxolane (DLin-K-MPZ), 2,2-dilinoleyl-4-dimethylaminomethyl-[1,3]-dioxolane (DLin-K-DMA), 2,2-dioleoyl-4-dimethylaminomethyl-[1,3]-dioxolane (DO-K-DMA), 2,2-distearoyl-4-dimethylaminomethyl-[1,3]-dioxolane (DS-K-DMA), 2,2-dilinoleyl-4-N-morpholino-[1,3]-dioxolane (DLin-K-MA), 2,2-Dilinoleyl-4-trimethylamino-[1,3]-dioxolane chloride (DLin-K-TMA.Cl), 2,2-dilinoleyl-4,5-bis(dimethylaminomethyl)-[1,3]-dioxolane (DLin-K$^2$-DMA), 2,2-dilinoleyl-4-methylpiperzine-[1,3]-dioxolane (D-Lin-K-N-methylpiperzine), (6Z,9Z,28Z,31Z)-heptatriaconta-6,9,28,31-tetraen-19-yl 4-(dimethylamino) butanoate (DLin-M-C3-DMA; "MC3"), dilinoleylmethyl-3-dimethylaminopropionate (DLin-M-C2-DMA; also known as DLin-M-K-DMA or DLin-M-DMA), 1,2-dioeylcarbamoyloxy-3-dimethylaminopropane (DO-C-DAP), 1,2-dimyristoleoyl-3-dimethylaminopropane (DMDAP), 1,2-dioleoyl-3-trimethylaminopropane chloride (DOTAP.Cl), 1,2-dilinoleylcarbamoyloxy-3-dimethylaminopropane (DLin-C-DAP), 1,2-dilinoleyoxy-3-(dimethylamino)acetoxypropane (DLin-DAC), 1,2-dilinoleyoxy-3-morpholinopropane (DLin-MA), 1,2-dilinoleoyl-3-dimethylaminopropane (DLinDAP), 1,2-dilinoleylthio-3-dimethylaminopropane (DLin-S-DMA), 1-linoleoyl-2-linoleyloxy-3-dimethylaminopropane (DLin-2-DMAP), 1,2-dilinoleyloxy-3-trimethylaminopropane chloride salt (DLin-TMA.Cl), 1,2-dilinoleoyl-3-trimethylaminopropane chloride salt (DLin-TAP.Cl), 1,2-dilinoleyloxy-3-(N-methylpiperazino)propane (DLin-MPZ), 3-(N,N-dilinoleylamino)-1,2-propanediol (DLinAP), 3-(N,N-dioleylamino)-1,2-propanedio (DOAP), 1,2-dilinoleyloxo-3-(2-N,N-dimethylamino)ethoxypropane (DLin-EG-DMA), 3-dimethylamino-2-(cholest-5-en-3-beta-oxybutan-4-oxy)-1-(cis,cis-9,12-octadecadienoxy)propane (CLinDMA), 2-[5'-(cholest-5-en-3-beta-oxy)-3'-oxapentoxy)-3-dimethy-1-(cis,cis-9',1-2'-octadecadienoxy)propane (CpLinDMA), N,N-dimethyl-3,4-dioleyloxybenzylamine (DMOBA), 1,2-N,N'-dioleylcarbamyl-3-dimethylaminopropane (DOcarbDAP), 1,2-N,N'-dilinoleylcarbamyl-3-dimethylaminopropane (DLincarbDAP), N,N-dioleyl-N,N-dimethylammonium chloride (DODAC), 1,2-dioleyloxy-N,N-dimethylaminopropane (DODMA), 1,2-distearyloxy-N,N-dimethylaminopropane (DSDMA), N-(1-(2,3-dioleyloxy)propyl)-N,N,N-trimethylammonium chloride (DOTMA), N,N-distearyl-N,N-dimethylammonium bromide (DDAB), N-(1-(2,3-dioleoyloxy)propyl)-N,N,N-trimethylammonium chloride (DOTAP), 3-(N—(N',N'-dimethylaminoethane)-carbamoyl)cholesterol (DC-Chol), N-(1,2-dimyristyloxyprop-3-yl)-N,N-dimethyl-N-hydroxyethyl ammonium bromide (DMRIE), 2,3-dioleyloxy-N-[2(sperminecarboxamido)ethyl]-N,N-dimethyl-1-propanaminiumtrifluoroacetate (DOSPA), dioctadecylamidoglycyl spermine (DOGS), and mixtures thereof.

Additional cationic lipids or salts thereof which may be present in the lipid particles described herein include novel cyclic cationic lipids such as CP-LenMC3, CP-7-LenMC3, CP-MC3, CP-DLen-C2K-DMA, CP-γDLen-C2K-DMA, CP-C2K-DMA, CP-DODMA, CP-DPetroDMA, CP-DLinDMA, CP-DLenDMA, CP-γDLenDMA, analogs thereof, and combinations thereof, as described in U.S. Provisional Application No. 61/334,096 entitled "Novel Cyclic Cationic Lipids and Methods of Use Thereof," filed May 12, 2010. Additional cationic lipids or salts thereof which may be present in the lipid particles described herein include novel cationic lipids such as 4-B10, 4-B12, 4-B13, 4-B14, 4-B15, 4-B16, 7-4-B10, N,N-dimethyl-2-((11Z,14Z)-3-((9Z,12Z)-octadeca-9,12-dienyloxy)icosa-11,14-dienyloxy)ethanamine (4-B10 Ether), (11Z,14Z)-3-(dimethylamino)propyl 3-((9Z,12Z)-octadeca-9,12-dienoyloxy)icosa-11,14-dienoate, CP-4-B10, analogs thereof, and combinations thereof, as described in U.S. Provisional Application No. 61/334,087 entitled "Novel Cationic Lipids and Methods of Use Thereof," filed May 12, 2010. Additional cationic lipids or salts thereof which may be present in the lipid particles described herein include the novel cationic lipids described in U.S. Provisional Application No. 61/295,134, entitled "Improved Cationic Lipids and Methods for the Delivery of Nucleic Acids," filed Jan. 14, 2010. Additional cationic lipids or salts thereof which may be present in the lipid particles described herein include the cationic lipids described in U.S. Patent Publication No. 20090023673. The disclosures of each of these patent documents are herein incorporated by reference in their entirety for all purposes.

In some embodiments, the additional cationic lipid forms a salt (preferably a crystalline salt) with one or more anions. In one particular embodiment, the additional cationic lipid is the oxalate (e.g., hemioxalate) salt thereof, which is preferably a crystalline salt.

The synthesis of cationic lipids such as DLinDMA and DLenDMA, as well as additional cationic lipids, is described in U.S. Patent Publication No. 20060083780, the disclosure of which is herein incorporated by reference in its entirety for all purposes.

The synthesis of cationic lipids such as γ-DLenDMA, C2-DLinDMA and C2-DLinDAP, as well as additional cationic lipids, is described in U.S. Provisional Application No. 61/295,134, entitled "Improved Cationic Lipids and Methods for the Delivery of Nucleic Acids," filed Jan. 14, 2010, the disclosure of which is herein incorporated by reference in its entirety for all purposes.

The synthesis of cationic lipids such as DLin-K-DMA, as well as additional cationic lipids, is described in PCT Publication No. WO 09/086558, the disclosure of which is herein incorporated by reference in its entirety for all purposes.

The synthesis of cationic lipids such as DLin-K-C2-DMA, DLin-K-C3-DMA, DLin-K-C4-DMA, DLin-K6-DMA, DLin-K-MPZ, DO-K-DMA, DS-K-DMA, DLin-K-MA, DLin-K-TMA.Cl, DLin-K$^2$-DMA, D-Lin-K-N- methylpiperzine, DLin-M-C2-DMA, DO-C-DAP, DMDAP, and DOTAP.Cl, as well as additional cationic lipids, is described in PCT Publication No. WO 2010/042877, entitled "Improved Amino Lipids and Methods for the Delivery of Nucleic Acids," filed Oct. 9, 2009, the disclosure of which is incorporated herein by reference in its entirety for all purposes.

The synthesis of DLin-M-C3-DMA ("MC3"), as well as additional cationic lipids (e.g., certain analogs of MC3), is described herein and in U.S. Provisional Application No. 61/185,800, entitled "Novel Lipids and Compositions for the Delivery of Therapeutics," filed Jun. 10, 2009, and U.S. Provisional Application No. 61/287,995, entitled "Methods and Compositions for Delivery of Nucleic Acids," filed Dec. 18, 2009, the disclosures of which are herein incorporated by reference in their entirety for all purposes.

The synthesis of cationic lipids such as DLin-C-DAP, DLinDAC, DLinMA, DLinDAP, DLin-S-DMA, DLin-2-DMAP, DLinTMA.Cl, DLinTAP.Cl, DLinMPZ, DLinAP, DOAP, and DLin-EG-DMA, as well as additional cationic lipids, is described in PCT Publication No. WO 09/086558, the disclosure of which is herein incorporated by reference in its entirety for all purposes.

The synthesis of cationic lipids such as CLinDMA, as well as additional cationic lipids, is described in U.S. Patent Publication No. 20060240554, the disclosure of which is herein incorporated by reference in its entirety for all purposes.

The synthesis of a number of other cationic lipids and related analogs has been described in U.S. Pat. Nos. 5,208,036; 5,264,618; 5,279,833; 5,283,185; 5,753,613; and 5,785,992; and PCT Publication No. WO 96/10390, the disclosures of which are each herein incorporated by reference in their entirety for all purposes. Additionally, a number of commercial preparations of cationic lipids can be used, such as, e.g., LIPOFECTIN® (including DOTMA and DOPE, available from GIBCO/BRL); LIPOFECTAMINE® (including DOSPA and DOPE, available from GIBCO/BRL); and TRANSFECTAM® (including DOGS, available from Promega Corp.).

In some embodiments, the cationic lipid comprises from about 50 mol % to about 90 mol %, from about 50 mol % to about 85 mol %, from about 50 mol % to about 80 mol %, from about 50 mol % to about 75 mol %, from about 50 mol % to about 70 mol %, from about 50 mol % to about 65 mol %, from about 50 mol % to about 60 mol %, from about 55 mol % to about 65 mol %, or from about 55 mol % to about 70 mol % (or any fraction thereof or range therein) of the total lipid present in the particle. In particular embodiments, the cationic lipid comprises about 50 mol %, 51 mol %, 52 mol %, 53 mol %, 54 mol %, 55 mol %, 56 mol %, 57 mol %, 58 mol %, 59 mol %, 60 mol %, 61 mol %, 62 mol %, 63 mol %, 64 mol %, or 65 mol % (or any fraction thereof) of the total lipid present in the particle.

In other embodiments, the cationic lipid comprises from about 2 mol % to about 60 mol %, from about 5 mol % to about 50 mol %, from about 10 mol % to about 50 mol %, from about 20 mol % to about 50 mol %, from about 20 mol % to about 40 mol %, from about 30 mol % to about 40 mol %, or about 40 mol % (or any fraction thereof or range therein) of the total lipid present in the particle.

Additional percentages and ranges of cationic lipids suitable for use in the lipid particles of the present invention are described in PCT Publication No. WO 09/127060, U.S. Provisional Application No. 61/184,652, filed Jun. 5, 2009, U.S. Provisional Application No. 61/295,134, filed Jan. 14, 2010, and U.S. Provisional Application No. 61/222,469, filed Jul. 1, 2009, the disclosures of which are herein incorporated by reference in their entirety for all purposes.

It should be understood that the percentage of cationic lipid present in the lipid particles of the invention is a target amount, and that the actual amount of cationic lipid present in the formulation may vary, for example, by ±5 mol %. For example, in the 1:57 lipid particle (e.g., SNALP) formulation, the target amount of cationic lipid is 57.1 mol %, but the actual amount of cationic lipid may be ±5 mol %, ±4 mol %, ±3 mol %, ±2 mol %, ±1 mol %, ±0.75 mol %, ±0.5 mol %, ±0.25 mol %, or ±0.1 mol % of that target amount, with the balance of the formulation being made up of other lipid components (adding up to 100 mol % of total lipids present in the particle).

B. Non-Cationic Lipids

The non-cationic lipids used in the lipid particles of the invention (e.g., SNALP) can be any of a variety of neutral uncharged, zwitterionic, or anionic lipids capable of producing a stable complex.

Non-limiting examples of non-cationic lipids include phospholipids such as lecithin, phosphatidylethanolamine, lysolecithin, lysophosphatidylethanolamine, phosphatidylserine, phosphatidylinositol, sphingomyelin, egg sphingomyelin (ESM), cephalin, cardiolipin, phosphatidic acid, cerebrosides, dicetylphosphate, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoyl-phosphatidylcholine (POPC), palmitoyloleoyl-phosphatidylethanolamine (POPE), palmitoyloleoyl-phosphatidylglycerol (POPG), dioleoylphosphatidylethanolamine 4-(N-maleimidomethyl)-cyclohexane-1-carboxylate (DOPE-mal), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethyl-phosphatidylethanolamine, dielaidoyl-phosphatidylethanolamine (DEPE), stearoyloleoyl-phosphatidylethanolamine (SOPE), lysophosphatidylcholine, dilinoleoylphosphatidylcholine, and mixtures thereof. Other diacylphosphatidylcholine and diacylphosphatidylethanolamine phospholipids can also be used. The acyl groups in these lipids are preferably acyl groups derived from fatty acids having $C_{10}$-$C_{24}$ carbon chains, e.g., lauroyl, myristoyl, palmitoyl, stearoyl, or oleoyl.

Additional examples of non-cationic lipids include sterols such as cholesterol and derivatives thereof. Non-limiting examples of cholesterol derivatives include polar analogues such as 5α-cholestanol, 5β-coprostanol, cholesteryl-(2'-hydroxy)-ethyl ether, cholesteryl-(4'-hydroxy)-butyl ether, and 6-ketocholestanol; non-polar analogues such as 5α-cholestane, cholestenone, 5α-cholestanone, 5β-cholestanone, and cholesteryl decanoate; and mixtures thereof. In preferred embodiments, the cholesterol derivative is a polar analogue such as cholesteryl-(4'-hydroxy)-butyl ether. The synthesis of cholesteryl-(2'-hydroxy)-ethyl ether is described in PCT Publication No. WO 09/127060, the disclosure of which is herein incorporated by reference in its entirety for all purposes.

In some embodiments, the non-cationic lipid present in the lipid particles (e.g., SNALP) comprises or consists of a mixture of one or more phospholipids and cholesterol or a derivative thereof. In other embodiments, the non-cationic lipid present in the lipid particles (e.g., SNALP) comprises or consists of one or more phospholipids, e.g., a cholesterol-free lipid particle formulation. In yet other embodiments, the non-cationic lipid present in the lipid particles (e.g., SNALP) comprises or consists of cholesterol or a derivative thereof, e.g., a phospholipid-free lipid particle formulation.

Other examples of non-cationic lipids suitable for use in the present invention include nonphosphorous containing lipids such as, e.g., stearylamine, dodecylamine, hexadecylamine, acetyl palmitate, glycerolricinoleate, hexadecyl stereate, isopropyl myristate, amphoteric acrylic polymers, triethanolamine-lauryl sulfate, alkyl-aryl sulfate polyethyl-oxylated fatty acid amides, dioctadecyldimethyl ammonium bromide, ceramide, sphingomyelin, and the like.

In some embodiments, the non-cationic lipid comprises from about 10 mol % to about 60 mol %, from about 20 mol % to about 55 mol %, from about 20 mol % to about 45 mol %, from about 20 mol % to about 40 mol %, from about 25 mol % to about 50 mol %, from about 25 mol % to about 45 mol %, from about 30 mol % to about 50 mol %, from about 30 mol % to about 45 mol %, from about 30 mol % to about 40 mol %, from about 35 mol % to about 45 mol %, from about 37 mol % to about 42 mol %, or about 35 mol %, 36 mol %, 37 mol %, 38 mol %, 39 mol %, 40 mol %, 41 mol %, 42 mol %, 43 mol %, 44 mol %, or 45 mol % (or any fraction thereof or range therein) of the total lipid present in the particle.

In embodiments where the lipid particles contain a mixture of phospholipid and cholesterol or a cholesterol derivative, the mixture may comprise up to about 40 mol %, 45 mol %, 50 mol %, 55 mol %, or 60 mol % of the total lipid present in the particle.

In some embodiments, the phospholipid component in the mixture may comprise from about 2 mol % to about 20 mol %, from about 2 mol % to about 15 mol %, from about 2 mol % to about 12 mol %, from about 4 mol % to about 15 mol %, or from about 4 mol % to about 10 mol % (or any fraction thereof or range therein) of the total lipid present in the particle. In certain preferred embodiments, the phospholipid component in the mixture comprises from about 5 mol % to about 10 mol %, from about 5 mol % to about 9 mol %, from about 5 mol % to about 8 mol %, from about 6 mol % to about 9 mol %, from about 6 mol % to about 8 mol %, or about 5 mol %, 6 mol %, 7 mol %, 8 mol %, 9 mol %, or 10 mol % (or any fraction thereof or range therein) of the total lipid present in the particle. As a non-limiting example, a 1:57 lipid particle formulation comprising a mixture of phospholipid and cholesterol may comprise a phospholipid such as DPPC or DSPC at about 7 mol % (or any fraction thereof), e.g., in a mixture with cholesterol or a cholesterol derivative at about 34 mol % (or any fraction thereof) of the total lipid present in the particle. As another non-limiting example, a 7:54 lipid particle formulation comprising a mixture of phospholipid and cholesterol may comprise a phospholipid such as DPPC or DSPC at about 7 mol % (or any fraction thereof), e.g., in a mixture with cholesterol or a cholesterol derivative at about 32 mol % (or any fraction thereof) of the total lipid present in the particle.

In other embodiments, the cholesterol component in the mixture may comprise from about 25 mol % to about 45 mol %, from about 25 mol % to about 40 mol %, from about 30 mol % to about 45 mol %, from about 30 mol % to about 40 mol %, from about 27 mol % to about 37 mol %, from about 25 mol % to about 30 mol %, or from about 35 mol % to about 40 mol % (or any fraction thereof or range therein) of the total lipid present in the particle. In certain preferred embodiments, the cholesterol component in the mixture comprises from about 25 mol % to about 35 mol %, from about 27 mol % to about 35 mol %, from about 29 mol % to about 35 mol %, from about 30 mol % to about 35 mol %, from about 30 mol % to about 34 mol %, from about 31 mol % to about 33 mol %, or about 30 mol %, 31 mol %, 32 mol %, 33 mol %, 34 mol %, or 35 mol % (or any fraction thereof or range therein) of the total lipid present in the particle. Typically, a 1:57 lipid particle formulation comprising a mixture of phospholipid and cholesterol may comprise cholesterol or a cholesterol derivative at about 34 mol % (or any fraction thereof), e.g., in a mixture with a phospholipid such as DPPC or DSPC at about 7 mol % (or any fraction thereof) of the total lipid present in the particle. Typically, a 7:54 lipid particle formulation comprising a mixture of phospholipid and cholesterol may comprise cholesterol or a cholesterol derivative at about 32 mol % (or any fraction thereof), e.g., in a mixture with a phospholipid such as DPPC or DSPC at about 7 mol % (or any fraction thereof) of the total lipid present in the particle.

In embodiments where the lipid particles are phospholipid-free, the cholesterol or derivative thereof may comprise up to about 25 mol %, 30 mol %, 35 mol %, 40 mol %, 45 mol %, 50 mol %, 55 mol %, or 60 mol % of the total lipid present in the particle.

In some embodiments, the cholesterol or derivative thereof in the phospholipid-free lipid particle formulation may comprise from about 25 mol % to about 45 mol %, from about 25 mol % to about 40 mol %, from about 30 mol % to about 45 mol %, from about 30 mol % to about 40 mol %, from about 31 mol % to about 39 mol %, from about 32 mol % to about 38 mol %, from about 33 mol % to about 37 mol %, from about 35 mol % to about 45 mol %, from about 30 mol % to about 35 mol %, from about 35 mol % to about 40 mol %, or about 30 mol %, 31 mol %, 32 mol %, 33 mol %, 34 mol %, 35 mol %, 36 mol %, 37 mol %, 38 mol %, 39 mol %, or 40 mol % (or any fraction thereof or range therein) of the total lipid present in the particle. As a non-limiting example, a 1:62 lipid particle formulation may comprise cholesterol at about 37 mol % (or any fraction thereof) of the total lipid present in the particle. As another non-limiting example, a 7:58 lipid particle formulation may comprise cholesterol at about 35 mol % (or any fraction thereof) of the total lipid present in the particle.

In other embodiments, the non-cationic lipid comprises from about 5 mol % to about 90 mol %, from about 10 mol % to about 85 mol %, from about 20 mol % to about 80 mol %, about 10 mol % (e.g., phospholipid only), or about 60 mol % (e.g., phospholipid and cholesterol or derivative thereof) (or any fraction thereof or range therein) of the total lipid present in the particle.

Additional percentages and ranges of non-cationic lipids suitable for use in the lipid particles of the present invention are described in PCT Publication No. WO 09/127060, U.S. Provisional Application No. 61/184,652, filed Jun. 5, 2009, U.S. Provisional Application No. 61/295,134, filed Jan. 14, 2010, and U.S. Provisional Application No. 61/222,469, filed Jul. 1, 2009, the disclosures of which are herein incorporated by reference in their entirety for all purposes.

It should be understood that the percentage of non-cationic lipid present in the lipid particles of the invention is a target amount, and that the actual amount of non-cationic lipid present in the formulation may vary, for example, by ±5 mol %. For example, in the 1:57 lipid particle (e.g., SNALP) formulation, the target amount of phospholipid is 7.1 mol % and the target amount of cholesterol is 34.3 mol %, but the actual amount of phospholipid may be ±2 mol %, ±1.5 mol %, ±1 mol %, ±0.75 mol %, ±0.5 mol %, ±0.25 mol %, or ±0.1 mol % of that target amount, and the actual amount of cholesterol may be ±3 mol %, ±2 mol %, ±1 mol %, ±0.75 mol %, ±0.5 mol %, ±0.25 mol %, or ±0.1 mol % of that target amount, with the balance of the formulation being made up of other lipid components (adding up to 100 mol % of total lipids present in the particle). Similarly, in the 7:54 lipid particle (e.g., SNALP) formulation, the target amount of phospholipid is 6.75 mol % and the target amount of cholesterol is 32.43 mol %, but the actual amount of phospholipid may be ±2 mol %, ±1.5 mol %, ±1 mol %, ±0.75 mol %, ±0.5 mol %, ±0.25 mol %, or ±0.1 mol % of that target amount, and the actual amount of cholesterol may be ±3 mol %, ±2 mol %, ±1 mol %, ±0.75 mol %, ±0.5 mol %, ±0.25 mol %, or ±±0.1 mol % of that target amount, with the balance of the formulation being made up of other lipid components (adding up to 100 mol % of total lipids present in the particle).

C. Lipid Conjugates

In addition to cationic and non-cationic lipids, the lipid particles of the invention (e.g., SNALP) may further comprise a lipid conjugate. The conjugated lipid is useful in that it prevents the aggregation of particles. Suitable conjugated lipids include, but are not limited to, PEG-lipid conjugates, POZ-lipid conjugates, ATTA-lipid conjugates, cationic-polymer-lipid conjugates (CPLs), and mixtures thereof. In certain embodiments, the particles comprise either a PEG-lipid conjugate or an ATTA-lipid conjugate together with a CPL.

In a preferred embodiment, the lipid conjugate is a PEG-lipid. Examples of PEG-lipids include, but are not limited to, PEG coupled to dialkyloxypropyls (PEG-DAA) as described in, e.g., PCT Publication No. WO 05/026372, PEG coupled to diacylglycerol (PEG-DAG) as described in, e.g., U.S. Patent Publication Nos. 20030077829 and 2005008689, PEG coupled to phospholipids such as phosphatidylethanolamine (PEG-PE), PEG conjugated to ceramides as described in, e.g., U.S. Pat. No. 5,885,613, PEG conjugated to cholesterol or a derivative thereof, and mixtures thereof. The disclosures of these patent documents are herein incorporated by reference in their entirety for all purposes.

Additional PEG-lipids suitable for use in the invention include, without limitation, mPEG2000-1,2-di-O-alkyl-sn3-carbomoylglyceride (PEG-C-DOMG). The synthesis of PEG-C-DOMG is described in PCT Publication No. WO 09/086558, the disclosure of which is herein incorporated by reference in its entirety for all purposes. Yet additional suitable PEG-lipid conjugates include, without limitation, 1-[8'-(1,2-dimyristoyl-3-propanoxy)-carboxamido-3',6'-di-oxaoctanyl]carbamoyl-o-methyl-poly(ethylene glycol) (2KPEG-DMG). The synthesis of 2KPEG-DMG is described in U.S. Pat. No. 7,404,969, the disclosure of which is herein incorporated by reference in its entirety for all purposes.

PEG is a linear, water-soluble polymer of ethylene PEG repeating units with two terminal hydroxyl groups. PEGs are classified by their molecular weights; for example, PEG 2000 has an average molecular weight of about 2,000 daltons, and PEG 5000 has an average molecular weight of about 5,000 daltons. PEGs are commercially available from Sigma Chemical Co. and other companies and include, but are not limited to, the following: monomethoxypolyethylene glycol (MePEG-OH), monomethoxypolyethylene glycol-succinate (MePEG-S), monomethoxypolyethylene glycol-succinimidyl succinate (MePEG-S-NHS), monomethoxypolyethylene glycol-amine (MePEG-NH$_2$), monomethoxypolyethylene glycol-tresylate (MePEG-TRES), monomethoxypolyethylene glycol-imidazolyl-carbonyl (MePEG-IM), as well as such compounds containing a terminal hydroxyl group instead of a terminal methoxy group (e.g., HO-PEG-S, HO-PEG-S-NHS, HO-PEG-NH$_2$, etc.). Other PEGs such as those described in U.S. Pat. Nos. 6,774,180 and 7,053,150 (e.g., mPEG (20 KDa) amine) are also useful for preparing the PEG-lipid conjugates of the present invention. The disclosures of these patents are herein incorporated by reference in their entirety for all purposes. In addition, monomethoxypolyethyleneglycol-acetic acid (MePEG-CH$_2$COOH) is particularly useful for preparing PEG-lipid conjugates including, e.g., PEG-DAA conjugates.

The PEG moiety of the PEG-lipid conjugates described herein may comprise an average molecular weight ranging from about 550 daltons to about 10,000 daltons. In certain instances, the PEG moiety has an average molecular weight of from about 750 daltons to about 5,000 daltons (e.g., from about 1,000 daltons to about 5,000 daltons, from about 1,500 daltons to about 3,000 daltons, from about 750 daltons to about 3,000 daltons, from about 750 daltons to about 2,000 daltons, etc.). In preferred embodiments, the PEG moiety has an average molecular weight of about 2,000 daltons or about 750 daltons.

In certain instances, the PEG can be optionally substituted by an alkyl, alkoxy, acyl, or aryl group. The PEG can be conjugated directly to the lipid or may be linked to the lipid via a linker moiety. Any linker moiety suitable for coupling the PEG to a lipid can be used including, e.g., non-ester containing linker moieties and ester-containing linker moieties. In a preferred embodiment, the linker moiety is a non-ester containing linker moiety. As used herein, the term "non-ester containing linker moiety" refers to a linker moiety that does not contain a carboxylic ester bond (—OC(O)—). Suitable non-ester containing linker moieties include, but are not limited to, amido (—C(O)NH—), amino (—NR—), carbonyl (—C(O)—), carbamate (—NHC(O)O—), urea (—NHC(O)NH—), disulphide (—S—S—), ether (—O—), succinyl (—(O)CCH$_2$CH$_2$C(O)—), succinamidyl (—NHC(O)CH$_2$CH$_2$C(O)NH—), ether, disulphide, as well as combinations thereof (such as a linker containing both a carbamate linker moiety and an amido linker moiety). In a preferred embodiment, a carbamate linker is used to couple the PEG to the lipid.

In other embodiments, an ester containing linker moiety is used to couple the PEG to the lipid. Suitable ester containing linker moieties include, e.g., carbonate (—OC(O)O—), succinoyl, phosphate esters (—O—(O)POH—O—), sulfonate esters, and combinations thereof.

Phosphatidylethanolamines having a variety of acyl chain groups of varying chain lengths and degrees of saturation can be conjugated to PEG to form the lipid conjugate. Such phosphatidylethanolamines are commercially available, or can be isolated or synthesized using conventional techniques known to those of skilled in the art. Phosphatidyl-ethanolamines containing saturated or unsaturated fatty acids with carbon chain lengths in the range of $C_{10}$ to $C_{20}$ are preferred. Phosphatidylethanolamines with mono- or diunsaturated fatty acids and mixtures of saturated and unsaturated fatty acids can also be used. Suitable phosphatidylethanolamines include, but are not limited to, dimyristoyl-phosphatidylethanolamine (DMPE), dipalmitoyl-phosphatidylethanolamine (DPPE), dioleoylphosphatidylethanolamine (DOPE), and distearoyl-phosphatidylethanolamine (DSPE).

The term "ATTA" or "polyamide" includes, without limitation, compounds described in U.S. Pat. Nos. 6,320,017 and 6,586,559, the disclosures of which are herein incorporated by reference in their entirety for all purposes. These compounds include a compound having the formula:

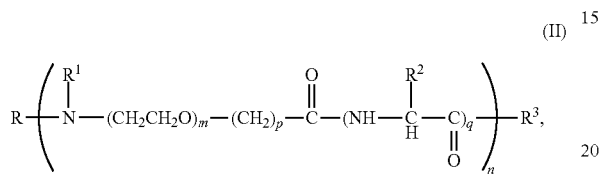

(II)

wherein R is a member selected from the group consisting of hydrogen, alkyl and acyl; $R^1$ is a member selected from the group consisting of hydrogen and alkyl; or optionally, R and $R^1$ and the nitrogen to which they are bound form an azido moiety; $R^2$ is a member of the group selected from hydrogen, optionally substituted alkyl, optionally substituted aryl and a side chain of an amino acid; $R^3$ is a member selected from the group consisting of hydrogen, halogen, hydroxy, alkoxy, mercapto, hydrazino, amino and $NR^4R5$, wherein $R^4$ and $R^5$ are independently hydrogen or alkyl; n is 4 to 80; m is 2 to 6; p is 1 to 4; and q is 0 or 1. It will be apparent to those of skill in the art that other polyamides can be used in the compounds of the present invention.

The term "diacylglycerol" or "DAG" includes a compound having 2 fatty acyl chains, $R^1$ and $R^2$, both of which have independently between 2 and 30 carbons bonded to the 1- and 2-position of glycerol by ester linkages. The acyl groups can be saturated or have varying degrees of unsaturation. Suitable acyl groups include, but are not limited to, lauroyl ($C_{12}$), myristoyl ($C_{14}$), palmitoyl ($C_{16}$), stearoyl ($C_{18}$), and icosoyl ($C_{20}$). In preferred embodiments, $R^1$ and $R^2$ are the same, i.e., $R^1$ and $R^2$ are both myristoyl (i.e., dimyristoyl), $R^1$ and $R^2$ are both stearoyl (i.e., distearoyl), etc. Diacylglycerols have the following general formula:

(III)

The term "dialkyloxypropyl" or "DAA" includes a compound having 2 alkyl chains, $R^1$ and $R^2$, both of which have independently between 2 and 30 carbons. The alkyl groups can be saturated or have varying degrees of unsaturation. Dialkyloxypropyls have the following general formula:

(IV)

In a preferred embodiment, the PEG-lipid is a PEG-DAA conjugate having the following formula:

(V)

wherein $R^1$ and $R^2$ are independently selected and are long-chain alkyl groups having from about 10 to about 22 carbon atoms; PEG is a polyethyleneglycol; and L is a non-ester containing linker moiety or an ester containing linker moiety as described above. The long-chain alkyl groups can be saturated or unsaturated. Suitable alkyl groups include, but are not limited to, decyl ($C_{10}$), lauryl ($C_{12}$), myristyl ($C_{14}$), palmityl ($C_{16}$), stearyl ($C_{18}$), and icosyl ($C_{20}$). In preferred embodiments, $R^1$ and $R^2$ are the same, i.e., $R^1$ and $R^2$ are both myristyl (i.e., dimyristyl), $R^1$ and $R^2$ are both stearyl (i.e., distearyl), etc.

In Formula V above, the PEG has an average molecular weight ranging from about 550 daltons to about 10,000 daltons. In certain instances, the PEG has an average molecular weight of from about 750 daltons to about 5,000 daltons (e.g., from about 1,000 daltons to about 5,000 daltons, from about 1,500 daltons to about 3,000 daltons, from about 750 daltons to about 3,000 daltons, from about 750 daltons to about 2,000 daltons, etc.). In preferred embodiments, the PEG has an average molecular weight of about 2,000 daltons or about 750 daltons. The PEG can be optionally substituted with alkyl, alkoxy, acyl, or aryl groups. In certain embodiments, the terminal hydroxyl group is substituted with a methoxy or methyl group.

In a preferred embodiment, "L" is a non-ester containing linker moiety. Suitable non-ester containing linkers include, but are not limited to, an amido linker moiety, an amino linker moiety, a carbonyl linker moiety, a carbamate linker moiety, a urea linker moiety, an ether linker moiety, a disulphide linker moiety, a succinamidyl linker moiety, and combinations thereof. In a preferred embodiment, the non-ester containing linker moiety is a carbamate linker moiety (i.e., a PEG-C-DAA conjugate). In another preferred embodiment, the non-ester containing linker moiety is an amido linker moiety (i.e., a PEG-A-DAA conjugate). In yet another preferred embodiment, the non-ester containing linker moiety is a succinamidyl linker moiety (i.e., a PEG-S-DAA conjugate).

In particular embodiments, the PEG-lipid conjugate is selected from:

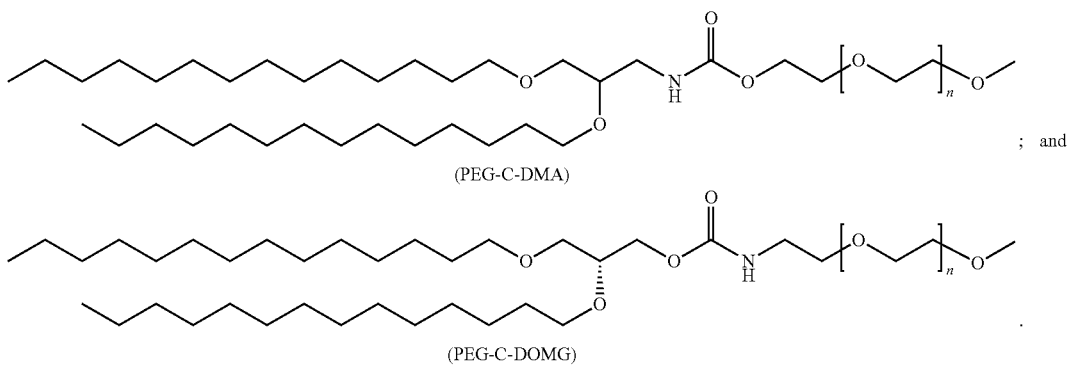

(PEG-C-DMA); and (PEG-C-DOMG)

The PEG-DAA conjugates are synthesized using standard techniques and reagents known to those of skill in the art. It will be recognized that the PEG-DAA conjugates will contain various amide, amine, ether, thio, carbamate, and urea linkages. Those of skill in the art will recognize that methods and reagents for forming these bonds are well known and readily available. See, e.g., March, ADVANCED ORGANIC CHEMISTRY (Wiley 1992); Larock, COMPREHENSIVE ORGANIC TRANSFORMATIONS (VCH 1989); and Furniss, VOGEL'S TEXTBOOK OF PRACTICAL ORGANIC CHEMISTRY, 5th ed. (Longman 1989). It will also be appreciated that any functional groups present may require protection and deprotection at different points in the synthesis of the PEG-DAA conjugates. Those of skill in the art will recognize that such techniques are well known. See, e.g., Green and Wuts, PROTECTIVE GROUPS IN ORGANIC SYNTHESIS (Wiley 1991).

Preferably, the PEG-DAA conjugate is a PEG-didecyloxypropyl ($C_{10}$) conjugate, a PEG-dilauryloxypropyl ($C_{12}$) conjugate, a PEG-dimyristyloxypropyl ($C_{14}$) conjugate, a PEG-dipalmityloxypropyl ($C_{16}$) conjugate, or a PEG-distearyloxypropyl ($C_{18}$) conjugate. In these embodiments, the PEG preferably has an average molecular weight of about 750 or about 2,000 daltons. In one particularly preferred embodiment, the PEG-lipid conjugate comprises PEG2000-C-DMA, wherein the "2000" denotes the average molecular weight of the PEG, the "C" denotes a carbamate linker moiety, and the "DMA" denotes dimyristyloxypropyl. In another particularly preferred embodiment, the PEG-lipid conjugate comprises PEG750-C-DMA, wherein the "750" denotes the average molecular weight of the PEG, the "C" denotes a carbamate linker moiety, and the "DMA" denotes dimyristyloxypropyl. In particular embodiments, the terminal hydroxyl group of the PEG is substituted with a methyl group. Those of skill in the art will readily appreciate that other dialkyloxypropyls can be used in the PEG-DAA conjugates of the present invention.

In addition to the foregoing, it will be readily apparent to those of skill in the art that other hydrophilic polymers can be used in place of PEG. Examples of suitable polymers that can be used in place of PEG include, but are not limited to, polyvinylpyrrolidone, polymethyloxazoline, polyethyloxazoline, polyhydroxypropyl methacrylamide, polymethacrylamide and polydimethylacrylamide, polylactic acid, polyglycolic acid, and derivatized celluloses such as hydroxymethylcellulose or hydroxyethylcellulose.

In addition to the foregoing components, the lipid particles (e.g., SNALP) of the present invention can further comprise cationic poly(ethylene glycol) (PEG) lipids or CPLs (see, e.g., Chen et al., Bioconj. Chem., 11:433-437 (2000); U.S. Pat. No. 6,852,334; PCT Publication No. WO 00/62813, the disclosures of which are herein incorporated by reference in their entirety for all purposes).

Suitable CPLs include compounds of Formula VI:

A-W-Y    (VI), wherein A, W, and Y are as described below.

With reference to Formula VI, "A" is a lipid moiety such as an amphipathic lipid, a neutral lipid, or a hydrophobic lipid that acts as a lipid anchor. Suitable lipid examples include, but are not limited to, diacylglycerolyls, dialkylglycerolyls, N—N-dialkylaminos, 1,2-diacyloxy-3-aminopropanes, and 1,2-dialkyl-3-aminopropanes.

"W" is a polymer or an oligomer such as a hydrophilic polymer or oligomer. Preferably, the hydrophilic polymer is a biocompatible polymer that is nonimmunogenic or possesses low inherent immunogenicity. Alternatively, the hydrophilic polymer can be weakly antigenic if used with appropriate adjuvants. Suitable nonimmunogenic polymers include, but are not limited to, PEG, polyamides, polylactic acid, polyglycolic acid, polylactic acid/polyglycolic acid copolymers, and combinations thereof. In a preferred embodiment, the polymer has a molecular weight of from about 250 to about 7,000 daltons.

"Y" is a polycationic moiety. The term polycationic moiety refers to a compound, derivative, or functional group having a positive charge, preferably at least 2 positive charges at a selected pH, preferably physiological pH. Suitable polycationic moieties include basic amino acids and their derivatives such as arginine, asparagine, glutamine, lysine, and histidine; spermine; spermidine; cationic dendrimers; polyamines; polyamine sugars; and amino polysaccharides. The polycationic moieties can be linear, such as linear tetralysine, branched or dendrimeric in structure. Polycationic moieties have between about 2 to about 15 positive charges, preferably between about 2 to about 12 positive charges, and more preferably between about 2 to about 8 positive charges at selected pH values. The selection of which polycationic moiety to employ may be determined by the type of particle application which is desired.

The charges on the polycationic moieties can be either distributed around the entire particle moiety, or alternatively, they can be a discrete concentration of charge density in one particular area of the particle moiety e.g., a charge spike. If the charge density is distributed on the particle, the charge density can be equally distributed or unequally distributed. All variations of charge distribution of the polycationic moiety are encompassed by the present invention.

The lipid "A" and the nonimmunogenic polymer "W" can be attached by various methods and preferably by covalent attachment. Methods known to those of skill in the art can be used for the covalent attachment of "A" and "W." Suitable linkages include, but are not limited to, amide, amine, carboxyl, carbonate, carbamate, ester, and hydrazone linkages. It will be apparent to those skilled in the art that "A" and "W" must have complementary functional groups to effectuate the linkage. The reaction of these two groups, one on the lipid and the other on the polymer, will provide the desired linkage. For example, when the lipid is a diacylglycerol and the terminal hydroxyl is activated, for instance with NHS and DCC, to form an active ester, and is then reacted with a polymer which contains an amino group, such as with a polyamide (see, e.g., U.S. Pat. Nos. 6,320,017 and 6,586,559, the disclosures of which are herein incorporated by reference in their entirety for all purposes), an amide bond will form between the two groups.

In certain instances, the polycationic moiety can have a ligand attached, such as a targeting ligand or a chelating moiety for complexing calcium. Preferably, after the ligand is attached, the cationic moiety maintains a positive charge. In certain instances, the ligand that is attached has a positive charge. Suitable ligands include, but are not limited to, a compound or device with a reactive functional group and include lipids, amphipathic lipids, carrier compounds, bio-affinity compounds, biomaterials, biopolymers, biomedical devices, analytically detectable compounds, therapeutically active compounds, enzymes, peptides, proteins, antibodies, immune stimulators, radiolabels, fluorogens, biotin, drugs, haptens, DNA, RNA, polysaccharides, liposomes, virosomes, micelles, immunoglobulins, functional groups, other targeting moieties, or toxins.

In some embodiments, the lipid conjugate (e.g., PEG-lipid) comprises from about 0.1 mol % to about 2 mol %, from about 0.5 mol % to about 2 mol %, from about 1 mol % to about 2 mol %, from about 0.6 mol % to about 1.9 mol %, from about 0.7 mol % to about 1.8 mol %, from about 0.8 mol % to about 1.7 mol %, from about 0.9 mol % to about 1.6 mol %, from about 0.9 mol % to about 1.8 mol %, from about 1 mol % to about 1.8 mol %, from about 1 mol % to about 1.7 mol %, from about 1.2 mol % to about 1.8 mol %, from about 1.2 mol % to about 1.7 mol %, from about 1.3 mol % to about 1.6 mol %, or from about 1.4 mol % to about 1.5 mol % (or any fraction thereof or range therein) of the total lipid present in the particle.

In other embodiments, the lipid conjugate (e.g., PEG-lipid) comprises from about 0 mol % to about 20 mol %, from about 0.5 mol % to about 20 mol %, from about 2 mol % to about 20 mol %, from about 1.5 mol % to about 18 mol %, from about 2 mol % to about 15 mol %, from about 4 mol % to about 15 mol %, from about 2 mol % to about 12 mol %, from about 5 mol % to about 12 mol %, or about 2 mol % (or any fraction thereof or range therein) of the total lipid present in the particle.

In further embodiments, the lipid conjugate (e.g., PEG-lipid) comprises from about 4 mol % to about 10 mol %, from about 5 mol % to about 10 mol %, from about 5 mol % to about 9 mol %, from about 5 mol % to about 8 mol %, from about 6 mol % to about 9 mol %, from about 6 mol % to about 8 mol %, or about 5 mol %, 6 mol %, 7 mol %, 8 mol %, 9 mol %, or 10 mol % (or any fraction thereof or range therein) of the total lipid present in the particle.

Additional examples, percentages, and/or ranges of lipid conjugates suitable for use in the lipid particles of the present invention are described in, e.g., PCT Publication No. WO 09/127060, U.S. Provisional Application No. 61/184,652, filed Jun. 5, 2009, U.S. Provisional Application No. 61/295,134, filed Jan. 14, 2010, U.S. Provisional Application No. 61/222,469, filed Jul. 1, 2009, U.S. Provisional Application No. 61/294,828, filed Jan. 13, 2010, U.S. Provisional Application No. 61/295,140, filed Jan. 14, 2010, and PCT Publication No. WO 2010/006282, the disclosures of which are herein incorporated by reference in their entirety for all purposes.

It should be understood that the percentage of lipid conjugate (e.g., PEG-lipid) present in the lipid particles of the invention is a target amount, and that the actual amount of lipid conjugate present in the formulation may vary, for example, by ±2 mol %. For example, in the 1:57 lipid particle (e.g., SNALP) formulation, the target amount of lipid conjugate is 1.4 mol %, but the actual amount of lipid conjugate may be ±0.5 mol %, ±0.4 mol %, ±0.3 mol %, ±0.2 mol %, ±0.1 mol %, or ±0.05 mol % of that target amount, with the balance of the formulation being made up of other lipid components (adding up to 100 mol % of total lipids present in the particle). Similarly, in the 7:54 lipid particle (e.g., SNALP) formulation, the target amount of lipid conjugate is 6.76 mol %, but the actual amount of lipid conjugate may be ±2 mol %, ±1.5 mol %, ±1 mol %, ±0.75 mol %, ±0.5 mol %, ±0.25 mol %, or ±0.1 mol % of that target amount, with the balance of the formulation being made up of other lipid components (adding up to 100 mol % of total lipids present in the particle).

One of ordinary skill in the art will appreciate that the concentration of the lipid conjugate can be varied depending on the lipid conjugate employed and the rate at which the lipid particle is to become fusogenic.

By controlling the composition and concentration of the lipid conjugate, one can control the rate at which the lipid conjugate exchanges out of the lipid particle and, in turn, the rate at which the lipid particle becomes fusogenic. For instance, when a PEG-DAA conjugate is used as the lipid conjugate, the rate at which the lipid particle becomes fusogenic can be varied, for example, by varying the concentration of the lipid conjugate, by varying the molecular weight of the PEG, or by varying the chain length and degree of saturation of the alkyl groups on the PEG-DAA conjugate. In addition, other variables including, for example, pH, temperature, ionic strength, etc. can be used to vary and/or control the rate at which the lipid particle becomes fusogenic. Other methods which can be used to control the rate at which the lipid particle becomes fusogenic will become apparent to those of skill in the art upon reading this disclosure. Also, by controlling the composition and concentration of the lipid conjugate, one can control the lipid particle (e.g., SNALP) size.

VI. Preparation of Lipid Particles

The lipid particles of the present invention, e.g., SNALP, in which an active agent or therapeutic agent such as an interfering RNA (e.g., siRNA) is entrapped within the lipid portion of the particle and is protected from degradation, can be formed by any method known in the art including, but not limited to, a continuous mixing method, a direct dilution process, and an in-line dilution process.

In particular embodiments, the cationic lipids may comprise one or more of the cationic lipids described herein or salts thereof, alone or in combination with other cationic lipids. In other embodiments, the non-cationic lipids are egg sphingomyelin (ESM), distearoylphosphatidylcholine (DSPC), dioleoylphosphatidylcholine (DOPC), 1-palmitoyl-2-oleoyl-phosphatidylcholine (POPC), dipalmitoyl-phosphatidylcholine (DPPC), monomethyl-phosphatidylethanolamine, dimethyl-phosphatidylethanolamine, 14:0 PE (1,2-dimyristoyl-phosphatidylethanolamine (DMPE)), 16:0 PE (1,2-dipalmitoyl-phosphatidylethanolamine (DPPE)), 18:0 PE (1,2-distearoyl-phosphatidylethanolamine (DSPE)), 18:1 PE (1,2-dioleoyl-phosphatidylethanolamine (DOPE)), 18:1 trans PE (1,2-dielaidoyl-phosphatidylethanolamine (DEPE)), 18:0-18:1 PE (1-stearoyl-2-oleoyl-phosphatidylethanolamine (SOPE)), 16:0-18:1 PE (1-palmitoyl-2-oleoyl-phosphatidylethanolamine (POPE)), polyethylene glycol-based polymers (e.g., PEG 2000, PEG 5000, PEG-modified diacylglycerols, or PEG-modified dialkyloxypropyls), cholesterol, derivatives thereof, or combinations thereof.

In a preferred embodiment, the present invention provides nucleic acid-lipid particles (e.g., SNALP) produced via a direct dilution process that includes forming a lipid vesicle (e.g., a non-lamellar lipid particle) solution and immediately and directly introducing the lipid vesicle solution into a collection vessel containing a controlled amount of dilution buffer. In preferred aspects, the collection vessel includes one or more elements configured to stir the contents of the collection vessel to facilitate dilution. In one aspect, the amount of dilution buffer present in the collection vessel is substantially equal to the volume of lipid vesicle solution introduced thereto. As a non-limiting example, a lipid vesicle solution in 45% ethanol when introduced into the collection vessel containing an equal volume of dilution buffer will advantageously yield smaller particles.

In a preferred embodiment, the present invention provides nucleic acid-lipid particles (e.g., SNALP) produced via an in-line dilution process in which a third reservoir containing dilution buffer is fluidly coupled to a second mixing region. In this embodiment, the lipid vesicle (e.g., non-lamellar lipid particle) solution formed in a first mixing region is immediately and directly mixed with dilution buffer in the second mixing region. In preferred aspects, the second mixing region includes a T-connector arranged so that the lipid vesicle solution and the dilution buffer flows meet as opposing 1800 flows; however, connectors providing shallower angles can be used, e.g., from about 270 to about 180° (e.g., about 90°). A pump mechanism delivers a controllable flow of buffer to the second mixing region. In one aspect, the flow rate of dilution buffer provided to the second mixing region is controlled to be substantially equal to the flow rate of lipid vesicle solution introduced thereto from the first mixing region. This embodiment advantageously allows for more control of the flow of dilution buffer mixing with the lipid vesicle solution in the second mixing region, and therefore also the concentration of lipid vesicle solution in buffer throughout the second mixing process. Such control of the dilution buffer flow rate advantageously allows for small particle size formation at reduced concentrations.

These processes and the apparatuses for carrying out these direct dilution and in-line dilution processes are described in detail in U.S. Patent Publication No. 20070042031, the disclosure of which is herein incorporated by reference in its entirety for all purposes.

The nucleic acid-lipid particles formed using the direct dilution and in-line dilution processes typically have a size of from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, less than about 120 nm, 110 nm, 100 nm, 90 nm, or 80 nm, or about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm (or any fraction thereof or range therein). The particles thus formed do not aggregate and are optionally sized to achieve a uniform particle size.

In other embodiments, the present invention provides nucleic acid-lipid particles (e.g., SNALP) produced via a continuous mixing method, e.g., a process that includes providing an aqueous solution comprising a nucleic acid (e.g., interfering RNA) in a first reservoir, providing an organic lipid solution in a second reservoir (wherein the lipids present in the organic lipid solution are solubilized in an organic solvent, e.g., a lower alkanol such as ethanol), and mixing the aqueous solution with the organic lipid solution such that the organic lipid solution mixes with the aqueous solution so as to substantially instantaneously produce a lipid vesicle (e.g., liposome) encapsulating the nucleic acid within the lipid vesicle. This process and the apparatus for carrying out this process are described in detail in U.S. Patent Publication No. 20040142025, the disclosure of which is herein incorporated by reference in its entirety for all purposes.

The action of continuously introducing lipid and buffer solutions into a mixing environment, such as in a mixing chamber, causes a continuous dilution of the lipid solution with the buffer solution, thereby producing a lipid vesicle substantially instantaneously upon mixing. As used herein, the phrase "continuously diluting a lipid solution with a buffer solution" (and variations) generally means that the lipid solution is diluted sufficiently rapidly in a hydration process with sufficient force to effectuate vesicle generation. By mixing the aqueous solution comprising a nucleic acid with the organic lipid solution, the organic lipid solution undergoes a continuous stepwise dilution in the presence of the buffer solution (i.e., aqueous solution) to produce a nucleic acid-lipid particle.

The nucleic acid-lipid particles formed using the continuous mixing method typically have a size of from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, less than about 120 nm, 110 nm, 100 nm, 90 nm, or 80 nm, or about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm (or any fraction thereof or range therein). The particles thus formed do not aggregate and are optionally sized to achieve a uniform particle size.

If needed, the lipid particles of the invention (e.g., SNALP) can be sized by any of the methods available for sizing liposomes. The sizing may be conducted in order to achieve a desired size range and relatively narrow distribution of particle sizes.

Several techniques are available for sizing the particles to a desired size. One sizing method, used for liposomes and equally applicable to the present particles, is described in U.S. Pat. No. 4,737,323, the disclosure of which is herein incorporated by reference in its entirety for all purposes. Sonicating a particle suspension either by bath or probe sonication produces a progressive size reduction down to particles of less than about 50 nm in size. Homogenization is another method which relies on shearing energy to fragment larger particles into smaller ones. In a typical homogenization procedure, particles are recirculated through a standard emulsion homogenizer until selected particle sizes, typically between about 60 and about 80 nm, are observed. In both methods, the particle size distribution can be monitored by conventional laser-beam particle size discrimination, or QELS.

Extrusion of the particles through a small-pore polycarbonate membrane or an asymmetric ceramic membrane is also an effective method for reducing particle sizes to a relatively well-defined size distribution. Typically, the suspension is cycled through the membrane one or more times until the desired particle size distribution is achieved. The particles may be extruded through successively smaller-pore membranes, to achieve a gradual reduction in size.

In some embodiments, the nucleic acids present in the particles are precondensed as described in, e.g., U.S. patent application Ser. No. 09/744,103, the disclosure of which is herein incorporated by reference in its entirety for all purposes.

In other embodiments, the methods may further comprise adding non-lipid polycations which are useful to effect the lipofection of cells using the present compositions. Examples of suitable non-lipid polycations include, hexadimethrine bromide (sold under the brand name POLYBRENE®, from Aldrich Chemical Co., Milwaukee, Wisconsin, USA) or other salts of hexadimethrine. Other suitable polycations include, for example, salts of poly-L-ornithine, poly-L-arginine, poly-L-lysine, poly-D-lysine, polyallylamine, and polyethyleneimine. Addition of these salts is preferably after the particles have been formed.

In some embodiments, the nucleic acid to lipid ratios (mass/mass ratios) in a formed nucleic acid-lipid particle (e.g., SNALP) will range from about 0.01 to about 0.2, from about 0.05 to about 0.2, from about 0.02 to about 0.1, from about 0.03 to about 0.1, or from about 0.01 to about 0.08. The ratio of the starting materials (input) also falls within this range. In other embodiments, the particle preparation uses about 400 μg nucleic acid per 10 mg total lipid or a nucleic acid to lipid mass ratio of about 0.01 to about 0.08 and, more preferably, about 0.04, which corresponds to 1.25 mg of total lipid per 50 μg of nucleic acid. In other preferred embodiments, the particle has a nucleic acid:lipid mass ratio of about 0.08.

In other embodiments, the lipid to nucleic acid ratios (mass/mass ratios) in a formed nucleic acid-lipid particle (e.g., SNALP) will range from about 1 (1:1) to about 100 (100:1), from about 5 (5:1) to about 100 (100:1), from about 1 (1:1) to about 50 (50:1), from about 2 (2:1) to about 50 (50:1), from about 3 (3:1) to about 50 (50:1), from about 4 (4:1) to about 50 (50:1), from about 5 (5:1) to about 50 (50:1), from about 1 (1:1) to about 25 (25:1), from about 2 (2:1) to about 25 (25:1), from about 3 (3:1) to about 25 (25:1), from about 4 (4:1) to about 25 (25:1), from about 5 (5:1) to about 25 (25:1), from about 5 (5:1) to about 20 (20:1), from about 5 (5:1) to about 15 (15:1), from about 5 (5:1) to about 10 (10:1), or about 5 (5:1), 6 (6:1), 7 (7:1), 8 (8:1), 9 (9:1), 10 (10:1), 11 (11:1), 12 (12:1), 13 (13:1), 14 (14:1), 15 (15:1), 16 (16:1), 17 (17:1), 18 (18:1), 19 (19:1), 20 (20:1), 21 (21:1), 22 (22:1), 23 (23:1), 24 (24:1), or 25 (25:1), or any fraction thereof or range therein. The ratio of the starting materials (input) also falls within this range.

As previously discussed, the conjugated lipid may further include a CPL. A variety of general methods for making SNALP-CPLs (CPL-containing SNALP) are discussed herein. Two general techniques include the "post-insertion" technique, that is, insertion of a CPL into, for example, a pre-formed SNALP, and the "standard" technique, wherein the CPL is included in the lipid mixture during, for example, the SNALP formation steps. The post-insertion technique results in SNALP having CPLs mainly in the external face of the SNALP bilayer membrane, whereas standard techniques provide SNALP having CPLs on both internal and external faces. The method is especially useful for vesicles made from phospholipids (which can contain cholesterol) and also for vesicles containing PEG-lipids (such as PEG-DAAs and PEG-DAGs). Methods of making SNALP-CPLs are taught, for example, in U.S. Pat. Nos. 5,705,385; 6,586,410; 5,981,501; 6,534,484; and 6,852,334; U.S. Patent Publication No. 20020072121; and PCT Publication No. WO 00/62813, the disclosures of which are herein incorporated by reference in their entirety for all purposes.

VII. Kits

The present invention also provides lipid particles (e.g., SNALP) in kit form. In some embodiments, the kit comprises a container which is compartmentalized for holding the various elements of the lipid particles (e.g., the active agents or therapeutic agents such as nucleic acids and the individual lipid components of the particles). Preferably, the kit comprises a container (e.g., a vial or ampoule) which holds the lipid particles of the invention (e.g., SNALP), wherein the particles are produced by one of the processes set forth herein. In certain embodiments, the kit may further comprise an endosomal membrane destabilizer (e.g., calcium ions). The kit typically contains the particle compositions of the invention, either as a suspension in a pharmaceutically acceptable carrier or in dehydrated form, with instructions for their rehydration (if lyophilized) and administration.

The lipid particles of the present invention can be tailored to preferentially target particular tissues, organs, or tumors of interest. In some instances, the 1:57 lipid particle (e.g., SNALP) formulation can be used to preferentially target the liver (e.g., normal liver tissue). In other instances, the 7:54 lipid particle (e.g., SNALP) formulation can be used to preferentially target solid tumors such as liver tumors and tumors outside of the liver. In preferred embodiments, the kits of the invention comprise these liver-directed and/or tumor-directed lipid particles, wherein the particles are present in a container as a suspension or in dehydrated form.

In certain other instances, it may be desirable to have a targeting moiety attached to the surface of the lipid particle to further enhance the targeting of the particle. Methods of attaching targeting moieties (e.g., antibodies, proteins, etc.) to lipids (such as those used in the present particles) are known to those of skill in the art.

VIII. Administration of Lipid Particles

Once formed, the lipid particles of the invention (e.g., SNALP) are useful for the introduction of active agents or therapeutic agents (e.g., nucleic acids such as interfering RNA) into cells. Accordingly, the present invention also provides methods for introducing an active agent or therapeutic agent such as a nucleic acid (e.g., interfering RNA) into a cell. In some instances, the cell is a liver cell such as, e.g., a hepatocyte present in liver tissue. In other instances, the cell is a tumor cell such as, e.g., a tumor cell present in a solid tumor. The methods are carried out in vitro or in vivo by first forming the particles as described above and then contacting the particles with the cells for a period of time sufficient for delivery of the active agent or therapeutic agent to the cells to occur.

The lipid particles of the invention (e.g., SNALP) can be adsorbed to almost any cell type with which they are mixed or contacted. Once adsorbed, the particles can either be endocytosed by a portion of the cells, exchange lipids with cell membranes, or fuse with the cells. Transfer or incorporation of the active agent or therapeutic agent (e.g., nucleic acid) portion of the particle can take place via any one of these pathways. In particular, when fusion takes place, the particle membrane is integrated into the cell membrane and the contents of the particle combine with the intracellular fluid.

The lipid particles of the invention (e.g., SNALP) can be administered either alone or in a mixture with a pharmaceutically acceptable carrier (e.g., physiological saline or phosphate buffer) selected in accordance with the route of administration and standard pharmaceutical practice. Generally, normal buffered saline (e.g., 135-150 mM NaCl) will be employed as the pharmaceutically acceptable carrier. Other suitable carriers include, e.g., water, buffered water, 0.4% saline, 0.3% glycine, and the like, including glycoproteins for enhanced stability, such as albumin, lipoprotein, globulin, etc. Additional suitable carriers are described in, e.g., REMINGTON'S PHARMACEUTICAL SCIENCES, Mack Publishing Company, Philadelphia, PA, 17th ed. (1985). As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The phrase "pharmaceutically acceptable" refers to molecular entities and compositions that do not produce an allergic or similar untoward reaction when administered to a human.

The pharmaceutically acceptable carrier is generally added following lipid particle formation. Thus, after the lipid particle (e.g., SNALP) is formed, the particle can be diluted into pharmaceutically acceptable carriers such as normal buffered saline.

The concentration of particles in the pharmaceutical formulations can vary widely, i.e., from less than about 0.05%, usually at or at least about 2 to 5%, to as much as about 10 to 90% by weight, and will be selected primarily by fluid volumes, viscosities, etc., in accordance with the particular mode of administration selected. For example, the concentration may be increased to lower the fluid load associated with treatment. This may be particularly desirable in patients having atherosclerosis-associated congestive heart failure or severe hypertension. Alternatively, particles composed of irritating lipids may be diluted to low concentrations to lessen inflammation at the site of administration.

The pharmaceutical compositions of the present invention may be sterilized by conventional, well-known sterilization techniques. Aqueous solutions can be packaged for use or filtered under aseptic conditions and lyophilized, the lyophilized preparation being combined with a sterile aqueous solution prior to administration. The compositions can contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, and calcium chloride. Additionally, the particle suspension may include lipid-protective agents which protect lipids against free-radical and lipid-peroxidative damages on storage. Lipophilic free-radical quenchers, such as alphatocopherol, and water-soluble iron-specific chelators, such as ferrioxamine, are suitable.

In some embodiments, the lipid particles of the invention (e.g., SNALP) are particularly useful in methods for the therapeutic delivery of one or more nucleic acids comprising an interfering RNA sequence (e.g., siRNA). In particular, it is an object of this invention to provide in vitro and in vivo methods for treatment of a disease or disorder in a mammal (e.g., a rodent such as a mouse or a primate such as a human, chimpanzee, or monkey) by downregulating or silencing the transcription and/or translation of one or more target nucleic acid sequences or genes of interest. As a non-limiting example, the methods of the invention are useful for in vivo delivery of interfering RNA (e.g., siRNA) to the liver and/or tumor of a mammalian subject. In certain embodiments, the disease or disorder is associated with expression and/or overexpression of a gene and expression or overexpression of the gene is reduced by the interfering RNA (e.g., siRNA). In certain other embodiments, a therapeutically effective amount of the lipid particle may be administered to the mammal. In some instances, an interfering RNA (e.g., siRNA) is formulated into a SNALP, and the particles are administered to patients requiring such treatment. In other instances, cells are removed from a patient, the interfering RNA is delivered in vitro (e.g., using a SNALP described herein), and the cells are reinjected into the patient.

A. In vivo Administration

Systemic delivery for in vivo therapy, e.g., delivery of a therapeutic nucleic acid to a distal target cell via body systems such as the circulation, has been achieved using nucleic acid-lipid particles such as those described in PCT Publication Nos. WO 05/007196, WO 05/121348, WO 05/120152, and WO 04/002453, the disclosures of which are herein incorporated by reference in their entirety for all purposes. The present invention also provides fully encapsulated lipid particles that protect the nucleic acid from nuclease degradation in serum, are non-immunogenic, are small in size, and are suitable for repeat dosing.

For in vivo administration, administration can be in any manner known in the art, e.g., by injection, oral administration, inhalation (e.g., intranasal or intratracheal), transdermal application, or rectal administration. Administration can be accomplished via single or divided doses. The pharmaceutical compositions can be administered parenterally, i.e., intraarticularly, intravenously, intraperitoneally, subcutaneously, or intramuscularly. In some embodiments, the pharmaceutical compositions are administered intravenously or intraperitoneally by a bolus injection (see, e.g., U.S. Pat. No. 5,286,634). Intracellular nucleic acid delivery has also been discussed in Straubringer et al., *Methods Enzymol.*, 101:512 (1983); Mannino et al., *Biotechniques*, 6:682 (1988); Nicolau et al., *Crit. Rev. Ther. Drug Carrier Syst.*, 6:239 (1989); and Behr, *Acc. Chem. Res.*, 26:274 (1993). Still other methods of administering lipid-based therapeutics are described in, for example, U.S. Pat. Nos. 3,993,754; 4,145,410; 4,235,871; 4,224,179; 4,522,803; and 4,588,578. The lipid particles can be administered by direct injection at the site of disease or by injection at a site distal from the site of disease (see, e.g., Culver, HUMAN GENE THERAPY, MaryAnn Liebert, Inc., Publishers, New York. pp. 70-71(1994)). The disclosures of the above-described references are herein incorporated by reference in their entirety for all purposes.

In embodiments where the lipid particles of the present invention (e.g., SNALP) are administered intravenously, at least about 5%, 10%, 15%, 20%, or 25% of the total injected dose of the particles is present in plasma about 8, 12, 24, 36, or 48 hours after injection. In other embodiments, more than about 20%, 30%, 40% and as much as about 60%, 70% or 80% of the total injected dose of the lipid particles is present in plasma about 8, 12, 24, 36, or 48 hours after injection. In certain instances, more than about 10% of a plurality of the particles is present in the plasma of a mammal about 1 hour after administration. In certain other instances, the presence of the lipid particles is detectable at least about 1 hour after administration of the particle. In certain embodiments, the presence of a therapeutic agent such as a nucleic acid is detectable in cells of the lung, liver, tumor, or at a site of inflammation at about 8, 12, 24, 36, 48, 60, 72 or 96 hours after administration. In other embodiments, downregulation of expression of a target sequence by an interfering RNA (e.g., siRNA) is detectable at about 8, 12, 24, 36, 48, 60, 72 or 96 hours after administration. In yet other embodiments, downregulation of expression of a target sequence by an interfering RNA (e.g., siRNA) occurs preferentially in liver cells (e.g., hepatocytes), tumor cells, or in cells at a site of inflammation. In further embodiments, the presence or effect of an interfering RNA (e.g., siRNA) in cells at a site proximal or distal to the site of administration or in cells of the lung, liver, or a tumor is detectable at about 12, 24, 48, 72, or 96 hours, or at about 6, 8, 10, 12, 14, 16, 18, 19, 20, 22, 24, 26, or 28 days after administration. In additional embodiments, the lipid particles (e.g., SNALP) of the invention are administered parenterally or intraperitoneally.

The compositions of the present invention, either alone or in combination with other suitable components, can be made into aerosol formulations (i.e., they can be "nebulized") to be administered via inhalation (e.g., intranasally or intratracheally) (see, Brigham et al., *Am. J. Sci.,* 298:278 (1989)). Aerosol formulations can be placed into pressurized acceptable propellants, such as dichlorodifluoromethane, propane, nitrogen, and the like.

In certain embodiments, the pharmaceutical compositions may be delivered by intranasal sprays, inhalation, and/or other aerosol delivery vehicles. Methods for delivering nucleic acid compositions directly to the lungs via nasal aerosol sprays have been described, e.g., in U.S. Pat. Nos. 5,756,353 and 5,804,212. Likewise, the delivery of drugs using intranasal microparticle resins and lysophosphatidylglycerol compounds (U.S. Pat. No. 5,725,871) are also well-known in the pharmaceutical arts. Similarly, transmucosal drug delivery in the form of a polytetrafluoroetheylene support matrix is described in U.S. Pat. No. 5,780,045. The disclosures of the above-described patents are herein incorporated by reference in their entirety for all purposes.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions are preferably administered, for example, by intravenous infusion, orally, topically, intraperitoneally, intravesically, or intrathecally.

Generally, when administered intravenously, the lipid particle formulations are formulated with a suitable pharmaceutical carrier. Many pharmaceutically acceptable carriers may be employed in the compositions and methods of the present invention. Suitable formulations for use in the present invention are found, for example, in REMINGTON'S PHARMACEUTICAL SCIENCES, Mack Publishing Company, Philadelphia, PA, 17th ed. (1985). A variety of aqueous carriers may be used, for example, water, buffered water, 0.4% saline, 0.3% glycine, and the like, and may include glycoproteins for enhanced stability, such as albumin, lipoprotein, globulin, etc. Generally, normal buffered saline (135-150 mM NaCl) will be employed as the pharmaceutically acceptable carrier, but other suitable carriers will suffice. These compositions can be sterilized by conventional liposomal sterilization techniques, such as filtration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc. These compositions can be sterilized using the techniques referred to above or, alternatively, they can be produced under sterile conditions. The resulting aqueous solutions may be packaged for use or filtered under aseptic conditions and lyophilized, the lyophilized preparation being combined with a sterile aqueous solution prior to administration.

In certain applications, the lipid particles disclosed herein may be delivered via oral administration to the individual. The particles may be incorporated with excipients and used in the form of ingestible tablets, buccal tablets, troches, capsules, pills, lozenges, elixirs, mouthwash, suspensions, oral sprays, syrups, wafers, and the like (see, e.g., U.S. Pat. Nos. 5,641,515, 5,580,579, and 5,792,451, the disclosures of which are herein incorporated by reference in their entirety for all purposes). These oral dosage forms may also contain the following: binders, gelatin; excipients, lubricants, and/or flavoring agents. When the unit dosage form is a capsule, it may contain, in addition to the materials described above, a liquid carrier. Various other materials may be present as coatings or to otherwise modify the physical form of the dosage unit. Of course, any material used in preparing any unit dosage form should be pharmaceutically pure and substantially non-toxic in the amounts employed.

Typically, these oral formulations may contain at least about 0.1% of the lipid particles or more, although the percentage of the particles may, of course, be varied and may conveniently be between about 1% or 2% and about 60% or 70% or more of the weight or volume of the total formulation. Naturally, the amount of particles in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

Formulations suitable for oral administration can consist of: (a) liquid solutions, such as an effective amount of a packaged therapeutic agent such as nucleic acid (e.g., interfering RNA) suspended in diluents such as water, saline, or PEG 400; (b) capsules, sachets, or tablets, each containing a predetermined amount of a therapeutic agent such as nucleic acid (e.g., interfering RNA), as liquids, solids, granules, or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise a therapeutic agent such as nucleic acid (e.g., interfering RNA) in a flavor, e.g., sucrose, as well as pastilles comprising the therapeutic agent in an inert base, such as gelatin and glycerin or sucrose and acacia emulsions, gels, and the like containing, in addition to the therapeutic agent, carriers known in the art.

In another example of their use, lipid particles can be incorporated into a broad range of topical dosage forms. For instance, a suspension containing nucleic acid-lipid particles such as SNALP can be formulated and administered as gels, oils, emulsions, topical creams, pastes, ointments, lotions, foams, mousses, and the like.

When preparing pharmaceutical preparations of the lipid particles of the invention, it is preferable to use quantities of the particles which have been purified to reduce or eliminate empty particles or particles with therapeutic agents such as nucleic acid associated with the external surface.

The methods of the present invention may be practiced in a variety of hosts. Preferred hosts include mammalian species, such as primates (e.g., humans and chimpanzees as well as other nonhuman primates), canines, felines, equines, bovines, ovines, caprines, rodents (e.g., rats and mice), lagomorphs, and swine.

The amount of particles administered will depend upon the ratio of therapeutic agent (e.g., nucleic acid) to lipid, the particular therapeutic agent (e.g., nucleic acid) used, the disease or disorder being treated, the age, weight, and condition of the patient, and the judgment of the clinician, but will generally be between about 0.01 and about 50 mg per kilogram of body weight, preferably between about 0.1 and about 5 mg/kg of body weight, or about $10^8$-$10^{10}$ particles per administration (e.g., injection).

B. In Vitro Administration

For in vitro applications, the delivery of therapeutic agents such as nucleic acids (e.g., interfering RNA) can be to any cell grown in culture, whether of plant or animal origin, vertebrate or invertebrate, and of any tissue or type. In preferred embodiments, the cells are animal cells, more preferably mammalian cells, and most preferably human cells (e.g., tumor cells or hepatocytes).

Contact between the cells and the lipid particles, when carried out in vitro, takes place in a biologically compatible medium. The concentration of particles varies widely depending on the particular application, but is generally between about 1 μmol and about 10 mmol. Treatment of the cells with the lipid particles is generally carried out at physiological temperatures (about 37° C.) for periods of time of from about 1 to 48 hours, preferably of from about 2 to 4 hours.

In one group of preferred embodiments, a lipid particle suspension is added to 60-80% confluent plated cells having a cell density of from about $10^3$ to about $10^5$ cells/ml, more preferably about $2 \times 10^4$ cells/ml. The concentration of the suspension added to the cells is preferably of from about 0.01 to 0.2 μg/ml, more preferably about 0.1 μg/ml.

To the extent that tissue culture of cells may be required, it is well-known in the art. For example, Freshney, Culture of Animal Cells, a Manual of Basic Technique, 3rd Ed., Wiley-Liss, New York (1994), Kuchler et al., Biochemical Methods in Cell Culture and Virology, Dowden, Hutchinson and Ross, Inc. (1977), and the references cited therein provide a general guide to the culture of cells. Cultured cell systems often will be in the form of monolayers of cells, although cell suspensions are also used.

Using an Endosomal Release Parameter (ERP) assay, the delivery efficiency of the SNALP or other lipid particle of the invention can be optimized. An ERP assay is described in detail in U.S. Patent Publication No. 20030077829, the disclosure of which is herein incorporated by reference in its entirety for all purposes. More particularly, the purpose of an ERP assay is to distinguish the effect of various cationic lipids and helper lipid components of SNALP or other lipid particle based on their relative effect on binding/uptake or fusion with/destabilization of the endosomal membrane. This assay allows one to determine quantitatively how each component of the SNALP or other lipid particle affects delivery efficiency, thereby optimizing the SNALP or other lipid particle. Usually, an ERP assay measures expression of a reporter protein (e.g., luciferase, 0-galactosidase, green fluorescent protein (GFP), etc.), and in some instances, a SNALP formulation optimized for an expression plasmid will also be appropriate for encapsulating an interfering RNA. In other instances, an ERP assay can be adapted to measure downregulation of transcription or translation of a target sequence in the presence or absence of an interfering RNA (e.g., siRNA). By comparing the ERPs for each of the various SNALP or other lipid particles, one can readily determine the optimized system, e.g., the SNALP or other lipid particle that has the greatest uptake in the cell.

C. Cells for Delivery of Lipid Particles

The compositions and methods of the present invention are used to treat a wide variety of cell types, in vivo and in vitro. Suitable cells include, but are not limited to, hepatocytes, reticuloendothelial cells (e.g., monocytes, macrophages, etc.), fibroblast cells, endothelial cells, platelet cells, other cell types infected and/or susceptible of being infected with viruses, hematopoietic precursor (stem) cells, keratinocytes, skeletal and smooth muscle cells, osteoblasts, neurons, quiescent lymphocytes, terminally differentiated cells, slow or noncycling primary cells, parenchymal cells, lymphoid cells, epithelial cells, bone cells, and the like.

In particular embodiments, an active agent or therapeutic agent such as a nucleic acid (e.g., an interfering RNA) is delivered to cancer cells (e.g., cells of a solid tumor) including, but not limited to, liver cancer cells, lung cancer cells, colon cancer cells, rectal cancer cells, anal cancer cells, bile duct cancer cells, small intestine cancer cells, stomach (gastric) cancer cells, esophageal cancer cells, gallbladder cancer cells, pancreatic cancer cells, appendix cancer cells, breast cancer cells, ovarian cancer cells, cervical cancer cells, prostate cancer cells, renal cancer cells, cancer cells of the central nervous system, glioblastoma tumor cells, skin cancer cells, lymphoma cells, choriocarcinoma tumor cells, head and neck cancer cells, osteogenic sarcoma tumor cells, and blood cancer cells.

In vivo delivery of lipid particles such as SNALP encapsulating a nucleic acid (e.g., an interfering RNA) is suited for targeting cells of any cell type. The methods and compositions can be employed with cells of a wide variety of vertebrates, including mammals, such as, e.g, canines, felines, equines, bovines, ovines, caprines, rodents (e.g., mice, rats, and guinea pigs), lagomorphs, swine, and primates (e.g. monkeys, chimpanzees, and humans).

D. Detection of Lipid Particles

In some embodiments, the lipid particles of the present invention (e.g., SNALP) are detectable in the subject at about 1, 2, 3, 4, 5, 6, 7, 8 or more hours. In other embodiments, the lipid particles of the present invention (e.g., SNALP) are detectable in the subject at about 8, 12, 24, 48, 60, 72, or 96 hours, or about 6, 8, 10, 12, 14, 16, 18, 19, 22, 24, 25, or 28 days after administration of the particles. The presence of the particles can be detected in the cells, tissues, or other biological samples from the subject.

The particles may be detected, e.g., by direct detection of the particles, detection of a therapeutic nucleic acid such as an interfering RNA (e.g., siRNA) sequence, detection of the target sequence of interest (i.e., by detecting expression or reduced expression of the sequence of interest), or a combination thereof.

1. Detection of Particles

Lipid particles of the invention such as SNALP can be detected using any method known in the art. For example, a label can be coupled directly or indirectly to a component of the lipid particle using methods well-known in the art. A wide variety of labels can be used, with the choice of label depending on sensitivity required, ease of conjugation with the lipid particle component, stability requirements, and available instrumentation and disposal provisions. Suitable labels include, but are not limited to, spectral labels such as fluorescent dyes (e.g., fluorescein and derivatives, such as fluorescein isothiocyanate (FITC) and Oregon Green™; rhodamine and derivatives such Texas red, tetrarhodimine isothiocynate (TRITC), etc., digoxigenin, biotin, phycoerythrin, AMCA, CyDyes™, and the like; radiolabels such as $^3$H, $^{125}$I, $^{35}$S, $^{14}$C, $^{32}$P, $^{33}$P, etc.; enzymes such as horse radish peroxidase, alkaline phosphatase, etc.; spectral colorimetric labels such as colloidal gold or colored glass or plastic beads such as polystyrene, polypropylene, latex, etc. The label can be detected using any means known in the art.

2. Detection of Nucleic Acids

Nucleic acids (e.g., interfering RNA) are detected and quantified herein by any of a number of means well-known to those of skill in the art. The detection of nucleic acids may proceed by well-known methods such as Southern analysis, Northern analysis, gel electrophoresis, PCR, radiolabeling, scintillation counting, and affinity chromatography. Additional analytic biochemical methods such as spectrophotometry, radiography, electrophoresis, capillary electrophoresis, high performance liquid chromatography (HPLC), thin layer chromatography (TLC), and hyperdiffusion chromatography may also be employed.

The selection of a nucleic acid hybridization format is not critical. A variety of nucleic acid hybridization formats are known to those skilled in the art. For example, common formats include sandwich assays and competition or displacement assays. Hybridization techniques are generally described in, e.g., "Nucleic Acid Hybridization, A Practical Approach," Eds. Hames and Higgins, IRL Press (1985).

The sensitivity of the hybridization assays may be enhanced through the use of a nucleic acid amplification system which multiplies the target nucleic acid being detected. In vitro amplification techniques suitable for amplifying sequences for use as molecular probes or for generating nucleic acid fragments for subsequent subcloning are known. Examples of techniques sufficient to direct persons of skill through such in vitro amplification methods, including the polymerase chain reaction (PCR), the ligase chain reaction (LCR), Qβ-replicase amplification, and other RNA polymerase mediated techniques (e.g., NASBA™) are found in Sambrook et al., *In Molecular Cloning: A Laboratory Manual*, Cold Spring Harbor Laboratory Press (2000); and Ausubel et al., SHORT PROTOCOLS IN MOLECULAR BIOLOGY, eds., *Current Protocols*, Greene Publishing Associates, Inc. and John Wiley & Sons, Inc. (2002); as well as U.S. Pat. No. 4,683,202; PCR Protocols, A Guide to Methods and Applications (Innis et al. eds.) Academic Press Inc. San Diego, CA (1990); Arnheim & Levinson (Oct. 1, 1990), C&EN36; *The Journal Of NIH Research*, 3:81 (1991); Kwoh et al., *Proc. Natl. Acad. Sci. USA*, 86:1173 (1989); Guatelli et al., *Proc. Natl. Acad. Sci. USA*, 87:1874 (1990); Lomell et al., *J. Clin. Chem.*, 35:1826 (1989); Landegren et al., *Science*, 241:1077 (1988); *Van Brunt, Biotechnology*, 8:291 (1990); Wu and Wallace, *Gene*, 4:560 (1989); Barringer et al., *Gene*, 89:117 (1990); and Sooknanan and Malek, *Biotechnology*, 13:563 (1995). Improved methods of cloning in vitro amplified nucleic acids are described in U.S. Pat. No. 5,426,039. Other methods described in the art are the nucleic acid sequence based amplification (NASBA™, Cangene, Mississauga, Ontario) and Qβ-replicase systems. These systems can be used to directly identify mutants where the PCR or LCR primers are designed to be extended or ligated only when a select sequence is present. Alternatively, the select sequences can be generally amplified using, for example, nonspecific PCR primers and the amplified target region later probed for a specific sequence indicative of a mutation. The disclosures of the above-described references are herein incorporated by reference in their entirety for all purposes.

Nucleic acids for use as probes, e.g., in in vitro amplification methods, for use as gene probes, or as inhibitor components are typically synthesized chemically according to the solid phase phosphoramidite triester method described by Beaucage et al., *Tetrahedron Letts.*, 22:1859 1862 (1981), e.g., using an automated synthesizer, as described in Needham VanDevanter et al., *Nucleic Acids Res.*, 12:6159 (1984). Purification of polynucleotides, where necessary, is typically performed by either native acrylamide gel electrophoresis or by anion exchange HPLC as described in Pearson et al., *J. Chrom.*, 255:137 149 (1983). The sequence of the synthetic polynucleotides can be verified using the chemical degradation method of Maxam and Gilbert (1980) in Grossman and Moldave (eds.) Academic Press, New York, *Methods in Enzymology*, 65:499.

An alternative means for determining the level of transcription is in situ hybridization. In situ hybridization assays are well-known and are generally described in Angerer et al., *Methods Enzymol.*, 152:649 (1987). In an in situ hybridization assay, cells are fixed to a solid support, typically a glass slide. If DNA is to be probed, the cells are denatured with heat or alkali. The cells are then contacted with a hybridization solution at a moderate temperature to permit annealing of specific probes that are labeled. The probes are preferably labeled with radioisotopes or fluorescent reporters.

IX. Examples

The present invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

Example 1. Characterization of SNALP Structure

This example demonstrates that by controlling the lipid composition of the SNALP formulation as well as the particle formation process, novel non-lamellar lipid nanoparticles (e.g., SNALP) can be produced that have enhanced activity. In this example, SNALP formulations of varying compositions were prepared using either a Stepwise Dilution Method or a Direct Dilution Method to study the effects the manufacturing process and/or the lipid composition had on particle size, encapsulation efficiency and morphology.

Figure 1A:
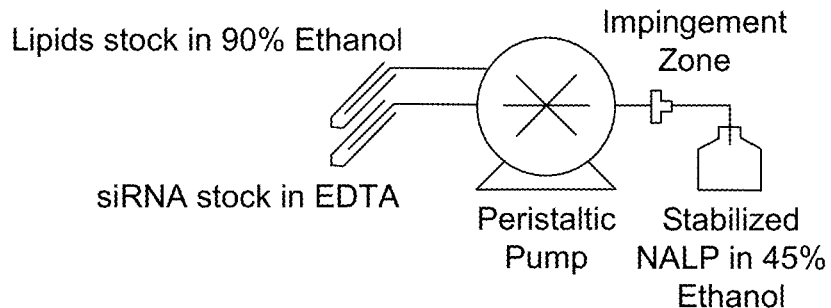
FIG. 1A shows a schematic of the Stepwise Dilution Method (SDM) or, alternatively, Lipomixer I method, used to make SNALP formulations.
Figure 1A:
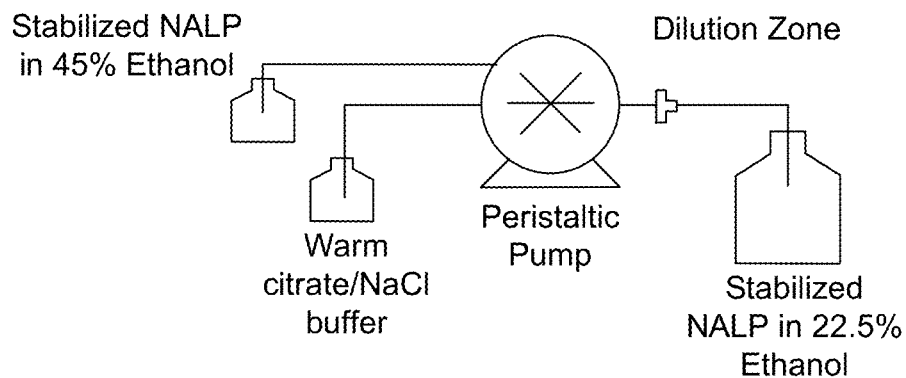

The Stepwise Dilution Method ("SDM"), which is also referred to herein as the Lipomixer I process, as well as the apparatuses for carrying out the SDM are described in detail in U.S. Patent Publication No. 20040142025 and in Jeffs, et al., "A Scalable, Extrusion-Free Method for Efficient Liposomal Encapsulation of Plasmid DNA," *Pharmaceutical Research,* 2005, Vol. 22, No. 3 pp 362-372, the disclosures of both of which are herein incorporated by reference in their entirety for all purposes. As illustrated in FIG. 1A, in the Stepwise Dilution method, a nucleic acid solution (e.g., ApoB-8, 100 mM EDTA, nuclease-free water) is blended with an equal volume of warmed lipid stock solution in 90% ethanol at 75 mL/min using a Watson-Marlow peristaltic pump. The blended solution, i.e., Stabilized NALP in 45% ethanol, is further diluted with an equal volume of warmed citrate/NaCl buffer at 75 mL/min, resulting in Stabilized NALP in 22.5% ethanol. The ethanol is removed from the stabilized NALP formulation by TFU hoop cartridges.

Figure 1B:
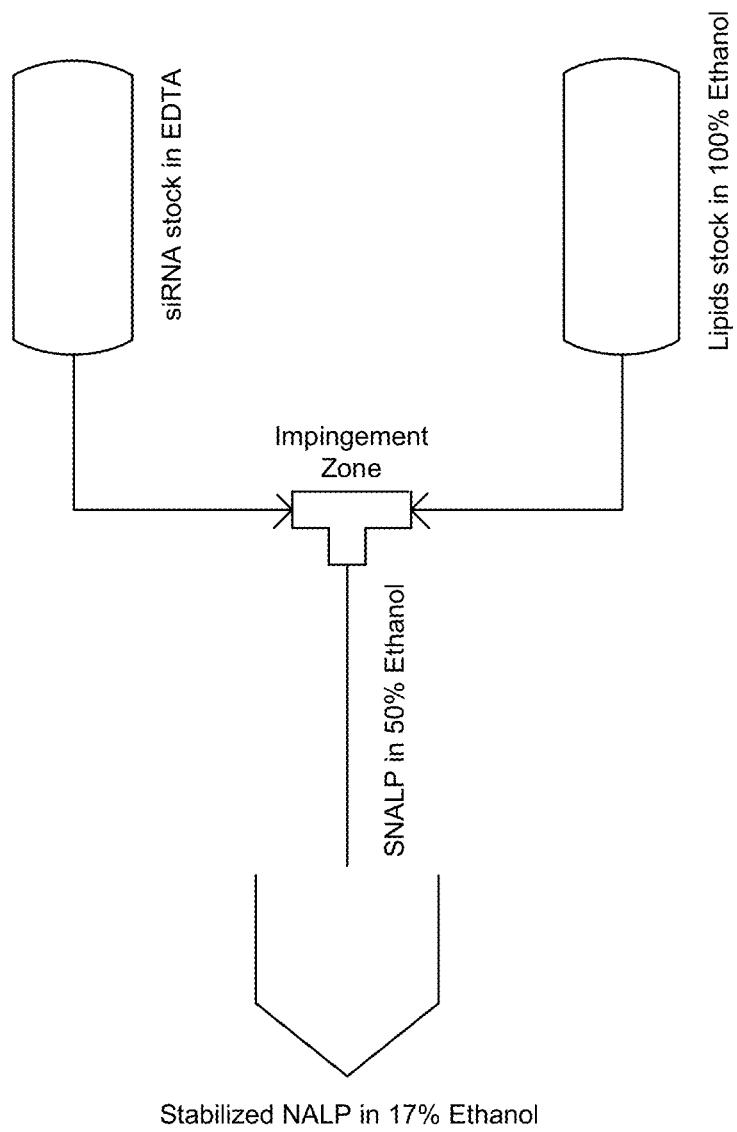
FIG. 1B illustrates a schematic of the Direct Dilution Method (DDM) or, alternatively, the Lipomixer II method used to make SNALP formulations.

The Direct Dilution Method ("DDM"), which is also referred to herein as the Lipomixer II process, as well as the apparatuses for carrying out the DDM are described in detail in U.S. Patent Publication No. 20070042031, the disclosure of which is herein incorporated by reference in its entirety for all purposes. As illustrated in FIG. 1B, in the Direct Dilution method, equal volumes of nucleic acid solution (e.g., ApoB-8, 100 mM EDTA, nuclease-free water) and lipid stock solution were blended at 200 mL/min using an automated syringe press (i.e., "Lipobot"), and diluted directly into PBS. The ethanol is removed from the stabilized NALP formulation by TFU hoop cartridge.

Table 1 sets forth a comparison of the process parameters for the Stepwise Dilution and Direct Dilution methods.

TABLE 1

Process Parameters for the Stepwise Dilution and Direct Dilution Methods

|  | SDM | DDM |
|---|---|---|
| Batch Size | 5-10 mg | 7-10 mg |
| Lipid Stocks | 90% ethanol | 100% ethanol |
| Equipment | Peristaltic Pump | Automated Syringe Press "Lipobot" |
| Blending Rate | 75 mL/min | 200 mL/min |
| T-connector | 1.6 mm ID | 200 mL/min |
| Dilution Buffer | 20 nM citrate/ 300 mM NaCl, pH | PBS, pH 7.4 |

All SNALP formulations used in this study were prepared with an siRNA targeting apolipoprotein B (ApoB) as the nucleic acid component. ApoB is the main apolipoprotein of chylomicrons and low density lipoproteins (LDL). Mutations in ApoB are associated with hypercholesterolemia. ApoB occurs in the plasma in 2 main forms, ApoB48 and ApoB 100, which are synthesized in the intestine and liver, respectively, due to an organ-specific stop codon. The ApoB siRNA used in this study is provided in Table 2, and is referred to herein as "siApoB-8." The modifications involved introducing 2'OMe-uridine or 2'OMe-guanosine at selected positions in the sense and antisense strands of the ApoB siRNA sequence, in which the siRNA duplex contained less than about 2000 2'OMe-modified nucleotides.

TABLE 2 siRNA duplex comprising sense and antisense ApoB RNA polynucleotides.

| Position | Modification | ApoB siRNA sequence | % 2'OMe- Modified | % Modified in DS Region |
|---|---|---|---|---|
| 10048 | U2/2 G1/2 | 5'-AGUGUCAUCACACUGAAUACC-3' (SEQ ID NO: 3) 3'-GUUCACAGUAGUGUGACUUAU-5' (SEQ ID No: 4) | 7/42 = 16.7% | 7/38 = 18.4% |

Column 1:
The number refers to the nucleotide position of the 5' base of the sense strand relative to the mouse ApoB mRNA sequence XM_137955.
Column 2:
The numbers refer to the distribution of 2'OMe chemical modifications in each strand.
Column 3:
2'OMe-modified nucleotides are indicated in bold and underlined. The siRNA duplex can alternatively or additionally comprise 2'-deoxy-2'-fluoro (2'F) nucleotides, 2'-deoxynucleotides, 2'-O-(2-methoxyethyl) (MOE) nucleotides, and/or locked nucleic acid (LNA) nucleotides.
Column 4:
The number and percentage of 2'OMe-modified nucleotides in the siRNA duplex are provided.
Column 5:
The number and percentage of modified nucleotides in the double-stranded (DS) region of the siRNA duplex are provided.

Regardless of the SNALP manufacturing process employed or the specific SNALP formulation screened, all SNALP formulations contained siApoB-8 as the nucleic acid component, and all SNALP formulations contained the following lipid components: the PEG-lipid conjugate PEG-cDMA (3-N-[(−Methoxypoly(ethylene glycol)2000)carbamoyl]-1,2-dimyristyloxypropylamine); the cationic lipid DLinDMA (1,2-Dilinoleyloxy-3-(N,N-dimethyl)aminopropane); the phospholipid DSPC (1,2-Distearoyl-sn-glycero-3-phosphocholine; Avanti Polar Lipids; Alabaster, AL); and synthetic cholesterol (Sigma-Aldrich Corp.; St. Louis, MO). The siRNAs were encapsulated into SNALP in one of the following formulations (all of which are described in molar percentages): (i) the "10:15" formulation: 10% PEG-cDMA;

15% DLinDMA; 20% DSPC; and 55% cholesterol (ii) the "2:30" formulation: 2% PEG-C-DMA, 30% DLinDMA, 20% DSPC, and 48% cholesterol; (iii) the "2:40" formulation: 1.4% PEG-cDMA; 57.1% DLinDMA; 7.1% DSPC; and 34.3% cholesterol; (iii) the "1:57" formulation: 1.4% PEG-cDMA; 57.1% DLinDMA; 7.1% DSPC; and 34.3% cholesterol; or (iv) the "1:62" formulation: 1.5% PEG-cDMA, 62 mol % DLinDMA, and 37% cholesterol. These various formulations are summarized in tabular form in Table 3.

TABLE 3

Lipid Components of SNALP Formulations

| | PEG2000-C-DMA (mol %) | DLinDMA (mol %) | Cholesterol (mol %) | DSPC (mol %) |
|---|---|---|---|---|
| 10:15 | 10 | 15 | 55 | 20 |
| 2:30 | 2 | 30 | 48 | 20 |
| 2:40 | 2 | 40 | 48 | 10 |
| 1:57 | 1.4 | 57 | 34 | 7 |
| 1:62 | 1.5 | 62 | 37 | 0 |

The lipid components and physical characteristics of the formulations prepared by the Stepwise Dilution Method are summarized in Table 4. The lipid:drug ratio is described in units of mg total lipid per mg nucleic acid. Mean particle size and polydispersity were measured on a Malvern Instruments Zetasizer. Encapsulation of nucleic acid was measured using a Ribogreen assay essentially as described in Heyes et al., *Journal of Controlled Release*, 107:276-287 (2005).

TABLE 4

Characterization of Formulations Prepared by Stepwise Dilution Method (SDM)

| Formulation (L/D) | Particle size (nm)/ Polydispersity | Initial Encapsulation (%) | Final Encapsulation (%) | Final L/D |
|---|---|---|---|---|
| 10:15 (L/D 16.4) | 93 (0.12) | 87 | 95 | 15.8 |
| 2:30 (L/D 12.9) | 95 (0.10) | 96 | 96 | 10.2 |
| 2:40 (L/D 12.5) | 114 (0.14) | 97 | 97 | 10.9 |
| 1:57 (L/D 9) | 116 (0.06) | 99 | 97 | 7.4 |
| 1:62 (L/D 8) | 108 (0.09) | 100 | 96 | 6.4 |

The particle size ranged from 93-116 nm, and the polydispersity values ranged from 0.06-0.14. Moreover, with the exception of the 10:15 formulation, all formulations had high initial encapsulation >95%.

The lipid components and physical characteristics of the formulations prepared by the Direct Dilution Method (DDM) are summarized in Table 5. As with Table 4, the lipid:drug ratio is described in units of mg total lipid per mg nucleic acid. Similarly, the mean particle size and polydispersity were measured on a Malvern Instruments Zetasizer, and the encapsulation of nucleic acid was measured using a Ribogreen assay essentially as described in Heyes et al., *Journal of Controlled Release*, 107:276-287 (2005).

TABLE 5

Characterization of Formulations Prepared By Direct Dilution Method (DDM)

| Formulation (L/D) | Particle size (nm)/ Polydispersity | Initial Encapsulation (%) | Final Encapsulation (%) | Final L/D |
|---|---|---|---|---|
| 10:15 (L/D 16.4) | 55 (0.09) | 30 | 94 | 47.2 |
| 2:30 (L/D 12.9) | 58 (0.07) | 97 | 97 | 11.6 |
| 2:40 (L/D 12.5) | 65 (0.11) | 95 | 97 | 12.3 |
| 1:57 (L/D 9) | 78 (0.03) | 93 | 96 | 8.5 |
| 1:62 (L/D 8) | 78 (0.04) | 86 | 97 | 8.7 |

The particle size ranged from 55-78 nm, and the polydispersity values ranged from 0.03-0.09. The 10:15 formulation had low encapsulation (30%) and high final L/D.

From Tables 4 and 5, it is apparent that SNALP prepared by DDM (Direct Dilution Method) possess smaller sizes and polydispersity values than those prepared by SDM (stepwise dilution method). Initial encapsulation for SDM formulations were generally higher than for DDM formulations, most likely due to the acidic blending conditions in SDM. Further, it is noted that the 10:15 SNALP prepared by DDM was problematic, with only 30% encapsulation and high final L/D ratio, an indication that this formulation is not compatible with this process method.

Example 2. Further Characterization of SNALP Structure Using Cryo-TEM

Figure 2A:
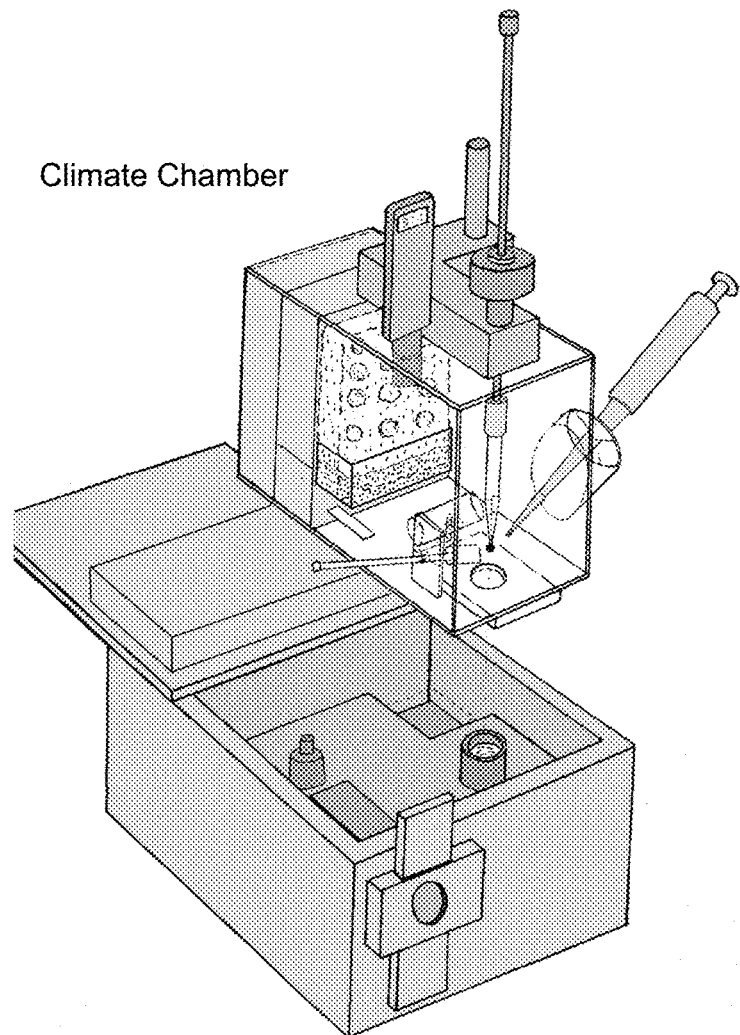
FIG. 2A-2C illustrates a schematic of an instrument used to carry out the Cryo-Transmission Electron Microscopy analysis of various SNALP formulations and the cryo vetrification technique employed.
Figure 2B:
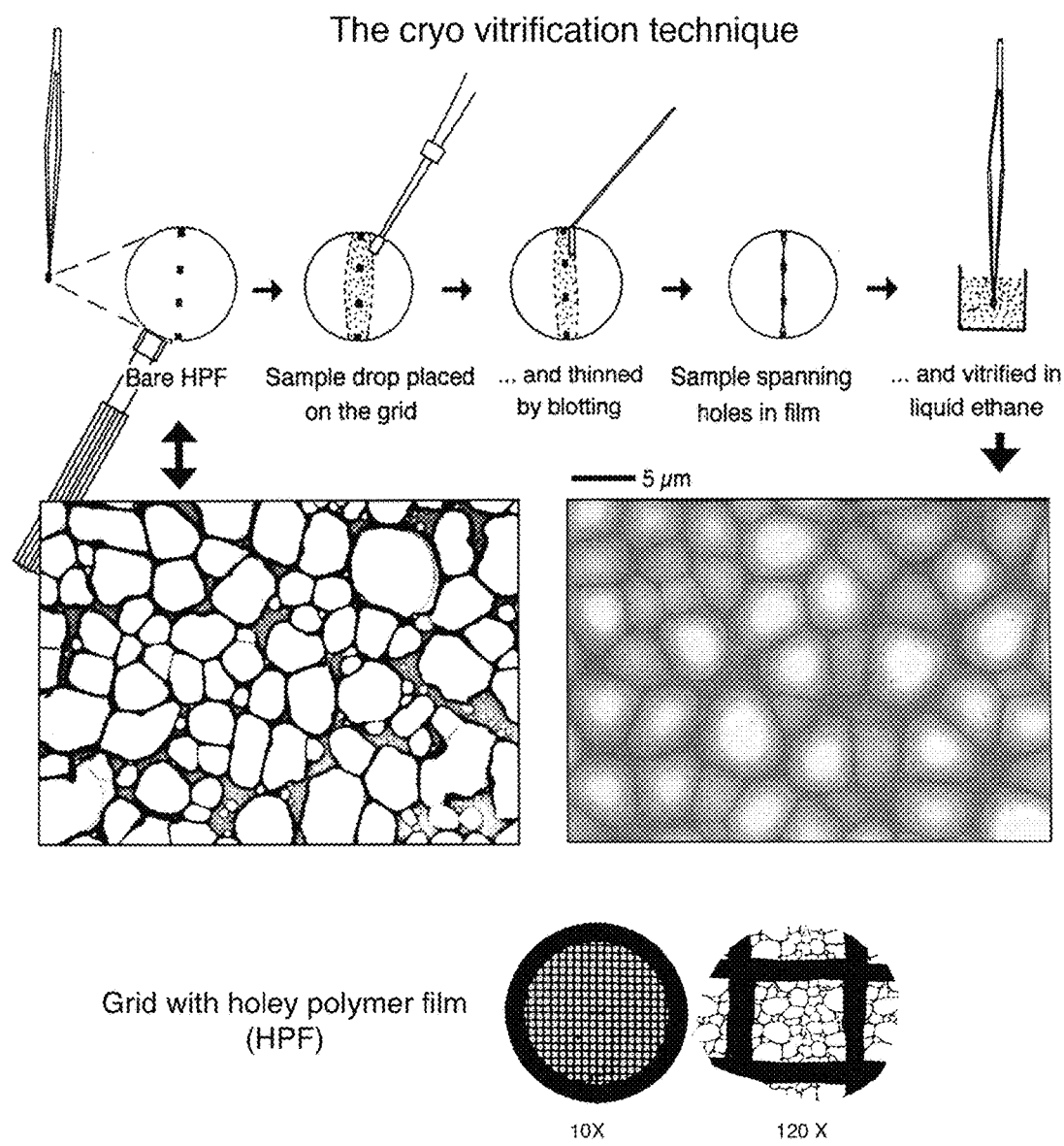
Figure 2C:
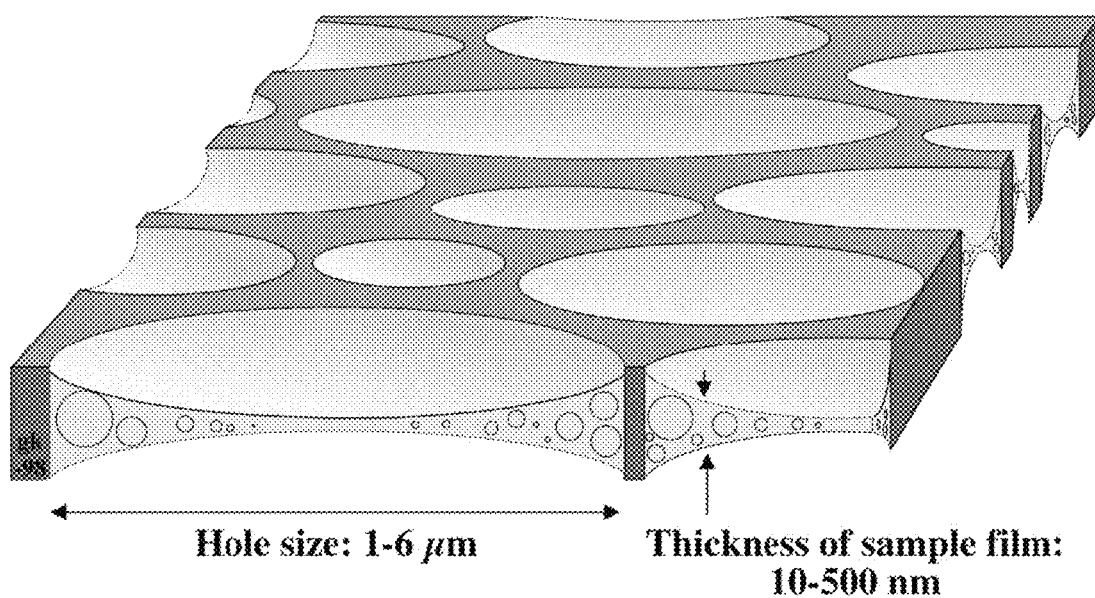

Various SNALP formulations prepared by the Stepwise Dilution Method and the Direct Dilution Method were further characterized by Cryo-Transmission Electron Microscopy ("Cryo-TEM"). As illustrated in FIGS. 2A-2C, Cryo-TEM is a microscopy technique, whereby a beam of electrons is transmitted through an ultra-thin frozen specimen, interacting with the specimen as it passes through. An image is then formed from the interaction of the electrons transmitted through the specimen, and the image is magnified and focused onto an imaging device.

Coded samples were sent to Uppsala University for Cryo-TEM imaging according to the method described by Almgren, M., et al., *Colloid Surf A* 174, 3-21 (2000). Briefly, the samples were incubated at 25° C. for 20-30 minutes before preparation. The climate chamber conditions were: 25° C., with >98% relative humidity. 0.5 μL of sample solution was deposited on copper grid with perforated polymer film. Excess solution was removed by blotting and the sample was vitrified in liquid ethane. Images at 100,000× total magnification were captured. Diametrical size of particles were calculated by number averaging (Scale Bars all=100 nm).

For all SNALP formulations analyzed, whether made by the SDM or the DDM, the resulting SNALP particles were categorized using the following criteria: (a) Non-lamellar particles: dense particles with no visible lamellar structures (e.g., no bilayers); and (b) Lamellar particles: particles possessing bilayer structures, including those with multiple compartments, LUVs and MLVs. It is noted that large structures with non-spherical, irregular shapes were not included as these were suspected to be artefacts. All SNALP samples analyzed contained 15 mg/mL total lipid and all samples were analyzed undiluted.

Table 6 sets forth the SNALP formulations prepared by the Stepwise Dilution Method (SDM) that were analyzed by Cryo-TEM.

TABLE 6

SNALP Formulations Prepared by SDM
and Analyzed by Cryo-TEM

| Lot No. | Composition |
| --- | --- |
| 284-050610-1 | 10:15 |
| 284-050610-2 | 2:30 |
| 284-050610-4 | 1:57 |
| 284-050610-5 | 1:62 |

Figure 3:
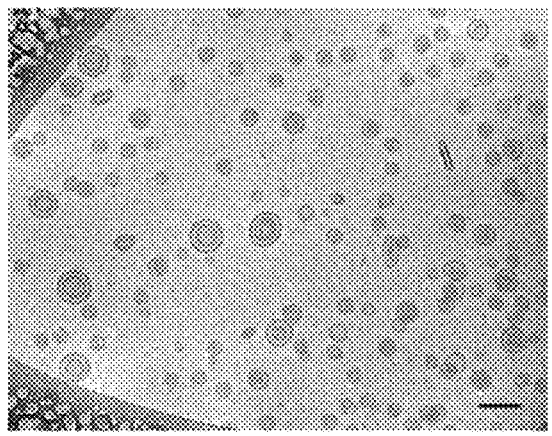
FIG. 3 shows Cryo-TEM data for the siApoB-8 10:15 SNALP formulation prepared by the Stepwise Dilution Method.
Figure 3:
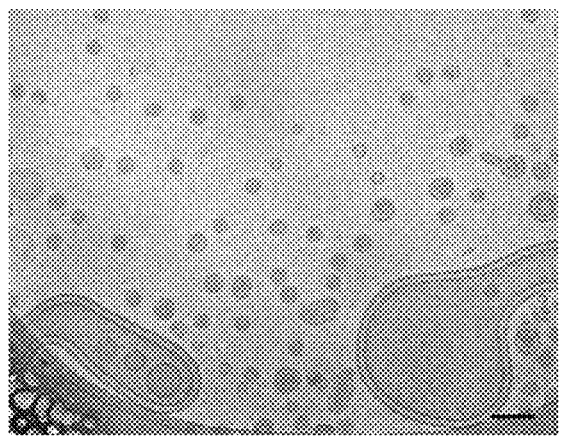
Figure 3:
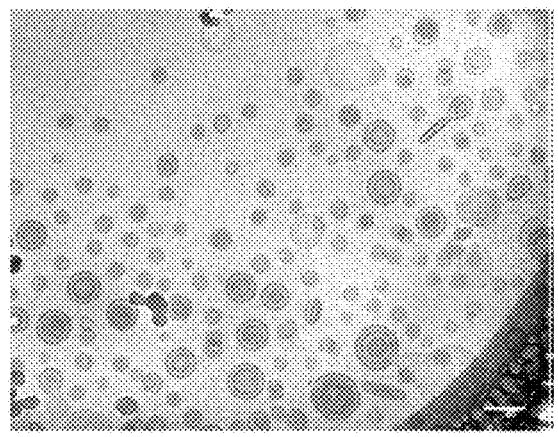

FIG. 3 sets forth representative Cryo-TEM data for the siApoB-8 10:15 SNALP formulation prepared by the Stepwise Dilution Method. It was found that spherical non-lamellar particles were more abundant (n=594) than lamellar particles (n=173). The particles varied in size, with rare large structures observed, which were thought to be artefacts.

Figure 4:
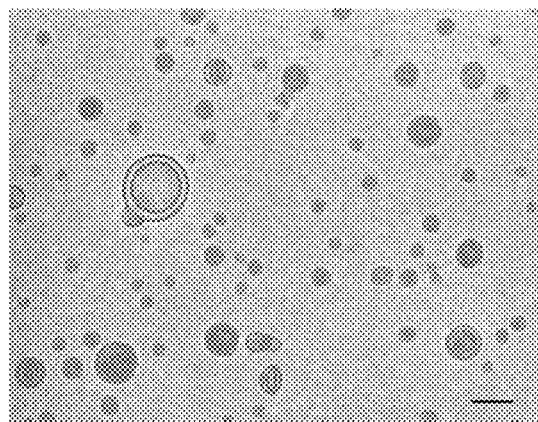
FIG. 4 shows Cryo-TEM data for the siApoB-8 2:30 SNALP formulation prepared by the Stepwise Dilution Method.
Figure 4:
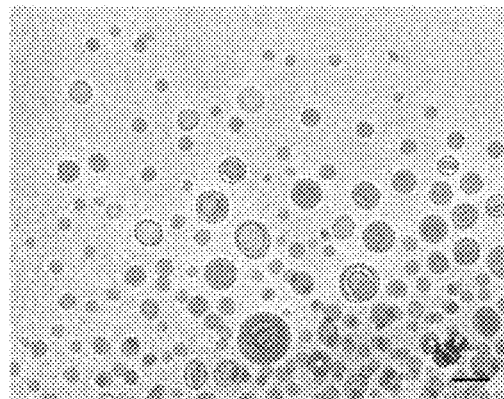
Figure 4:
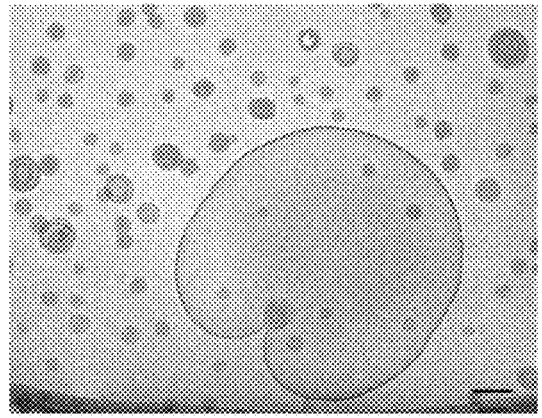

FIG. 4 sets forth representative Cryo-TEM data for the siApoB-8 2:30 SNALP formulation prepared by the Stepwise Dilution Method. This 2:30 SNALP formulation had similar heterogeneous particle morphology to that of the 10:15 formulation. It was found that non-lamellar particles were more abundant (n=665) than lamellar particles (n=67). The particles varied in size, with some non-spherical particles being observed.

Figure 5:
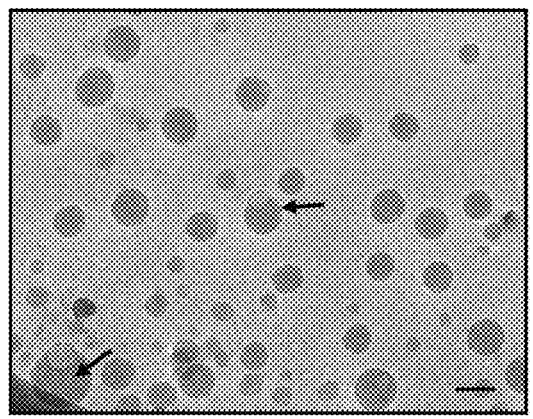
FIG. 5 shows representative Cryo-TEM data (3 images) for the siApoB-8 1:57 SNALP formulation prepared by the Stepwise Dilution Method. Examples of lamellar structures that possess non-lamellar compartments are marked with arrows.
Figure 5:
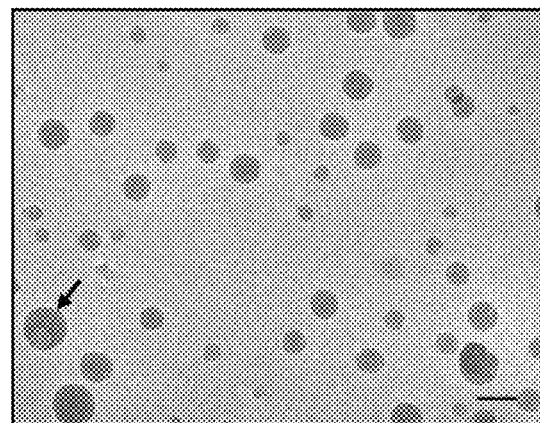
Figure 5:
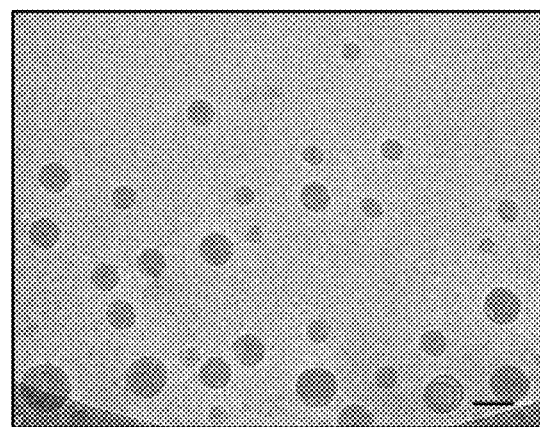

FIG. 5 sets forth representative Cryo-TEM data for the siApoB-8 1:57 formulation prepared by the Stepwise Dilution Method. It was found that predominantly (>95%) non-lamellar particles were present (325 of 341); however, approximately half of the lamellar structure possess non-lamellar compartments (see, examples marked with arrows in FIG. 5). It is clear from the Cryo-TEM data that the particles size is more homogeneous, with no large structures being found.

Figure 6:
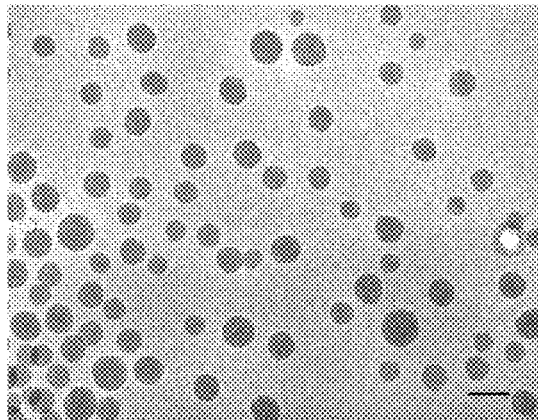
FIG. 6 shows representative Cryo-TEM data (3 images) for the siApoB-8 1:62 SNALP formulation prepared by the Stepwise Dilution Method. Examples of particles with dual compartments are marked with arrows.
Figure 6:
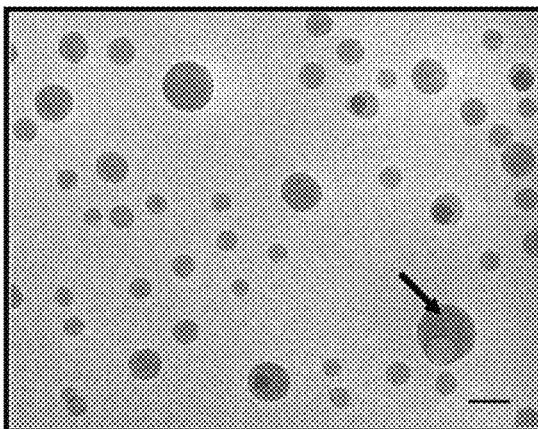
Figure 6:
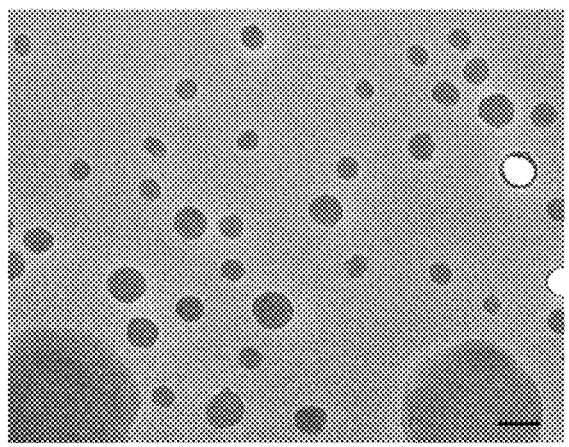

FIG. 6 sets forth representative Cryo-TEM data for the siApoB-8 1:62 formulation prepared by the Stepwise Dilution Method. The 1:62 SNALP formulation has similar particle morphology to the 1:57 formulation with >98% of the particles being non-lamellar particles (313 of 317). Similar to the 1:57 formulation, particle size is more homogeneous, with large particles rarely being found. Further, with the 1:62 formulation, fewer particles with dual compartments were present compared to the 1:57 formulation (see, examples marked with arrows in FIG. 6).

Figure 7:
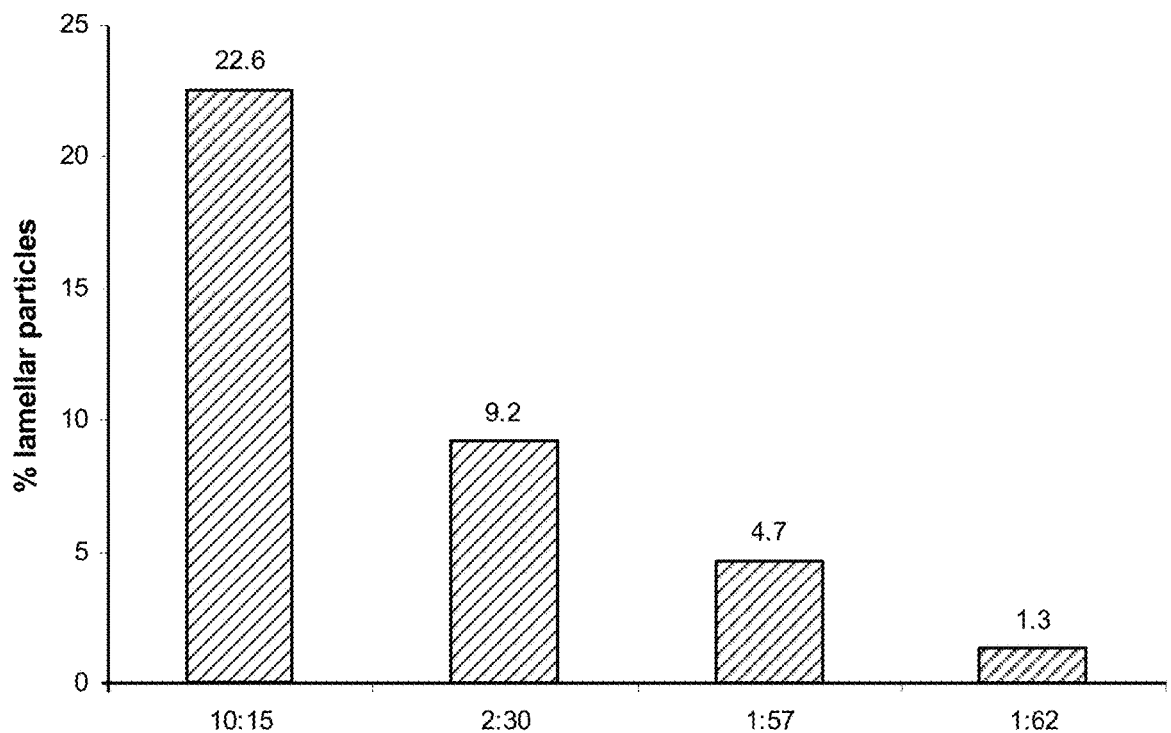
FIG. 7 shows the summary of particle morphology (non-lamellar particles vs. lamellar particles) for the 10:15, the 2:30, the 1:57 and the 1:62 formulations, all of which were prepared using the Stepwise Dilution Method. The 10:15, the 2:30, the 1:57 and the 1:62 formulations are plotted on the x-axis of the graph and the y-axis of the graph shows the % lamellar particles in each formulation.

FIG. 7 illustrates the presence of lamellar particles in the 10:15, the 2:30, the 1:57 and the 1:62 SNALP formulations prepared using the Stepwise Dilution Method. From FIG. 7, it is apparent that using the Stepwise Dilution Methodology, an increase in the molar percentage of cationic lipid in the SNALP formulation decreases the incidence of lamellar particles.

Table 7 sets forth the SNALP formulations prepared by the Direct Dilution Method (DDM) that were analyzed by Cryo-TEM.

TABLE 7

SNALP Formulations Prepared by DDM
and Analyzed by Cryo-TEM

| Lot No. | Composition |
| --- | --- |
| 280-060710-3 | 2:30 |
| 280-060710-2 | 2:40 |
| 280-060710-4 | 1:57 |
| 280-060710-5 | 1:62 |

Figure 8:
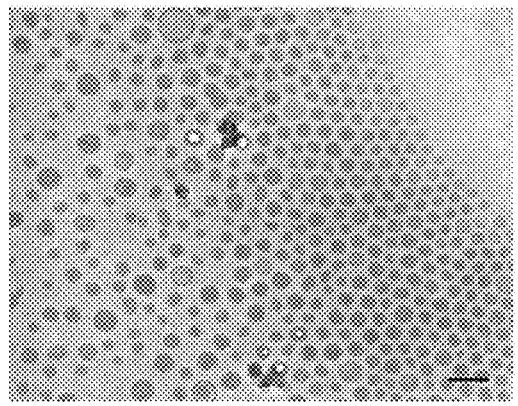
FIG. 8 shows representative Cryo-TEM data (3 images) for the siApoB-8 2:30 SNALP formulation prepared by the Direct Dilution Method. The vast majority of particles are non-lamellar (1386 of 1400).
Figure 8:
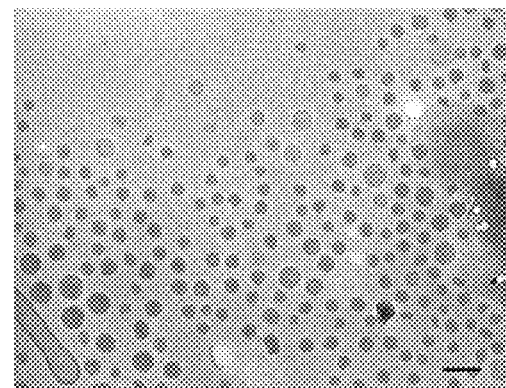
Figure 8:
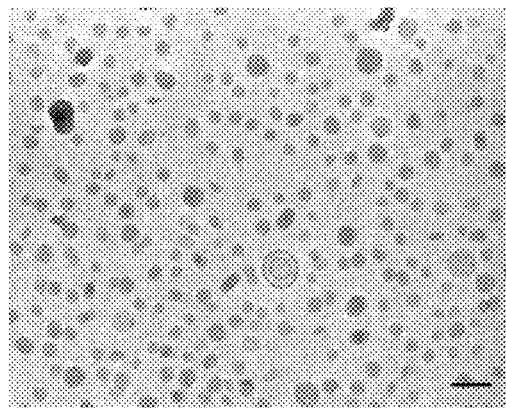

FIG. 8 sets forth representative Cryo-TEM data for the siApoB-8 2:30 formulation prepared by the Direct Dilution Method. As seen in FIG. 8, the vast majority of particles in the 2:30 SNALP formulation are non-lamellar (1386 of 1400).

Figure 9:
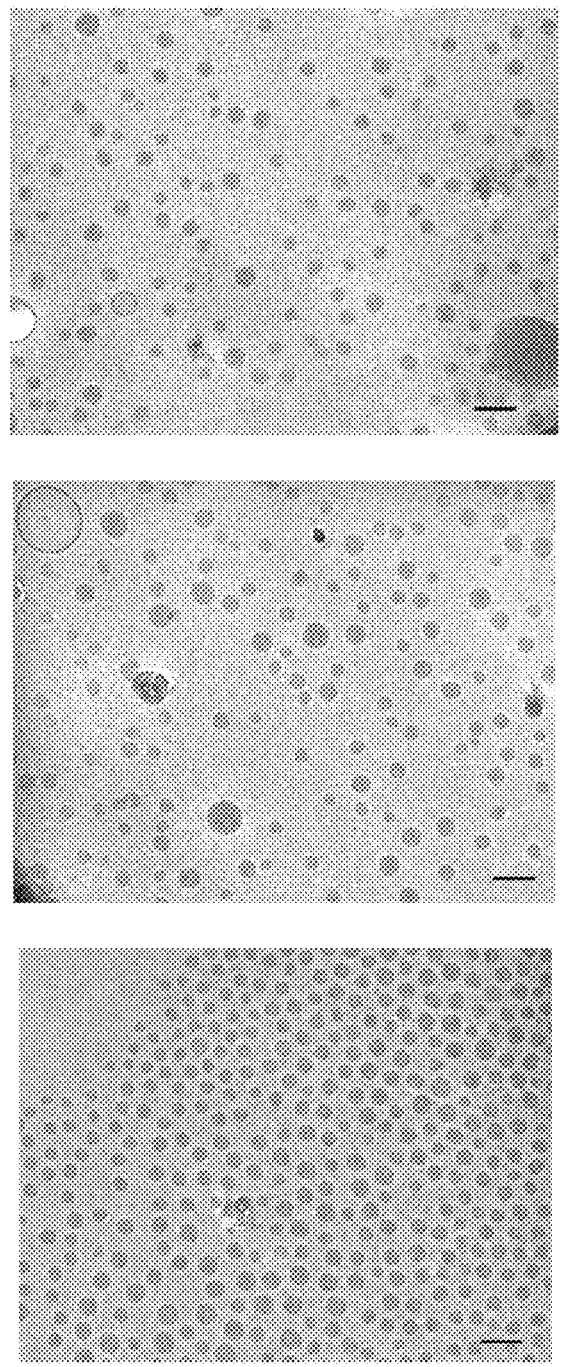
FIG. 9 shows representative Cryo-TEM data (3 images) for the siApoB-8 2:40 SNALP formulation prepared by the Direct Dilution Method. The vast majority of particles are non-lamellar (1191 of 1201 (or greater than 99% of the particles)).

FIG. 9 sets forth representative Cryo-TEM data for the siApoB-8 2:40 formulation prepared by the Direct Dilution Method. As with the 2:30 formulation, the vast majority of particles in the 2:40 SNALP formulation are non-lamellar (1191 of 1201 (or greater than 99% of the particles)).

Figure 10:
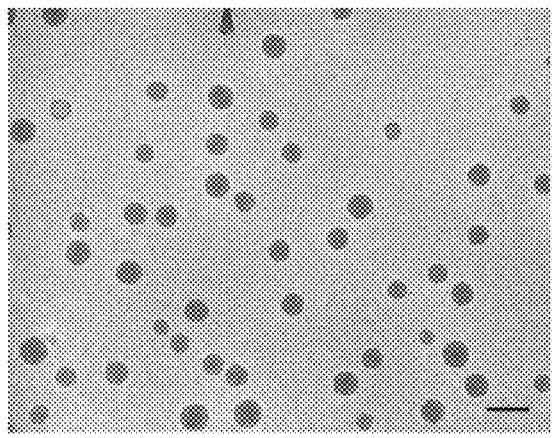
FIG. 10 shows representative Cryo-TEM data (3 images) for the siApoB-8 1:57 SNALP formulation prepared by the Direct Dilution Method. The vast majority of particles are non-lamellar, with lamellar particles being very rare (2 of 696).
Figure 10:
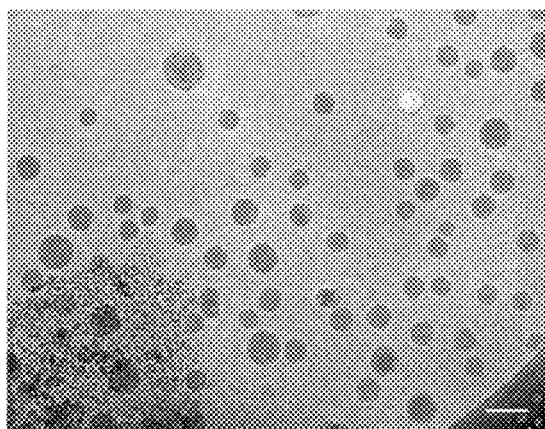
Figure 10:
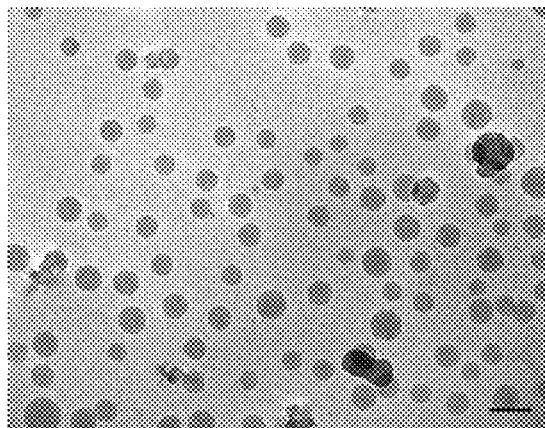

FIG. 10 sets forth representative Cryo-TEM data for the siApoB-8 1:57 formulation prepared by the Direct Dilution Method. As with the 2:30 and 2:40 formulations, the vast majority of particles in the 1:57 SNALP formulation are non-lamellar, with lamellar particles being very rare (2 of 696). Advantageously, the particle size distribution is very homogeneous, with very low polydispersity.

Figure 11:
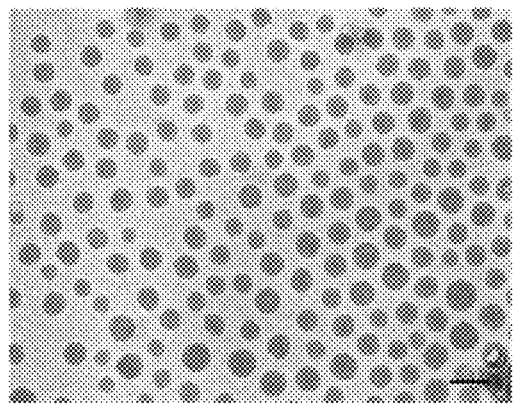
FIG. 11 shows representative Cryo-TEM data (3 images) for the siApoB-8 1:62 SNALP formulation prepared by the Direct Dilution Method. The vast majority of particles are non-lamellar, with lamellar particles being very rare (2 of 709).
Figure 11:
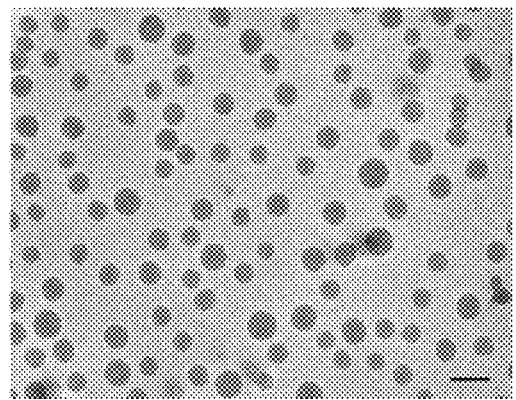
Figure 11:
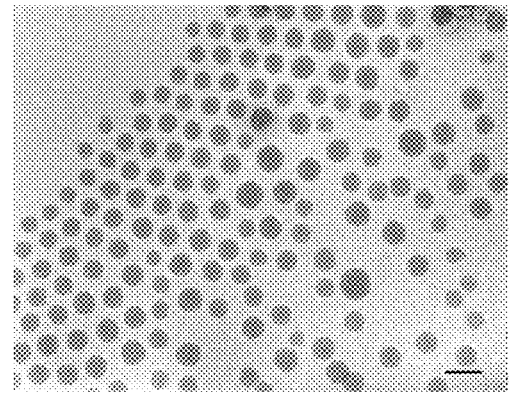

FIG. 11 sets forth representative Cryo-TEM data for the siApoB-8 1:62 formulation prepared by the Direct Dilution Method. As with the 2:30, the 2:40 and the 1:57 formulations, the vast majority of particles in the 1:62 SNALP formulation are non-lamellar, with lamellar particles being very rare (2 of 709). Advantageously, and similar to the 1:57 formulation, particle size distribution is very homogeneous in the 1:62 formulation, with very low polydispersity.

Figure 12:
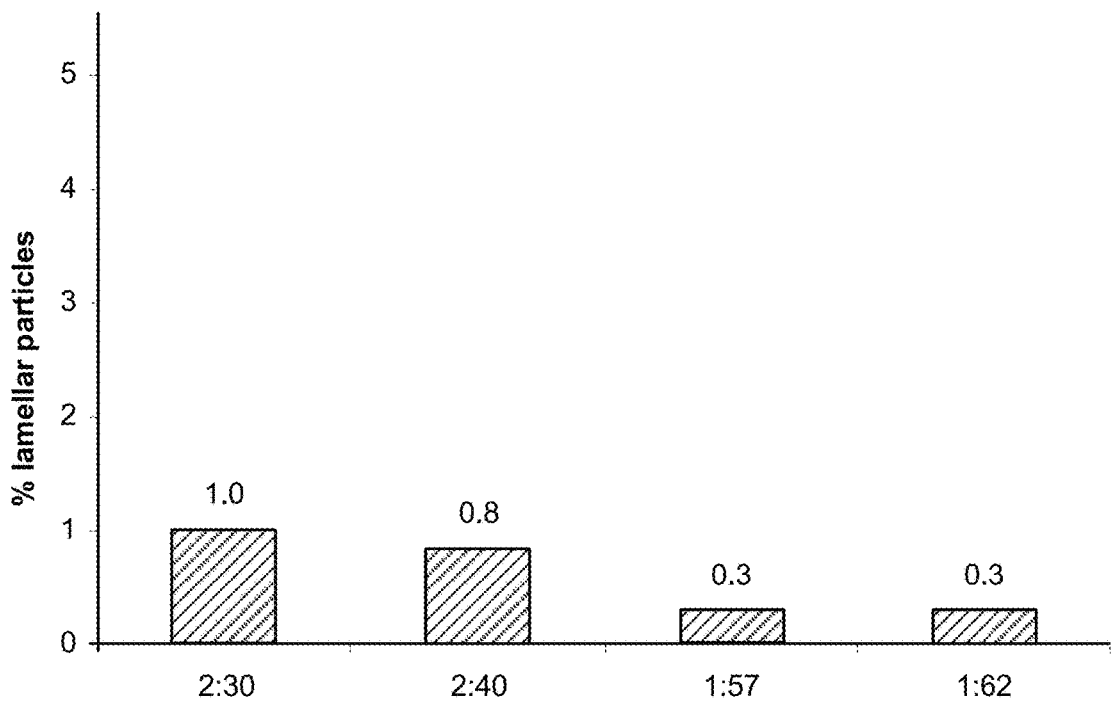
FIG. 12 shows the summary of particle morphology (non-lamellar particles vs. lamellar particles) for the 2:30, the 2:40, the 1:57 and the 1:62 formulations, all of which were prepared using the Direct Dilution Method. The 2:30, the 2:40, the 1:57 and the 1:62 formulations are plotted on the x-axis of the graph and the y-axis of the graph shows the % lamellar particles in each formulation.

FIG. 12 illustrates the presence of lamellar particles in the 2:30, the 2:40, the 1:57 and the 1:62 SNALP formulations prepared using the Direct Dilution Method. From FIG. 12, it is seen that the Direct Dilution Method favors non-lamellar particle formation. Moreover, it is seen that increasing the cationic lipid content has a minor effect on reducing the incidence of lamellar particles.

Based on the Cryo-TEM data, it is clear that the Stepwise Dilution Method (SMD) produces SNALP with a higher proportion of lamellar particles compared to SNALP prepared using the Direct Dilution Method. The 1:57 and 1:62 SNALP formulations produce particles with very homogeneous morphologies. With these formulations, the SNALP formation method has a large impact on particle size, but only a minor effect on particle morphology (since with both the SDM and the DDM, the vast majority of particles were non-lamellar).

For certain other formulations (e.g., the 10:15 and the 2:30 SNALP formulations), particle morphology is, in fact, dependent on formation method (SDM vs. DDM). Interestingly, it was found that the Direct Dilution Method is unable to produce the 10:15 SNALP formulation with acceptable siRNA encapsulation.

This Cryo-TEM data clearly demonstrates that a novel, non-liposomal lipid nanoparticle can be prepared using the Direct Dilution Method described herein. The resulting SNALP particles contain pH titratable aminolipids, are charge-free at physiological pH and encapsulate polar nucleic acid. Importantly, the Direct Dilution Method yielded smaller particle sizes and smaller polydispersity than those prepared by the SDM. It is thought that tightening the particle size distribution using the Direct Dilution Method helps to reduce the incidence of lamellar particles.

Example 3. Characterization of 7:54 SNALP Formulation Using Cryo-TEM

In this example, the 7:54 formulation as well as variations of the 7:54 formulation were analyzed using methods similar to those set forth in Examples 1 and 2. All of the 7:54 SNALP formulations were prepared with an siRNA targeting polo-like kinase 1 (PLK-1) (Genbank Accession No. NM_005030) as the nucleic acid component. The PLK-1 siRNA sequence used in this study is provided in Table 8.

TABLE 8

| siRNA | PLK-1 siRNA Sequence | % 2'OMe-Modified | % Modified in DS Region |
|---|---|---|---|
| PLK1424 2/6 | 5'-AGAUCACCCUCCUUAAAUAUU-3' (SEQ ID NO: 1)<br>3'-CUUCUAGUGGGAGGAAUUUAU-5' (SEQ ID NO: 2) | 9/42 = 21.4% | 7/38 = 18.4% |

Column 1:
The number after "PLK" refers to the nucleotide position of the 5' base of the sense strand relative to the start codon (ATG) of the human PLK-1 mRNA sequence NM_005030.
Column 2:
2'OMe nucleotides are indicated in bold and underlined. The 3'-overhangs on one or both strands of the siRNA molecule may alternatively comprise 1-4 deoxythymidine (dT) nucleotides, 1-4 modified and/or unmodified uridine (U) ribonucleotides, or 1-2 additional ribonucleotides having complementarity to the target sequence or the complementary strand thereof.
Column 3:
The number and percentage of 2'OMe-modified nucleotides in the siRNA molecule are provided.
Column 4:
The number and percentage of modified nucleotides in the double-stranded (DS) region of the siRNA molecule are provided.

The lipid components and physical characteristics of the various 7:54 formulations prepared by the Direct Dilution Method are summarized in Table 9. Mean particle size and polydispersity were measured on a Malvern Instruments Zetasizer. Encapsulation of nucleic acid was measured using a Ribogreen assay essentially as described in Heyes et al., *Journal of Controlled Release*, 107:276-287 (2005).

TABLE 9

Characterization of 7:54 Formulations Prepared by Direct Dilution Method

| Lot | Description | Composition (mol %)<br>PEG750-C-DMA \| DLinDMA \| Chol \| DPPC | Finished Product SNALP |||
|---|---|---|---|---|---|
| | | | Zavg (nm) | Poly | Encaps (%) |
| 121-050709-1 | 7:54 | 6.76\|54.06\|32.43\|6.75 | 79.01 | 0.075 | 93 |
| 121-050709-2 | 7:54 – 25% PEG (5:55) | 5.15\|54.98\|32.99\|6.87 | 89.03 | 0.037 | 93 |
| 121-050709-4 | 7:54 + 50% PEG (10:52) | 9.80\|52.29\|31.37\|6.5 | 67.57 | 0.085 | 94 |

"Zavg" = median diameter of particle;
"Poly" = polydispersity;
"Encaps" = encapsulation efficiency.

The various 7:54 formulations were further characterized by Cryo-Transmission Electron Microscopy ("Cryo-TEM") as described in Example 2. Coded samples were sent to Uppsala University for Cryo-TEM imaging according to the method described by Almgren, M., et al., *Colloid Surf A* 174, 3-21 (2000). Briefly, the samples were incubated at 25° C. for 20-30 minutes before preparation. The climate chamber conditions were: 25° C., with >98% relative humidity. 0.5 μL of sample solution was deposited on copper grid with perforated polymer film. Excess solution was removed by blotting and the sample was vitrified in liquid ethane. Images at 100,000× total magnification were captured. Diametrical size of particles were calculated by number averaging (Scale Bars all=100 nm).

Figure 13:
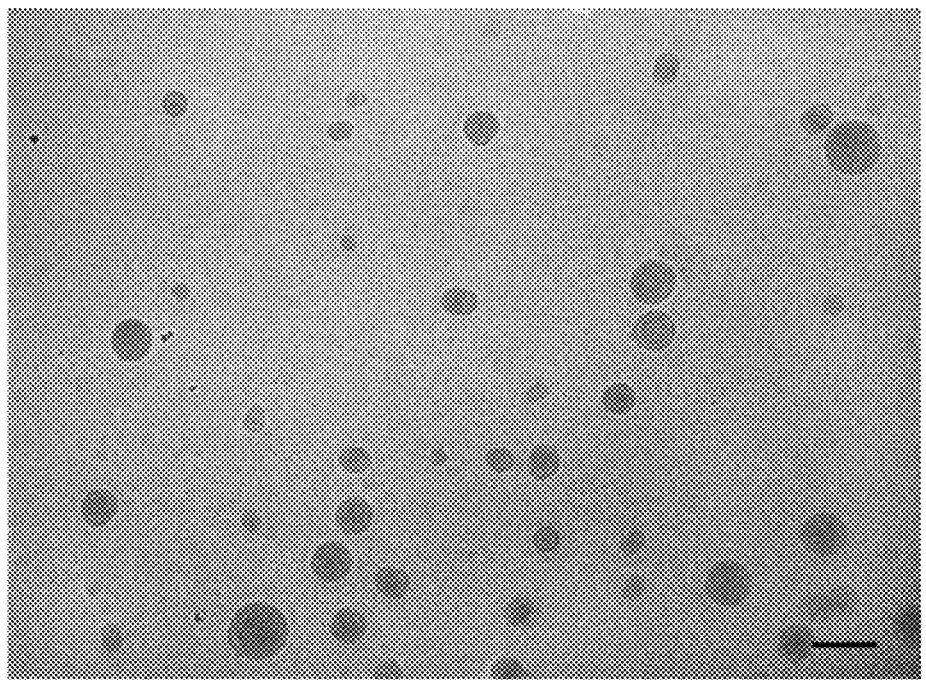
FIG. 13 shows representative Cryo-TEM data (2 images) for the 7:54 $PEG_{750}$-C-DMA PLK-1 SNALP Formulation. The vast majority of particles are non-lamellar, with lamellar particles being very rare.
Figure 13:
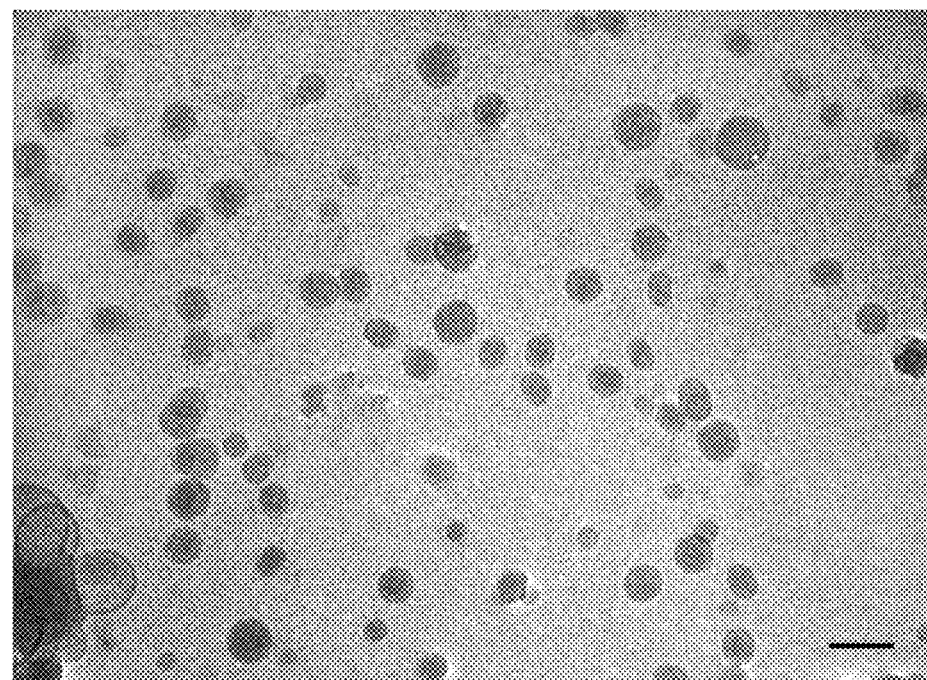

FIG. 13 sets forth representative Cryo-TEM data for the PLK-1 7:54 formulation prepared by the Direct Dilution Method. As with the 1:57 and 1:62 formulations, the vast majority of particles in the 7:54 SNALP formulation are non-lamellar, with lamellar particles being very rare. Also, similar to the 1:57 and 1:62 formulations, particle size distribution is very homogeneous in the 7:54 formulation, with very low polydispersity.

Figure 14:
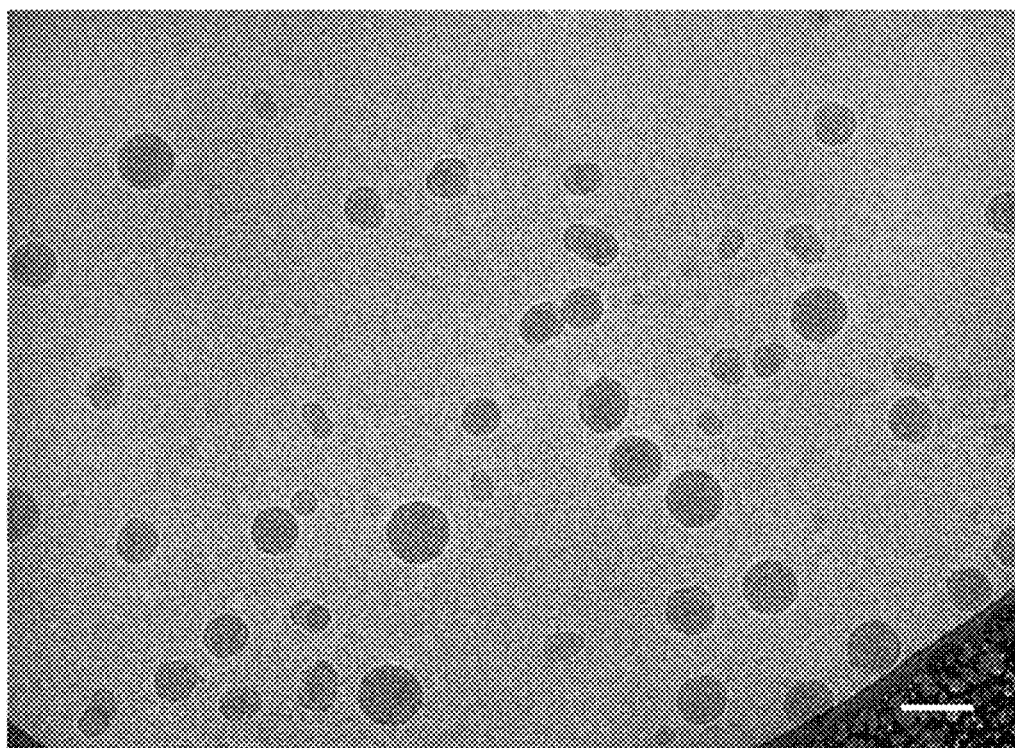
FIG. 14 shows representative Cryo-TEM data for the 7:54 $PEG_{750}$-C-DMA (~25% SNALP) PLK-1 SNALP Formulation. The vast majority of particles are non-lamellar, with lamellar particles being very rare.
Figure 15:
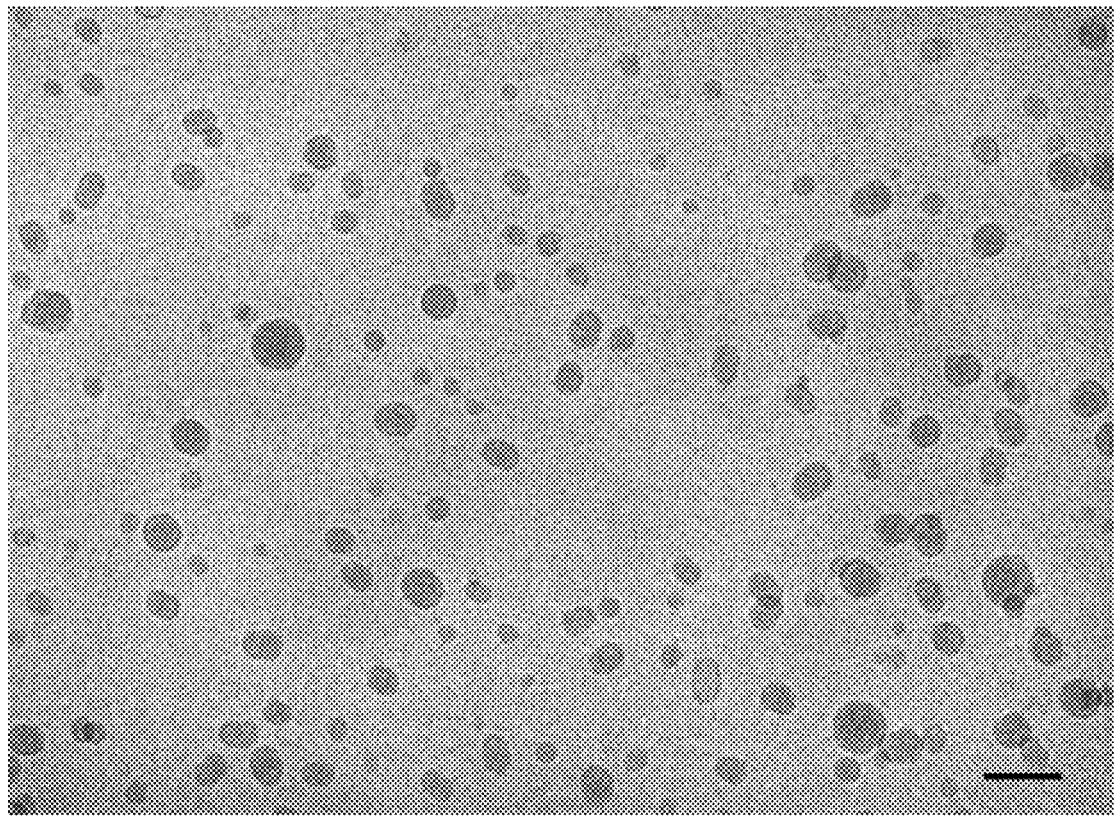
FIG. 15 shows representative Cryo-TEM data for the 7:54 $PEG_{750}$-C-DMA (+50% SNALP) PLK-1 SNALP Formulation. The vast majority of particles are non-lamellar, with lamellar particles being very rare.

FIGS. 14 and 15 also set forth representative Cryo-TEM data for the 7:54 PEG$_{750}$-C-DMA (−25% PEG) PLK SNALP and the 7:54 PEG750-C-DMA (+50% PEG) PLK SNALP formulations, respectively, prepared by the Direct Dilution Method. As with the 7:54 SNALP formulation, the vast majority of particles in these variations of the 7:54 SNALP formulation are non-lamellar, with lamellar particles being very rare. Also, similar to the 7:54 formulation, particle size distribution is very homogeneous in these variations of the 7:54 SNALP formulations, with very low polydispersity.

Example 4. Comparison of the Silencing Activity of ApoB siRNA Formulated as 2:30 SNALP and 2:40 SNALP SNALP formulations were prepared with the ApoB siRNA set forth in Table 2. The 2:30 SNALP formulation used in this study is lipid composition 2:30:20:48 as described in molar percentages of PEG-C-DMA, DLinDMA, DSPC, and cholesterol (in that order). The 2:40 SNALP formulation used in this study is lipid composition 2:40:10:48 as described in molar percentages of PEG-C-DMA, DLinDMA, DPPC, and cholesterol (in that order).

BALB/c mice (female, 4 weeks old) were obtained from Harlan Labs. After an acclimation period (of at least 7 days), animals were administered a single dose of SNALP by intravenous (IV) injection in the lateral tail vein. The dose was 5 mg encapsulated siRNA per kg body weight. As a negative control, one group of animals was given IV injections of phosphate buffered saline (PBS) vehicle. 96 h after the treatment, animals were euthanized and liver tissue was collected in RNAlater.

Liver tissues were analyzed for ApoB mRNA levels normalized against glyceraldehyde-3-phosphate dehydrogenase (GAPDH) mRNA levels using the QuantiGene assay (Panomics; Fremont, CA) essentially as described in Judge et al., *Molecular Therapy*, 13:494 (2006).

Figure 16:
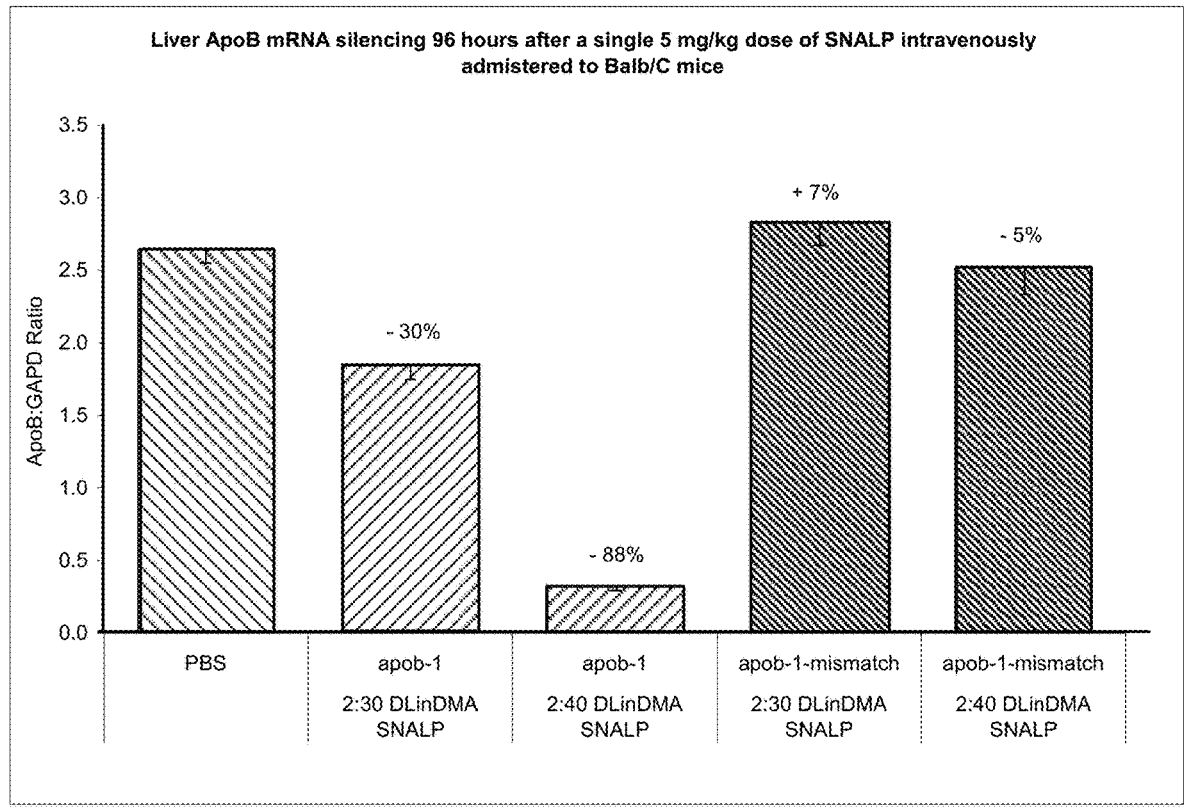
FIG. 16 illustrates data demonstrating that the 2:40 siApoB-8 SNALP formulation has enhanced ApoB silencing activity compared to the 2:30 siApoB-8 SNALP formulation following intravenous administration in mice.

FIG. 16 shows that the 2:40 SNALP containing ApoB 10048 U2/2 G1/2 siRNA was about 3 times as efficacious as the 2:30 SNALP in mediating ApoB gene silencing in mouse liver.

Example 5. ApoB siRNA Formulated as 1:57 SNALP have Potent Silencing Activity In Vivo SNALP formulations were prepared with the ApoB siRNA set forth in Table 2.

The lipid components and physical characteristics of the formulations are summarized in Table 10. The lipid:drug ratio is described in units of mg total lipid per mg nucleic acid. Mean particle size and polydispersity were measured on a Malvern Instruments Zetasizer. Encapsulation of nucleic acid was measured using a Ribogreen assay essentially as described in Heyes et al., *Journal of Controlled Release*, 107:276-287 (2005).

TABLE 10

Characteristics of the SNALP formulations used in this study.

| SNALP (L:D ratio) | siRNA Payload | Particle Size (Polydispersity) | % Encapsulation |
|---|---|---|---|
| 2:30 (13) | ApoB-10048 U2/2 G1/2 | 65 nm (0.16) | 88 |
| 1:57 (9) | ApoB-10048 U2/2 G1/2 | 74 nm (0.10) | 89 |

The 2:30 SNALP formulation used in this study is lipid composition 2:30:20:48 as described in molar percentages of PEG-C-DMA, DLinDMA, DSPC, and cholesterol (in that order). This formulation was prepared by syringe press at an input lipid to drug (L:D) ratio (mg:mg) of 13:1.

The 1:57 SNALP formulation used in this study is lipid composition 1.5:57.1:7:34.3 as described in molar percentages of PEG-C-DMA, DLinDMA, DPPC, and cholesterol (in that order). This formulation was prepared by syringe press at an input lipid to drug (L:D) ratio (mg:mg) of 9:1.

BALB/c mice (female, 4 weeks old) were obtained from Harlan Labs. After an acclimation period (of at least 7 days), animals were administered SNALP by intravenous (IV) injection in the lateral tail vein once daily on Study Days 0, 1, 2, 3 & 4 for a total of 5 doses per animal. Daily dosage was either 1.0 (for 2:30 SNALP) or 0.1 (for 1:57 SNALP) mg encapsulated siRNA per kg body weight, corresponding to 10 ml/kg (rounded to the nearest 10 μl). As a negative control, one group of animals was given IV injections of phosphate buffered saline (PBS) vehicle. On Study Day 7, 72 h after the last treatment, animals were euthanized and liver tissue was collected in RNAlater.

Liver tissues were analyzed for ApoB mRNA levels normalized against glyceraldehyde-3-phosphate dehydrogenase (GAPDH) mRNA levels using the QuantiGene assay (Panomics; Fremont, CA) essentially as described in Judge et al., *Molecular Therapy*, 13:494 (2006).

Figure 17:
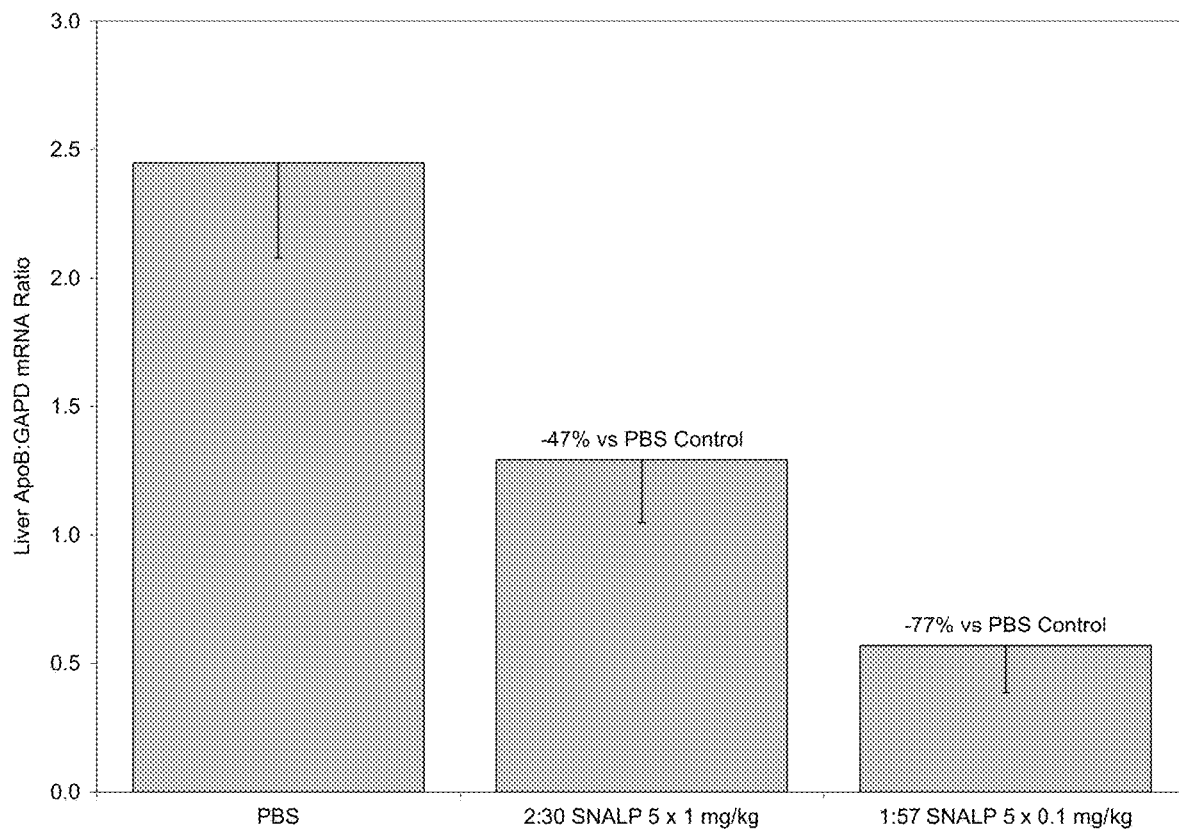
FIG. 17 illustrates data demonstrating the activity of 1:57 SNALP containing ApoB siRNA following intravenous administration in mice. Each bar represents the group mean of five animals. Error bars indicate the standard deviation.

FIG. 17 shows that the 1:57 SNALP containing ApoB 10048 U2/2 G1/2 siRNA was more efficacious than the 2:30 SNALP in mediating ApoB gene silencing in mouse liver at a 10-fold lower dose.

Example 6. Comparison of the Silencing Activity of ApoB siRNA Formulated as 2:40 SNALP and 1:57 SNALP SNALP formulations were prepared with the ApoB siRNA set forth in Table 2, i.e., siApoB-8. The 2:40 SNALP formulation used in this study is lipid composition 2:40:10:48 as described in molar percentages of PEG-C-DMA, DLinDMA, DPPC, and cholesterol (in that order). The 1:57 SNALP formulation used in this study is lipid composition 1.5:57.1:7:34.3 as described in molar percentages of PEG-C-DMA, DLinDMA, DPPC, and cholesterol (in that order).

BALB/c mice (female, 4 weeks old) were obtained from Harlan Labs. After an acclimation period (of at least 7 days), animals were administered a single dose of SNALP by intravenous (IV) injection in the lateral tail vein. Dosage was either 0.5 or 0.75 (for the 2:40 SNALP), or 0.10, 0.25, 0.5 or 0.75 (for the 1:57 SNALP) mg encapsulated siRNA per kg body weight, corresponding to 10 ml/kg (rounded to the nearest 10 μl). As a negative control, one group of animals was given IV injections of phosphate buffered saline (PBS) vehicle. 48 h after the treatment, animals were euthanized and liver tissue was collected in RNAlater.

Liver tissues were analyzed for ApoB mRNA levels normalized against glyceraldehyde-3-phosphate dehydrogenase (GAPDH) mRNA levels using the QuantiGene assay (Panomics; Fremont, CA) essentially as described in Judge et al., *Molecular Therapy*, 13:494 (2006).

Figure 18:
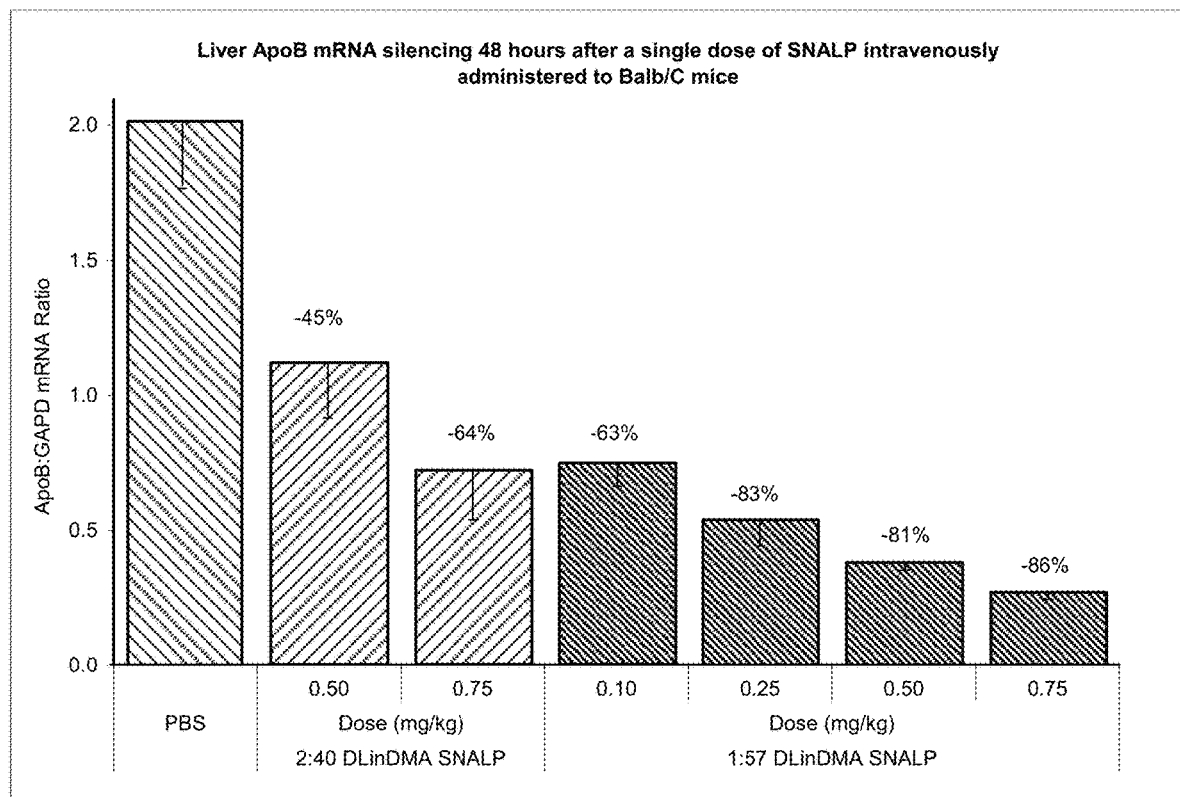
FIG. 18 illustrates data demonstrating that the 1:57 siApoB-8 SNALP formulation has enhanced ApoB silencing activity compared to the 2:40 siApoB-8 SNALP formulation following intravenous administration in mice.

FIG. 18 shows that the 1:57 SNALP containing ApoB 10048 U2/2 G1/2 siRNA was as efficacious as the 2:40 SNALP in mediating ApoB gene silencing in mouse liver at a 7.5-fold lower dose, i.e., 64% knockdown at a 0.75 mg/kg dose of 2:40 SNALP versus 63% knockdown at a 0.10 mg/kg dose of 1:57 SNALP.

Example 7. Activity of the 7:54 DLinDMA SNALP Formulation in Normal Liver Versus Liver Tumors 7:54 or 1:57 DLinDMA SNALP formulations were prepared with PLK-1 (Table 8) or ApoB (Table 2) siRNA as the nucleic acid component. Mice with normal livers were administered either phosphate buffered saline (PBS), ApoB 1:57 DLinDMA SNALP, or ApoB 7:54 DLinDMA SNALP by intravenous (IV) injection via the lateral tail vein. Mice with established Hep3B intrahepatic tumors were administered either PBS, PLK-1 1:57 DLinDMA SNALP, or PLK-1 7:54 DLinDMA SNALP by IV injection via the lateral tail vein.

Figure 19:
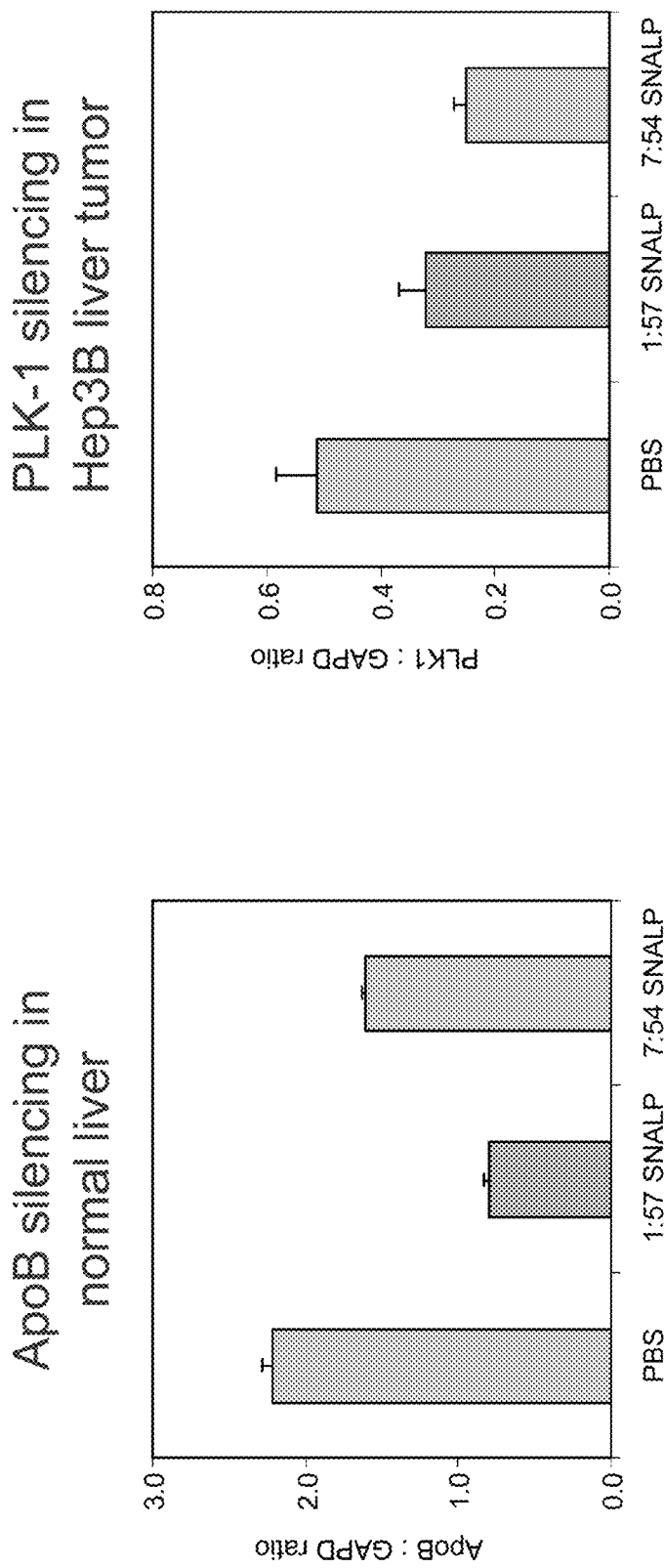
FIG. 19 shows a comparison of the silencing activity of exemplary 1:57 and 7:54 DLinDMA SNALP formulations in normal liver tissue and liver tumors.

FIG. 19 shows that the 1:57 DLinDMA SNALP formulation was capable of silencing ApoB expression in normal liver tissue and PLK-1 expression in Hep3B liver tumors, while the 7:54 DLinDMA SNALP formulation displayed enhanced silencing activity in liver tumors compared to normal liver tissue. As such, this example demonstrates that the 7:54 DLinDMA SNALP formulation preferentially targets tumor cells compared to the normal liver, whereas the 1:57 DLinDMA SNALP formulation preferentially targets normal liver cells compared to solid tumors.

This example further demonstrates that the 7:54 DLinDMA SNALP formulation may help limit PLK-1 silencing in proliferating hepatocytes (e.g., diseased liver state). Hepatocytes in the healthy liver are typically non-dividing and therefore do not express PLK-1. However, in diseased states (e.g., in a cancerous liver), normal hepatocytes are more proliferative (as they attempt to repair the damage) and therefore express PLK-1. Use of the PLK-1 7:54 DLinDMA SNALP formulation avoids the undesired targeting of normal proliferating hepatocytes, thereby limiting PLK-1 silencing in these cells. As a result, there is a reduction or abrogation in the death of these healthy hepatocytes, while PLK-1 expression is effectively silenced in tumor cells.

Figure 20:
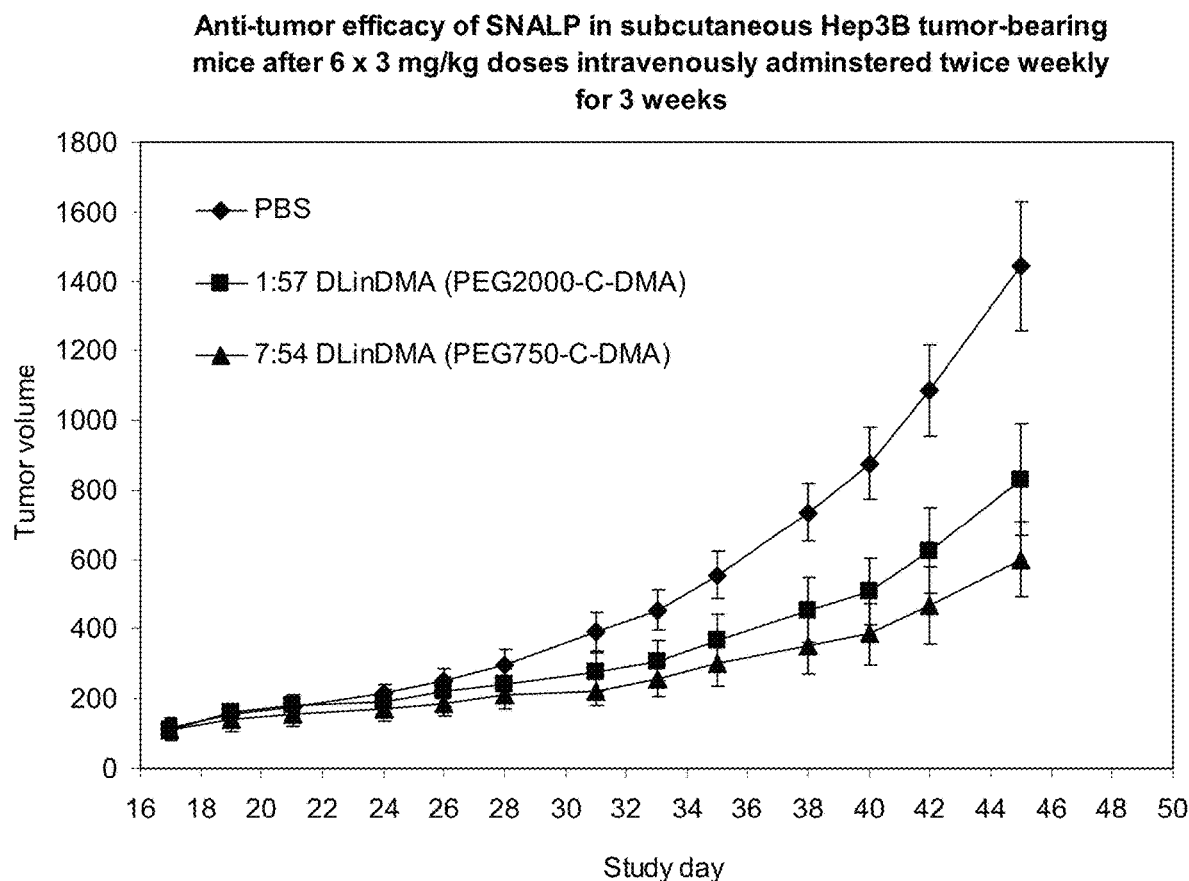
FIG. 20 shows a comparison of the silencing activity of exemplary 1:57 and 7:54 DLinDMA SNALP formulations in subcutaneous tumors.

Example 8. Activity of the 7:54 DLinDMA SNALP Formulation in Tumors Outside of the Liver 7:54 or 1:57 DLinDMA SNALP formulations were prepared with PLK-1 siRNA as the nucleic acid component (Table 8). Mice with established Hep3B subcutaneous (SC) tumors were administered either PBS (Control), PLK-1 1:57 DLinDMA SNALP, or PLK-1 7:54 DLinDMA SNALP by IV injection via the lateral tail vein at a dose of 6×3 mg/kg SNALP twice weekly for 3 weeks (Days 17, 20, 24, 27, 31, 34). FIG. 20 shows that while multiple doses of PLK-1 1:57 DLinDMA SNALP were effective at inducing the regression of established SC Hep3B tumors compared to control mice, multiple doses of PLK-1 7:54 DLinDMA SNALP were more effective at inducing the regression of these SC solid tumors compared to the PLK-1 1:57 DLinDMA SNALP formulation.

Thus, this study shows that the 7:54 DLinDMA SNALP formulation displays increased potency in SC tumors and can be used to preferentially target tumors outside of the liver.

Example 9. Synthesis of MC3

MC3 (Compound 1) having the structure shown below was synthesized as described in Scheme 1 below.

STEP 1: Magnesium bromide etherate (34 g, 110 mmol) and a stir bar were added to a 2000 mL round bottom flask. The flask was sealed and flushed with nitrogen. Anhydrous diethyl ether (400 mL) was added via cannula. A solution of linolenyl mesylate (20 g, 58 mmol) in anhydrous ether (300 mL) was then added, and the suspension stirred overnight. The suspension was poured into 500 mL of chilled water and transferred to a 2000-mL separating funnel. After shaking, the organic phase was separated. The aqueous phase was then extracted with ether (2×250 mL) and all ether phases combined. The ether phase was washed with water (2×250 mL), brine (250 mL) and dried over anhydrous $Mg_2SO_4$. The solution was filtered, concentrated and purified by flash chromatography. Final yield 18.9 g, 99%.

STEP 2: A 1 liter RBF was charged with magnesium turnings (11.1 g, 463 mmol), anhydrous THF (65 mL) and stir-bar and flushed with nitrogen. In a separate flask, a solution of linoleyl bromide (140 g, 425 mL) in anhydrous THF (150 mL) was prepared, and 20 mL of this solution added to the magnesium. When most of the heat had dissipated, the remainder of the bromide was added over a period of 15 minutes. Temperature was then maintained at 45° C. for 4 h. The reaction was then cooled (0° C.). Using a dropping funnel, a solution of ethyl formate (32.4 g, 438 mmol) in anhydrous THF (150 mL) was added over a 40 minute period. The reaction was stirred overnight at room

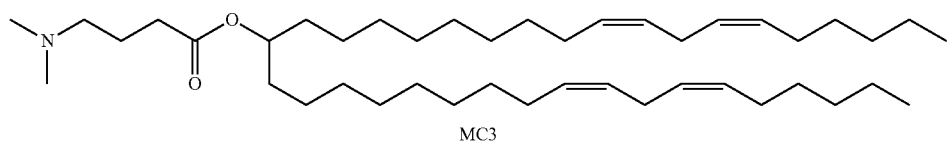 [SMILES: CCCCC/C=C\C/C=C\CCCCCCCCC(CCCCCCCC/C=C\C/C=C\CCCCC)OC(=O)CCCN(C)C]

MC3

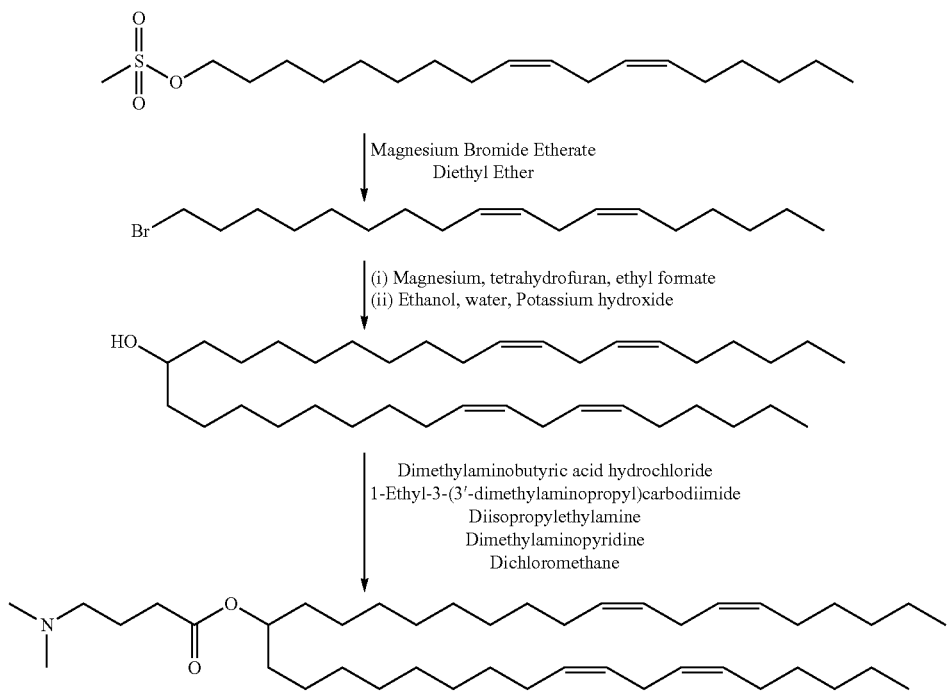

Scheme 1 temperature. The reaction was cooled to −15° C. and 5N HCl (185 mL) added slowly. The mixture was transferred to a 2 L separating funnel separated. Water (150 mL) and hexane (150 mL) were added, the mixture washed, and again the aqueous removed. The organic was washed a final time with water (150 mL) and then concentrated to a yellow oil. The yellow oil was stirred with a mixture of EtOH (210 mL), water (30 mL) and KOH (15.8 g) for 1.5 h at room temp. The EtOH was evaporated and the residue treated with hexane (50 mL). 5N HCl (200 mL) was added via dropping funnel. The organic was washed with water (2×50 mL) evaporated, dried and purified by chromatography (0-5% EtOAc in hexane, 91 g, 81%).

STEP 3: Dilinoleylmethanol (7.8 g, 14.9 mmol), dimethylaminobutyric acid hydrochloride (2.99 g, 17.8 mmol) and a stir bar were added to 500 mL RBF. The flask was flushed with nitrogen and anh. DCM (120 mL) added, followed by EDCI (3.6 g, 18.8 mmol), DIPEA (6.3 mL, 36.3 mmol) and DMAP (450 mg, 3.69 mmol). The reaction was stirred overnight. The reaction was diluted with DCM (300 mL) and washed with sat. NaHCO$_3$ (200 mL), water (300 mL) and sat. NaCL (200 mL). Each aq. wash was extracted once with DCM (50 mL). Organics were combined, dried (MgSO$_4$) and concentrated to yield a yellow oil with some crystalline matter. This was purified by chromatography (0-2% MeOH in CHCl$_3$) to yield Lin-MC3 as a pale yellow oil (9.0 g, 14.1 mmol, 95%).

Example 10. Synthesis of LenMC3 and CP-LenMC3

LenMC3 (Compound 4) and CP-LenMC3 (Compound 5) having the structures shown below were synthesized as described in Scheme 2 below. LenMC3 is also known as linolenyl-MC3 and DLen-MC3. CP-LenMC3 is also known as CP-linolenyl-MC3 and CP-DLen-MC3.

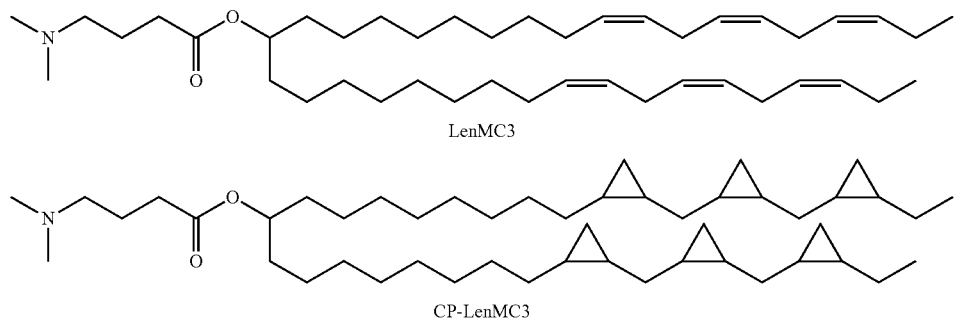

LenMC3

CP-LenMC3

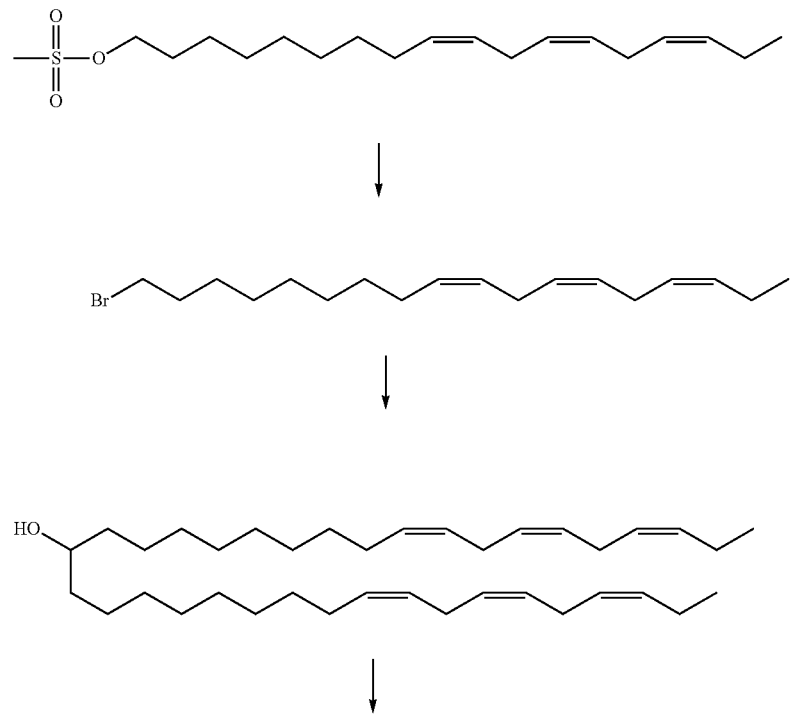

Scheme 2

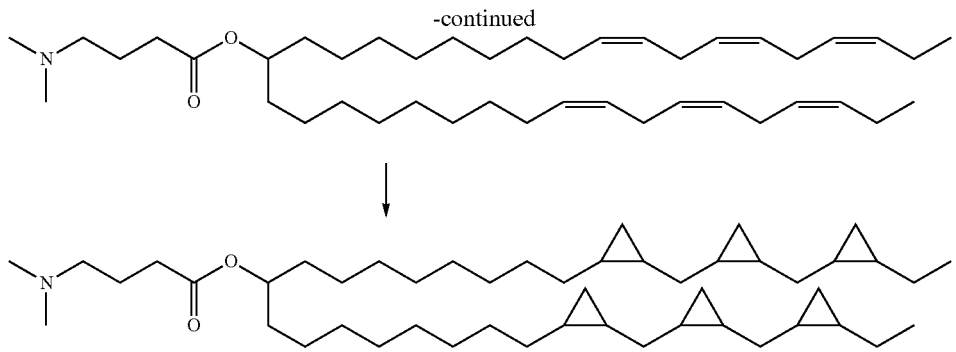

Synthesis of Linolenyl Bromide (Compound 2)

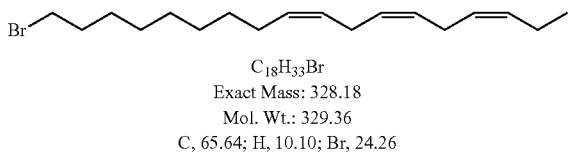 [SMILES: CC/C=C\C/C=C\C/C=C\CCCCCCCCBr]

C₁₈H₃₃Br
Exact Mass: 328.18
Mol. Wt.: 329.36
C, 65.64; H, 10.10; Br, 24.26

Magnesium bromide etherate (34 g, 110 mmol) and a stir bar were added to a 2000 mL round bottom flask. The flask was sealed and flushed with nitrogen. Anhydrous diethyl ether (400 mL) was added via cannula. A solution of linolenyl mesylate (20 g, 58 mmol) in anhydrous ether (300 mL) was then added, and the suspension stirred overnight. The suspension was poured into 500 mL of chilled water and transferred to a 2000-mL separating funnel. After shaking, the organic phase was separated. The aqueous phase was then extracted with ether (2×250 mL) and all ether phases combined. The ether phase was washed with water (2×250 mL), brine (250 mL) and dried over anhydrous Mg$_2$SO$_4$. The solution was filtered, concentrated and purified by flash chromatography. Final yield 19.1 g, 100%.

mmol) added via syringe. The addition was made dropwise, directly into the reaction mixture, and the cloudy suspension again stirred overnight. During this time the reaction turned bright yellow. The R.M. was transferred to a 2000-mL sep. funnel with ether (50 mL), and washed with 10% H$_2$SO$_4$ (200 mL), water (2×200 mL) and brine (200 mL). The organic was dried over anhydrous MgSO$_4$, filtered and concentrated. Crude yield was 14.5 g. TLC indicated that majority of product was the methyl formate, which was purified by column chromatography. The purified formate (9.3 g, 16.7 mmol) was transferred to a 1000 mL round bottom flask and EtOH (600 mL) and a stirbar added. With stirring, water (25 mL—forming ~5% aqueous solution) was slowly added, followed by KOH (2.0 g, 35.7 mmol). After 1 hour, the solution had turned pale yellow. TLC indicated reaction had gone to completion. The solution was concentrated by rotovap to 50% of its volume and then poured into 200 mL of 5% HCl. The aqueous phase was extracted with ether (3×200 mL). The ether fractions were combined and washed with water (3×200 mL), dried (MgSO$_4$) and concentrated to yield 8.9 g of dilinolenyl methanol (16.8 mmol, 58%).

Synthesis of Len-MC3 (Compound 4)

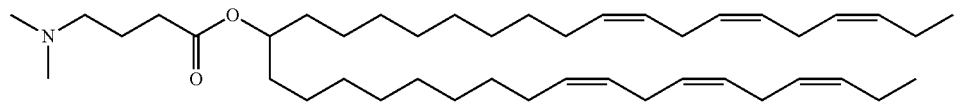

Synthesis of Dilinolenyl Methanol (Compound 3)

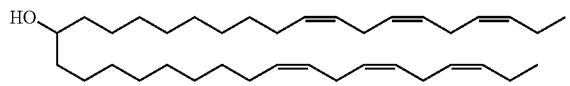 [SMILES: CC/C=C\C/C=C\C/C=C\CCCCCCCCC(O)CCCCCCCC/C=C\C/C=C\C/C=C\CC]

Magnesium turnings (2.1 g, 87 mmol), 5 crystals of iodine and a stirbar were added to a 1000 mL round-bottom flask. The flask was flushed with nitrogen and a solution of linolenyl bromide (Compound 2) (19.1 g, 58 mmol) in anhydrous diethyl ether (500 mL) added via cannula. The mixture turned cloudy and was refluxed overnight. The mixture was cooled to RT and ethyl formate (4.66 mL, 58

Dilinolenyl methanol (Compound 3) (2.5 g, 4.76 mmol), dimethylaminobutyric acid hydrochloride (970 mg, 5.77 mmol) and a stir bar were added to 100 mL RBF. The flask was flushed with nitrogen and anhydrous DCM (40 mL) added, followed by EDCI (FW 191.7, 1.2 g, 6.26 mmol), DIPEA (2.1 mL, 12.1 mmol) and DMAP (150 mg, 1.23 mmol). The reaction was stirred overnight, whereupon TLC indicated >80% conversion. Reaction was diluted with DCM (100 mL) and washed with sat. NaHCO$_3$ (100 mL), water (200 mL) and sat. NaCL (100 mL). Aqueous washes were combined and extracted with DCM (2×50 mL). Organics were then combined, dried (MgSO$_4$) and concentrated to yield a yellow oil with some crystalline matter. This was purified by chromatography to yield Len-MC3 as a pale yellow oil (2.3 g, 3.6 mmol, 76%).

Synthesis of CP-LenMC3 (Compound 5)

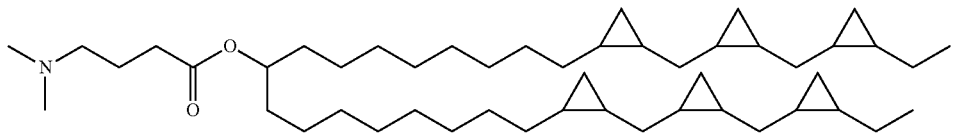

Chemical Formula: $C_{49}H_{87}NO_2$
Exact Mass: 721.7
Molecular Weight: 722.2
Elemental Analysis: C, 81.49; H, 12.14; N, 1.94; O, 4.43

To a 250 mL RBF was added Len-MC3 (Compound 4) (1.1 g, 1.72 mmol), a stirbar and anhydrous DCM (40 mL). The flask was flushed with $N_2$ and cooled to 0° C., then a 1M solution of diethylzinc in hexanes added (30 mL, 30 mmol). The solution was stirred for 1 hour at 0° C., then diiodomethane (2.4 mL 30 mmol) added and the reaction stirred overnight at RT. The reaction mixture was concentrated and then redissolved in EtOAc (50 mL). The EtOAc was washed successively with 5% HCl (2×50 mL), water (50 mL), $NaHCO_3$ (50 mL), water (50 mL), and brine (50 mL). The aqueous washes were combined and extracted with DCM (2×50 mL). All organics were combined, dried and concentrated to yield crude CP-Len-MC3. $^1$H-NMR indicated some olefins still to be present, so the compound was treated again, using the same procedures and amounts outlined above. This time, after chromatography, $^1$H-NMR indicated total conversion of the olefins. Final yield 1.0 g, 1.39 mmol, 81%.

Example 11. Synthesis of γ-LenMC3 and CP-γ-LenMC3

γ-LenMC3 (Compound 8) and CP-γ-LenMC3 (Compound 9) having the structures shown below were synthesized as described in Scheme 3 below. γ-LenMC3 is also known as γlinolenyl-MC3, γDLen-MC3, and D-γ-Len-MC3. CP-γ-LenMC3 is also known as CP-γlinolenyl-MC3, CP-γDLen-MC3, and CP-D-γ-Len-MC3.

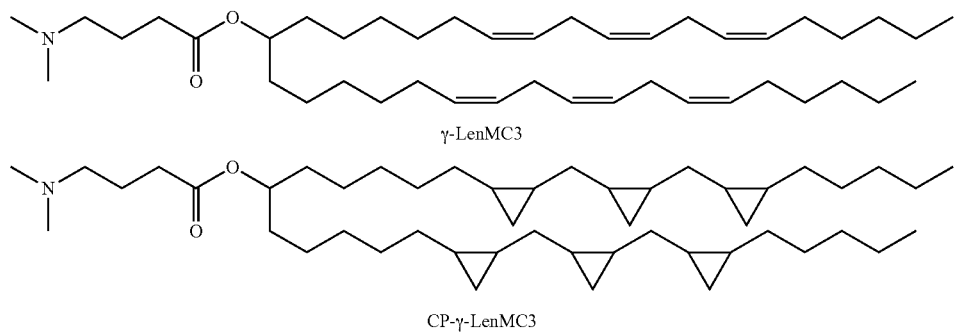

γ-LenMC3

CP-γ-LenMC3

Scheme 3

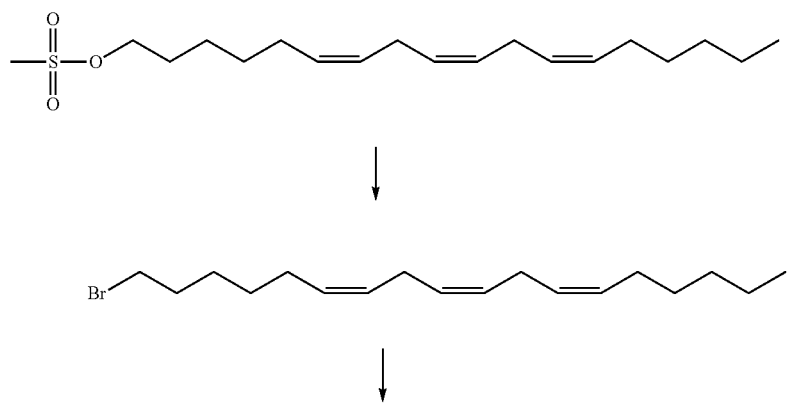

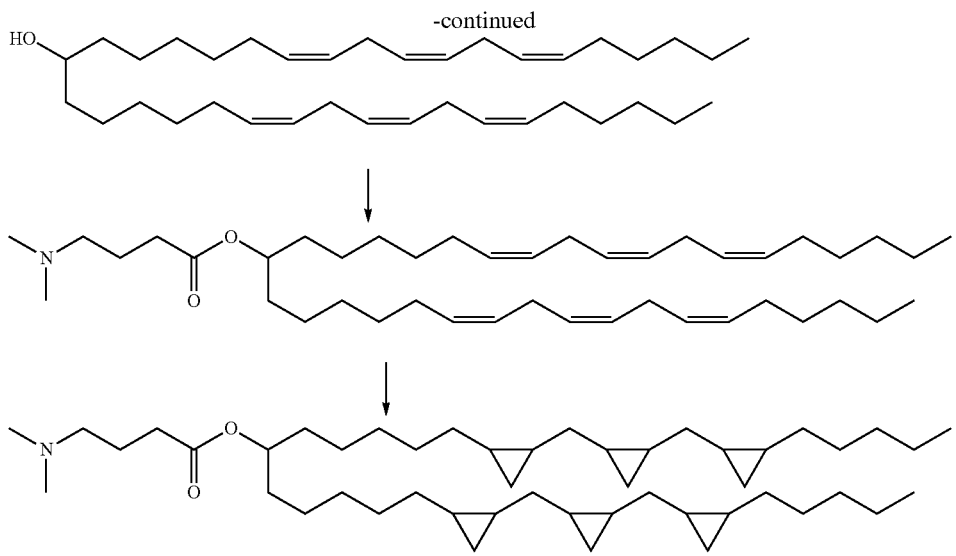

Synthesis of γ-Linolenyl Bromide (Compound 6)

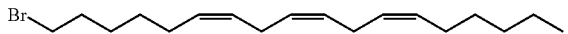

Magnesium bromide etherate (34 g, 110 mmol) and a stir bar were added to a 2000 mL round bottom flask. The flask was sealed and flushed with nitrogen. Anhydrous diethyl ether (400 mL) was added via cannula. A solution of γ-linolenyl mesylate (20 g, 58 mmol) in anhydrous ether (300 mL) was then added, and the suspension stirred overnight. The suspension was poured into 500 mL of chilled water and transferred to a 2000-mL separating funnel. After shaking, the organic phase was separated. The aqueous phase was then extracted with ether (2×250 mL) and all ether phases combined. The ether phase was washed with water (2×250 mL), brine (250 mL) and dried over anhydrous $Mg_2SO_4$. The solution was filtered, concentrated and purified by flash chromatography. Final yield 18.9 g, 99%.

Synthesis of di-γ-Linolenyl Methanol (Compound 7)

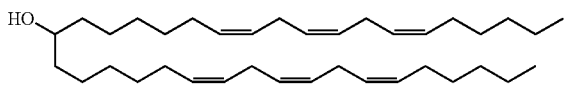 [SMILES: CCCCC/C=C\C/C=C\C/C=C\CCCCCC(O)CCCCC/C=C\C/C=C\C/C=C\CCCCC]

Magnesium turnings (2.1 g, 87 mmol), 5 crystals of iodine and a stirbar were added to a 1000 mL round-bottom flask. The flask was flushed with nitrogen and a solution of γ-linolenyl bromide (Compound 6) (18.9 g, 57 mmol) in anhydrous diethyl ether (500 mL) added via cannula. The mixture turned cloudy and was refluxed overnight. The mixture was cooled to RT and ethyl formate (4.66 mL, 58 mmol) added dropwise. The suspension was stirred overnight, turning bright yellow. The R.M. was transferred to a 2000-mL sep. funnel with ether (50 mL), and washed with 10% sulphuric acid (200 mL), water (2×200 mL) and brine (200 mL). The organic was dried over anhydrous $MgSO_4$, filtered and concentrated. Crude yield was 14.5 g. TLC indicated that majority of product was the methyl formate, which was purified by column chromatography. The purified formate was transferred to a 1000 mL round bottom flask and EtOH (600 mL) and a stirbar added. With stirring, water (25 mL—forming ~5% aqueous solution) was slowly added, followed by KOH (2.0 g, 35.7 mmol). After 1 hour, solution had turned pale yellow. TLC indicated reaction had gone to completion. The solution was concentrated by rotovap to 50% of its volume and then poured into 200 mL of 5% HCl. The aqueous phase was extracted with ether (3×200 mL). The ether fractions were combined and washed with water (3×200 mL), dried ($MgSO_4$) and concentrated to yield 8.8 g of di-γ-linolenyl methanol (16.8 mmol, 58%).

Synthesis of γ-LenMC3 (Compound 8)

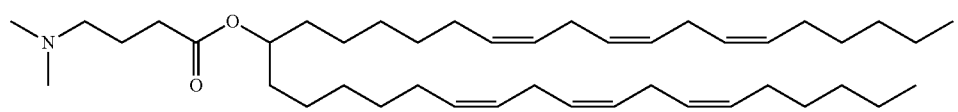 [SMILES: CCCCC/C=C\C/C=C\C/C=C\CCCCCC(CCCCC/C=C\C/C=C\C/C=C\CCCCC)OC(=O)CCCN(C)C]

Di-γ-linolenyl methanol (Compound 7) (2.5 g, 4.76 mmol), dimethylaminobutyric acid hydrochloride (970 mg, 5.77 mmol) and a stir bar were added to 100 mL RBF. The flask was flushed with nitrogen and anhydrous DCM (40 mL) added, followed by EDCI (1.2 g, 6.26 mmol), DIPEA (2.1 mL, 12.1 mmol) and DMAP (150 mg, 1.23 mmol). The reaction was stirred overnight. The reaction was diluted with DCM (100 mL) and washed with sat. NaHCO$_3$ (100 mL), water (200 mL) and sat. NaCL (100 mL). Aqueous washes were combined and extracted with DCM (2×50 mL). Organics were then combined, dried (MgSO$_4$) and concentrated to yield a yellow oil. This was purified by chromatography to yield γ-Len-MC3 as a pale yellow oil (2.6 g, 4.1 mmol, 86%).

Synthesis of CP-γ-LenMC3 (Compound 9)

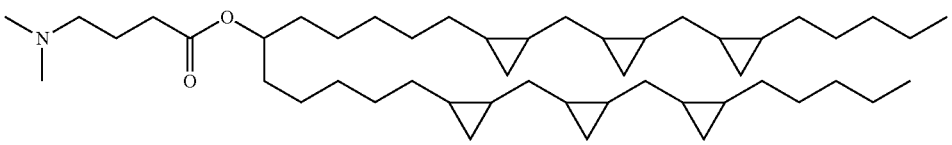 [SMILES: CCCCCC1CC1CC1CC1CC1CC1CCCCCC(CCCCCC1CC1CC1CC1CC1CC1CCCCC)OC(=O)CCCN(C)C]

To a 250 mL RBF was added γ-LenMC3 (Compound 8) (1.28 g, 2.0 mmol), a stirbar and anhydrous DCM (40 mL). The flask was flushed with N$_2$ and cooled to 0° C., then a 1M solution of diethylzinc in hexanes added (30 mL, 30 mmol, ~5 equivalents per olefin). The solution was stirred for 1 hour at 0° C., then diiodomethane (2.4 mL 50 mmol) added and the reaction stirred overnight at RT. The reaction mixture was concentrated and then redissolved in EtOAc (50 mL). The EtOAc was washed successively with 5% HCl (2×50 mL), water (50 mL), NaHCO$_3$ (50 mL), water (50 mL), and brine (50 mL). The aqueous washes were combined and extracted with DCM (2×50 mL). All organics were combined, dried and concentrated to yield crude CP-γ-LenMC3. $^1$H-NMR indicated some olefins still to be present, so the compound was treated again, using the same procedures and amounts outlined above. This time $^1$H-NMR indicated total conversion of the olefins. Final yield after chromatography was 1.3 g, 1.8 mmol, 90%.

Example 12. Synthesis of MC3MC

MC3MC (Compound 10) having the structure shown below was synthesized as described in Schemes 4 and 5 below.

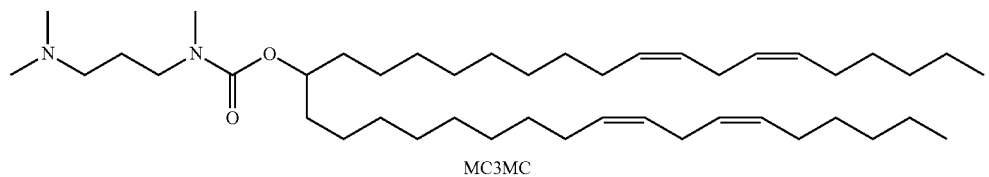 [SMILES: CCCCC/C=C\C/C=C\CCCCCCCCC(CCCCCCCC/C=C\C/C=C\CCCCC)OC(=O)N(C)CCCN(C)C]

MC3MC

Scheme 4

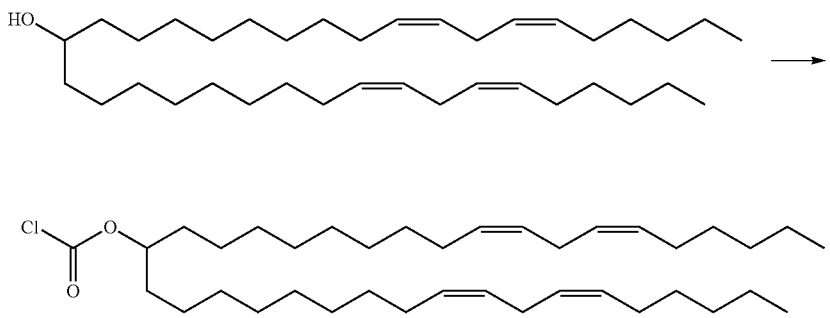

A 50 mL round bottom flask was charged with dilinoleyl methanol (3.06 g, 5.78 mmol) and a stir bar and flushed with nitrogen. Anhydrous DCM (30 mL) was added, followed by diphosgene (1.75 mL, 14.46 mmol, 2.5 eqv.). The reaction was stirred overnight and then concentrated by rotovap and purified by chromatography. This yielded the product as a colourless oil (2.6 g, 4.4 mmol, 76%).

Scheme 5

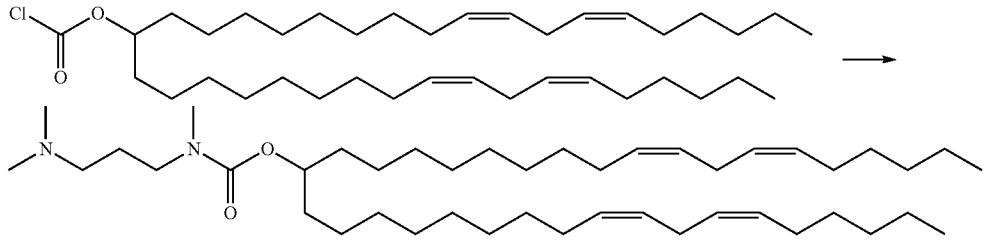

A 50 mL r.b.f. containing the chloroformate (350 mg, 0.59 mmol) and a stir bar was flushed with nitrogen and sealed. Anhydrous DCM (10 mL) and N,N,N'-trimethyl-1,3-propanediamine (580 mg, 5 mmol) were added and the reaction stirred for 4 h. TLC indicated the reaction to have gone to completion. The mixture was diluted to a volume of 40 mL with DCM and washed with sat. NaHCO$_3$ (30 mL), water (30 mL) and brine (30 mL). The aqueous phases were combined and extracted once with DCM (20 mL). Organics were then combined, dried over MgSO$_4$, and concentrated by rotovap. Purification yielded the product as a pale oil, 350 mg, 0.52 mmol, 89%.

Example 13. Synthesis of MC2MC

MC2MC (Compound 11) having the structure shown below was synthesized as described in Scheme 6 below.

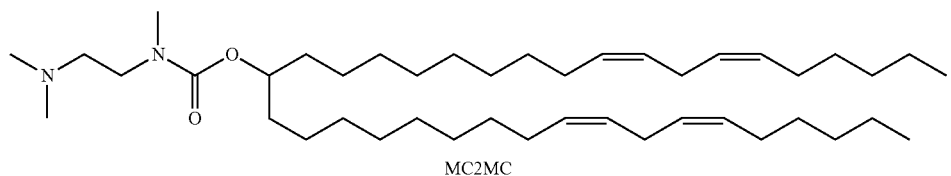 [SMILES: CCCCC/C=C\C/C=C\CCCCCCCCC(CCCCCCCC/C=C\C/C=C\CCCCC)OC(=O)N(C)CCN(C)C]

MC2MC

Scheme 6

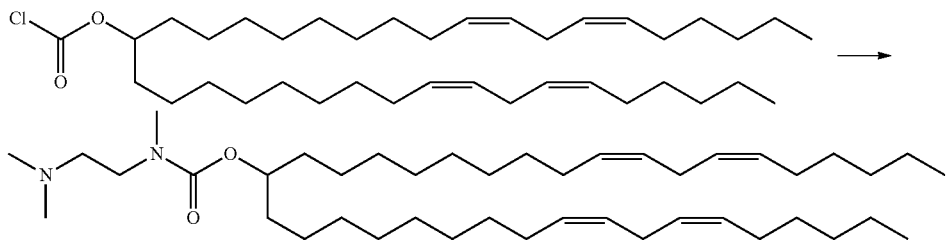

A 50 mL round bottom flask containing the chloroformate (400 mg, 0.68 mmol) and a stir bar was flushed with nitrogen and sealed. Anhydrous DCM (10 mL) and N,N,N'-trimethyl-1,2-ethanediamine (510 mg, 5 mmol) were added and the reaction stirred for overnight. TLC indicated the reaction to have gone to completion. The mixture was concentrated by rotovap and purified by column chromatography to yield the product as a pale oil (350 mg, 0.53 mmol, 78%).

Example 14. Synthesis of MC2C

MC2C (Compound 12) having the structure shown below was synthesized as described in Scheme 7 below.

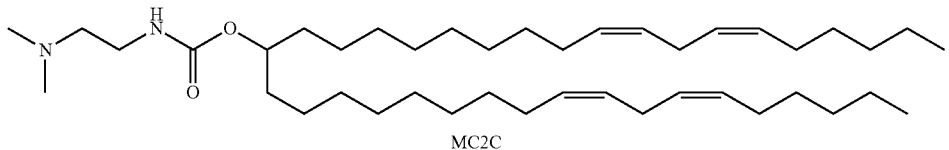

MC2C

Scheme 7

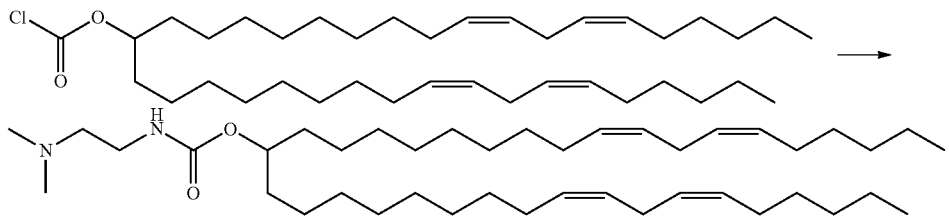

A 50 mL round bottom flask containing the chloroformate (400 mg, 0.68 mmol) and a stir bar was flushed with nitrogen and sealed. Anhydrous DCM (10 mL) and N,N,-dimethyl-ethylenediamine (440 mg, 5 mmol) were added and the reaction stirred for overnight. TLC indicated the reaction to have gone to completion. The mixture was concentrated by rotovap and purified by column chromatography to yield the product as a pale yellow oil (350 mg, 0.54 mmol, 80%).

Example 15. Synthesis of MC3 Ether

MC3 Ether (Compound 13) having the structure shown below was synthesized as described in Scheme 8 below.

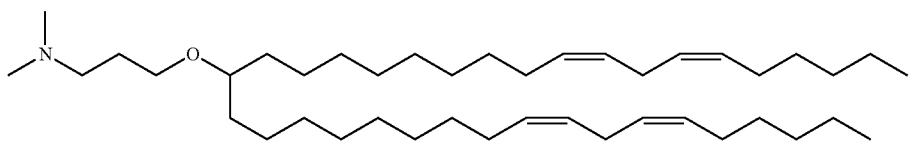

Chemical Formula: $C_{42}H_{79}NO$
Exact Mass: 613.6
Molecular Weight: 614.1
Elemental Analysis: C, 82.15; H, 12.97; N, 2.28; O, 2.61

Scheme 8

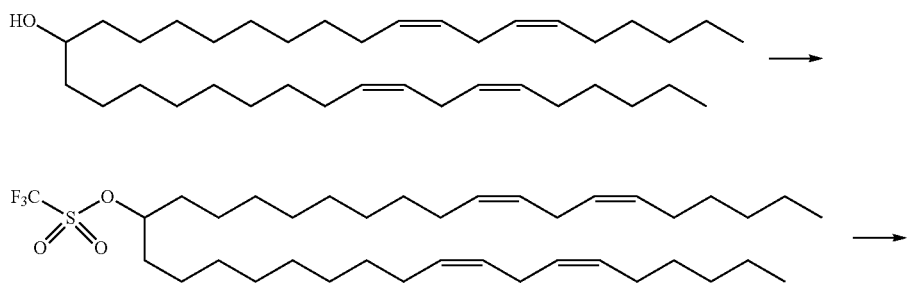

A 50 mL RBF with stir-bar was flushed with nitrogen and anhydrous DCM (4 mL). Triflic anhydride (0.7 g, 420 μL, 2.5 mmol) was added and the flask cooled to −15° C. Anhydrous pyridine (198 mg, 202 μL, 2.5 mmol) was slowly added, causing fuming and a white precipitate to form. A solution of dlinoleyl methanol (1.06 g, 2 mmol) in anhydrous DCM (2 mL) was added slowly over a period of 2 minutes. After stirring for 2 h at ~−15° C. the reaction was off-white in color. TLC showed triflate formation and water (2 mL) was added to quench the reaction. DCM (10 mL) was added and the mixture washed with water (2×20 mL), dried (MgSO$_4$), filtered and transferred to a 25 mL round bottom flask. Proton Sponge (1.07 g, 5 mmol, min 2.5 eqv.), dimethylaminopropanol (515 mg, 5 mmol, min. 2.5 eqv) and a stir bar added and the vessel flushed with nitrogen, fitted with a condenser and refluxed for 48 h. Water (10 mL) was added, and after stirring vigorously for several minutes, separated in a 30 mL sep funnel. The organic was washed again with water (10 mL), dried over MgSO$_4$, concentrated and purified by chromatography (MeOH/CHCl$_3$) to yield the product as a pale yellow oil (400 mg, 33%).

Alternatively, MC3 Ether (Compound 13) was synthesized starting from dilinoleyl methanol (DLinMeOH) as follows:

Synthesis of Compound 14

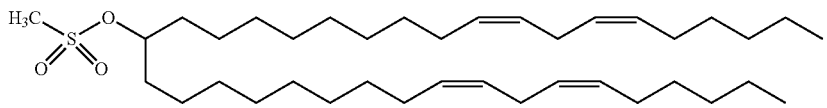

Chemical Formula: C$_{38}$H$_{70}$O$_3$S
Exact Mass: 606.5
Molecular Weight: 607.0
Elemental Analysis: C, 75.19; H, 11.62; O, 7.91; S, 5.28

A 50 mL RBF with stir-bar was flushed with nitrogen, and DLinMeOH (1060 mg, 2 mmol), TEA (6 mmol, 834 μL) and anh. DCM (20 mL) added. Flask was cooled to 0° C. and either MsCl (6 mmol) added. Reaction was stirred overnight. Reaction was diluted to 70 mL with DCM, washed with sat. NaHCO$_3$ (2×50 mL) and sat. NaCl (50 mL), dried (MgSO$_4$), filtered, concentrated and purified by column chromatography (14% EtOAc in hexane). Yield 900 mg, 75%.

Synthesis of MC3 Ether

A 50 mL RBF with stir-bar were flushed with nitrogen, and NaH (220 mg, 9 mmol), dimethylaminopropanol (927 mg, 1.06 mL, 9 mmol) and anh. benzene (10 mL) added. After effervescence subsided, Compound 14 (440 mg, 0.75 mmol) was added and RM refluxed overnight at 90° C. TLC indicated 30-50% product formation. RM was refluxed a second night, but TLC did not appear to indicate further reaction. The reaction was diluted to 40 mL with benzene, and quenched with ethanol (25 mL). It was then washed with water (40 mL), dried and concentrated. The crude product was purified to yield product as a pale yellow oil, 157 mg, 33%.

Example 16. Synthesis of MC4 Ether

MC4 Ether (Compound 15) having the structure shown below was synthesized as described below.

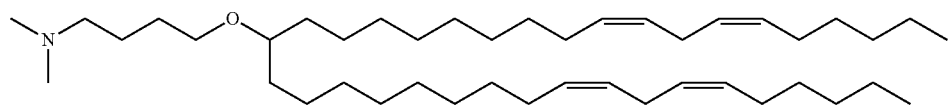

Chemical Formula: C$_{43}$H$_{81}$NO
Exact Mass: 627.6
Molecular Weight: 628.1
Elemental Analysis: C, 82.22; H, 13.00; N, 2.23; O, 2.55

A 50 mL RBF with stir-bar were flushed with nitrogen, and NaH (220 mg, 9 mmol), dimethylaminobutanol (1.05 g, 9 mmol) and anh. benzene (10 mL) added. After effervescence subsided, Compound 14 (440 mg, 0.75 mmol) was added and RM refluxed overnight at 90° C. TLC indicated some product formation. The reaction was diluted to 40 mL with benzene, and quenched with ethanol (25 mL). It was then washed with water (40 mL), dried and concentrated. The crude product was purified to yield product as a pale yellow oil, 145 mg, 31%.

Example 17. Synthesis of MC3 Amide

MC3 Amide (Compound 16) having the structure shown below was synthesized as described in Schemes 9-11 below.

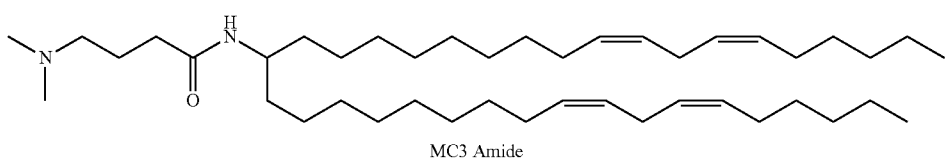 [SMILES: CCCCC/C=C\C/C=C\CCCCCCCCC(CCCCCCCC/C=C\C/C=C\CCCCC)NC(=O)CCCN(C)C]

MC3 Amide

Scheme 9

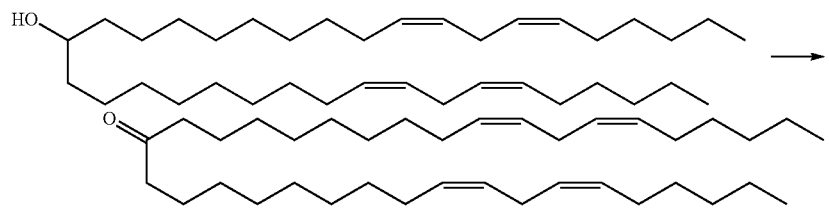

To a 500 mL RBF containing a solution of dilinoleyl methanol (10 g, 18.9 mmol) in DCM (200 mL) was added pyridinium chlorochromate (12.24 g, 56.7 mmol), anh. sodium carbonate (1.0 g, 9.5 mmol) and a stir bar. The resulting suspension was stirred under nitrogen at RT for 3 h, after which time TLC indicated all SM to have been consumed. Ether (300 mL) was then added to the mixture and the resulting brown suspension filtered through a pad of silica (300 mL), washing the pad with ether (3×100 mL). The ether phases were combined, concentrated and purified to yield 9.0 g (17.1 mmol, 90%) of ketone.

Scheme 10

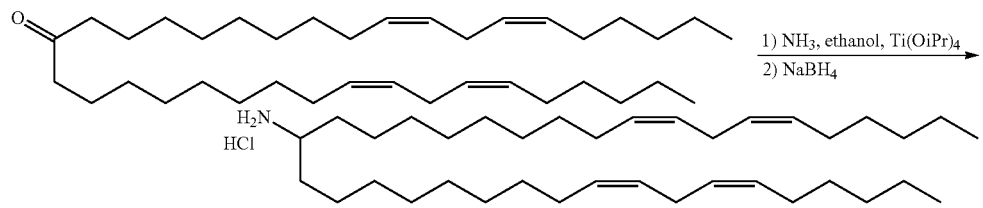

To a solution of dilinoleyl ketone (1.0 g, 1.9 mmol) in 2M ammonia in ethanol (5 mL) was added titanium(IV) isopropoxide (1.15 mL, 3.8 mmol). The solution was stirred under nitrogen at room temperature for 6 hours then sodium borohydride (110 mg, 3.8 mmol) was added. The solution effervesced for approximately 5 minutes, and then a colorless precipitate began to form. The solution was stirred for 16 hours at room temperature, quenched with 10% NH₄OH (25 mL) and diluted with ethyl acetate (50 mL). The inorganic solids were filtered and the aqueous phase was washed with ethyl acetate (2×75 mL). The combine ethyl acetate extracts were washed with 2M HCl (2×50 mL), dried on magnesium sulfate, filtered and concentrated to dryness to afford the product as a pale yellow HCl salt (1.1 g, quantitative).

Scheme 11

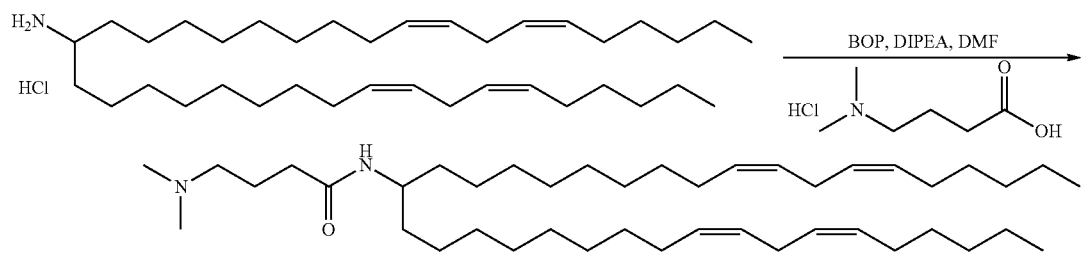

To a solution of dilinoleyl methylamine hydrochloride (1.1 g, 1.95 mmol), BOP (1.1 g, 2.4 mmol) and 4-(dimethylamino)butanoic acid hydrochloride (402 mg, 2.4 mmol) in anhydrous DMF (20 mL) was added diisopropylethylamine (1.4 mL, 7.8 mmol). The solution was stirred for 16 hours at room temperature. The solution was concentrated in vacuo to dryness and dissolved in ethyl acetate (100 mL). The ethyl acetate was washed with brine (3×50 mL), dried on magnesium sulfate, filtered and concentrated in vacuo to dryness. The residue was purified by column chromatography (1% to 2.5% MeOH in CHCl$_3$) to afford the product as an orange oil. Decolorization through a pad of silica gel (eluted with 50% hexanes ethyl acetate to 100% ethyl acetate) afforded the product as a pale yellow oil (151 mg, 12%).

Example 18. Synthesis of Pan-MC3

Phytanyl-MC3 ("Pan-MC3") (Compound 17) having the structure shown below was synthesized as described in Scheme 12 below.

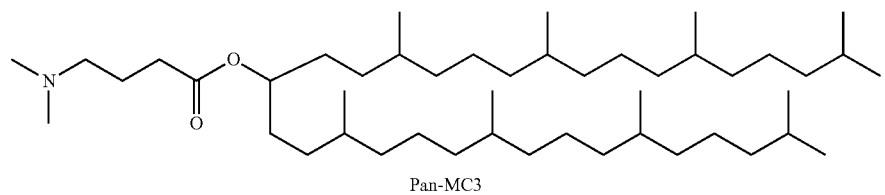 [SMILES: CC(C)CCCC(C)CCCC(C)CCCC(C)CCC(CCC(C)CCCC(C)CCCC(C)CCCC(C)C)OC(=O)CCCN(C)C]

Pan-MC3

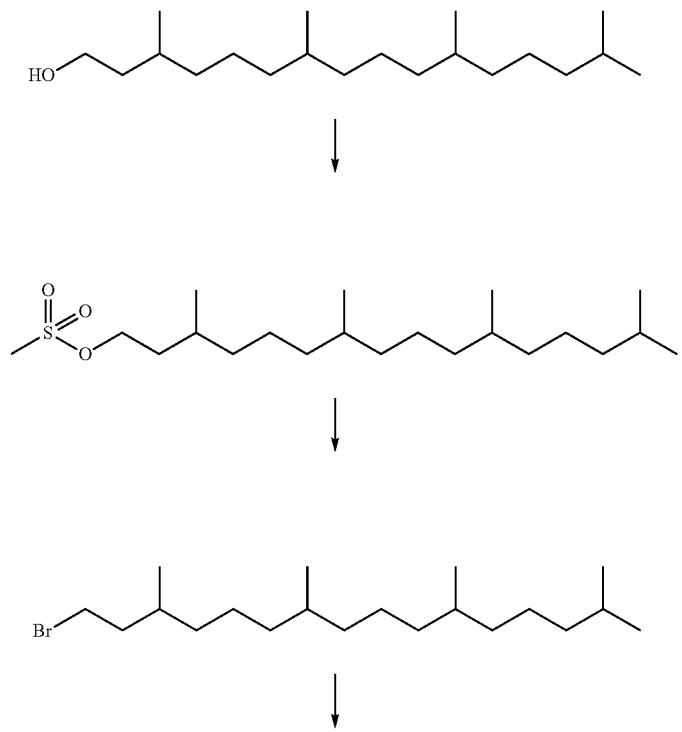

Scheme 12

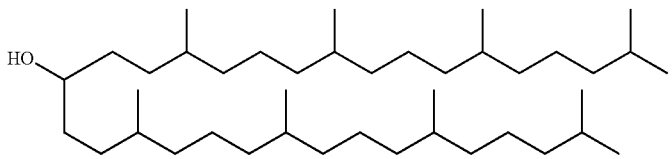

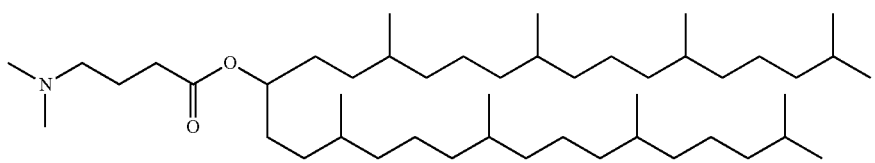

Synthesis of Phytanyl Mesylate

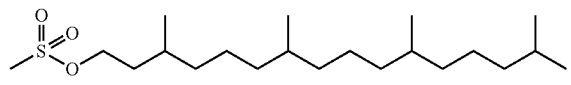 [SMILES: CC(C)CCCC(C)CCCC(C)CCCC(C)CCOS(C)(=O)=O]

To a solution of phytanol (14.98 g, 50.2 mmol) in anhydrous dichloromethane (150 mL) under nitrogen was added triethylamine (7.7 mL, 55.2 mmol). The solution was cooled to −10° C. and then a solution of methanesulfonyl chloride (11.51 g, 100.5 mmol) in anhydrous dichloromethane (100 mL) was added dropwise over 30 minutes. Upon completion, the solution was diluted to 500 mL using dichloromethane. The solution was washed twice with saturated NaHCO$_3$, dried over MgSO$_4$, filtered, and concentrated to dryness to afford the product as a colorless oil (18.9 g, 100%).

Synthesis of Phytanyl Bromide

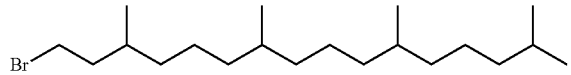 [SMILES: CC(C)CCCC(C)CCCC(C)CCCC(C)CCBr]

To a suspension of magnesium bromide diethyl etherate (25.9 g, 100.3 mmol) in anhydrous diethyl ether (250 mL) under nitrogen at room temperature was added a solution of phytanyl mesylate (18.9 g, 50.2 mmol) in anhydrous diethyl ether (200 mL) dropwise over 15 minutes. The resulting slurry was stirred for 72 hours at room temperature. Upon completion, the reaction mixture was cooled to 0° C. and ice cold water was added dropwise until all solid dissolved and bubbling stopped. Diethyl ether (300 mL) was added, and the organic and aqueous layers separated. The aqueous layer was back-extracted with diethyl ether (200 mL). The combined diethyl ether extracts were dried on MgSO$_4$, filtered, and concentrated. The resulting oil was purified by column chromatography (column 10" L×2" W; eluted with 100% hexanes) to afford the product as a pale yellow oil (16.3 g, 90%).

Synthesis of Diphytanyl Methanol

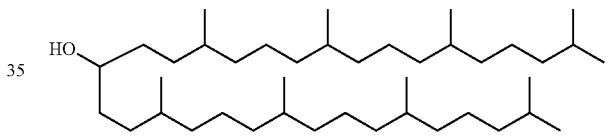

Magnesium turnings (1.18 g, 48.5 mmol) were heated at 250° C. in an oven for 1 hour and then stirred at room temperature under nitrogen for 2 hours. Anhydrous diethyl ether (300 mL) and a single crystal of iodine were added, followed by a solution of phytanyl bromide (15.2 g, 42.1 mmol) in anhydrous diethyl ether (30 mL). The resulting cloudy mixture was heated to reflux overnight. The solution was cooled (0° C.) and a solution of ethyl formate (3.9 mL, 48.5 mmol) in anhydrous diethyl ether (15 mL) was added dropwise over 25 minutes. The resulting yellow solution was again stirred overnight. The yellow solution was cooled (0° C.) and quenched using 5M HCl (15 mL), and then hexanes (100 mL) and water (150 mL) were added. The aqueous and organic layers were separated and the aqueous layer back-extracted twice with hexanes. The combined organics were washed with water, dried on MgSO$_4$, filtered, and concentrated in vacuo to dryness.

The resulting pale yellow oil was dissolved in ethanol (25 mL) and transferred to a flask containing a solution of potassium hydroxide (2.2 g, 39.2 mmol) in water (5 mL). The resulting biphasic solution was stirred at 10° C. for 2.5 hours. Ethanol was removed in vacuo and hexanes (25 mL) and 5M HCl (35 mL) were added. The organic and aqueous layers were separated and the organic layer washed twice with water. The combined organics were dried over MgSO$_4$, filtered, and concentrated. The resulting pale yellow oil was purified by column chromatography (column 12" L×2" W; eluted with a gradient of 100% hexanes→2%-4% ethyl ether in hexanes) to afford the product as a pale yellow oil (6.4 g, 49%).

Synthesis of Phytanyl-MC3

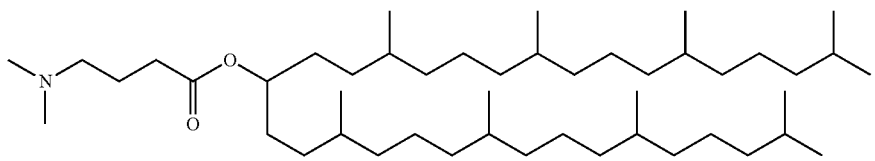 [SMILES: CC(C)CCCC(C)CCCC(C)CCCC(C)CCC(CCC(C)CCCC(C)CCCC(C)CCCC(C)C)OC(=O)CCCN(C)C]

To a solution of diphytanyl methanol (6.4 g, 10.3 mmol) and 4-(dimethylamino) butyric acid hydrochloride (2.25 g, 13.4 mmol) in anhydrous dichloromethane (60 mL) under nitrogen at room temperature was added EDC (2.77 g, 18.0 mmol), diisopropylethylamine (5.4 mL, 31.0 mmol), and 4-dimethylaminopyridine (45 mg, 0.37 mmol). After 16 hours the reaction mixture was diluted with dichloromethane (75 mL). The organic layer was washed with saturated NaHCO$_3$, water, and brine, and then dried on MgSO$_4$, filtered, and concentrated. The resulting yellow oil was purified by column chromatography (column 10" L×2" W; eluted with a gradient of 100% hexanes→10%→50% ethyl acetate in hexanes) to afford the product as a pale yellow oil (3.53 g, 49%) with recovery of some phytanyl methanol (2.81 g, 44%).

Example 19. Synthesis of Pan-MC4

Phytanyl-MC4 ("Pan-MC4") (Compound 18) having the structure shown below was synthesized as described in Scheme 13 below.

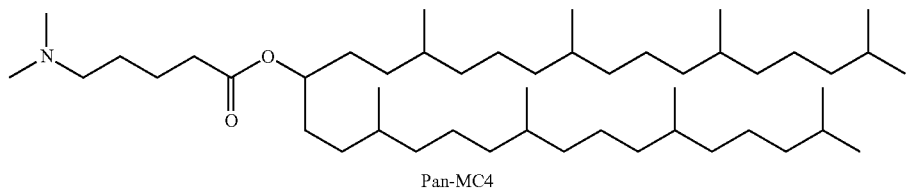 [SMILES: CC(C)CCCC(C)CCCC(C)CCCC(C)CCC(CCC(C)CCCC(C)CCCC(C)CCCC(C)C)OC(=O)CCCCN(C)C]

Pan-MC4

Scheme 13

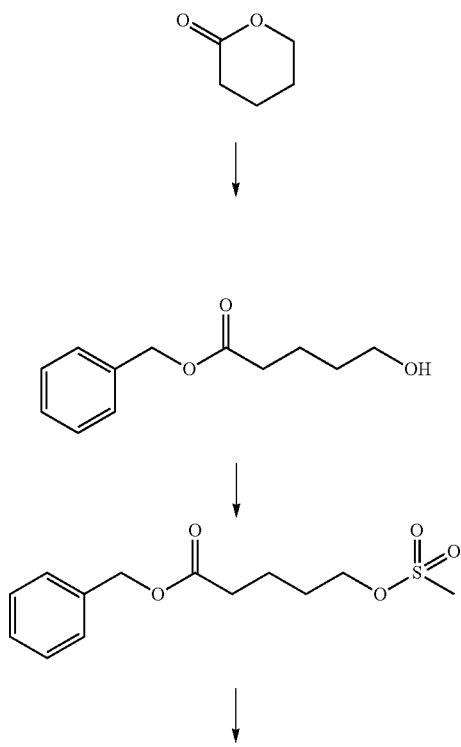

-continued

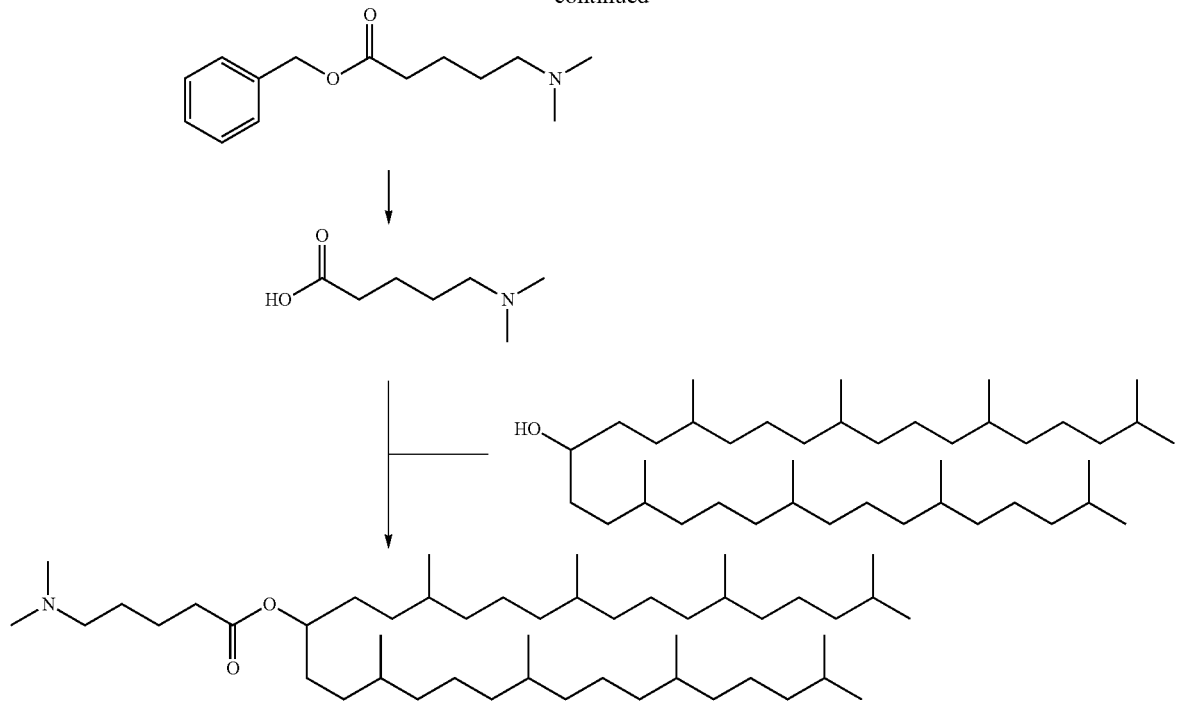

Synthesis of Benzyl 5-Hydroxypentanoate

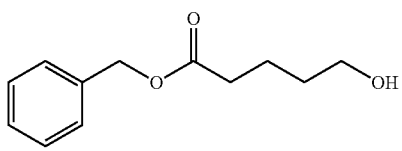 [SMILES: O=C(CCCCO)OCc1ccccc1]

A solution of δ-valerolactone (10 g, 100 mmol) in 1M aqueous sodium hydroxide (100 mL) was heated overnight with stirring at 65° C. The solution was concentrated in vacuo to dryness and any residual water removed under high vacuum at −190° C. The resulting white powder was broken up and suspended in acetone (40 mL). With stirring, benzyl bromide (17 g, 101.4 mmol) and tetrabutylammonium bromide (0.82 g, 2.539 mmol) were added. The mixture was heated at 45° C. with stirring for 72 hours, cooled, and concentrated. The resulting white oily powder was dissolved in ethyl acetate (300 mL) and washed twice each with saturated NaHCO₃ and brine. The organic portion was dried over anhydrous MgSO₄, filtered, and then concentrated. The result was a yellow oil, which was purified by column chromatography (column 10″ L×2″ W; eluted with a gradient of 100% hexanes→30%→50% ethyl acetate in hexanes) to afford the product as a pale yellow oil (3.11 g, 15%).

Synthesis of Benzyl 5-(Methanesulfonyl)Pentanoate

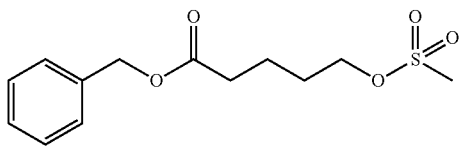 [SMILES: CS(=O)(=O)OCCCCC(=O)OCc1ccccc1]

To a solution of benzyl 5-hydroxypentanoate (2.01 g, 9.65 mmol) in anhydrous dichloromethane (30 mL) under nitrogen at −15° C. was added triethylamine (2.7 mL, 19.3 mmol) followed by a solution of methanesulfonyl chloride (1.5 mL, 19.3 mmol) dropwise over 20 minutes. The reaction was stirred at room temperature overnight and then diluted to 75 mL using dichloromethane. The organic layer was washed three times with saturated NaHCO₃ and the combined aqueous layers backextracted with dichloromethane. The combined organic phases were dried over MgSO₄, filtered, and concentrated. The resulting dark orange oil was purified by column chromatography (column 5″ L×1″ W; eluted with a gradient of 100% hexanes→10%→20%→25% diethyl ether in hexanes) to afford the product as a pale yellow oil (1.39 g, 50%).

Synthesis of Benzyl 5-(Dimethylamino)Pentanoate

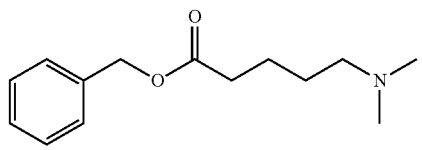 [SMILES: CN(C)CCCCC(=O)OCc1ccccc1]

Benzyl 5-(methanesulfonyl)pentanoate (1.39 g, 4.85 mmol) was allowed to react in a 5.6M solution of dimethylamine in ethanol (100 mL) for 20 hours. The solution was then concentrated in vacuo to dryness. The resulting brown oil was purified by column chromatography (column 10″ L×1″ W; eluted with a gradient of 100% dichloromethane→2%/0.5%→4%/0.5% MeOH/NH₄OH in dichloromethane) to afford the product as a yellow oil (0.79 g, 69%).

Synthesis of 5-(Dimethylamino)Pentanoic Acid

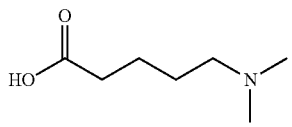

To a solution of 5-(dimethylamino)benzyl pentanoate (0.79 g, 33.6 mmol) in anhydrous ethyl acetate (20 mL) under nitrogen at room temperature was added 10% palladium on carbon (250 mg). The solution was stirred vigorously under a hydrogen atmosphere. After 16 hours additional palladium on carbon (100 mg) was added to encourage the reaction, and at 24 hours hydrogen gas was bubbled through the solution. At 40 hours the solution was filtered through celite and concentrated in vacuo to dryness to afford the product as a yellow oil (295 mg, 60.4%).

Synthesis of Phytanyl-MC4

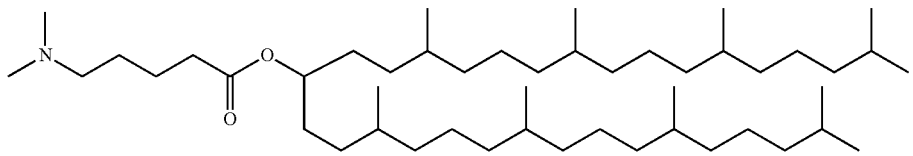 [SMILES: CC(C)CCCC(C)CCCC(C)CCCC(C)CCC(CCC(C)CCCC(C)CCCC(C)CCCC(C)C)OC(=O)CCCCN(C)C]

A solution of diphytanyl methanol (0.8 g, 1.3 mmol) and 4-(dimethylamino) pentanoic acid (0.24 g, 1.7 mmol) in anhydrous dichloromethane (10 mL) under nitrogen at room temperature was added EDC (0.347 g, 1.8 mmol), diisopropylethylamine (0.67 mL, 3.9 mmol), and 4-dimethylaminopyridine (45 mg, 0.37 mmol). After 20 hours additional 5-(dimethylamino)pentanoic acid (0.05 g, 0.34 mmol) was added to encourage the reaction. The reaction was stirred for an additional 52 hours and then diluted to 50 mL using dichloromethane. The organic phase was washed with saturated NaHCO$_3$, water, and brine, and the combined aqueous layers backextracted with dichloromethane. The combined organic layers were dried on MgSO$_4$, filtered, and concentrated. The resulting yellow oil was purified by column chromatography (column 10" L×1¼" W; eluted with a gradient of 100% hexanes→10%→50% ethyl acetate in hexanes) to afford the product as a pale yellow oil (474 mg, 51%) with recovery of some diphytanyl methanol (348 mg, 43.5%).

Example 20. Synthesis of Pan-MC5

Phytanyl-MC5 ("Pan-MC5") (Compound 19) having the structure shown below was synthesized as described in Scheme 14 below.

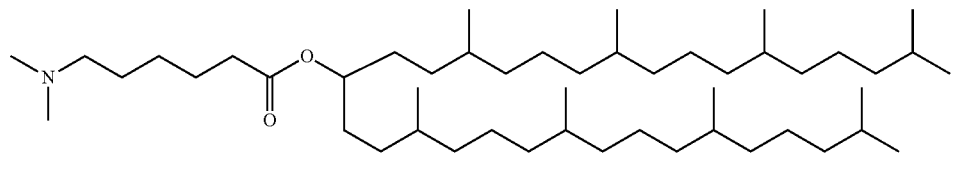

Pan-MC5

Scheme 14

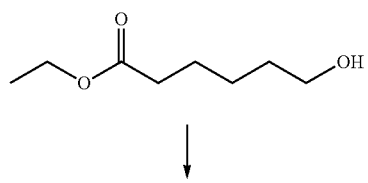

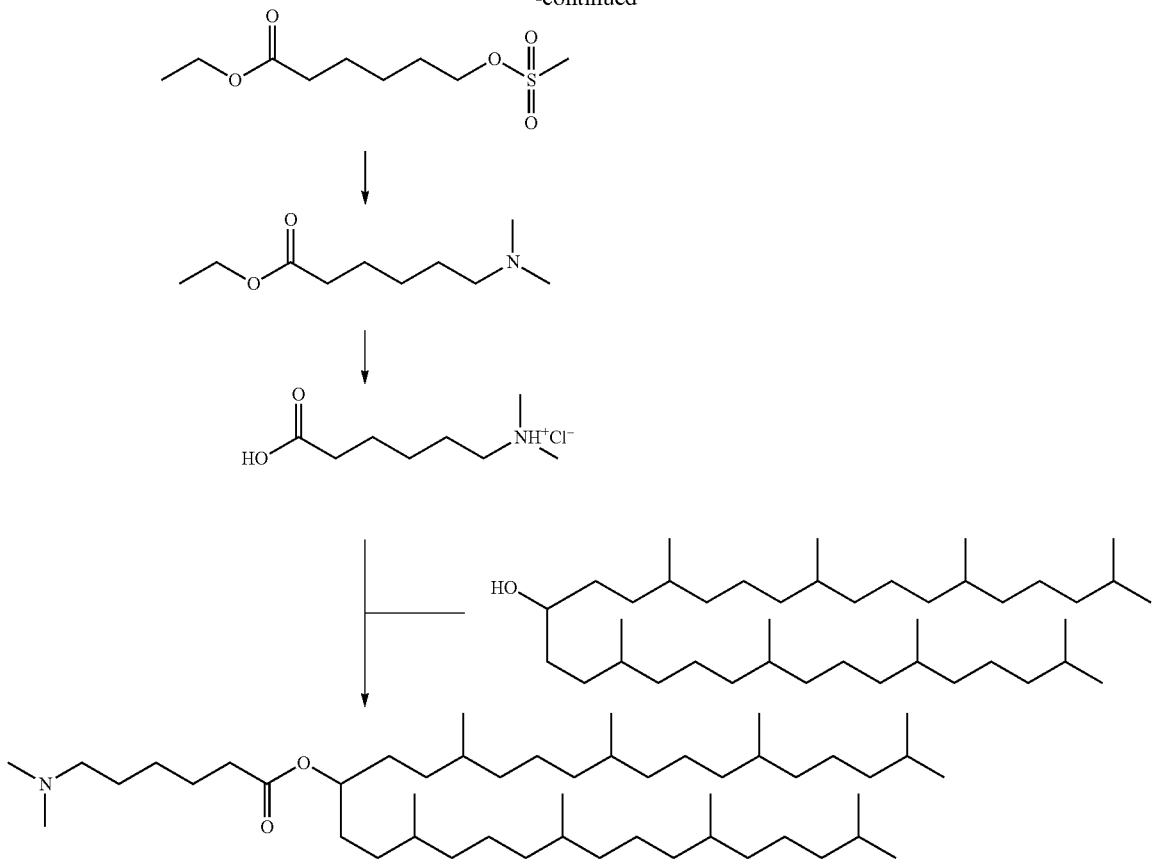

Synthesis of Ethyl 6-(Methanesulfonyl)Hexanoate

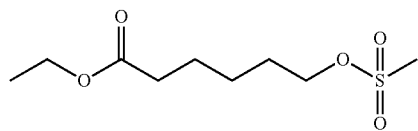

To a solution of ethyl 6-hydroxyhexanoate (5 g, 31.2 mmol) in anhydrous dichloromethane (115 mL) under nitrogen at −10° C. was added triethylamine (8.7 mL, 62.5 mmol) followed by methanesulfonyl chloride (4.8 mL, 62.5 mmol) dropwise over 1 hour. The resulting solution was stirred at room temperature for 6 hours and then diluted to 300 mL using dichloromethane. The solution was washed with twice saturated NaHCO$_3$, and the aqueous layers backextracted with dichloromethane. The combined organics were dried over MgSO$_4$, filtered, and concentrated. The resulting dark orange oil was purified by column chromatography (column 5" L×2" W; eluted with a gradient of 100% hexanes→10%→20% ethyl acetate in hexanes) to afford the product as a pale yellow oil.

Synthesis of Ethyl 6-(dimethylamino)hexanoate

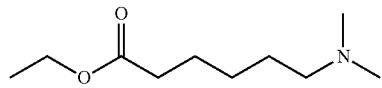

Ethyl 6-(methanesulfonyl)hexanoate was allowed to react in a 5.6M solution of dimethylamine in ethanol (100 mL) for 17 hours. The solution was then concentrated in vacuo to dryness. The resulting bright orange paste was purified by column chromatography (column 5" L×2" W; eluted with a gradient of 100% dichloromethane→1%/0.25%→2%/0.5% MeOH/NH$_4$OH in dichloromethane) to afford the product as a yellow oil.

Synthesis of 6-(Dimethylamino)Hexanoic Acid Hydrochloride

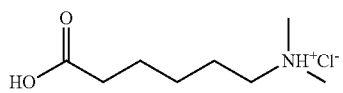

To a solution of Ethyl 6-(dimethylamino)hexanoate (5.85 g, 31.2 mmol) in dioxane (200 mL) was added 1M NaOH (200 mL). The solution was stirred vigorously at room temperature for 2 hours and then dioxane was removed in vacuo. The resulting aqueous solution was made slightly acidic using concentrated HCl (15 mL). At this point, dichloromethane and ether were used in an attempt to extract the product from solution. However, all attempts failed. Instead, water was removed under high vacuum to afford the product as an off-white solid, a mixture of approximately 35% 6-(dimethylamino)hexanoic acid hydrochloride in NaCl by weight.

Synthesis of Phytanyl-MC5

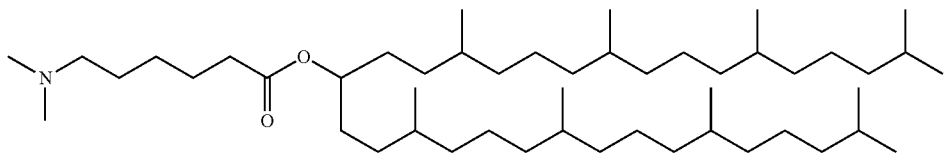 [SMILES: CC(C)CCCC(C)CCCC(C)CCCC(C)CCC(CCC(C)CCCC(C)CCCC(C)CCCC(C)C)OC(=O)CCCCCN(C)C]

To a solution of diphytanyl methanol (1.5 g, 2.4 mmol) and 35% 6-(dimethylamino) hexanoic acid hydrochloride (1.79 g, 3.2 mmol) in anhydrous dichloromethane (15 mL) under nitrogen at room temperature was added EDC (0.65 g, 3.4 mmol), diisopropylethylamine (1.26 mL, 7.2 mmol) and 4-dimethylaminopyridine (10 mg). After 48 hours additional 35% 6-(dimethylamino)hexanoic acid (1 g, 1.8 mmol), EDC (0.32 g, 1.7 mmol) and 4-dimethylaminopyridine (15 mg) were added. After an additional 72 hours the reaction mixture was diluted to 75 mL using dichloromethane and then washed with water, saturated NaHCO$_3$, and brine. The combined aqueous layers were backextracted twice with dichloromethane and the combined organic layers dried over MgSO$_4$, filtered, and concentrated. The resulting yellow oil was purified by column chromatography (column 1¼" W×10" L; eluted with a gradient of 100% hexanes→1%→50% ethyl acetate in hexanes) to afford the product as a yellow oil (175 mg, 10%) with some recovery of diphytanyl methanol.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications, patents, PCT publications, and Genbank Accession Nos., are incorporated herein by reference for all purposes.

---

What is claimed is:

1. A composition comprising:
a plurality of nucleic acid-lipid particles, wherein each particle in the plurality of particles comprises:
(a) a nucleic acid;
(b) a cationic lipid comprising one or more diastereomers;
(c) a non-cationic lipid; and
(d) a conjugated lipid that inhibits aggregation of particles,
wherein at least about 95% of the particles in the plurality of particles are electron-dense.

2. The composition of claim 1, wherein the nucleic acid is RNA.

3. The composition of claim 1, wherein the nucleic acid is mRNA.

4. The composition of claim 1, wherein the cationic lipid comprises a mixture of diastereomers.

5. The composition of claim 1, wherein the cationic lipid consists of one or more diastereomers.

6. The composition of claim 1, wherein the cationic lipid has a protonatable group with a pK$_a$ of from about 4 to about 7.

7. The composition of claim 1, wherein the non-cationic lipid is a mixture of (i) a phospholipid and cholesterol or (ii) a phospholipid and a cholesterol derivative.

8. The composition of claim 1, wherein the conjugated lipid that inhibits aggregation of particles is a polyethyleneglycol (PEG)-lipid conjugate.

9. The composition of claim 8, wherein the PEG-lipid conjugate is selected from the group consisting of a PEG-diacylglycerol (PEG-DAG) conjugate, a PEG dialkyloxypropyl (PEG-DAA) conjugate, a PEG-phospholipid conjugate, a PEG-ceramide (PEG-Cer) conjugate, and a mixture thereof.

10. The composition of claim 1, wherein the electron-dense particles comprise an inverse hexagonal (H$_{II}$) or cubic phase structure.

11. The composition of claim 1, wherein greater than 95% of the particles are electron-dense.

12. The composition of claim 1, wherein at least 96% of the particles are electron-dense.

13. The composition of claim 1, wherein at least 97% of the particles are electron-dense.

14. The composition of claim 1, wherein at least 98% of the particles are electron-dense.

15. The composition of claim 1, wherein at least 99% of the particles are electron-dense.

16. The composition of claim 1, wherein the nucleic acid is fully encapsulated in the particles.

17. The composition of claim 1, wherein the particles have a mean diameter of from about 60 nm to about 130 nm.

18. The composition of claim 1, wherein the particles have a mean diameter of from about 70 nm to about 110 nm.

19. The composition of claim 1, wherein the particles have a mean diameter of from about 90 nm to about 100 nm.

20. The composition of claim 1, wherein the particles have a lipid:nucleic acid ratio of from about 2 to about 25.

21. The composition of claim 1, wherein the particles have a lipid:nucleic acid ratio of from about 3 to about 20.

22. A pharmaceutical composition comprising a composition of claim 1 and a pharmaceutically acceptable carrier.

23. A method for introducing a therapeutic agent into a cell, the method comprising:

contacting the cell with a composition of claim 1.

24. A method for the in vivo delivery of a therapeutic agent, the method comprising:

administering to a mammal a composition of claim 1.

* * * * *

UNITED STATES PATENT AND TRADEMARK OFFICE
CERTIFICATE OF CORRECTION

PATENT NO. : 12,129,467 B2
APPLICATION NO. : 18/410136
DATED : October 29, 2024
INVENTOR(S) : Ed Yaworski, Lloyd B. Jeffs and Lorne R. Palmer Page 1 of 1

It is certified that error appears in the above-identified patent and that said Letters Patent is hereby corrected as shown below:

In the Claims

Column 151, Claim 1, Line 47: After "diastereomers", insert --and not including 3-(N-(N',N'-dimethylaminoethane)-carbamoyl)cholesterol (DC-Chol), 2,3-dioleyloxy-N-[2-(spermine-carboxamido)ethyl]-N,N-dimethyl-1-propanaminium (DOSPA), 3-dimethylamino-2-(cholest-5-en-3-beta-oxybutan-4-oxy)-1-(cis,cis-9,12-octadecadienoxy)propane (CLinDMA), or 2-[5'-(cholest-5-en-3-beta-oxy)-3'-oxapentoxy]-3-dimethy-1-(cis,cis-9',12'-octadecadienoxy)propane (CpLinDMA)--

Column 153, Claim 22, Line 9: Before "composition", delete "a" and replace with --the--

Column 153, Claim 23, Line 13: Before "composition", delete "a" and replace with --the--

Column 153, Claim 24, Line 16: Before "composition", delete "a" and replace with --the--

Signed and Sealed this
Seventh Day of October, 2025

John A. Squires
*Director of the United States Patent and Trademark Office*

SEQUENCE LISTING

```
Sequence total quantity: 4
SEQ ID NO: 1            moltype = RNA  length = 21
FEATURE                 Location/Qualifiers
misc_feature            1..21
                        note = synthetic serine/threonine protein kinase 13
                          (STPK13), polo-like kinase 1 (PLK-1) siRNA PLK1424 2/6
                          sense strand
source                  1..21
                        mol_type = other RNA
                        organism = synthetic construct
modified_base           10
                        mod_base = um
modified_base           14
                        mod_base = um
modified_base           4
                        mod_base = um
modified_base           18
                        mod_base = um
modified_base           20
                        mod_base = um
ncRNA                   1..21
                        ncRNA_class = siRNA
SEQUENCE: 1
agatcaccct ccttaaatat t                                                   21

SEQ ID NO: 2            moltype = RNA  length = 21
FEATURE                 Location/Qualifiers
misc_feature            1..21
                        note = synthetic serine/threonine protein kinase 13
                          (STPK13), polo-like kinase 1 (PLK-1) siRNA PLK1424 2/6
                          antisense strand
source                  1..21
                        mol_type = other RNA
                        organism = synthetic construct
modified_base           20
                        mod_base = um
modified_base           17
                        mod_base = um
modified_base           15
                        mod_base = gm
modified_base           8
                        mod_base = gm
ncRNA                   1..21
```

-continued

```
                       ncRNA_class = siRNA
SEQUENCE: 2
tatttaagga gggtgatctt c                                                  21

SEQ ID NO: 3          moltype = RNA   length = 21
FEATURE               Location/Qualifiers
misc_feature          1..21
                      note = synthetic apolipoprotein B (APOB, ApoB, Apo B-100,
                        apob-100, apob-48, FLDB, LDLCQ4, AI315052), transcript
                        variant 1 siRNA siApoB-8 sense strand
modified_base         4
                      mod_base = gm
modified_base         8
                      mod_base = um
source                1..21
                      mol_type = other RNA
                      organism = synthetic construct
modified_base         14
                      mod_base = um
ncRNA                 1..21
                      ncRNA_class = siRNA
SEQUENCE: 3
agtgtcatca cactgaatac c                                                  21

SEQ ID NO: 4          moltype = RNA   length = 21
FEATURE               Location/Qualifiers
misc_feature          1..21
                      note = synthetic apolipoprotein B (APOB, ApoB, Apo B-100,
                        apob-100, apob-48, FLDB, LDLCQ4, AI315052), transcript
                        variant 1 siRNA siApoB-8 antisense strand
source                1..21
                      mol_type = other RNA
                      organism = synthetic construct
modified_base         4
                      mod_base = um
modified_base         19
                      mod_base = um
modified_base         7
                      mod_base = gm
modified_base         9
                      mod_base = gm
ncRNA                 1..21
                      ncRNA_class = siRNA
SEQUENCE: 4
tattcagtgt gatgacactt g                                                  21
```